US010894079B2

(12) United States Patent
Müllner et al.

(10) Patent No.: US 10,894,079 B2
(45) Date of Patent: Jan. 19, 2021

(54) CHROMATOGRAPHY BASED PURIFICATION STRATEGIES FOR VIRUSES

(71) Applicant: Themis Bioscience GmbH, Vienna (AT)

(72) Inventors: Matthias Müllner, Pixendorf (AT); Erich Tauber, Muckendorf (AT); Patrick Csar, Königstetten (AT); Angelika Irmler, Vienna (AT); Katrin Ramsauer, Vienna (AT); Sabrina Schrauf, Mörbisch am See (AT)

(73) Assignee: THEMIS BIOSCIENCE GMBH, Vienna (AT)

( * ) Notice: Subject to any disclaimer, the term of this patent is extended or adjusted under 35 U.S.C. 154(b) by 16 days.

(21) Appl. No.: 16/063,240

(22) PCT Filed: Dec. 23, 2016

(86) PCT No.: PCT/EP2016/082628
§ 371 (c)(1),
(2) Date: Jun. 15, 2018

(87) PCT Pub. No.: WO2017/109211
PCT Pub. Date: Jun. 29, 2017

(65) Prior Publication Data

US 2018/0371426 A1 Dec. 27, 2018

(30) Foreign Application Priority Data

Dec. 23, 2015 (EP) .................................... 15202480
Mar. 29, 2016 (EP) .................................... 16162688

(51) Int. Cl.

| | |
|---|---|
| ***B01D 15/38*** | (2006.01) |
| ***C12N 7/00*** | (2006.01) |
| ***A61K 39/12*** | (2006.01) |
| ***C12N 15/86*** | (2006.01) |
| ***A61K 39/165*** | (2006.01) |
| ***B01J 20/282*** | (2006.01) |
| ***C12N 7/02*** | (2006.01) |
| ***A61P 31/14*** | (2006.01) |
| *B01D 15/36* | (2006.01) |

(52) U.S. Cl.
CPC ............ *A61K 39/12* (2013.01); *A61K 39/165* (2013.01); *A61P 31/14* (2018.01); *B01D 15/3804* (2013.01); *B01J 20/282* (2013.01); *C12N 7/00* (2013.01); *C12N 7/02* (2013.01); *C12N 15/86* (2013.01); *B01D 15/361* (2013.01); *C12N 2760/00034* (2013.01); *C12N 2760/00051* (2013.01); *C12N 2760/18051* (2013.01); *C12N 2760/18434* (2013.01); *C12N 2760/18443* (2013.01); *C12N 2770/24121* (2013.01); *C12N 2770/24122* (2013.01); *C12N 2770/24134* (2013.01); *C12N 2770/24151* (2013.01); *C12N 2800/22* (2013.01); *C12N 2840/105* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 7,759,104 B2 * | 7/2010 | Federspiel | C12N 7/00 | 424/212.1 |
| 2009/0304729 A1 * | 12/2009 | Gregersen | A61K 39/12 | 424/186.1 |

FOREIGN PATENT DOCUMENTS

| | | | |
|---|---|---|---|
| EP | 1 375 512 | B1 | 7/2009 |
| EP | 1 599 495 | B9 | 8/2012 |
| EP | 1 939 214 | B1 | 7/2013 |
| WO | 2004/000876 | A1 | 12/2003 |
| WO | 2008/078198 | A2 | 7/2008 |
| WO | 2014/049094 | A1 | 4/2014 |
| WO | WO-2014049094 | A1 * | 4/2014 |

OTHER PUBLICATIONS

Rager et al., The EMBO Journal, 2002, 21(10):2364-2372. (Year: 2002).*

BIA Separations, 2010, Poster "Virus Downstream Processing Using CIM Monoliths", available from http://wolfson.huji.ac.il/purification/PDF/Columns/BIAseparations%20_Virus_DSP_brochure.pdf, 4 page printout. (Year: 2010).*

Sviben et al., Journal of Chromatography B, 2017, 1054:10-19. (Year: 2017).*

Brandler et al., "A recombinant measles vaccine expressing chikungunya virus-like particles is strongly immunogenic and protects mice from lethal challenge with chikungunya virus," *Vaccine 31*:3718-3725, 2013.

Branovic et al., "Application of short monolithic columns for improved detection of viruses," *Journal of Virological Methods 110*:163-171, 2003.

(Continued)

*Primary Examiner* — Stacy B Chen
(74) *Attorney, Agent, or Firm* — Seed Intellectual Property Law Group LLP

(57) ABSTRACT

The present invention provides purification strategies for sterically demanding, i.e. large and pleomorphic, infectious virus particles or VLPs derived therefrom, preferably having a measles virus scaffold to yield fractions or compositions with a significantly reduced content of contaminating host cell DNA and a reduced content of further process-related impurities. Further provided are methods of propagating and purifying infectious virus particles having a measles virus scaffold suitable to provide a preparation having a strongly reduced content of contaminating host cell DNA and a reduced content of further process-related impurities for immunogenic or anti-tumor purposes. In addition, immunogenic and vaccine compositions based on the above methods are provided. Finally, there are provided immunogenic or vaccine compositions produced by the disclosed methods, which are suitable for use in immunogenic or prophylactic vaccination treatment of a subject in need thereof.

10 Claims, No Drawings

Specification includes a Sequence Listing.

(56) References Cited

OTHER PUBLICATIONS

FDA Briefing Document, Vaccines and Related Biological Products Advisory Committee Meeting, "Cell Lines Derived from Human Tumors for Vaccine Manufacture," Sep. 19, 2012 (30 pages).
Herzer et al., "Isoelectric titration curves of viral particles as an evaluation tool for ion exchange chromatography," *Life Science News 13*: 2003 (3 pages).
Jungbauer et al., "Monoliths for fast bioseparation and bioconversion and their applications in biotechnology," *J. Sep. Sci 27*:767-778, 2004.
GenBank, "Human herpesvirus 3, complete genome," Accession No. NC_001348.1, Aug. 13, 2018, 54 pages.
GenBank, "Human papillomavirus type 41, complete genome," Accession No. NC_001354.1, Aug. 13, 2018, 5 pages.
GenBank, "Human papillomavirus-1, complete genome," Accession No. NC_001356.1, Aug. 13, 2018, 5 pages.
GenBank, "Hepatitis E virus, complete genome," Accession No. NC_001434.1, Aug. 13, 2018, 4 pages.
GenBank, "Japanese encephalitis virus, genome," Accession No. NC_001437.1, May 24, 2019, 6 pages.
GenBank, "Human papillomavirus type 4, complete genome," Accession No. NC_001457.1, Aug. 13, 2018, 5 pages.
GenBank, "Dengue virus 1, complete genome," Accession No. NC_001477.1, May 3, 2019, 6 pages.
GenBank, "Human papillomavirus type 16, complete genome," Accession No. NC_001526.2, Oct. 27, 2010, 5 pages.
GenBank, "Human papillomoavirus type 5, complete genome," Accession No. NC_001531.1, Aug. 13, 2018, 5 pages.
GenBank, "Human enterovirus A, complete genome," Accession No. NC_001612.1, Aug. 13, 2018, 5 pages.
GenBank, "Tick-borne encephalitis virus, complete genome," Accession No. NC_001672.1, May 23, 2019, 5 pages.
GenBank, "Human orthopneumovirus Subgroup B, complete genome," Accession No. NC_001781.1, Oct. 30, 2018, 7 pages.
GenBank, "Norovirus GI, complete genome," Accession No. NC_001959.2, Aug. 13, 2018, 5 pages.
GenBank, "Yellow fever virus, complete genome," Accession No. NC_002031.1, May 23, 2019, 5 pages.
GenBank, "Poliovirus, complete genome," Accession No. NC_002058.3, Aug. 13, 2018, 11 pages.
GenBank, "SARS coronavirus, complete genome," Accession No. NC_004718.3, Aug. 13, 2018, 16 pages.
GenBank, "Human herpesvirus 5 strain Merlin, complete genome," Accession No. NC_006273.2, Aug. 13, 2018, 100 pages.
GenBank, "Human gammaherpesvirus 4, complete genome," Accession No. NC_007605.1, Aug. 13, 2018, 81 pages.
GenBank, "Human herpesvirus 4, complete genome," Accession No. NC_009334.1, Aug. 13, 2018, 60 pages.
GenBank, "West Nile virus lineage 1, complete genome," Accession No. NC_009942.1, Aug. 1, 2019, 7 pages.
GenBank, "Zika virus, complete genome," Accession No. NC_012532.1, Aug. 1, 2019, 5 pages.
GenBank, "Middle East respiratory syndrome coronavirus, complete genome," Accession No. NC_019843.3, Aug. 13, 2018, 14 pages.
Nestola et al., "Improved Virus Purification Processes for Vaccines and Gene Therapy," *Biotechnology and Bioengineering 112*(5):843-857, 2015.
Radecke et al., "Rescue of measles viruses from cloned DNA," *EMBO J. 14*(23):5773-5784, 1995.
Rajamanickam et al., "Monoliths in Bioprocess Technology," *Chromatography 2*:195-212, 2015.
Ungerechts et al., "Moving oncolytic viruses into the clinic: clinical-grade production, purification, and characterization of diverse oncolytic viruses," *Molecular Therapy—Methods & Clinical Development 3*(16018): 1-12, 2016.
Vicente et al., "Large-scale production and purification of VLP-based vaccines," *Journal of Invertebrate Pathology 107*: S42-S48, 2011.
Victoria et al., "Viral Nucleic Acids in Live-Attenuated Vaccines: Detection of Minority Variants and an Adventitious Virus," *J. Virol. 84*(12):6033-6040, 2010.
Merten eds., "Viral Vectors for Gene Therapy: Methods and Protocols," Methods in Molecular Biology 737, Humana Press c/o Springer Science & Business Media, LLC, New York, NY, USA, 2011.
Wolff et al., "Downstream processing of cell culture-derived virus particles," *Expert Rev. Vaccines 10*(10): 1451-1475, 2011.

* cited by examiner

SEQUENCE LISTING

```
<160> NUMBER OF SEQ ID NOS: 9

<210> SEQ ID NO 1
<211> LENGTH: 18994
<212> TYPE: DNA
<213> ORGANISM: Measles virus Schwarz strain pTM - pTM MV Schw

<400> SEQUENCE: 1

tcatgaacgc ggccgctaat acgactcact atagggccaa ctttgtttgg tctgatgagt      60

ccgtgaggac gaaacccgga gtcccgggtc accaaacaaa gttgggtaag gatagttcaa     120

tcaatgatca tcttctagtg cacttaggat tcaagatcct attatcaggg acaagagcag     180

gattagggat atccgagatg gccacacttt taaggagctt agcattgttc aaaagaaaca     240

aggacaaacc acccattaca tcaggatccg gtggagccat cagaggaatc aaacacatta     300

ttatagtacc aatccctgga gattcctcaa ttaccactcg atccagactt ctggaccggt     360

tggtgaggtt aattggaaac ccggatgtga gcgggcccaa actaacaggg gcactaatag     420

gtatattatc cttatttgtg gagtctccag gtcaattgat tcagaggatc accgatgacc     480

ctgacgttag cataaggctg ttagaggttg tccagagtga ccagtcacaa tctggcctta     540
```

```
ccttcgcatc aagaggtacc aacatggagg atgaggcgga ccaatacttt tcacatgatg    600
atccaattag tagtgatcaa tccaggttcg gatggttcgg gaacaaggaa atctcagata    660
ttgaagtgca agaccctgag ggattcaaca tgattctggg taccatccta gcccaaattt    720
gggtcttgct cgcaaaggcg gttacggccc cagacacggc agctgattcg gagctaagaa    780
ggtggataaa gtacacccaa caaagaaggg tagttggtga atttagattg gagagaaaat    840
ggttggatgt ggtgaggaac aggattgccg aggacctctc cttacgccga ttcatggtcg    900
ctctaatcct ggatatcaag agaacacccg gaaacaaacc caggattgct gaaatgatat    960
gtgacattga tacatatatc gtagaggcag gattagccag ttttatcctg actattaagt   1020
ttgggataga aactatgtat cctgctcttg gactgcatga atttgctggt gagttatcca   1080
cacttgagtc cttgatgaac ctttaccagc aaatggggga aactgcaccc tacatggtaa   1140
tcctggagaa ctcaattcag aacaagttca gtgcaggatc ataccctctg ctctggagct   1200
atgccatggg agtaggagtg gaacttgaaa actccatggg aggtttgaac tttggccgat   1260
cttactttga tccagcatat tttagattag ggcaagagat ggtaaggagg tcagctggaa   1320
aggtcagttc cacattggca tctgaactcg gtatcactgc cgaggatgca aggcttgttt   1380
cagagattgc aatgcatact actgaggaca agatcagtag agcggttgga cccagacaag   1440
cccaagtatc atttctacac ggtgatcaaa gtgagaatga gctaccgaga ttgggggca   1500
aggaagatag gagggtcaaa cagagtcgag gagaagccag ggagagctac agagaaaccg   1560
ggcccagcag agcaagtgat gcgagagctg cccatcttcc aaccggcaca ccccctagaca   1620
ttgacactgc aacggagtcc agccaagatc cgcaggacag tcgaaggtca gctgacgccc   1680
tgcttaggct gcaagccatg gcaggaatct cggaagaaca aggctcagac acggacaccc   1740
ctatagtgta caatgacaga aatcttctag actaggtgcg agaggccgag ggccagaaca   1800
acatccgcct accatccatc attgttataa aaaacttagg aaccaggtcc acacagccgc   1860
cagcccatca accatccact cccacgattg gagccaatgg cagaagagca ggcacgccat   1920
gtcaaaaacg gactggaatg catccgggct ctcaaggccg agcccatcgg ctcactggcc   1980
atcgaggaag ctatggcagc atggtcagaa atatcagaca acccaggaca ggagcgagcc   2040
acctgcaggg aagagaaggc aggcagttcg ggtctcagca aaccatgcct ctcagcaatt   2100
ggatcaactg aaggcggtgc acctcgcatc cgcggtcagg gacctggaga gagcgatgac   2160
gacgctgaaa ctttgggaat ccccccaaga aatctccagg catcaagcac tgggttacag   2220
tgttattacg tttatgatca cagcggtgaa gcggttaagg gaatccaaga tgctgactct   2280
atcatggttc aatcaggcct tgatggtgat agcaccctct caggaggaga caatgaatct   2340
gaaaacagcg atgtggatat tggcgaacct gataccgagg gatatgctat cactgaccgg   2400
ggatctgctc ccatctctat ggggttcagg gcttctgatg ttgaaactgc agaaggaggg   2460
gagatccacg agctcctgag actccaatcc agaggcaaca actttccgaa gcttgggaaa   2520
actctcaatg ttcctccgcc cccggacccc ggtagggcca gcacttccgg gacacccatt   2580
aaaaagggca cagacgcgag attagcctca tttggaacgg agatcgcgtc tttattgaca   2640
ggtggtgcaa cccaatgtgc tcgaaagtca ccctcggaac catcagggcc aggtgcacct   2700
gcggggaatg tccccgagtg tgtgagcaat gccgcactga tacaggagtg gacacccgaa   2760
tctggtacca caatctcccc gagatcccag aataatgaag aagggggaga ctattatgat   2820
gatgagctgt tctctgatgt ccaagatatt aaaacagcct tggccaaaat acacgaggat   2880
aatcagaaga taatctccaa gctagaatca ctgctgttat tgaagggaga agttgagtca   2940
```

```
attaagaagc agatcaacag gcaaaatatc agcatatcca ccctggaagg acacctctca   3000
agcatcatga tcgccattcc tggacttggg aaggatccca acgaccccac tgcagatgtc   3060
gaaatcaatc ccgacttgaa acccatcata ggcagagatt caggccgagc actggccgaa   3120
gttctcaaga aacccgttgc cagccgacaa ctccaaggaa tgacaaatgg acggaccagt   3180
tccagaggac agctgctgaa ggaatttcag ctaaagccga tcgggaaaaa gatgagctca   3240
gccgtcgggt ttgttcctga caccggccct gcatcacgca gtgtaatccg ctccattata   3300
aaatccagcc ggctagagga ggatcggaag cgttacctga tgactctcct tgatgatatc   3360
aaaggagcca atgatcttgc caagttccac cagatgctga tgaagataat aatgaagtag   3420
ctacagctca acttacctgc caaccccatg ccagtcgacc caactagtac aacctaaatc   3480
cattataaaa aacttaggag caaagtgatt gcctcccaag gtccacaatg acagagacct   3540
acgacttcga caagtcggca tgggacatca aagggtcgat cgctccgata caacccacca   3600
cctacagtga tggcaggctg gtgccccagg tcagagtcat agatcctggt ctaggcgaca   3660
ggaaggatga atgctttatg tacatgtttc tgctgggggt tgttgaggac agcgattccc   3720
tagggcctcc aatcgggcga gcatttgggt tcctgccctt aggtgttggc agatccacag   3780
caaagcccga aaaactcctc aaagaggcca ctgagcttga catagttgtt agacgtacag   3840
cagggctcaa tgaaaaactg gtgttctaca acaacacccc actaactctc ctcacacctt   3900
ggagaaaggt cctaacaaca gggagtgtct tcaacgcaaa ccaagtgtgc aatgcggtta   3960
atctgatacc gctcgatacc ccgcagaggt tccgtgttgt ttatatgagc atcacccgtc   4020
tttcggataa cgggtattac accgttccta gaagaatgct ggaattcaga tcggtcaatg   4080
cagtggcctt caacctgctg gtgaccctta ggattgacaa ggcgataggc cctgggaaga   4140
tcatcgacaa tacagagcaa cttcctgagg caacatttat ggtccacatc gggaacttca   4200
ggagaaagaa gagtgaagtc tactctgccg attattgcaa aatgaaaatc gaaaagatgg   4260
gcctggtttt tgcacttggt gggatagggg gcaccagtct tcacattaga agcacaggca   4320
aaatgagcaa gactctccat gcacaactcg ggttcaagaa gaccttatgt tacccgctga   4380
tggatatcaa tgaagacctt aatcgattac tctggaggag cagatgcaag atagtaagaa   4440
tccaggcagt tttgcagcca tcagttcctc aagaattccg catttacgac gacgtgatca   4500
taaatgatga ccaaggacta ttcaaagttc tgtagaccgt agtgcccagc aatgcccgaa   4560
aacgaccccc ctcacaatga cagccagaag gcccggacaa aaaagccccc tccgaaagac   4620
tccacggacc aagcgagagg ccagccagca gccgacggca agcgcgaaca ccaggcggcc   4680
ccagcacaga acagccctga cacaaggcca ccaccagcca ccccaatctg catcctcctc   4740
gtgggacccc cgaggaccaa cccccaaggc tgcccccgat ccaaaccacc aaccgcatcc   4800
ccaccacccc cgggaaagaa acccccagca attggaaggc ccctccccct cttcctcaac   4860
acaagaactc cacaaccgaa ccgcacaagc gaccgaggtg acccaaccgc aggcatccga   4920
ctccctagac agatcctctc tccccggcaa actaaacaaa acttagggcc aaggaacata   4980
cacacccaac agaacccaga ccccggccca cggcgccgcg cccccaaccc ccgacaacca   5040
gagggagccc ccaaccaatc ccgccggctc ccccggtgcc cacaggcagg gacaccaacc   5100
cccgaacaga cccagcaccc aaccatcgac aatccaagac gggggggccc ccccaaaaaa   5160
aggcccccag gggccgacag ccagcaccgc gaggaagccc acccaccccca cacacgacca   5220
cggcaaccaa accagaaccc agaccaccct gggccaccag ctcccagact cggccatcac   5280
```

-continued

```
cccgcagaaa ggaaaggcca caacccgcgc accccagccc cgatccggcg gggagccacc   5340
caacccgaac cagcacccaa gagcgatccc cgaaggaccc ccgaaccgca aaggacatca   5400
gtatcccaca gcctctccaa gtcccccggt ctcctcctct tctcgaaggg accaaaagat   5460
caatccacca cacccgacga cactcaactc cccaccccta aaggagacac cgggaatccc   5520
agaatcaaga ctcatccaat gtccatcatg ggtctcaagg tgaacgtctc tgccatattc   5580
atggcagtac tgttaactct ccaaacaccc accggtcaaa tccattgggg caatctctct   5640
aagatagggg tggtaggaat aggaagtgca agctacaaag ttatgactcg ttccagccat   5700
caatcattag tcataaaatt aatgcccaat ataactctcc tcaataactg cacgagggta   5760
gagattgcag aatacaggag actactgaga acagttttgg aaccaattag agatgcactt   5820
aatgcaatga cccagaatat aagaccggtt cagagtgtag cttcaagtag gagacacaag   5880
agatttgcgg gagtagtcct ggcaggtgcg gccctaggcg ttgccacagc tgctcagata   5940
acagccggca ttgcacttca ccagtccatg ctgaactctc aagccatcga caatctgaga   6000
gcgagcctgg aaactactaa tcaggcaatt gagacaatca gacaagcagg gcaggagatg   6060
atattggctg ttcagggtgt ccaagactac atcaataatg agctgatacc gtctatgaac   6120
caactatctt gtgatttaat cggccagaag ctcgggctca aattgctcag atactataca   6180
gaaatcctgt cattatttgg ccccagttta cgggacccca tatctgcgga gatatctatc   6240
caggctttga gctatgcgct tggaggagac atcaataagg tgttagaaaa gctcggatac   6300
agtggaggtg atttactggg catcttagag agcggaggaa taaaggcccg gataactcac   6360
gtcgacacag agtcctactt cattgtcctc agtatagcct atccgacgct gtccgagatt   6420
aagggggtga ttgtccaccg gctagagggg gtctcgtaca acataggctc tcaagagtgg   6480
tataccactg tgcccaagta tgttgcaacc caagggtacc ttatctcgaa ttttgatgag   6540
tcatcgtgta ctttcatgcc agaggggact gtgtgcagcc aaaatgcctt gtacccgatg   6600
agtcctctgc tccaagaatg cctccggggg tacaccaagt cctgtgctcg tacactcgta   6660
tccgggtctt ttgggaaccg gttcatttta tcacaaggga acctaatagc caattgtgca   6720
tcaatccttt gcaagtgtta cacaacagga acgatcatta atcaagaccc tgacaagatc   6780
ctaacataca ttgctgccga tcactgcccg gtagtcgagg tgaacggcgt gaccatccaa   6840
gtcgggagca ggaggtatcc agacgctgtg tacttgcaca gaattgacct cggtcctccc   6900
atatcattgg agaggttgga cgtagggaca aatctgggga atgcaattgc taagttggag   6960
gatgccaagg aattgttgga gtcatcggac cagatattga ggagtatgaa aggtttatcg   7020
agcactagca tagtctacat cctgattgca gtgtgtcttg gagggttgat agggatcccc   7080
gctttaatat gttgctgcag gggggcgttgt aacaaaaagg gagaacaagt tggtatgtca   7140
agaccaggcc taaagcctga tcttacggga acatcaaaat cctatgtaag gtcgctctga   7200
tcctctacaa ctcttgaaac acaaatgtcc cacaagtctc ctcttcgtca tcaagcaacc   7260
accgcaccca gcatcaagcc cacctgaaat tatctccggc ttccctctgg ccgaacaata   7320
tcggtagtta atcaaaactt agggtgcaag atcatccaca atgtcaccac aacgagaccg   7380
gataaatgcc ttctacaaag ataacccccca tcccaaggga agtaggatag tcattaacag   7440
agaacatctt atgattgata gaccttatgt tttgctggct gttctgtttg tcatgtttct   7500
gagcttgatc gggttgctag ccattgcagg cattagactt catcgggcag ccatctacac   7560
cgcagagatc cataaaagcc tcagcaccaa tctagatgta actaactcaa tcgagcatca   7620
ggtcaaggac gtgctgacac cactcttcaa aatcatcggt gatgaagtgg gcctgaggac   7680
```

```
acctcagaga ttcactgacc tagtgaaatt aatctctgac aagattaaat tccttaatcc   7740
ggatagggag tacgacttca gagatctcac ttggtgtatc aacccgccag agagaatcaa   7800
attggattat gatcaatact gtgcagatgt ggctgctgaa gagctcatga atgcattggt   7860
gaactcaact ctactggaga ccagaacaac caatcagttc ctagctgtct caaagggaaa   7920
ctgctcaggg cccactacaa tcagaggtca attctcaaac atgtcgctgt ccctgttaga   7980
cttgtattta ggtcgaggtt acaatgtgtc atctatagtc actatgacat cccagggaat   8040
gtatgggggga acttacctag tggaaaagcc taatctgagc agcaaaaggt cagagttgtc   8100
acaactgagc atgtaccgag tgtttgaagt aggtgttatc agaaatccgg gtttgggggc   8160
tccggtgttc catatgacaa actatcttga gcaaccagtc agtaatgatc tcagcaactg   8220
tatggtggct ttgggggagc tcaaactcgc agccctttgt cacggggaag attctatcac   8280
aattccctat cagggatcag ggaaaggtgt cagcttccag ctcgtcaagc taggtgtctg   8340
gaaatcccca accgacatgc aatcctgggt ccccttatca acggatgatc cagtgataga   8400
caggctttac ctctcatctc acagaggtgt tatcgctgac aatcaagcaa aatgggctgt   8460
cccgacaaca cgaacagatg acaagttgcg aatggagaca tgcttccaac aggcgtgtaa   8520
gggtaaaatc caagcactct gcgagaatcc cgagtgggca ccattgaagg ataacaggat   8580
tccttcatac ggggtcttgt ctgttgatct gagtctgaca gttgagctta aaatcaaaat   8640
tgcttcggga ttcgggccat tgatcacaca cggttcaggg atggacctat acaaatccaa   8700
ccacaacaat gtgtattggc tgactatccc gccaatgaag aacctagcct taggtgtaat   8760
caacacattg gagtggatac cgagattcaa ggttagtccc tacctcttca ctgtcccaat   8820
taaggaagca ggcgaagact gccatgcccc aacataccta cctgcggagg tggatggtga   8880
tgtcaaactc agttccaatc tggtgattct acctggtcaa gatctccaat atgttttggc   8940
aacctacgat acttccaggg ttgaacatgc tgtggtttat tacgtttaca gcccaagccg   9000
ctcattttct tacttttatc cttttaggtt gcctataaag ggggtcccca tcgaattaca   9060
agtggaatgc ttcacatggg accaaaaact ctggtgccgt cacttctgtg tgcttgcgga   9120
ctcagaatct ggtggacata tcactcactc tgggatggtg ggcatgggag tcagctgcac   9180
agtcacccgg gaagatggaa ccaatcgcag atagggctgc tagtgaacca atcacatgat   9240
gtcacccaga catcaggcat acccactagt gtgaaataga catcagaatt aagaaaaacg   9300
tagggtccaa gtggttcccc gttatggact cgctatctgt caaccagatc ttataccctg   9360
aagttcacct agatagcccg atagttacca ataagatagt agccatcctg gagtatgctc   9420
gagtccctca cgcttacagc ctggaggacc ctacactgtg tcagaacatc aagcaccgcc   9480
taaaaaacgg attttccaac caaatgatta taaacaatgt ggaagttggg aatgtcatca   9540
agtccaagct taggagttat ccggcccact ctcatattcc atatccaaat tgtaatcagg   9600
atttatttaa catagaagac aaagagtcaa cgaggaagat ccgtgaactc ctcaaaaagg   9660
ggaattcgct gtactccaaa gtcagtgata aggttttcca atgcttaagg gacactaact   9720
cacggcttgg cctaggctcc gaattgaggg aggacatcaa ggagaaagtt attaacttgg   9780
gagtttacat gcacagctcc cagtggtttg agccctttct gttttggttt acagtcaaga   9840
ctgagatgag gtcagtgatt aaatcacaaa cccatacttg ccataggagg agacacacac   9900
ctgtattctt cactggtagt tcagttgagt tgctaatctc tcgtgacctt gttgctataa   9960
tcagtaaaga gtctcaacat gtatattacc tgacatttga actggttttg atgtattgtg  10020
```

```
atgtcataga ggggaggtta atgacagaga ccgctatgac tattgatgct aggtatacag  10080
agcttctagg aagagtcaga tacatgtgga aactgataga tggtttcttc cctgcactcg  10140
ggaatccaac ttatcaaatt gtagccatgc tggagcctct ttcacttgct tacctgcagc  10200
tgagggatat aacagtagaa ctcagaggtg ctttccttaa ccactgcttt actgaaatac  10260
atgatgttct tgaccaaaac gggttttctg atgaaggtac ttatcatgag ttaactgaag  10320
ctctagatta cattttcata actgatgaca tacatctgac aggggagatt ttctcatttt  10380
tcagaagttt cggccacccc agacttgaag cagtaacggc tgctgaaaat gttaggaaat  10440
acatgaatca gcctaaagtc attgtgtatg agactctgat gaaaggtcat gccatatttt  10500
gtggaatcat aatcaacggc tatcgtgaca ggcacggagg cagttggcca ccgctgaccc  10560
tcccccctgca tgctgcagac acaatccgga atgctcaagc ttcaggtgaa gggttaacac  10620
atgagcagtg cgttgataac tggaaatctt ttgctggagt gaaatttggc tgctttatgc  10680
ctcttagcct ggatagtgat ctgacaatgt acctaaagga caaggcactt gctgctctcc  10740
aaagggaatg ggattcagtt tacccgaaag agttcctgcg ttacgaccct cccaagggaa  10800
ccgggtcacg gaggcttgta gatgttttcc ttaatgattc gagctttgac ccatatgatg  10860
tgataaatgta tgttgtaagt ggagcttacc tccatgaccc tgagttcaac ctgtcttaca  10920
gcctgaaaga aaaggagatc aaggaaacag gtagactttt tgctaaaatg acttacaaaa  10980
tgagggcatg ccaagtgatt gctgaaaatc taatctcaaa cgggattggc aaatatttta  11040
aggacaatgg gatggccaag gatgagcacg atttgactaa ggcactccac actctagctg  11100
tctcaggagt ccccaaagat ctcaaagaaa gtcacagggg ggggccagtc ttaaaaacct  11160
actcccgaag cccagtccac acaagtacca ggaacgtgag agcagcaaaa gggtttatag  11220
ggttccctca agtaattcgg caggaccaag acactgatca tccggagaat atggaagctt  11280
acgagacagt cagtgcattt atcacgactg atctcaagaa gtactgcctt aattggagat  11340
atgagaccat cagcttgttt gcacagaggc taaatgagat ttacggattg ccctcatttt  11400
tccagtggct gcataagagg cttgagacct ctgtcctgta tgtaagtgac cctcattgcc  11460
cccccgacct tgacgcccat atcccgttat ataaagtccc caatgatcaa atcttcatta  11520
agtaccctat gggaggtata gaagggtatt gtcagaagct gtggaccatc agcaccattc  11580
cctatctata cctggctgct tatgagagcg gagtaaggat tgcttcgtta gtgcaagggg  11640
acaatcagac catagccgta acaaaaaggg tacccagcac atggccctac aaccttaaga  11700
aacgggaagc tgctagagta actagagatt actttgtaat tcttaggcaa aggctacatg  11760
atattggcca tcacctcaag gcaaatgaga caattgtttc atcacatttt tttgtctatt  11820
caaaaggaat atattatgat gggctacttg tgtcccaatc actcaagagc atcgcaagat  11880
gtgtattctg gtcagagact atagttgatg aaacaagggc agcatgcagt aatattgcta  11940
caacaatggc taaaagcatc gagagaggtt atgaccgtta ccttgcatat tccctgaacg  12000
tcctaaaagt gatacagcaa attctgatct ctcttggctt cacaatcaat tcaaccatga  12060
cccgggatgt agtcataccc ctcctcacaa acaacgacct cttaataagg atggcactgt  12120
tgcccgctcc tattgggggg atgaattatc tgaatatgag caggctgttt gtcagaaaca  12180
tcggtgatcc agtaacatca tcaattgctg atctcaagag aatgattctc gcctcactaa  12240
tgcctgaaga gaccctccat caagtaatga cacaacaacc gggggactct tcattcctag  12300
actgggctag cgacccttac tcagcaaatc ttgtatgtgt ccagagcatc actagactcc  12360
tcaagaacat aactgcaagg tttgtcctga tccatagtcc aaacccaatg ttaaaaggat  12420
```

```
tattccatga tgacagtaaa gaagaggacg agggactggc ggcattcctc atggacaggc  12480
atattatagt acctagggca gctcatgaaa tcctggatca tagtgtcaca ggggcaagag  12540
agtctattgc aggcatgctg gataccacaa aaggcttgat tcgagccagc atgaggaagg  12600
gggggttaac ctctcgagtg ataaccagat tgtccaatta tgactatgaa caattcagag  12660
cagggatggt gctattgaca ggaagaaaga gaaatgtcct cattgacaaa gagtcatgtt  12720
cagtgcagct ggcgagagct ctaagaagcc atatgtgggc gaggctagct cgaggacggc  12780
ctatttacgg ccttgaggtc cctgatgtac tagaatctat gcgaggccac cttattcggc  12840
gtcatgagac atgtgtcatc tgcgagtgtg gatcagtcaa ctacggatgg tttttgtcc  12900
cctcgggttg ccaactggat gatattgaca aggaaacatc atccttgaga gtcccatata  12960
ttggttctac cactgatgag agaacagaca tgaagcttgc cttcgtaaga gccccaagtc  13020
gatccttgcg atctgctgtt agaatagcaa cagtgtactc atgggcttac ggtgatgatg  13080
atagctcttg gaacgaagcc tggttgttgg ctaggcaaag ggccaatgtg agcctggagg  13140
agctaagggt gatcactccc atctcaactt cgactaattt agcgcatagg ttgagggatc  13200
gtagcactca agtgaaatac tcaggtacat cccttgtccg agtggcgagg tataccacaa  13260
tctccaacga caatctctca tttgtcatat cagataagaa ggttgatact aactttatat  13320
accaacaagg aatgcttcta gggttgggtg ttttagaaac attgtttcga ctcgagaaag  13380
ataccggatc atctaacacg gtattacatc ttcacgtcga aacagattgt tgcgtgatcc  13440
cgatgataga tcatcccagg atacccagct cccgcaagct agagctgagg gcagagctat  13500
gtaccaaccc attgatatat gataatgcac ctttaattga cagagatgca acaaggctat  13560
acacccagag ccataggagg caccttgtgg aatttgttac atggtccaca ccccaactat  13620
atcacatttt agctaagtcc acagcactat ctatgattga cctggtaaca aaatttgaga  13680
aggaccatat gaatgaaatt tcagctctca taggggatga cgatatcaat agtttcataa  13740
ctgagtttct gctcatagag ccaagattat tcactatcta cttgggccag tgtgcggcca  13800
tcaattgggc atttgatgta cattatcata gaccatcagg gaaatatcag atgggtgagc  13860
tgttgtcatc gttcctttct agaatgagca aaggagtgtt taaggtgctt gtcaatgctc  13920
taagccaccc aaagatctac aagaaattct ggcattgtgg tattatagag cctatccatg  13980
gtccttcact tgatgctcaa aacttgcaca caactgtgtg caacatggtt tacacatgct  14040
atatgaccta cctcgacctg ttgttgaatg aagagttaga agagttcaca tttctcttgt  14100
gtgaaagcga cgaggatgta gtaccggaca gattcgacaa catccaggca aaacacttat  14160
gtgttctggc agatttgtac tgtcaaccag ggacctgccc accaattcga ggtctaagac  14220
cggtagagaa atgtgcagtt ctaaccgacc atatcaaggc agaggctatg ttatctccag  14280
caggatcttc gtggaacata aatccaatta ttgtagacca ttactcatgc tctctgactt  14340
atctccggcg aggatcgatc aaacagataa gattgagagt tgatccagga ttcattttcg  14400
acgccctcgc tgaggtaaat gtcagtcagc caaagatcgg cagcaacaac atctcaaata  14460
tgagcatcaa ggctttcaga cccccacacg atgatgttgc aaaattgctc aaagatatca  14520
acacaagcaa gcacaatctt cccatttcag ggggcaatct cgccaattat gaaatccatg  14580
ctttccgcag aatcgggttg aactcatctg cttgctacaa agctgttgag atatcaacat  14640
taattaggag atgccttgag ccaggggagg acggcttgtt cttgggtgag ggatcgggtt  14700
ctatgttgat cacttataaa gagatactta aactaaacaa gtgcttctat aatagtgggg  14760
```

```
tttccgccaa ttctagatct ggtcaaaggg aattagcacc ctatccctcc gaagttggcc  14820
ttgtcgaaca cagaatggga gtaggtaata ttgtcaaagt gctctttaac gggaggcccg  14880
aagtcacgtg ggtaggcagt gtagattgct tcaatttcat agttagtaat atccctacct  14940
ctagtgtggg gtttatccat tcagatatag agaccttgcc tgacaaagat actatagaga  15000
agctagagga attggcagcc atcttatcga tggctctgct cctgggcaaa ataggatcaa  15060
tactggtgat taagcttatg cctttcagcg gggattttgt tcagggattt ataagttatg  15120
tagggtctca ttatagagaa gtgaaccttg tataccctag atacagcaac ttcatctcta  15180
ctgaatctta tttggttatg acagatctca aggctaaccg gctaatgaat cctgaaaaga  15240
ttaagcagca gataattgaa tcatctgtga ggacttcacc tggacttata ggtcacatcc  15300
tatccattaa gcaactaagc tgcatacaag caattgtggg agacgcagtt agtagaggtg  15360
atatcaatcc tactctgaaa aaacttacac ctatagagca ggtgctgatc aattgcgggt  15420
tggcaattaa cggacctaag ctgtgcaaag aattgatcca ccatgatgtt gcctcagggc  15480
aagatggatt gcttaattct atactcatcc tctacaggga gttggcaaga ttcaaagaca  15540
accaaagaag tcaacaaggg atgttccacg cttaccccgt attggtaagt agcaggcaac  15600
gagaacttat atctaggatc acccgcaaat tctgggggca cattcttctt tactccggga  15660
acaaaaagtt gataaataag tttatccaga atctcaagtc cggctatctg atactagact  15720
tacaccagaa tatcttcgtt aagaatctat ccaagtcaga gaaacagatt attatgacgg  15780
ggggtttgaa acgtgagtgg gtttttaagg taacagtcaa ggagaccaaa gaatggtata  15840
agttagtcgg atacagtgcc ctgattaagg actaattggt tgaactccgg aaccctaatc  15900
ctgccctagg tggttaggca ttatttgcaa tatattaaag aaaactttga aaatacgaag  15960
tttctattcc cagctttgtc tggtggccgg catggtccca gcctcctcgc tggcgccggc  16020
tgggcaacat tccgagggga ccgtcccctc ggtaatggcg aatgggacgc ggccgatccg  16080
gctgctaaca aagcccgaaa ggaagctgag ttggctgctg ccaccgctga gcaataacta  16140
gcataacccc ttggggcctc taaacgggtc ttgaggggtt ttttgctgaa aggaggaact  16200
atatccggat gcggccgcgg gccctatggt acccagcttt tgttcccttt agtgagggtt  16260
aattccgagc ttggcgtaat catggtcata gctgtttcct gtgtgaaatt gttatccgct  16320
cacaattcca cacaacatag gagccggaag cataaagtgt aaagcctggg gtgcctaatg  16380
agtgaggtaa ctcacattaa ttgcgttgcg ctcactgccc gctttccagt cgggaaacct  16440
gtcgtgccag ctgcattaat gaatcggcca acgcgcgggg agaggcggtt tgcgtattgg  16500
gcgctcttcc gcttcctcgc tcactgactc gctgcgctcg gtcgttcggc tgcggcgagc  16560
ggtatcagct cactcaaagg cggtaatacg gttatccaca gaatcagggg ataacgcagg  16620
aaagaacatg tgagcaaaag gccagcaaaa ggccaggaac cgtaaaaagg ccgcgttgct  16680
ggcgtttttc cataggctcg gcccccctga cgagcatcac aaaaatcgac gctcaagtca  16740
gaggtggcga aacccgacag gactataaag ataccaggcg tttccccctg gaagctccct  16800
cgtgcgctct cctgttccga ccctgccgct taccggatac ctgtccgcct ttctcccttc  16860
gggaagcgtg gcgctttctc aatgctcacg ctgtaggtat ctcagttcgg tgtaggtcgt  16920
tcgctccaag ctgggctgtg tgcacgaacc ccccgttcag cccgaccgct gcgccttatc  16980
cggtaactat cgtcttgagt ccaacccggt aagacacgac ttatcgccac tggcagcagc  17040
cactggtaac aggattagca gagcgaggta tgtaggcggt gctacagagt tcttgaagtg  17100
gtggcctaac tacggctaca ctagaaggac agtatttggt atctgcgctc tgctgaagcc  17160
```

```
agttaccttc ggaaaaagag ttggtagctc ttgatccggc aaacaaacca ccgctggtag  17220

cggtggtttt tttgtttgca agcagcagat tacgcgcaga aaaaaaggat ctcaagaaga  17280

tcctttgatc ttttctacgg ggtctgacgc tcagtggaac gaaaactcac gttaagggat  17340

tttggtcatg agattatcaa aaaggatctt cacctagatc cttttaaatt aaaaatgaag  17400

ttttaaatca atctaaagta tatatgagta aacttggtct gacagttacc aatgcttaat  17460

cagtgaggca cctatctcag cgatctgtct atttcgttca tccatagttg cctgactgcc  17520

cgtcgtgtag ataactacga tacgggaggg cttaccatct ggccccagtg ctgcaatgat  17580

accgcgagac ccacgctcac cggctccaga tttatcagca ataaaccagc cagccggaag  17640

ggccgagcgc agaagtggtc ctgcaacttt atccgcctcc atccagtcta ttaattgttg  17700

ccgggaagct agagtaagta gttcgccagt taatagtttg cgcaacgttg ttgccattgc  17760

tacaggcatc gtggtgtcac gctcgtcgtt tggtatggct tcattcagct ccggttccca  17820

acgatcaagg cgagttacat gatcccccat gttgtgaaaa aaagcggtta gctccttcgg  17880

tcctccgatc gttgtcagaa gtaagttggc cgcagtgtta tcactcatgc ttatggcagc  17940

actgcataat tctcttactg tcatgccatc cgtaagatgc ttttctgtga ctggtgagta  18000

ctcaaccaag tcattctgag aatagtgtat gcggcgaccg agttgctctt gcccggcgtc  18060

aatacgggat aataccgcgc cacatagcag aactttaaaa gtgctcatca ttggaaaacg  18120

ttcttcgggg cgaaaactct caaggatctt accgctgttg agatccagtt cgatgtaacc  18180

cactcgtgca cccaactgat cttcagcatc ttttactttc accagcgttt ctgggtgagc  18240

aaaaacagga aggcaaaatg ccgcaaaaaa gggaataagg gcgacacgga aatgttgaat  18300

actcatactc ttcctttttc aatattattg aagcatttat cagggttatt gtctcatgag  18360

cggatacata tttgaatgta tttagaaaaa taaacaaata ggggttccgc gcacatttcc  18420

ccgaaaagtg ccacctgaaa ttgtaaacgt taatattttg ttaaaattcg cgttaaattt  18480

ttgttaaatc agctcatttt ttaaccaata ggccgaaatc ggcaaaatcc cttataaatc  18540

aaaagaatag accgagatag ggttgagtgt tgttccagtt tggaacaaga gtccactatt  18600

aaagaacgtg gactccaacg tcaaagggcg aaaaaccgtc tatcagggcg atggcccact  18660

acgtgaacca tcaccctaat caagtttttt ggggtcgagg tgccgtaaag cactaaatcg  18720

gaaccctaaa gggagccccc gatttagagc ttgacgggga aagccggcga acgtggcgag  18780

aaaggaaggg aagaaagcga aaggagcggg cgctagggcg ctggcaagtg tagcggtcac  18840

gctgcgcgta accaccacac ccgccgcgct taatgcgccg ctacagggcg cgtcccattc  18900

gccattcagg ctgcgcaact gttgggaagg gcgatcggtg cgggcctctt cgctattacg  18960

ccagccaccg cggtgatcct tataaagcta gatg                              18994
```

<210> SEQ ID NO 2
<211> LENGTH: 22857
<212> TYPE: DNA
<213> ORGANISM: artificial sequence
<220> FEATURE:
<223> OTHER INFORMATION: pTM 2ATU MV CHIK - Chikungunya antigens cloned into ATU2

<400> SEQUENCE: 2

```
tccaaccgcg cgcgcggccg ctaatacgac tcactatagg gccaactttg tttggtctga     60

tgagtccgtg aggacgaaac ccggagtccc gggtcaccaa acaaagttgg gtaaggatag    120

ttcaatcaat gatcatcttc tagtgcactt aggattcaag atcctattat cagggacaag    180
```

```
agcaggatta gggatatccg agatggccac acttttaagg agcttagcat tgttcaaaag    240
aaacaaggac aaaccaccca ttacatcagg atccggtgga gccatcagag gaatcaaaca    300
cattattata gtaccaatcc ctggagattc ctcaattacc actcgatcca gacttctgga    360
ccggttggtg aggttaattg gaaacccgga tgtgagcggg cccaaactaa caggggcact    420
aataggtata ttatccttat ttgtggagtc tccaggtcaa ttgattcaga ggatcaccga    480
tgaccctgac gttagcataa ggctgttaga ggttgtccag agtgaccagt cacaatctgg    540
ccttaccttc gcatcaagag gtaccaacat ggaggatgag gcggaccaat acttttcaca    600
tgatgatcca attagtagtg atcaatccag gttcggatgg ttcgggaaca aggaaatctc    660
agatattgaa gtgcaagacc ctgagggatt caacatgatt ctgggtacca tcctagccca    720
aatttgggtc ttgctcgcaa aggcggttac ggccccagac acggcagctg attcggagct    780
aagaaggtgg ataaagtaca cccaacaaag aagggtagtt ggtgaattta gattggagag    840
aaaatggttg gatgtggtga ggaacaggat tgccgaggac ctctccttac gccgattcat    900
ggtcgctcta atcctggata tcaagagaac acccggaaac aaacccagga ttgctgaaat    960
gatatgtgac attgatacat atatcgtaga ggcaggatta gccagtttta tcctgactat   1020
taagtttggg atagaaacta tgtatcctgc tcttggactg catgaatttg ctggtgagtt   1080
atccacactt gagtccttga tgaaccttta ccagcaaatg ggggaaactg caccctacat   1140
ggtaatcctg gagaactcaa ttcagaacaa gttcagtgca ggatcatacc ctctgctctg   1200
gagctatgcc atgggagtag gagtggaact tgaaaactcc atgggaggtt tgaactttgg   1260
ccgatcttac tttgatccag catattttag attagggcaa gagatggtaa ggaggtcagc   1320
tggaaaggtc agttccacat tggcatctga actcggtatc actgccgagg atgcaaggct   1380
tgtttcagag attgcaatgc atactactga ggacaagatc agtagagcgg ttggacccag   1440
acaagcccaa gtatcatttc tacacggtga tcaaagtgag aatgagctac cgagattggg   1500
gggcaaggaa gataggaggg tcaaacagag tcgaggagaa gccagggaga gctacagaga   1560
aaccgggccc agcagagcaa gtgatgcgag agctgcccat cttccaaccg gcacacccct   1620
agacattgac actgcaacgg agtccagcca agatccgcag gacagtcgaa ggtcagctga   1680
cgccctgctt aggctgcaag ccatggcagg aatctcggaa gaacaaggct cagacacgga   1740
cacccctata gtgtacaatg acagaaatct tctagactag gtgcgagagg ccgagggcca   1800
gaacaacatc cgcctaccat ccatcattgt tataaaaaac ttaggaacca ggtccacaca   1860
gccgccagcc catcaaccat ccactcccac gattggagcc aatggcagaa gagcaggcac   1920
gccatgtcaa aaacggactg gaatgcatcc gggctctcaa ggccgagccc atcggctcac   1980
tggccatcga ggaagctatg gcagcatggt cagaaatatc agacaaccca ggacaggagc   2040
gagccacctg cagggaagag aaggcaggca gttcgggtct cagcaaacca tgcctctcag   2100
caattggatc aactgaaggc ggtgcacctc gcatccgcgg tcagggacct ggagagagcg   2160
atgacgacgc tgaaactttg ggaatccccc caagaaatct ccaggcatca agcactgggt   2220
tacagtgtta ttacgtttat gatcacagcg gtgaagcggt taagggaatc caagatgctg   2280
actctatcat ggttcaatca ggccttgatg gtgatagcac cctctcagga ggagacaatg   2340
aatctgaaaa cagcgatgtg gatattggcg aacctgatac cgagggatat gctatcactg   2400
accggggatc tgctcccatc tctatggggt tcagggcttc tgatgttgaa actgcagaag   2460
gaggggagat ccacgagctc ctgagactcc aatccagagg caacaacttt ccgaagcttg   2520
```

```
ggaaaactct caatgttcct ccgcccccgg accccggtag ggccagcact tccgggacac   2580
ccattaaaaa gggcacagac gcgagattag cctcatttgg aacggagatc gcgtctttat   2640
tgacaggtgg tgcaacccaa tgtgctcgaa agtcaccctc ggaaccatca gggccaggtg   2700
cacctgcggg gaatgtcccc gagtgtgtga gcaatgccgc actgatacag gagtggacac   2760
ccgaatctgg taccacaatc tccccgagat cccagaataa tgaagaaggg ggagactatt   2820
atgatgatga gctgttctct gatgtccaag atattaaaac agccttggcc aaaatacacg   2880
aggataatca gaagataatc tccaagctag aatcactgct gttattgaag ggagaagttg   2940
agtcaattaa gaagcagatc aacaggcaaa atatcagcat atccaccctg gaaggacacc   3000
tctcaagcat catgatcgcc attcctggac ttgggaagga tcccaacgac cccactgcag   3060
atgtcgaaat caatcccgac ttgaaaccca tcataggcag agattcaggc cgagcactgg   3120
ccgaagttct caagaaaccc gttgccagcc gacaactcca aggaatgaca aatggacgga   3180
ccagttccag aggacagctg ctgaaggaat ttcagctaaa gccgatcggg aaaaagatga   3240
gctcagccgt cgggtttgtt cctgacaccg gccctgcatc acgcagtgta atccgctcca   3300
ttataaaatc cagccggcta gaggaggatc ggaagcgtta cctgatgact ctccttgatg   3360
atatcaaagg agccaatgat cttgccaagt tccaccagat gctgatgaag ataataatga   3420
agtagctaca gctcaactta cctgccaacc ccatgccagt cgacccaact agcctaccct   3480
ccatcattgt tataaaaaac ttaggaacca ggtccacaca gccgccagcc catcaacgcg   3540
tacgatggag ttcatcccaa cccaaacttt ttacaatagg aggtaccagc ctcgaccctg   3600
gactccgcgc cctactatcc aagtcatcag gcccagaccg cgccctcaga ggcaagctgg   3660
gcaacttgcc cagctgatct cagcagttaa taaactgaca atgagagcgg taccccaaca   3720
gaagccacgc aggaatcgga agaataagaa gcaaaagcaa aaacaacagg cgccacaaaa   3780
caacacaaat caaaagaagc agccacctaa aaagaaaccg gctcaaaaga aaaagaagcc   3840
gggccgcaga gagaggatgt gcatgaaaat cgaaaatgat tgtattttcg aagtcaagca   3900
cgaaggtaag gtaacaggtt acgcgtgcct ggtgggggac aaagtaatga aaccagcaca   3960
cgtcaagggc accatcgata acgcggacct ggccaaactg gcctttaagc ggtcatctaa   4020
gtatgacctt gaatgcgctc agatacccgt gcacatgaag tccgacgctt cgaagttcac   4080
ccatgagaaa ccggaggggt actacaactg gcaccacgga gcagtacagt actcaggagg   4140
ccggttcacc atccctacag gtgctggcaa accaggggac agcggcagac cgatcttcga   4200
caacaaggga cgcgtggtgg ccatagtctt aggaggagct aatgaaggag cccgtacagc   4260
cctctcggtg gtgacctgga ataaagacat tgtcactaaa atcacccccg agggggccga   4320
agagtggagt cttgccatcc cagttatgtg cctgttggca aacaccacgt tcccatgctc   4380
ccagccacct tgcacgccct gctgctacga gaaggaaccg gaggaaaccc tacgcatgct   4440
tgaggacaac gtcatgagac ctgggtacta tcagctgcta caagcatcct taacatgttc   4500
tccccaccgc cagcgacgca gcaccaagga caacttcaat gtctataaag ccacaagacc   4560
atacttagct cactgtcccg actgtggaga agggcactcg tgccatagtc ccgtagcact   4620
agaacgcatc agaaatgaag cgacagacgg gacgctgaaa atccaggtct ccttgcaaat   4680
cggaataaag acggatgaca gccacgattg gaccaagctg cgttatatgg acaaccacat   4740
gccagcagac gcagagaggg cggggctatt tgtaagaaca tcagcaccgt gtacgattac   4800
tggaacaatg ggacacttca tcctggcccg atgtcctaaa ggcgaaactc tgacggtggg   4860
attcactgac agtaggaaga ttagtcactc atgtacgcac ccatttcacc acgaccctcc   4920
```

```
tgtgataggt cgggagaaat tccattcccg accgcagcac ggtaaagagc taccttgcag   4980
cacctacgtg cagagcaccg ccgcaactac cgaggagata gaggtacaca tgcccccaga   5040
cacccctgat cgcacattaa tgtcacaaca gtccggcaac gtaaagatca cagtcaatgg   5100
ccagacggtg cggtacaagt gtaattgcgg tggctcaaat gaaggactaa caactacaga   5160
caaagtgatt aataactgca aggttgatca atgtcatgcc gcggtcacca atcacaaaaa   5220
gtggcagtat aactcccctc tggtcccgcg taatgctgaa cttggggacc ggaaaggaaa   5280
aattcacatc ccgtttccgc tggcaaatgt aacatgcagg gtgcctaaag caaggaaccc   5340
caccgtgacg tatggcaaaa accaagtcat catgctactg tatcctgacc acccaacact   5400
cctgtcctac cggaatatgg gagaagaacc aaactatcaa gaagagtggg tgatgcataa   5460
gaaggaagtc gtgctaaccg tgccgactga agggctcgag gtcacgtggg gcaacaacga   5520
gccgtataag tattggccgc agttatctac aaacggtaca gcccatggcc acccgcacga   5580
gataattctg tattattatg agctgtaccc cactatgact gtagtagttg tgtcagtggc   5640
cacgttcata ctcctgtcga tggtgggtat ggcagcgggg atgtgcatgt gtgcacgacg   5700
cagatgcatc acaccgtatg aactgacacc aggagctacc gtcccattcc tgcttagcct   5760
aatatgctgc atcagaacag ctaaagcggc cacataccaa gaggctgcga tatacctgtg   5820
gaacgagcag caacctttgt tttggctaca agcccttatt ccgctggcag ccctgattgt   5880
tctatgcaac tgtctgagac tcttaccatg ctgctgtaaa acgttggctt ttttagccgt   5940
aatgagcgtc ggtgcccaca ctgtgagcgc ttacgaacac gtaacagtga tcccgaacac   6000
ggtgggagta ccgtataaga ctctagtcaa tagacctggc tacagcccca tggtattgga   6060
gatggaacta ctgtcagtca ctttggagcc aacactatcg cttgattaca tcacgtgcga   6120
gtacaaaacc gtcatcccgt ctccttacgt gaagtgctgc ggtacagcag agtgcaagga   6180
caaaaaccta cctgactaca gctgtaaggt cttcaccggc gtctacccat ttatgtgggg   6240
cggcgcctac tgcttctgcg acgctgaaaa cacgcagttg agcgaagcac acgtggagaa   6300
gtccgaatca tgcaaaacag aatttgcatc agcatacagg gctcataccg catctgcatc   6360
agctaagctc cgcgtccttt accaaggaaa taacatcact gtaactgcct atgcaaacgg   6420
cgaccatgcc gtcacagtta aggacgccaa attcattgtg gggccaatgt cttcagcctg   6480
gacacctttc gacaacaaaa ttgtggtgta caaaggtgac gtctataaca tggactaccc   6540
gcccttcggc gcaggaagac caggacaatt tggcgatatc caaagtcgca cacctgagag   6600
taaagacgtc tatgctaata cacaactggt actgcagaga ccggctgtgg gtacggtaca   6660
cgtgccatac tctcaggcac catctggctt taagtattgg ctaaaagaac gcggggcgtc   6720
gctgcagcac acagcaccat ttggctgcca aatagcaaca aacccggtaa gagcggtgaa   6780
ctgcgccgta gggaacatgc ccatctccat cgacataccg gaagcggcct tcactagggt   6840
cgtcgacgcg ccctctttaa cggacatgtc gtgcgaggta ccagcctgca cccattcctc   6900
agactttggg ggcgtcgcca ttattaaata tgcagccagc aagaaaggca agtgtgcggt   6960
gcattcgatg actaacgccg tcactattcg ggaagctgag atagaagttg aagggaattc   7020
tcagctgcaa atctctttct cgacggcctt agccagcgcc gaattccgcg tacaagtctg   7080
ttctacacaa gtacactgtg cagccgagtg ccacccccccg aaggaccaca tagtcaacta   7140
cccggcgtca cataccaccc tcggggtcca ggacatctcc gctacggcga tgtcatgggt   7200
gcagaagatc acgggaggtg tgggactggt tgttgctgtt gccgcactga ttctaatcgt   7260
```

```
ggtgctatgc gtgtcgttca gcaggcacta ataggcgcgc agcgcttaga cgtctcgcga   7320
tcgatactag tacaacctaa atccattata aaaaacttag gagcaaagtg attgcctccc   7380
aaggtccaca atgacagaga cctacgactt cgacaagtcg gcatgggaca tcaaagggtc   7440
gatcgctccg atacaaccca ccacctacag tgatggcagg ctggtgcccc aggtcagagt   7500
catagatcct ggtctaggcg acaggaagga tgaatgcttt atgtacatgt ttctgctggg   7560
ggttgttgag gacagcgatt ccctagggcc tccaatcggg cgagcatttg ggttcctgcc   7620
cttaggtgtt ggcagatcca cagcaaagcc cgaaaaactc ctcaaagagg ccactgagct   7680
tgacatagtt gttagacgta cagcagggct caatgaaaaa ctggtgttct acaacaacac   7740
cccactaact ctcctcacac cttggagaaa ggtcctaaca acagggagtg tcttcaacgc   7800
aaaccaagtg tgcaatgcgg ttaatctgat accgctcgat accccgcaga ggttccgtgt   7860
tgtttatatg agcatcaccc gtctttcgga taacgggtat tacaccgttc ctagaagaat   7920
gctggaattc agatcggtca atgcagtggc cttcaacctg ctggtgaccc ttaggattga   7980
caaggcgata ggccctggga agatcatcga caatacagag caacttcctg aggcaacatt   8040
tatggtccac atcgggaact tcaggagaaa gaagagtgaa gtctactctg ccgattattg   8100
caaaatgaaa atcgaaaaga tgggcctggt ttttgcactt ggtgggatag ggggcaccag   8160
tcttcacatt agaagcacag gcaaaatgag caagactctc catgcacaac tcgggttcaa   8220
gaagacctta tgttacccgc tgatggatat caatgaagac cttaatcgat tactctggag   8280
gagcagatgc aagatagtaa gaatccaggc agttttgcag ccatcagttc ctcaagaatt   8340
ccgcatttac gacgacgtga tcataaatga tgaccaagga ctattcaaag ttctgtagac   8400
cgtagtgccc agcaatgccc gaaaacgacc cccctcacaa tgacagccag aaggcccgga   8460
caaaaaagcc ccctccgaaa gactccacgg accaagcgag aggccagcca gcagccgacg   8520
gcaagcgcga acaccaggcg gccccagcac agaacagccc tgacacaagg ccaccaccag   8580
ccaccccaat ctgcatcctc ctcgtgggac ccccgaggac caacccccaa ggctgccccc   8640
gatccaaacc accaaccgca tccccaccac ccccgggaaa gaaaccccca gcaattggaa   8700
ggcccctccc cctcttcctc aacacaagaa ctccacaacc gaaccgcaca agcgaccgag   8760
gtgacccaac cgcaggcatc cgactcccta gacagatcct ctctccccgg caaactaaac   8820
aaaacttagg gccaaggaac atacacaccc aacagaaccc agaccccggc ccacggcgcc   8880
gcgcccccaa cccccgacaa ccagagggag cccccaacca atcccgccgg ctcccccggt   8940
gcccacaggc agggacacca acccccgaac agacccagca cccaaccatc gacaatccaa   9000
gacggggggg cccccccaaa aaaaggcccc caggggccga cagccagcac cgcgaggaag   9060
cccacccacc ccacacacga ccacggcaac caaaccagaa cccagaccac cctgggccac   9120
cagctcccag actcggccat cacccccgcag aaaggaaagg ccacaacccg cgcaccccag   9180
ccccgatccg gcggggagcc acccaacccg aaccagcacc caagagcgat ccccgaagga   9240
cccccgaacc gcaaaggaca tcagtatccc acagcctctc caagtccccc ggtctcctcc   9300
tcttctcgaa gggaccaaaa gatcaatcca ccacacccga cgacactcaa ctccccaccc   9360
ctaaaggaga caccgggaat cccagaatca agactcatcc aatgtccatc atgggtctca   9420
aggtgaacgt ctctgccata ttcatggcag tactgttaac tctccaaaca cccaccggtc   9480
aaatccattg ggcaatctc tctaagatag gggtggtagg aataggaagt gcaagctaca   9540
aagttatgac tcgttccagc catcaatcat tagtcataaa attaatgccc aatataactc   9600
tcctcaataa ctgcacgagg gtagagattg cagaatacag gagactactg agaacagttt   9660
```

```
tggaaccaat tagagatgca cttaatgcaa tgacccagaa tataagaccg gttcagagtg   9720
tagcttcaag taggagacac aagagatttg cgggagtagt cctggcaggt gcggccctag   9780
gcgttgccac agctgctcag ataacagccg gcattgcact tcaccagtcc atgctgaact   9840
ctcaagccat cgacaatctg agagcgagcc tggaaactac taatcaggca attgagacaa   9900
tcagacaagc agggcaggag atgatattgg ctgttcaggg tgtccaagac tacatcaata   9960
atgagctgat accgtctatg aaccaactat cttgtgattt aatcggccag aagctcgggc  10020
tcaaattgct cagatactat acagaaatcc tgtcattatt tggccccagt ttacgggacc  10080
ccatatctgc ggagatatct atccaggctt tgagctatgc gcttggagga gacatcaata  10140
aggtgttaga aaagctcgga tacagtggag gtgatttact gggcatctta gagagcggag  10200
gaataaaggc ccggataact cacgtcgaca cagagtccta cttcattgtc ctcagtatag  10260
cctatccgac gctgtccgag attaaggggg tgattgtcca ccggctagag gggtctcgt   10320
acaacatagg ctctcaagag tggtatacca ctgtgcccaa gtatgttgca acccaagggt  10380
accttatctc gaattttgat gagtcatcgt gtactttcat gccagagggg actgtgtgca  10440
gccaaaatgc cttgtacccg atgagtcctc tgctccaaga atgcctccgg gggtacacca  10500
agtcctgtgc tcgtacactc gtatccgggt cttttgggaa ccggttcatt ttatcacaag  10560
ggaacctaat agccaattgt gcatcaatcc tttgcaagtg ttacacaaca ggaacgatca  10620
ttaatcaaga ccctgacaag atcctaacat acattgctgc cgatcactgc ccggtagtcg  10680
aggtgaacgg cgtgaccatc caagtcggga gcaggaggta tccagacgct gtgtacttgc  10740
acagaattga cctcggtcct cccatatcat tggagaggtt ggacgtaggg acaaatctgg  10800
ggaatgcaat tgctaagttg gaggatgcca aggaattgtt ggagtcatcg gaccagatat  10860
tgaggagtat gaaaggttta tcgagcacta gcatagtcta catcctgatt gcagtgtgtc  10920
ttggagggtt gatagggatc cccgctttaa tatgttgctg cagggggcgt tgtaacaaaa  10980
agggagaaca agttggtatg tcaagaccag gcctaaagcc tgatcttacg ggaacatcaa  11040
aatcctatgt aaggtcgctc tgatcctcta caactcttga aacacaaatg tcccacaagt  11100
ctcctcttcg tcatcaagca accaccgcac ccagcatcaa gcccacctga aattatctcc  11160
ggcttccctc tggccgaaca atatcggtag ttaatcaaaa cttagggtgc aagatcatcc  11220
acaatgtcac cacaacgaga ccggataaat gccttctaca aagataaccc ccatcccaag  11280
ggaagtagga tagtcattaa cagagaacat cttatgattg atagacctta tgttttgctg  11340
gctgttctgt ttgtcatgtt tctgagcttg atcgggttgc tagccattgc aggcattaga  11400
cttcatcggg cagccatcta caccgcagag atccataaaa gcctcagcac caatctagat  11460
gtaactaact caatcgagca tcaggtcaag gacgtgctga caccactctt caaaatcatc  11520
ggtgatgaag tgggcctgag gacacctcag agattcactg acctagtgaa attaatctct  11580
gacaagatta aattccttaa tccggatagg gagtacgact tcagagatct cacttggtgt  11640
atcaacccgc cagagagaat caaattggat tatgatcaat actgtgcaga tgtggctgct  11700
gaagagctca tgaatgcatt ggtgaactca actctactgg agaccagaac aaccaatcag  11760
ttcctagctg tctcaaaggg aaactgctca gggcccacta caatcagagg tcaattctca  11820
aacatgtcgc tgtccctgtt agacttgtat ttaggtcgag gttacaatgt gtcatctata  11880
gtcactatga catcccaggg aatgtatggg ggaacttacc tagtggaaaa gcctaatctg  11940
agcagcaaaa ggtcagagtt gtcacaactg agcatgtacc gagtgtttga agtaggtgtt  12000
```

```
atcagaaatc cgggtttggg ggctccggtg ttccatatga caaactatct tgagcaacca  12060
gtcagtaatg atctcagcaa ctgtatggtg gctttggggg agctcaaact cgcagccctt  12120
tgtcacgggg aagattctat cacaattccc tatcagggat cagggaaagg tgtcagcttc  12180
cagctcgtca agctaggtgt ctggaaatcc ccaaccgaca tgcaatcctg ggtcccctta  12240
tcaacggatg atccagtgat agacaggctt tacctctcat ctcacagagg tgttatcgct  12300
gacaatcaag caaaatgggc tgtcccgaca acacgaacag atgacaagtt gcgaatggag  12360
acatgcttcc aacaggcgtg taagggtaaa atccaagcac tctgcgagaa tcccgagtgg  12420
gcaccattga aggataacag gattccttca tacggggtct tgtctgttga tctgagtctg  12480
acagttgagc ttaaaatcaa aattgcttcg ggattcgggc cattgatcac acacggttca  12540
gggatggacc tatacaaatc caaccacaac aatgtgtatt ggctgactat cccgccaatg  12600
aagaacctag ccttaggtgt aatcaacaca ttggagtgga taccgagatt caaggttagt  12660
ccctacctct tcactgtccc aattaaggaa gcaggcgaag actgccatgc cccaacatac  12720
ctacctgcgg aggtggatgg tgatgtcaaa ctcagttcca atctggtgat tctacctggt  12780
caagatctcc aatatgtttt ggcaacctac gatacttcca gggttgaaca tgctgtggtt  12840
tattacgttt acagcccaag ccgctcattt tcttactttt atccttttag gttgcctata  12900
aagggggtcc ccatcgaatt acaagtggaa tgcttcacat gggaccaaaa actctggtgc  12960
cgtcacttct gtgtgcttgc ggactcagaa tctggtggac atatcactca ctctgggatg  13020
gtgggcatgg gagtcagctg cacagtcacc cgggaagatg gaaccaatcg cagatagggc  13080
tgctagtgaa ccaatcacat gatgtcaccc agacatcagg catacccact agtgtgaaat  13140
agacatcaga attaagaaaa acgtagggtc caagtggttc cccgttatgg actcgctatc  13200
tgtcaaccag atcttatacc ctgaagttca cctagatagc ccgatagtta ccaataagat  13260
agtagccatc ctggagtatg ctcgagtccc tcacgcttac agcctggagg accctacact  13320
gtgtcagaac atcaagcacc gcctaaaaaa cggattttcc aaccaaatga ttataaacaa  13380
tgtggaagtt gggaatgtca tcaagtccaa gcttaggagt tatccggccc actctcatat  13440
tccatatcca aattgtaatc aggatttatt taacatagaa gacaaagagt caacgaggaa  13500
gatccgtgaa ctcctcaaaa aggggaattc gctgtactcc aaagtcagtg ataaggtttt  13560
ccaatgctta agggacacta actcacggct tggcctaggc tccgaattga gggaggacat  13620
caaggagaaa gttattaact tgggagttta catgcacagc tcccagtggt ttgagccctt  13680
tctgttttgg tttacagtca agactgagat gaggtcagtg attaaatcac aaacccatac  13740
ttgccatagg aggagacaca cacctgtatt cttcactggt agttcagttg agttgctaat  13800
ctctcgtgac cttgttgcta taatcagtaa agagtctcaa catgtatatt acctgacatt  13860
tgaactggtt ttgatgtatt gtgatgtcat agaggggagg ttaatgacag agaccgctat  13920
gactattgat gctaggtata cagagcttct aggaagagtc agatacatgt ggaaactgat  13980
agatggtttc ttccctgcac tcgggaatcc aacttatcaa attgtagcca tgctggagcc  14040
tctttcactt gcttacctgc agctgaggga tataacagta gaactcagag gtgctttcct  14100
taaccactgc tttactgaaa tacatgatgt tcttgaccaa aacgggtttt ctgatgaagg  14160
tacttatcat gagttaactg aagctctaga ttacattttc ataactgatg acatacatct  14220
gacaggggag attttctcat tttcagaag tttcggccac cccagacttg aagcagtaac  14280
ggctgctgaa aatgttagga aatacatgaa tcagcctaaa gtcattgtgt atgagactct  14340
gatgaaaggt catgccatat tttgtggaat cataatcaac ggctatcgtg acaggcacgg  14400
```

```
aggcagttgg ccaccgctga ccctccccct gcatgctgca gacacaatcc ggaatgctca  14460
agcttcaggt gaagggttaa cacatgagca gtgcgttgat aactggaaat cttttgctgg  14520
agtgaaattt ggctgcttta tgcctcttag cctggatagt gatctgacaa tgtacctaaa  14580
ggacaaggca cttgctgctc tccaaaggga atgggattca gtttacccga aagagttcct  14640
gcgttacgac cctcccaagg gaaccgggtc acggaggctt gtagatgttt tccttaatga  14700
ttcgagcttt gacccatatg atgtgataat gtatgttgta agtggagctt acctccatga  14760
ccctgagttc aacctgtctt acagcctgaa agaaaaggag atcaaggaaa caggtagact  14820
ttttgctaaa atgacttaca aaatgagggc atgccaagtg attgctgaaa atctaatctc  14880
aaacgggatt ggcaaatatt ttaaggacaa tgggatggcc aaggatgagc acgatttgac  14940
taaggcactc cacactctag ctgtctcagg agtccccaaa gatctcaaag aaagtcacag  15000
ggggggccca gtcttaaaaa cctactcccg aagcccagtc cacacaagta ccaggaacgt  15060
gagagcagca aaagggttta tagggttccc tcaagtaatt cggcaggacc aagacactga  15120
tcatccggag aatatggaag cttacgagac agtcagtgca tttatcacga ctgatctcaa  15180
gaagtactgc cttaattgga gatatgagac catcagcttg tttgcacaga ggctaaatga  15240
gatttacgga ttgccctcat tttccagtg gctgcataag aggcttgaga cctctgtcct  15300
gtatgtaagt gaccctcatt gcccccccga ccttgacgcc catatcccgt tatataaagt  15360
ccccaatgat caaatcttca ttaagtaccc tatgggaggt atagaagggt attgtcagaa  15420
gctgtggacc atcagcacca ttccctatct atacctggct gcttatgaga gcggagtaag  15480
gattgcttcg ttagtgcaag gggacaatca gaccatagcc gtaacaaaaa gggtacccag  15540
cacatggccc tacaacctta agaaacggga agctgctaga gtaactagag attactttgt  15600
aattcttagg caaaggctac atgatattgg ccatcacctc aaggcaaatg agacaattgt  15660
ttcatcacat ttttttgtct attcaaaagg aatatattat gatgggctac ttgtgtccca  15720
atcactcaag agcatcgcaa gatgtgtatt ctggtcagag actatagttg atgaaacaag  15780
ggcagcatgc agtaatattg ctacaacaat ggctaaaagc atcgagagag gttatgaccg  15840
ttaccttgca tattccctga acgtcctaaa agtgatacag caaattctga tctctcttgg  15900
cttcacaatc aattcaacca tgacccggga tgtagtcata cccctcctca caaacaacga  15960
cctcttaata aggatggcac tgttgcccgc tcctattggg gggatgaatt atctgaatat  16020
gagcaggctg tttgtcagaa acatcggtga tccagtaaca tcatcaattg ctgatctcaa  16080
gagaatgatt ctcgcctcac taatgcctga agagaccctc catcaagtaa tgacacaaca  16140
accgggggac tcttcattcc tagactgggc tagcgaccct tactcagcaa atcttgtatg  16200
tgtccagagc atcactagac tcctcaagaa cataactgca aggtttgtcc tgatccatag  16260
tccaaaccca atgttaaaag gattattcca tgatgacagt aaagaagagg acgagggact  16320
ggcggcattc ctcatggaca ggcatattat agtacctagg gcagctcatg aaatcctgga  16380
tcatagtgtc acaggggcaa gagagtctat tgcaggcatg ctggatacca caaaaggctt  16440
gattcgagcc agcatgagga aggggggtt aacctctcga gtgataacca gattgtccaa  16500
ttatgactat gaacaattca gagcagggat ggtgctattg acaggaagaa agagaaatgt  16560
cctcattgac aaagagtcat gttcagtgca gctggcgaga gctctaagaa gccatatgtg  16620
ggcgaggcta gctcgaggac ggcctattta cggccttgag gtccctgatg tactagaatc  16680
tatgcgaggc caccttattc ggcgtcatga gacatgtgtc atctgcgagt gtggatcagt  16740
```

-continued

```
caactacgga tggtttttg tcccctcggg ttgccaactg gatgatattg acaaggaaac 16800
atcatccttg agagtcccat atattggttc taccactgat gagagaacag acatgaagct 16860
tgccttcgta agagccccaa gtcgatcctt gcgatctgct gttagaatag caacagtgta 16920
ctcatgggct tacggtgatg atgatagctc ttggaacgaa gcctggttgt tggctaggca 16980
aagggccaat gtgagcctgg aggagctaag ggtgatcact cccatctcaa cttcgactaa 17040
tttagcgcat aggttgaggg atcgtagcac tcaagtgaaa tactcaggta catcccttgt 17100
ccgagtggcg aggtatacca caatctccaa cgacaatctc tcatttgtca tatcagataa 17160
gaaggttgat actaacttta tataccaaca aggaatgctt ctagggttgg gtgttttaga 17220
aacattgttt cgactcgaga aagataccgg atcatctaac acggtattac atcttcacgt 17280
cgaaacagat tgttgcgtga tcccgatgat agatcatccc aggataccca gctcccgcaa 17340
gctagagctg agggcagagc tatgtaccaa cccattgata tatgataatg cacctttaat 17400
tgacagagat gcaacaaggc tatacaccca gagccatagg aggcaccttg tggaatttgt 17460
tacatggtcc acaccccaac tatatcacat tttagctaag tccacagcac tatctatgat 17520
tgacctggta acaaaatttg agaaggacca tatgaatgaa atttcagctc tcataggga 17580
tgacgatatc aatagtttca taactgagtt tctgctcata gagccaagat tattcactat 17640
ctacttgggc cagtgtgcgg ccatcaattg ggcatttgat gtacattatc atagaccatc 17700
agggaaatat cagatgggtg agctgttgtc atcgttcctt tctagaatga gcaaaggagt 17760
gtttaaggtg cttgtcaatg ctctaagcca cccaaagatc tacaagaaat tctggcattg 17820
tggtattata gagcctatcc atggtccttc acttgatgct caaaacttgc acacaactgt 17880
gtgcaacatg gtttacacat gctatatgac ctacctcgac ctgttgttga atgaagagtt 17940
agaagagttc acatttctct tgtgtgaaag cgacgaggat gtagtaccgg acagattcga 18000
caacatccag gcaaaacact tatgtgttct ggcagatttg tactgtcaac cagggacctg 18060
cccaccaatt cgaggtctaa gaccggtaga gaaatgtgca gttctaaccg accatatcaa 18120
ggcagaggct atgttatctc cagcaggatc ttcgtggaac ataaatccaa ttattgtaga 18180
ccattactca tgctctctga cttatctccg gcgaggatcg atcaaacaga taagattgag 18240
agttgatcca ggattcattt tcgacgccct cgctgaggta aatgtcagtc agccaaagat 18300
cggcagcaac aacatctcaa atatgagcat caaggctttc agacccccac acgatgatgt 18360
tgcaaaattg ctcaaagata tcaacacaag caagcacaat cttcccattt caggggggcaa 18420
tctcgccaat tatgaaatcc atgctttccg cagaatcggg ttgaactcat ctgcttgcta 18480
caaagctgtt gagatatcaa cattaattag gagatgcctt gagccagggg aggacggctt 18540
gttcttgggt gagggatcgg gttctatgtt gatcacttat aaagagatac ttaaactaaa 18600
caagtgcttc tataatagtg ggtttccgc caattctaga tctggtcaaa gggaattagc 18660
accctatccc tccgaagttg gccttgtcga acacagaatg ggagtaggta atattgtcaa 18720
agtgctcttt aacgggaggc ccgaagtcac gtgggtaggc agtgtagatt gcttcaattt 18780
catagttagt aatatcccta cctctagtgt ggggtttatc cattcagata tagagacctt 18840
gcctgacaaa gatactatag agaagctaga ggaattggca gccatcttat cgatggctct 18900
gctcctgggc aaaataggat caatactggt gattaagctt atgcctttca gcggggattt 18960
tgttcaggga tttataagtt atgtagggtc tcattataga gaagtgaacc ttgtataccc 19020
tagatacagc aacttcatct ctactgaatc ttatttggtt atgacagatc tcaaggctaa 19080
ccggctaatg aatcctgaaa agattaagca gcagataatt gaatcatctg tgaggacttc 19140
```

```
acctggactt ataggtcaca tcctatccat taagcaacta agctgcatac aagcaattgt  19200
gggagacgca gttagtagag gtgatatcaa tcctactctg aaaaaactta cacctataga  19260
gcaggtgctg atcaattgcg ggttggcaat taacggacct aagctgtgca aagaattgat  19320
ccaccatgat gttgcctcag ggcaagatgg attgcttaat tctatactca tcctctacag  19380
ggagttggca agattcaaag acaaccaaag aagtcaacaa gggatgttcc acgcttaccc  19440
cgtattggta agtagcaggc aacgagaact tatatctagg atcacccgca aattctgggg  19500
gcacattctt ctttactccg ggaacaaaaa gttgataaat aagtttatcc agaatctcaa  19560
gtccggctat ctgatactag acttacacca gaatatcttc gttaagaatc tatccaagtc  19620
agagaaacag attattatga cggggggttt gaaacgtgag tgggttttta aggtaacagt  19680
caaggagacc aaagaatggt ataagttagt cggatacagt gccctgatta aggactaatt  19740
ggttgaactc cggaacccta atcctgccct aggtggttag gcattatttg caatatatta  19800
aagaaaactt tgaaaatacg aagtttctat tcccagcttt gtctggtggc cggcatggtc  19860
ccagcctcct cgctggcgcc ggctgggcaa cattccgagg ggaccgtccc ctcggtaatg  19920
gcgaatggga cgcggccgat ccggctgcta acaaagcccg aaaggaagct gagttggctg  19980
ctgccaccgc tgagcaataa ctagcataac cccttggggc ctctaaacgg gtcttgaggg  20040
gtttttgct gaaaggagga actatatccg gatgcggccg cgggccctat ggtacccagc  20100
ttttgttccc tttagtgagg gttaattccg agcttggcgt aatcatggtc atagctgttt  20160
cctgtgtgaa attgttatcc gctcacaatt ccacacaaca taggagccgg aagcataaag  20220
tgtaaagcct ggggtgccta atgagtgagg taactcacat taattgcgtt gcgctcactg  20280
cccgctttcc agtcgggaaa cctgtcgtgc cagctgcatt aatgaatcgg ccaacgcgcg  20340
gggagaggcg gtttgcgtat tgggcgctct tccgcttcct cgctcactga ctcgctgcgc  20400
tcggtcgttc ggctgcggcg agcggtatca gctcactcaa aggcggtaat acggttatcc  20460
acagaatcag gggataacgc aggaaagaac atgtgagcaa aaggccagca aaaggccagg  20520
aaccgtaaaa aggccgcgtt gctggcgttt ttccataggc tcggcccccc tgacgagcat  20580
cacaaaaatc gacgctcaag tcagaggtgg cgaaacccga caggactata aagataccag  20640
gcgttccccc ctggaagctc cctcgtgcgc tctcctgttc cgaccctgcc gcttaccgga  20700
tacctgtccg cctttctccc ttcgggaagc gtggcgcttt ctcaatgctc acgctgtagg  20760
tatctcagtt cggtgtaggt cgttcgctcc aagctgggct gtgtgcacga accccccgtt  20820
cagcccgacc gctgcgcctt atccggtaac tatcgtcttg agtccaaccc ggtaagacac  20880
gacttatcgc cactggcagc agccactggt aacaggatta gcagagcgag gtatgtaggc  20940
ggtgctacag agttcttgaa gtggtggcct aactacggct acactagaag gacagtattt  21000
ggtatctgcg ctctgctgaa gccagttacc ttcggaaaaa gagttggtag ctcttgatcc  21060
ggcaaacaaa ccaccgctgg tagcggtggt ttttttgttt gcaagcagca gattacgcgc  21120
agaaaaaaag gatctcaaga agatcctttg atcttttcta cggggtctga cgctcagtgg  21180
aacgaaaact cacgttaagg gattttggtc atgagattat caaaaaggat cttcacctag  21240
atccttttaa attaaaaatg aagttttaaa tcaatctaaa gtatatatga gtaaacttgg  21300
tctgacagtt accaatgctt aatcagtgag gcacctatct cagcgatctg tctatttcgt  21360
tcatccatag ttgcctgact gccccgtcgtg tagataacta cgatacggga gggcttacca  21420
tctggcccca gtgctgcaat gataccgcga gacccacgct caccggctcc agatttatca  21480
```

```
gcaataaacc agccagccgg aagggccgag cgcagaagtg gtcctgcaac tttatccgcc  21540

tccatccagt ctattaattg ttgccgggaa gctagagtaa gtagttcgcc agttaatagt  21600

ttgcgcaacg ttgttgccat tgctacaggc atcgtggtgt cacgctcgtc gtttggtatg  21660

gcttcattca gctccggttc ccaacgatca aggcgagtta catgatcccc catgttgtga  21720

aaaaaagcgg ttagctcctt cggtcctccg atcgttgtca gaagtaagtt ggccgcagtg  21780

ttatcactca tgcttatggc agcactgcat aattctctta ctgtcatgcc atccgtaaga  21840

tgcttttctg tgactggtga gtactcaacc aagtcattct gagaatagtg tatgcggcga  21900

ccgagttgct cttgcccggc gtcaatacgg gataataccg cgccacatag cagaacttta  21960

aaagtgctca tcattggaaa acgttcttcg gggcgaaaac tctcaaggat cttaccgctg  22020

ttgagatcca gttcgatgta acccactcgt gcacccaact gatcttcagc atcttttact  22080

ttcaccagcg tttctgggtg agcaaaaaca ggaaggcaaa atgccgcaaa aaagggaata  22140

agggcgacac ggaaatgttg aatactcata ctcttccttt ttcaatatta ttgaagcatt  22200

tatcagggtt attgtctcat gagcggatac atatttgaat gtatttagaa aaataaacaa  22260

ataggggttc cgcgcacatt tccccgaaaa gtgccacctg aaattgtaaa cgttaatatt  22320

ttgttaaaat tcgcgttaaa tttttgttaa atcagctcat tttttaacca ataggccgaa  22380

atcggcaaaa tcccttataa atcaaaagaa tagaccgaga tagggttgag tgttgttcca  22440

gtttggaaca agagtccact attaaagaac gtggactcca acgtcaaagg gcgaaaaacc  22500

gtctatcagg gcgatggccc actacgtgaa ccatcaccct aatcaagttt tttggggtcg  22560

aggtgccgta aagcactaaa tcggaaccct aaagggagcc cccgatttag agcttgacgg  22620

ggaaagccgg cgaacgtggc gagaaaggaa gggaagaaag cgaaaggagc gggcgctagg  22680

gcgctggcaa gtgtagcggt cacgctgcgc gtaaccacca cacccgccgc gcttaatgcg  22740

ccgctacagg gcgcgtccca ttcgccattc aggctgcgca actgttggga agggcgatcg  22800

gtgcgggcct cttcgctatt acgccagcca ccgcggtgat ccttataaag ctagatg     22857
```

```
<210> SEQ ID NO 3
<211> LENGTH: 20629
<212> TYPE: DNA
<213> ORGANISM: artificial sequence
<220> FEATURE:
<223> OTHER INFORMATION: pTM 2ATU MV DVAX1 - Dengue virus antigens
      cloned into ATU2

<400> SEQUENCE: 3

gcggccgcta atacgactca ctatagggcc aactttgttt ggtctgatga gtccgtgagg     60

acgaaacccg gagtcccggg tcaccaaaca aagttgggta aggatagttc aatcaatgat    120

catcttctag tgcacttagg attcaagatc ctattatcag ggacaagagc aggattaggg    180

atatccgaga tggccacact tttaaggagc ttagcattgt tcaaaagaaa caaggacaaa    240

ccacccatta catcaggatc cggtggagcc atcagaggaa tcaaacacat tattatagta    300

ccaatccctg gagattcctc aattaccact cgatccagac ttctggaccg gttggtgagg    360

ttaattggaa acccggatgt gagcgggccc aaactaacag gggcactaat aggtatatta    420

tccttatttg tggagtctcc aggtcaattg attcagagga tcaccgatga ccctgacgtt    480

agcataaggc tgttagaggt tgtccagagt gaccagtcac aatctggcct taccttcgca    540

tcaagaggta ccaacatgga ggatgaggcg gaccaatact tttcacatga tgatccaatt    600

agtagtgatc aatccaggtt cggatggttc gggaacaagg aaatctcaga tattgaagtg    660
```

```
caagaccctg agggattcaa catgattctg ggtaccatcc tagcccaaat ttgggtcttg    720
ctcgcaaagg cggttacggc cccagacacg gcagctgatt cggagctaag aaggtggata    780
aagtacaccc aacaaagaag ggtagttggt gaatttagat tggagagaaa atggttggat    840
gtggtgagga acaggattgc cgaggacctc tccttacgcc gattcatggt cgctctaatc    900
ctggatatca agagaacacc cggaaacaaa cccaggattg ctgaaatgat atgtgacatt    960
gatacatata tcgtagaggc aggattagcc agttttatcc tgactattaa gtttgggata   1020
gaaactatgt atcctgctct tggactgcat gaatttgctg gtgagttatc cacacttgag   1080
tccttgatga acctttacca gcaaatgggg gaaactgcac cctacatggt aatcctggag   1140
aactcaattc agaacaagtt cagtgcagga tcataccctc tgctctggag ctatgccatg   1200
ggagtaggag tggaacttga aaactccatg ggaggtttga actttggccg atcttacttt   1260
gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg gacccagaca agcccaagta   1440
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccoctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cggtctcag caaaccatgc ctctcagcaa ttggatcaac    2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
```

```
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac gatgggcatc   3540
atattcattc ttcttatgct ggttacaccg tctatggcgg agaaacttcg aatcaaaggt   3600
atgagctata cgatgtgcag cggcaagttc aagatcgaga aggaaatggc tgaaacccag   3660
cacggtacaa ctgtggtcaa agtcaaatat gagggggctg gcgctccctg taaagtaccc   3720
attgagatta gggacgtcaa taaagagaag gtggtaggtc gcatcatctc cagtacacct   3780
ttggccgaga acacgaactc cgtcacaaac atagagttgg aacccccgtt cggagactca   3840
tacattgtga tcggggtggg caactctgca ctcacactgc attggttcaa gaagggaagc   3900
agtatcggcc gcagggataa gagagacaaa ctgaaattga aaggtatgtc ctatgccatg   3960
tgcacgaata ctttcgttct caagaaagaa gtatctgaga ctcagcacgg aaccatcctg   4020
atcaaagtcg agtacaaagg agaagacgtg ccctgtaaga tcccattcag taccgaggat   4080
ggacagggca aggcccataa cggcaggctg ataaccgcca accctgtggt tacaaagaag   4140
gaagagccag tcaatatcga agctgagcca ccgttcgggg agagcaacat agtaattggc   4200
ataggggata atgctttgaa gatcaactgg tacaagaaag gaagctccat tggccgaaga   4260
gataagcgcg acaaactcca gctgaaagga atgagctact ccatgtgtac tgggaagttc   4320
aagattgtca aggaaatcgc cgaaactcag catggcacta ttgtgatccg cgtgcagtat   4380
gaaggcgatg gtagcccctg caagatacca tttgaaatca ccgatttgga gaaacggcac   4440
gtcctgggtc ggctcattac cgtgaaccca atcgtgaccg agaaggacag tccagttaat   4500
atcgaggccg agcctccttt cggcgacagt tacatcattg taggggtgga accagggcaa   4560
ctgaagctga actggttcaa gaaaggcagc agtataggac ggcgggataa acgggacaaa   4620
ctcacactga aaggcatgtc atacgttatg tgcaccggct cattcaaact ggagaaggaa   4680
gttgcagaga cacagcatgg gaccgtgctc gtgcaggtca aatacgaggg caccgacgct   4740
ccttgcaaga ttccgttcag tacacaggac gagaaaggcg tgactcagaa cggcagattg   4800
attacagcga accctatcgt gactgacaag gagaagccag ttaacatcga gactgagccg   4860
cctttcggag aatcatacat tatcgtggga gccggcgaga aggcactgaa actcagctgg   4920
ttcaagaagg gcagctcaat cggtcggaga gacaagcggt ctgtcgccct cgcaccgcac   4980
gtgggcctgg gtctggaaac gaggaccgag acgtggatga gttccgaagg cgcatggaag   5040
caaatccaga aagtggagac gtgggccctc aggcatccgt aatgagcgcg cagcgcttag   5100
acgtctcgcg atcgatacta gtacaaccta aatccattat aaaaaactta ggagcaaagt   5160
gattgcctcc caaggtccac aatgacagag acctacgact tcgacaagtc ggcatgggac   5220
atcaaagggt cgatcgctcc gatacaaccc accacctaca gtgatggcag gctggtgccc   5280
caggtcagag tcatagatcc tggtctaggc gacaggaagg atgaatgctt tatgtacatg   5340
tttctgctgg gggttgttga ggacagcgat tccctagggc ctccaatcgg gcgagcattt   5400
```

-continued

```
gggttcctgc ccttaggtgt tggcagatcc acagcaaagc ccgaaaaact cctcaaagag   5460
gccactgagc ttgacatagt tgttagacgt acagcagggc tcaatgaaaa actggtgttc   5520
tacaacaaca ccccactaac tctcctcaca ccttggagaa aggtcctaac aacagggagt   5580
gtcttcaacg caaaccaagt gtgcaatgcg gttaatctga taccgctcga taccccgcag   5640
aggttccgtg ttgtttatat gagcatcacc cgtctttcgg ataacgggta ttacaccgtt   5700
cctagaagaa tgctggaatt cagatcggtc aatgcagtgg ccttcaacct gctggtgacc   5760
cttaggattg acaaggcgat aggccctggg aagatcatcg acaatacaga gcaacttcct   5820
gaggcaacat ttatggtcca catcgggaac ttcaggagaa agaagagtga agtctactct   5880
gccgattatt gcaaaatgaa aatcgaaaag atgggcctgg tttttgcact tggtgggata   5940
gggggcacca gtcttcacat tagaagcaca ggcaaaatga gcaagactct ccatgcacaa   6000
ctcgggttca agaagacctt atgttacccg ctgatggata tcaatgaaga ccttaatcga   6060
ttactctgga ggagcagatg caagatagta agaatccagg cagttttgca gccatcagtt   6120
cctcaagaat tccgcattta cgacgacgtg atcataaatg atgaccaagg actattcaaa   6180
gttctgtaga ccgtagtgcc cagcaatgcc cgaaaacgac cccccctcaca atgacagcca   6240
gaaggcccgg acaaaaaagc cccctccgaa agactccacg gaccaagcga gaggccagcc   6300
agcagccgac ggcaagcgcg aacaccaggc ggccccagca cagaacagcc ctgacacaag   6360
gccaccacca gccaccccaa tctgcatcct cctcgtggga cccccgagga ccaaccccca   6420
aggctgcccc cgatccaaac caccaaccgc atccccacca cccccgggaa agaaaccccc   6480
agcaattgga aggcccctcc ccctcttcct caacacaaga actccacaac cgaaccgcac   6540
aagcgaccga ggtgacccaa ccgcaggcat ccgactccct agacagatcc tctctccccg   6600
gcaaactaaa caaaacttag ggccaaggaa catacacacc caacagaacc cagaccccgg   6660
cccacggcgc cgcgccccca acccccgaca accagaggga gcccccaacc aatcccgccg   6720
gctcccccgg tgcccacagg cagggacacc aacccccgaa cagacccagc acccaaccat   6780
cgacaatcca agacgggggg gcccccccaa aaaaaggccc ccaggggccg acagccagca   6840
ccgcgaggaa gcccacccac cccacacacg accacggcaa ccaaaccaga acccagacca   6900
ccctgggcca ccagctccca gactcggcca tcaccccgca gaaaggaaag gccacaaccc   6960
gcgcaccccca gccccgatcc ggcggggagc cacccaaccc gaaccagcac ccaagagcga   7020
tccccgaagg acccccgaac cgcaaaggac atcagtatcc cacagcctct ccaagtcccc   7080
cggtctcctc ctcttctcga agggaccaaa agatcaatcc accacacccg acgacactca   7140
actccccacc cctaaaggag acaccgggaa tcccagaatc aagactcatc caatgtccat   7200
catgggtctc aaggtgaacg tctctgccat attcatggca gtactgttaa ctctccaaac   7260
acccaccggt caaatccatt ggggcaatct ctctaagata ggggtggtag gaataggaag   7320
tgcaagctac aaagttatga ctcgttccag ccatcaatca ttagtcataa aattaatgcc   7380
caatataact ctcctcaata actgcacgag ggtagagatt gcagaataca ggagactact   7440
gagaacagtt ttggaaccaa ttagagatgc acttaatgca atgacccaga atataagacc   7500
ggttcagagt gtagcttcaa gtaggagaca caagagattt gcgggagtag tcctggcagg   7560
tgcggcccta ggcgttgcca cagctgctca gataacagcc ggcattgcac ttcaccagtc   7620
catgctgaac tctcaagcca tcgacaatct gagagcgagc ctggaaacta ctaatcaggc   7680
aattgagaca atcagacaag cagggcagga gatgatattg gctgttcagg gtgtccaaga   7740
ctacatcaat aatgagctga taccgtctat gaaccaacta tcttgtgatt taatcggcca   7800
```

```
gaagctcggg ctcaaattgc tcagatacta tacagaaatc ctgtcattat ttggccccag   7860
tttacgggac cccatatctg cggagatatc tatccaggct ttgagctatg cgcttggagg   7920
agacatcaat aaggtgttag aaaagctcgg atacagtgga ggtgatttac tgggcatctt   7980
agagagcgga ggaataaagg cccggataac tcacgtcgac acagagtcct acttcattgt   8040
cctcagtata gcctatccga cgctgtccga gattaagggg gtgattgtcc accggctaga   8100
gggggtctcg tacaacatag gctctcaaga gtggtatacc actgtgccca agtatgttgc   8160
aacccaaggg taccttatct cgaattttga tgagtcatcg tgtactttca tgccagaggg   8220
gactgtgtgc agccaaaatg ccttgtaccc gatgagtcct ctgctccaag aatgcctccg   8280
ggggtacacc aagtcctgtg ctcgtacact cgtatccggg tcttttggga accggttcat   8340
tttatcacaa gggaacctaa tagccaattg tgcatcaatc ctttgcaagt gttacacaac   8400
aggaacgatc attaatcaag accctgacaa gatcctaaca tacattgctg ccgatcactg   8460
cccggtagtc gaggtgaacg gcgtgaccat ccaagtcggg agcaggaggt atccagacgc   8520
tgtgtacttg cacagaattg acctcggtcc tcccatatca ttggagaggt tggacgtagg   8580
gacaaatctg gggaatgcaa ttgctaagtt ggaggatgcc aaggaattgt tggagtcatc   8640
ggaccagata ttgaggagta tgaaaggttt atcgagcact agcatagtct acatcctgat   8700
tgcagtgtgt cttggagggt tgatagggat ccccgcttta atatgttgct gcagggggcg   8760
ttgtaacaaa aagggagaac aagttggtat gtcaagacca ggcctaaagc ctgatcttac   8820
gggaacatca aaatcctatg taaggtcgct ctgatcctct acaactcttg aaacacaaat   8880
gtcccacaag tctcctcttc gtcatcaagc aaccaccgca cccagcatca agcccacctg   8940
aaattatctc cggcttccct ctggccgaac aatatcggta gttaatcaaa acttagggtg   9000
caagatcatc cacaatgtca ccacaacgag accggataaa tgccttctac aaagataacc   9060
cccatcccaa gggaagtagg atagtcatta acagagaaca tcttatgatt gatagacctt   9120
atgttttgct ggctgttctg tttgtcatgt ttctgagctt gatcgggttg ctagccattg   9180
caggcattag acttcatcgg gcagccatct acaccgcaga gatccataaa agcctcagca   9240
ccaatctaga tgtaactaac tcaatcgagc atcaggtcaa ggacgtgctg acaccactct   9300
tcaaaatcat cggtgatgaa gtgggcctga ggacacctca gagattcact gacctagtga   9360
aattaatctc tgacaagatt aaattcctta atccggatag ggagtacgac ttcagagatc   9420
tcacttggtg tatcaacccg ccagagagaa tcaaattgga ttatgatcaa tactgtgcag   9480
atgtggctgc tgaagagctc atgaatgcat tggtgaactc aactctactg gagaccagaa   9540
caaccaatca gttcctagct gtctcaaagg gaaactgctc agggcccact acaatcagag   9600
gtcaattctc aaacatgtcg ctgtccctgt tagacttgta tttaggtcga ggttacaatg   9660
tgtcatctat agtcactatg acatcccagg gaatgtatgg gggaacttac ctagtggaaa   9720
agcctaatct gagcagcaaa aggtcagagt tgtcacaact gagcatgtac cgagtgtttg   9780
aagtaggtgt tatcagaaat ccgggtttgg gggctccggt gttccatatg acaaactatc   9840
ttgagcaacc agtcagtaat gatctcagca actgtatggt ggctttgggg gagctcaaac   9900
tcgcagccct ttgtcacggg gaagattcta tcacaattcc ctatcaggga tcagggaaag   9960
gtgtcagctt ccagctcgtc aagctaggtg tctggaaatc ccccaaccgac atgcaatcct  10020
gggtcccctt atcaacggat gatccagtga tagacaggct ttacctctca tctcacagag  10080
gtgttatcgc tgacaatcaa gcaaaatggg ctgtcccgac aacacgaaca gatgacaagt  10140
```

```
tgcgaatgga gacatgcttc caacaggcgt gtaagggtaa aatccaagca ctctgcgaga  10200
atcccgagtg ggcaccattg aaggataaca ggattccttc atacggggtc ttgtctgttg  10260
atctgagtct gacagttgag cttaaaatca aaattgcttc gggattcggg ccattgatca  10320
cacacggttc agggatggac ctatacaaat ccaaccacaa caatgtgtat tggctgacta  10380
tcccgccaat gaagaaccta gccttaggtg taatcaacac attggagtgg ataccgagat  10440
tcaaggttag tccctacctc ttcactgtcc caattaagga agcaggcgaa gactgccatg  10500
ccccaacata cctacctgcg gaggtggatg gtgatgtcaa actcagttcc aatctggtga  10560
ttctacctgg tcaagatctc caatatgttt tggcaaccta cgatacttcc agggttgaac  10620
atgctgtggt ttattacgtt tacagcccaa gccgctcatt ttcttacttt tatcctttta  10680
ggttgcctat aaagggggtc cccatcgaat tacaagtgga atgcttcaca tgggaccaaa  10740
aactctggtg ccgtcacttc tgtgtgcttg cggactcaga atctggtgga catatcactc  10800
actctgggat ggtgggcatg ggagtcagct gcacagtcac ccgggaagat ggaaccaatc  10860
gcagataggg ctgctagtga accaatcaca tgatgtcacc cagacatcag gcatacccac  10920
tagtgtgaaa tagacatcag aattaagaaa aacgtagggt ccaagtggtt ccccgttatg  10980
gactcgctat ctgtcaacca gatcttatac cctgaagttc acctagatag cccgatagtt  11040
accaataaga tagtagccat cctggagtat gctcgagtcc ctcacgctta cagcctggag  11100
gaccctacac tgtgtcagaa catcaagcac cgcctaaaaa acggattttc caaccaaatg  11160
attataaaca atgtggaagt tgggaatgtc atcaagtcca agcttaggag ttatccggcc  11220
cactctcata ttccatatcc aaattgtaat caggatttat ttaacataga agacaaagag  11280
tcaacgagga agatccgtga actcctcaaa aaggggaatt cgctgtactc caaagtcagt  11340
gataaggttt tccaatgctt aagggacact aactcacggc ttggcctagg ctccgaattg  11400
agggaggaca tcaaggagaa agttattaac ttgggagttt acatgcacag ctcccagtgg  11460
tttgagccct ttctgttttg gtttacagtc aagactgaga tgaggtcagt gattaaatca  11520
caaacccata cttgccatag gaggagacac acacctgtat tcttcactgg tagttcagtt  11580
gagttgctaa tctctcgtga ccttgttgct ataatcagta aagagtctca acatgtatat  11640
tacctgacat ttgaactggt tttgatgtat tgtgatgtca tagaggggag gttaatgaca  11700
gagaccgcta tgactattga tgctaggtat acagagcttc taggaagagt cagatacatg  11760
tggaaactga tagatggttt cttccctgca ctcgggaatc caacttatca aattgtagcc  11820
atgctggagc ctctttcact tgcttacctg cagctgaggg atataacagt agaactcaga  11880
ggtgctttcc ttaaccactg ctttactgaa atacatgatg ttcttgacca aaacgggttt  11940
tctgatgaag gtacttatca tgagttaact gaagctctag attacatttt cataactgat  12000
gacatacatc tgacagggga gattttctca tttttcagaa gtttcggcca ccccagactt  12060
gaagcagtaa cggctgctga aaatgttagg aaatacatga atcagcctaa agtcattgtg  12120
tatgagactc tgatgaaagg tcatgccata ttttgtggaa tcataatcaa cggctatcgt  12180
gacaggcacg gaggcagttg gccaccgctg accctccccc tgcatgctgc agacacaatc  12240
cggaatgctc aagcttcagg tgaagggtta acacatgagc agtgcgttga taactggaaa  12300
tcttttgctg gagtgaaatt tggctgcttt atgcctctta gcctggatag tgatctgaca  12360
atgtacctaa aggacaaggc acttgctgct ctccaaaggg aatgggattc agtttacccg  12420
aaagagttcc tgcgttacga ccctcccaag ggaaccgggt cacggaggct tgtagatgtt  12480
ttccttaatg attcgagctt tgacccatat gatgtgataa tgtatgttgt aagtggagct  12540
```

```
tacctccatg accctgagtt caacctgtct tacagcctga aagaaaagga gatcaaggaa  12600
acaggtagac tttttgctaa aatgacttac aaaatgaggg catgccaagt gattgctgaa  12660
aatctaatct caaacgggat tggcaaatat tttaaggaca atgggatggc caaggatgag  12720
cacgatttga ctaaggcact ccacactcta gctgtctcag gagtccccaa agatctcaaa  12780
gaaagtcaca gggggggcc agtcttaaaa acctactccc gaagcccagt ccacacaagt  12840
accaggaacg tgagagcagc aaaagggttt atagggttcc ctcaagtaat tcggcaggac  12900
caagacactg atcatccgga gaatatggaa gcttacgaga cagtcagtgc atttatcacg  12960
actgatctca agaagtactg ccttaattgg agatatgaga ccatcagctt gtttgcacag  13020
aggctaaatg agatttacgg attgccctca tttttccagt ggctgcataa gaggcttgag  13080
acctctgtcc tgtatgtaag tgaccctcat tgccccccg accttgacgc ccatatcccg  13140
ttatataaag tccccaatga tcaaatcttc attaagtacc ctatgggagg tatagaaggg  13200
tattgtcaga agctgtggac catcagcacc attccctatc tatacctggc tgcttatgag  13260
agcggagtaa ggattgcttc gttagtgcaa ggggacaatc agaccatagc cgtaacaaaa  13320
agggtaccca gcacatggcc ctacaacctt aagaaacggg aagctgctag agtaactaga  13380
gattactttg taattcttag gcaaaggcta catgatattg gccatcacct caaggcaaat  13440
gagacaattg tttcatcaca tttttttgtc tattcaaaag gaatatatta tgatgggcta  13500
cttgtgtccc aatcactcaa gagcatcgca agatgtgtat tctggtcaga gactatagtt  13560
gatgaaacaa gggcagcatg cagtaatatt gctacaacaa tggctaaaag catcgagaga  13620
ggttatgacc gttaccttgc atattccctg aacgtcctaa aagtgataca gcaaattctg  13680
atctctcttg gcttcacaat caattcaacc atgacccggg atgtagtcat acccctcctc  13740
acaaacaacg acctcttaat aaggatggca ctgttgcccg ctcctattgg ggggatgaat  13800
tatctgaata tgagcaggct gtttgtcaga aacatcggtg atccagtaac atcatcaatt  13860
gctgatctca agagaatgat tctcgcctca ctaatgcctg aagagaccct ccatcaagta  13920
atgacacaac aaccggggga ctcttcattc ctagactggg ctagcgaccc ttactcagca  13980
aatcttgtat gtgtccagag catcactaga ctcctcaaga acataactgc aaggtttgtc  14040
ctgatccata gtccaaaccc aatgttaaaa ggattattcc atgatgacag taaagaagag  14100
gacgagggac tggcggcatt cctcatggac aggcatatta tagtacctag ggcagctcat  14160
gaaatcctgg atcatagtgt cacaggggca agagagtcta ttgcaggcat gctggatacc  14220
acaaaaggct tgattcgagc cagcatgagg aaggggggt taacctctcg agtgataacc  14280
agattgtcca attatgacta tgaacaattc agagcaggga tggtgctatt gacaggaaga  14340
aagagaaatg tcctcattga caaagagtca tgttcagtgc agctggcgag agctctaaga  14400
agccatatgt gggcgaggct agctcgagga cggcctattt acggccttga ggtccctgat  14460
gtactagaat ctatgcgagg ccaccttatt cggcgtcatg agacatgtgt catctgcgag  14520
tgtggatcag tcaactacgg atggtttttt gtcccctcgg gttgccaact ggatgatatt  14580
gacaaggaaa catcatcctt gagagtccca tatattggtt ctaccactga tgagagaaca  14640
gacatgaagc ttgccttcgt aagagcccca agtcgatcct tgcgatctgc tgttagaata  14700
gcaacagtgt actcatgggc ttacggtgat gatgatagct cttggaacga agcctggttg  14760
ttggctaggc aaagggccaa tgtgagcctg gaggagctaa gggtgatcac tcccatctca  14820
acttcgacta atttagcgca taggttgagg gatcgtagca ctcaagtgaa atactcaggt  14880
```

```
acatcccttg tccgagtggc gaggtatacc acaatctcca acgacaatct ctcatttgtc  14940
atatcagata agaaggttga tactaacttt atataccaac aaggaatgct tctagggttg  15000
ggtgttttag aaacattgtt tcgactcgag aaagataccg gatcatctaa cacggtatta  15060
catcttcacg tcgaaacaga ttgttgcgtg atcccgatga tagatcatcc caggataccc  15120
agctcccgca agctagagct gagggcagag ctatgtacca acccattgat atatgataat  15180
gcacctttaa ttgacagaga tgcaacaagg ctatacaccc agagccatag gaggcacctt  15240
gtggaatttg ttacatggtc cacaccccaa ctatatcaca ttttagctaa gtccacagca  15300
ctatctatga ttgacctggt aacaaaattt gagaaggacc atatgaatga aatttcagct  15360
ctcatagggg atgacgatat caatagtttc ataactgagt ttctgctcat agagccaaga  15420
ttattcacta tctacttggg ccagtgtgcg gccatcaatt gggcatttga tgtacattat  15480
catagaccat cagggaaata tcagatgggt gagctgttgt catcgttcct ttctagaatg  15540
agcaaaggag tgtttaaggt gcttgtcaat gctctaagcc acccaaagat ctacaagaaa  15600
ttctggcatt gtggtattat agagcctatc catggtcctt cacttgatgc tcaaaacttg  15660
cacacaactg tgtgcaacat ggtttacaca tgctatatga cctacctcga cctgttgttg  15720
aatgaagagt tagaagagtt cacatttctc ttgtgtgaaa gcgacgagga tgtagtaccg  15780
gacagattcg acaacatcca ggcaaaacac ttatgtgttc tggcagattt gtactgtcaa  15840
ccagggacct gcccaccaat tcgaggtcta agaccggtag agaaatgtgc agttctaacc  15900
gaccatatca aggcagaggc tatgttatct ccagcaggat cttcgtggaa cataaatcca  15960
attattgtag accattactc atgctctctg acttatctcc ggcgaggatc gatcaaacag  16020
ataagattga gagttgatcc aggattcatt ttcgacgccc tcgctgaggt aaatgtcagt  16080
cagccaaaga tcggcagcaa caacatctca aatatgagca tcaaggcttt cagaccccca  16140
cacgatgatg ttgcaaaatt gctcaaagat atcaacacaa gcaagcacaa tcttcccatt  16200
tcagggggca atctcgccaa ttatgaaatc catgctttcc gcagaatcgg gttgaactca  16260
tctgcttgct acaaagctgt tgagatatca acattaatta ggagatgcct tgagccaggg  16320
gaggacggct tgttcttggg tgagggatcg ggttctatgt tgatcactta taaagagata  16380
cttaaactaa acaagtgctt ctataatagt ggggtttccg ccaattctag atctggtcaa  16440
agggaattag caccctatcc ctccgaagtt ggccttgtcg aacacagaat gggagtaggt  16500
aatattgtca aagtgctctt taacgggagg cccgaagtca cgtgggtagg cagtgtagat  16560
tgcttcaatt tcatagttag taatatccct acctctagtg tggggtttat ccattcagat  16620
atagagacct tgcctgacaa agatactata gagaagctag aggaattggc agccatctta  16680
tcgatggctc tgctcctggg caaaatagga tcaatactgg tgattaagct tatgcctttc  16740
agcggggatt ttgttcaggg atttataagt tatgtagggt ctcattatag agaagtgaac  16800
cttgtatacc ctagatacag caacttcatc tctactgaat cttatttggt tatgacagat  16860
ctcaaggcta accggctaat gaatcctgaa aagattaagc agcagataat tgaatcatct  16920
gtgaggactt cacctggact tataggtcac atcctatcca ttaagcaact aagctgcata  16980
caagcaattg tgggagacgc agttagtaga ggtgatatca atcctactct gaaaaaactt  17040
acacctatag agcaggtgct gatcaattgc gggttggcaa ttaacggacc taagctgtgc  17100
aaagaattga tccaccatga tgttgcctca gggcaagatg gattgcttaa ttctatactc  17160
atcctctaca gggagttggc aagattcaaa gacaaccaaa gaagtcaaca agggatgttc  17220
cacgcttacc ccgtattggt aagtagcagg caacgagaac ttatatctag gatcacccgc  17280
```

```
aaattctggg ggcacattct tctttactcc gggaacaaaa agttgataaa taagtttatc  17340
cagaatctca agtccggcta tctgatacta gacttacacc agaatatctt cgttaagaat  17400
ctatccaagt cagagaaaca gattattatg acggggggtt tgaaacgtga gtgggttttt  17460
aaggtaacag tcaaggagac caaagaatgg tataagttag tcggatacag tgccctgatt  17520
aaggactaat tggttgaact ccggaaccct aatcctgccc taggtggtta ggcattattt  17580
gcaatatatt aaagaaaact ttgaaaatac gaagtttcta ttcccagctt tgtctggtgg  17640
ccggcatggt cccagcctcc tcgctggcgc cggctgggca acattccgag gggaccgtcc  17700
cctcggtaat ggcgaatggg acgcggccga tccggctgct aacaaagccc gaaaggaagc  17760
tgagttggct gctgccaccg ctgagcaata actagcataa ccccttgggg cctctaaacg  17820
ggtcttgagg ggttttttgc tgaaaggagg aactatatcc ggatgcggcc gcgggcccta  17880
tggtacccag cttttgttcc ctttagtgag ggttaattcc gagcttggcg taatcatggt  17940
catagctgtt tcctgtgtga aattgttatc cgctcacaat tccacacaac ataggagccg  18000
gaagcataaa gtgtaaagcc tggggtgcct aatgagtgag gtaactcaca ttaattgcgt  18060
tgcgctcact gcccgctttc cagtcgggaa acctgtcgtg ccagctgcat taatgaatcg  18120
gccaacgcgc ggggagaggc ggtttgcgta ttgggcgctc ttccgcttcc tcgctcactg  18180
actcgctgcg ctcggtcgtt cggctgcggc gagcggtatc agctcactca aaggcggtaa  18240
tacggttatc cacagaatca ggggataacg caggaaagaa catgtgagca aaaggccagc  18300
aaaaggccag gaaccgtaaa aaggccgcgt tgctggcgtt tttccatagg ctcggccccc  18360
ctgacgagca tcacaaaaat cgacgctcaa gtcagaggtg gcgaaacccg acaggactat  18420
aaagatacca ggcgttcccc cctggaagct ccctcgtgcg ctctcctgtt ccgaccctgc  18480
cgcttaccgg atacctgtcc gcctttctcc cttcgggaag cgtggcgctt tctcaatgct  18540
cacgctgtag gtatctcagt tcggtgtagg tcgttcgctc caagctgggc tgtgtgcacg  18600
aaccccccgt tcagcccgac cgctgcgcct tatccggtaa ctatcgtctt gagtccaacc  18660
cggtaagaca cgacttatcg ccactggcag cagccactgg taacaggatt agcagagcga  18720
ggtatgtagg cggtgctaca gagttcttga agtggtggcc taactacggc tacactagaa  18780
ggacagtatt tggtatctgc gctctgctga agccagttac cttcggaaaa agagttggta  18840
gctcttgatc cggcaaacaa accaccgctg gtagcggtgg tttttttgtt tgcaagcagc  18900
agattacgcg cagaaaaaaa ggatctcaag aagatccttt gatcttttct acggggtctg  18960
acgctcagtg gaacgaaaac tcacgttaag ggattttggt catgagatta tcaaaaagga  19020
tcttcaccta gatcctttta aattaaaaat gaagttttaa atcaatctaa agtatatatg  19080
agtaaacttg gtctgacagt taccaatgct taatcagtga ggcacctatc tcagcgatct  19140
gtctatttcg ttcatccata gttgcctgac tgcccgtcgt gtagataact acgatacggg  19200
agggcttacc atctggcccc agtgctgcaa tgataccgcg agacccacgc tcaccggctc  19260
cagatttatc agcaataaac cagccagccg gaagggccga gcgcagaagt ggtcctgcaa  19320
ctttatccgc ctccatccag tctattaatt gttgccggga agctagagta agtagttcgc  19380
cagttaatag tttgcgcaac gttgttgcca ttgctacagg catcgtggtg tcacgctcgt  19440
cgtttggtat ggcttcattc agctccggtt cccaacgatc aaggcgagtt acatgatccc  19500
ccatgttgtg aaaaaaagcg gttagctcct tcggtcctcc gatcgttgtc agaagtaagt  19560
tggccgcagt gttatcactc atgcttatgg cagcactgca taattctctt actgtcatgc  19620
```

catccgtaag atgcttttct gtgactggtg agtactcaac caagtcattc tgagaatagt 19680
gtatgcggcg accgagttgc tcttgcccgg cgtcaatacg ggataatacc gcgccacata 19740
gcagaacttt aaaagtgctc atcattggaa aacgttcttc ggggcgaaaa ctctcaagga 19800
tcttaccgct gttgagatcc agttcgatgt aacccactcg tgcacccaac tgatcttcag 19860
catcttttac tttcaccagc gtttctgggt gagcaaaaac aggaaggcaa aatgccgcaa 19920
aaaagggaat aagggcgaca cggaaatgtt gaatactcat actcttcctt tttcaatatt 19980
attgaagcat ttatcagggt tattgtctca tgagcggata catatttgaa tgtatttaga 20040
aaaataaaca aataggggtt ccgcgcacat ttccccgaaa agtgccacct gaaattgtaa 20100
acgttaatat tttgttaaaa ttcgcgttaa atttttgtta aatcagctca ttttttaacc 20160
aataggccga aatcggcaaa atcccttata aatcaaaaga atagaccgag atagggttga 20220
gtgttgttcc agtttggaac aagagtccac tattaaagaa cgtggactcc aacgtcaaag 20280
ggcgaaaaac cgtctatcag ggcgatggcc cactacgtga accatcaccc taatcaagtt 20340
ttttggggtc gaggtgccgt aaagcactaa atcggaaccc taaagggagc ccccgattta 20400
gagcttgacg gggaaagccg gcgaacgtgg cgagaaagga agggaagaaa gcgaaaggag 20460
cgggcgctag ggcgctggca agtgtagcgg tcacgctgcg cgtaaccacc acacccgccg 20520
cgcttaatgc gccgctacag ggcgcgtccc attcgccatt caggctgcgc aactgttggg 20580
aagggcgatc ggtgcgggcc tcttcgctat tacgccagcc accgcggtg 20629

<210> SEQ ID NO 4
<211> LENGTH: 19107
<212> TYPE: DNA
<213> ORGANISM: artificial sequence
<220> FEATURE:
<223> OTHER INFORMATION: pTM 2ATU MV Schw - Measles virus scaffold with ATU

<400> SEQUENCE: 4
tccaaccgcg cgcgcggccg ctaatacgac tcactatagg gccaactttg tttggtctga 60
tgagtccgtg aggacgaaac ccggagtccc gggtcaccaa acaaagttgg gtaaggatag 120
ttcaatcaat gatcatcttc tagtgcactt aggattcaag atcctattat cagggacaag 180
agcaggatta gggatatccg agatggccac acttttaagg agcttagcat tgttcaaaag 240
aaacaaggac aaaccaccca ttacatcagg atccggtgga gccatcagag gaatcaaaca 300
cattattata gtaccaatcc ctggagattc ctcaattacc actcgatcca gacttctgga 360
ccggttggtg aggttaattg gaaacccgga tgtgagcggg cccaaactaa caggggcact 420
aataggtata ttatccttat ttgtggagtc tccaggtcaa ttgattcaga ggatcaccga 480
tgaccctgac gttagcataa ggctgttaga ggttgtccag agtgaccagt cacaatctgg 540
ccttaccttc gcatcaagag gtaccaacat ggaggatgag gcggaccaat acttttcaca 600
tgatgatcca attagtagtg atcaatccag gttcggatgg ttcgggaaca aggaaatctc 660
agatattgaa gtgcaagacc ctgagggatt caacatgatt ctgggtacca tcctagccca 720
aatttgggtc ttgctcgcaa aggcggttac ggccccagac acggcagctg attcggagct 780
aagaaggtgg ataaagtaca cccaacaaag aagggtagtt ggtgaattta gattggagag 840
aaaatggttg gatgtggtga ggaacaggat tgccgaggac ctctccttac gccgattcat 900
ggtcgctcta atcctggata tcaagagaac acccggaaac aaacccagga ttgctgaaat 960
gatatgtgac attgatacat atatcgtaga ggcaggatta gccagtttta tcctgactat 1020

```
taagtttggg atagaaacta tgtatcctgc tcttggactg catgaatttg ctggtgagtt   1080
atccacactt gagtccttga tgaaccttta ccagcaaatg ggggaaactg caccctacat   1140
ggtaatcctg gagaactcaa ttcagaacaa gttcagtgca ggatcatacc ctctgctctg   1200
gagctatgcc atgggagtag gagtggaact tgaaaactcc atgggaggtt tgaactttgg   1260
ccgatcttac tttgatccag catattttag attagggcaa gagatggtaa ggaggtcagc   1320
tggaaaggtc agttccacat tggcatctga actcggtatc actgccgagg atgcaaggct   1380
tgtttcagag attgcaatgc atactactga ggacaagatc agtagagcgg ttggacccag   1440
acaagcccaa gtatcatttc tacacggtga tcaaagtgag aatgagctac cgagattggg   1500
gggcaaggaa gataggaggg tcaaacagag tcgaggagaa gccagggaga gctacagaga   1560
aaccgggccc agcagagcaa gtgatgcgag agctgcccat cttccaaccg gcacacccct   1620
agacattgac actgcaacgg agtccagcca agatccgcag gacagtcgaa ggtcagctga   1680
cgccctgctt aggctgcaag ccatggcagg aatctcggaa gaacaaggct cagacacgga   1740
cacccctata gtgtacaatg acagaaatct tctagactag gtgcgagagg ccgagggcca   1800
gaacaacatc cgcctaccat ccatcattgt tataaaaaac ttaggaacca ggtccacaca   1860
gccgccagcc catcaaccat ccactcccac gattggagcc aatggcagaa gagcaggcac   1920
gccatgtcaa aaacggactg gaatgcatcc gggctctcaa ggccgagccc atcggctcac   1980
tggccatcga ggaagctatg gcagcatggt cagaaatatc agacaaccca ggacaggagc   2040
gagccacctg cagggaagag aaggcaggca gttcgggtct cagcaaacca tgcctctcag   2100
caattggatc aactgaaggc ggtgcacctc gcatccgcgg tcagggacct ggagagagcg   2160
atgacgacgc tgaaactttg ggaatccccc caagaaatct ccaggcatca agcactgggt   2220
tacagtgtta ttacgtttat gatcacagcg gtgaagcggt taagggaatc caagatgctg   2280
actctatcat ggttcaatca ggccttgatg gtgatagcac cctctcagga ggagacaatg   2340
aatctgaaaa cagcgatgtg gatattggcg aacctgatac cgagggatat gctatcactg   2400
accggggatc tgctcccatc tctatggggt tcagggcttc tgatgttgaa actgcagaag   2460
gaggggagat ccacgagctc ctgagactcc aatccagagg caacaacttt ccgaagcttg   2520
ggaaaactct caatgttcct ccgcccccgg accccggtag ggccagcact tccgggacac   2580
ccattaaaaa gggcacagac gcgagattag cctcatttgg aacggagatc gcgtctttat   2640
tgacaggtgg tgcaacccaa tgtgctcgaa agtcaccctc ggaaccatca gggccaggtg   2700
cacctgcggg gaatgtcccc gagtgtgtga gcaatgccgc actgatacag gagtggacac   2760
ccgaatctgg taccacaatc tccccgagat cccagaataa tgaagaaggg ggagactatt   2820
atgatgatga gctgttctct gatgtccaag atattaaaac agccttggcc aaaatacacg   2880
aggataatca gaagataatc tccaagctag aatcactgct gttattgaag ggagaagttg   2940
agtcaattaa gaagcagatc aacaggcaaa atatcagcat atccaccctg gaaggacacc   3000
tctcaagcat catgatcgcc attcctggac ttgggaagga tcccaacgac cccactgcag   3060
atgtcgaaat caatcccgac ttgaaaccca tcataggcag agattcaggc cgagcactgg   3120
ccgaagttct caagaaaccc gttgccagcc gacaactcca aggaatgaca aatggacgga   3180
ccagttccag aggacagctg ctgaaggaat ttcagctaaa gccgatcggg aaaaagatga   3240
gctcagccgt cgggtttgtt cctgacaccg gccctgcatc acgcagtgta atccgctcca   3300
ttataaaatc cagccggcta gaggaggatc ggaagcgtta cctgatgact ctccttgatg   3360
atatcaaagg agccaatgat cttgccaagt tccaccagat gctgatgaag ataataatga   3420
```

```
agtagctaca gctcaactta cctgccaacc ccatgccagt cgacccaact agcctaccct   3480
ccatcattgt tataaaaaac ttaggaacca ggtccacaca gccgccagcc catcaacgcg   3540
tacggcgcgc agcgcttaga cgtctcgcga tcgatactag tacaacctaa atccattata   3600
aaaaacttag gagcaaagtg attgcctccc aaggtccaca atgacagaga cctacgactt   3660
cgacaagtcg gcatgggaca tcaaagggtc gatcgctccg atacaaccca ccacctacag   3720
tgatggcagg ctggtgcccc aggtcagagt catagatcct ggtctaggcg acaggaagga   3780
tgaatgcttt atgtacatgt ttctgctggg ggttgttgag gacagcgatt ccctagggcc   3840
tccaatcggg cgagcatttg ggttcctgcc cttaggtgtt ggcagatcca cagcaaagcc   3900
cgaaaaactc ctcaaagagg ccactgagct tgacatagtt gttagacgta cagcagggct   3960
caatgaaaaa ctggtgttct acaacaacac cccactaact ctcctcacac cttggagaaa   4020
ggtcctaaca acagggagtg tcttcaacgc aaaccaagtg tgcaatgcgg ttaatctgat   4080
accgctcgat accccgcaga ggttccgtgt tgtttatatg agcatcaccc gtctttcgga   4140
taacgggtat tacaccgttc ctagaagaat gctggaattc agatcggtca atgcagtggc   4200
cttcaacctg ctggtgaccc ttaggattga caaggcgata ggccctggga agatcatcga   4260
caatacagag caacttcctg aggcaacatt tatggtccac atcgggaact tcaggagaaa   4320
gaagagtgaa gtctactctg ccgattattg caaaatgaaa atcgaaaaga tgggcctggt   4380
ttttgcactt ggtgggatag gggcaccag tcttcacatt agaagcacag gcaaaatgag   4440
caagactctc catgcacaac tcgggttcaa gaagacctta tgttacccgc tgatggatat   4500
caatgaagac cttaatcgat tactctggag gagcagatgc aagatagtaa gaatccaggc   4560
agttttgcag ccatcagttc ctcaagaatt ccgcatttac gacgacgtga tcataaatga   4620
tgaccaagga ctattcaaag ttctgtagac cgtagtgccc agcaatgccc gaaaacgacc   4680
cccctcacaa tgacagccag aaggcccgga caaaaaagcc ccctccgaaa gactccacgg   4740
accaagcgag aggccagcca gcagccgacg gcaagcgcga acaccaggcg gccccagcac   4800
agaacagccc tgacacaagg ccaccaccag ccaccccaat ctgcatcctc ctcgtgggac   4860
ccccgaggac caacccccaa ggctgccccc gatccaaacc accaaccgca tccccaccac   4920
ccccgggaaa gaaaccccca gcaattggaa ggcccctccc cctcttcctc aacacaagaa   4980
ctccacaacc gaaccgcaca agcgaccgag gtgacccaac cgcaggcatc cgactcccta   5040
gacagatcct ctctccccgg caaactaaac aaaacttagg gccaaggaac atacacaccc   5100
aacagaaccc agaccccggc ccacggcgcc gcgcccccaa cccccgacaa ccagagggag   5160
cccccaacca atcccgccgg ctcccccggt gcccacaggc agggacacca acccccgaac   5220
agacccagca cccaaccatc gacaatccaa gacggggggg ccccccccaaa aaaaggcccc   5280
caggggccga cagccagcac cgcgaggaag cccacccacc ccacacacga ccacggcaac   5340
caaaccagaa cccagaccac cctgggccac cagctcccag actcggccat caccccgcag   5400
aaaggaaagg ccacaacccg cgcaccccag ccccgatccg gcggggagcc acccaacccg   5460
aaccagcacc caagagcgat ccccgaagga cccccgaacc gcaaaggaca tcagtatccc   5520
acagcctctc caagtccccc ggtctcctcc tcttctcgaa gggaccaaaa gatcaatcca   5580
ccacacccga cgacactcaa ctccccaccc ctaaaggaga caccgggaat cccagaatca   5640
agactcatcc aatgtccatc atgggtctca aggtgaacgt ctctgccata ttcatggcag   5700
tactgttaac tctccaaaca cccaccggtc aaatccattg ggcaatctc tctaagatag   5760
```

```
gggtggtagg aataggaagt gcaagctaca aagttatgac tcgttccagc catcaatcat   5820
tagtcataaa attaatgccc aatataactc tcctcaataa ctgcacgagg gtagagattg   5880
cagaatacag gagactactg agaacagttt tggaaccaat tagagatgca cttaatgcaa   5940
tgacccagaa tataagaccg gttcagagtg tagcttcaag taggagacac aagagatttg   6000
cgggagtagt cctggcaggt gcggccctag gcgttgccac agctgctcag ataacagccg   6060
gcattgcact tcaccagtcc atgctgaact ctcaagccat cgacaatctg agagcgagcc   6120
tggaaactac taatcaggca attgagacaa tcagacaagc agggcaggag atgatattgg   6180
ctgttcaggg tgtccaagac tacatcaata atgagctgat accgtctatg aaccaactat   6240
cttgtgattt aatcggccag aagctcgggc tcaaattgct cagatactat acagaaatcc   6300
tgtcattatt tggccccagt ttacgggacc ccatatctgc ggagatatct atccaggctt   6360
tgagctatgc gcttggagga gacatcaata aggtgttaga aaagctcgga tacagtggag   6420
gtgatttact gggcatctta gagagcggag gaataaaggc ccggataact cacgtcgaca   6480
cagagtccta cttcattgtc ctcagtatag cctatccgac gctgtccgag attaaggggg   6540
tgattgtcca ccggctagag ggggtctcgt acaacatagg ctctcaagag tggtatacca   6600
ctgtgcccaa gtatgttgca acccaagggt accttatctc gaattttgat gagtcatcgt   6660
gtactttcat gccagagggg actgtgtgca gccaaaatgc cttgtacccg atgagtcctc   6720
tgctccaaga atgcctccgg gggtacacca agtcctgtgc tcgtacactc gtatccgggt   6780
cttttgggaa ccggttcatt ttatcacaag ggaacctaat agccaattgt gcatcaatcc   6840
tttgcaagtg ttacacaaca ggaacgatca ttaatcaaga ccctgacaag atcctaacat   6900
acattgctgc cgatcactgc ccggtagtcg aggtgaacgg cgtgaccatc caagtcggga   6960
gcaggaggta tccagacgct gtgtacttgc acagaattga cctcggtcct cccatatcat   7020
tggagaggtt ggacgtaggg acaaatctgg ggaatgcaat tgctaagttg gaggatgcca   7080
aggaattgtt ggagtcatcg gaccagatat tgaggagtat gaaaggttta tcgagcacta   7140
gcatagtcta catcctgatt gcagtgtgtc ttggagggtt gatagggatc cccgctttaa   7200
tatgttgctg cagggggcgt tgtaacaaaa agggagaaca agttggtatg tcaagaccag   7260
gcctaaagcc tgatcttacg ggaacatcaa aatcctatgt aaggtcgctc tgatcctcta   7320
caactcttga aacacaaatg tcccacaagt ctcctcttcg tcatcaagca accaccgcac   7380
ccagcatcaa gcccacctga aattatctcc ggcttccctc tggccgaaca atatcggtag   7440
ttaatcaaaa cttagggtgc aagatcatcc acaatgtcac cacaacgaga ccggataaat   7500
gccttctaca aagataaccc ccatcccaag ggaagtagga tagtcattaa cagagaacat   7560
cttatgattg atagacctta tgttttgctg gctgttctgt ttgtcatgtt tctgagcttg   7620
atcgggttgc tagccattgc aggcattaga cttcatcggg cagccatcta caccgcagag   7680
atccataaaa gcctcagcac caatctagat gtaactaact caatcgagca tcaggtcaag   7740
gacgtgctga caccactctt caaaatcatc ggtgatgaag tgggcctgag gacacctcag   7800
agattcactg acctagtgaa attaatctct gacaagatta aattccttaa tccggatagg   7860
gagtacgact tcagagatct cacttggtgt atcaacccgc cagagagaat caaattggat   7920
tatgatcaat actgtgcaga tgtggctgct gaagagctca tgaatgcatt ggtgaactca   7980
actctactgg agaccagaac aaccaatcag ttcctagctg tctcaaaggg aaactgctca   8040
gggcccacta caatcagagg tcaattctca aacatgtcgc tgtccctgtt agacttgtat   8100
ttaggtcgag gttacaatgt gtcatctata gtcactatga catcccaggg aatgtatggg   8160
```

```
ggaacttacc tagtggaaaa gcctaatctg agcagcaaaa ggtcagagtt gtcacaactg   8220
agcatgtacc gagtgtttga agtaggtgtt atcagaaatc cgggtttggg ggctccggtg   8280
ttccatatga caaactatct tgagcaacca gtcagtaatg atctcagcaa ctgtatggtg   8340
gctttggggg agctcaaact cgcagccctt tgtcacgggg aagattctat cacaattccc   8400
tatcagggat cagggaaagg tgtcagcttc cagctcgtca agctaggtgt ctggaaatcc   8460
ccaaccgaca tgcaatcctg ggtcccctta tcaacggatg atccagtgat agacaggctt   8520
tacctctcat ctcacagagg tgttatcgct gacaatcaag caaaatgggc tgtcccgaca   8580
acacgaacag atgacaagtt gcgaatggag acatgcttcc aacaggcgtg taagggtaaa   8640
atccaagcac tctgcgagaa tcccgagtgg gcaccattga aggataacag gattccttca   8700
tacggggtct tgtctgttga tctgagtctg acagttgagc ttaaaatcaa aattgcttcg   8760
ggattcgggc cattgatcac acacggttca gggatggacc tatacaaatc caaccacaac   8820
aatgtgtatt ggctgactat cccgccaatg aagaacctag ccttaggtgt aatcaacaca   8880
ttggagtgga taccgagatt caaggttagt ccctacctct tcactgtccc aattaaggaa   8940
gcaggcgaag actgccatgc cccaacatac ctacctgcgg aggtggatgg tgatgtcaaa   9000
ctcagttcca atctggtgat tctacctggt caagatctcc aatatgtttt ggcaacctac   9060
gatacttcca gggttgaaca tgctgtggtt tattacgttt acagcccaag ccgctcattt   9120
tcttactttt atcctttttag gttgcctata aagggggtcc ccatcgaatt acaagtggaa   9180
tgcttcacat gggaccaaaa actctggtgc cgtcacttct gtgtgcttgc ggactcagaa   9240
tctggtggac atatcactca ctctgggatg gtgggcatgg gagtcagctg cacagtcacc   9300
cgggaagatg gaaccaatcg cagatagggc tgctagtgaa ccaatcacat gatgtcaccc   9360
agacatcagg catacccact agtgtgaaat agacatcaga attaagaaaa acgtagggtc   9420
caagtggttc cccgttatgg actcgctatc tgtcaaccag atcttatacc ctgaagttca   9480
cctagatagc ccgatagtta ccaataagat agtagccatc ctggagtatg ctcgagtccc   9540
tcacgcttac agcctggagg accctacact gtgtcagaac atcaagcacc gcctaaaaaa   9600
cggattttcc aaccaaatga ttataaacaa tgtggaagtt gggaatgtca tcaagtccaa   9660
gcttaggagt tatccggccc actctcatat tccatatcca aattgtaatc aggatttatt   9720
taacatagaa gacaaagagt caacgaggaa gatccgtgaa ctcctcaaaa aggggaattc   9780
gctgtactcc aaagtcagtg ataaggtttt ccaatgctta agggacacta actcacggct   9840
tggcctaggc tccgaattga gggaggacat caaggagaaa gttattaact tgggagttta   9900
catgcacagc tcccagtggt ttgagccctt tctgttttgg tttacagtca agactgagat   9960
gaggtcagtg attaaatcac aaacccatac ttgccatagg aggagacaca cacctgtatt  10020
cttcactggt agttcagttg agttgctaat ctctcgtgac cttgttgcta taatcagtaa  10080
agagtctcaa catgtatatt acctgacatt tgaactggtt ttgatgtatt gtgatgtcat  10140
agaggggagg ttaatgacag agaccgctat gactattgat gctaggtata cagagcttct  10200
aggaagagtc agatacatgt ggaaactgat agatggtttc ttccctgcac tcgggaatcc  10260
aacttatcaa attgtagcca tgctggagcc tctttcactt gcttacctgc agctgaggga  10320
tataacagta gaactcagag gtgctttcct taaccactgc tttactgaaa tacatgatgt  10380
tcttgaccaa aacgggtttt ctgatgaagg tacttatcat gagttaactg aagctctaga  10440
ttacattttc ataactgatg acatacatct gacaggggag attttctcat tttcagaag   10500
```

```
tttcggccac cccagacttg aagcagtaac ggctgctgaa aatgttagga aatacatgaa  10560
tcagcctaaa gtcattgtgt atgagactct gatgaaaggt catgccatat tttgtggaat  10620
cataatcaac ggctatcgtg acaggcacgg aggcagttgg ccaccgctga ccctccccct  10680
gcatgctgca gacacaatcc ggaatgctca agcttcaggt gaagggttaa cacatgagca  10740
gtgcgttgat aactggaaat cttttgctgg agtgaaattt ggctgcttta tgcctcttag  10800
cctggatagt gatctgacaa tgtacctaaa ggacaaggca cttgctgctc tccaaaggga  10860
atgggattca gtttacccga aagagttcct gcgttacgac cctcccaagg gaaccgggtc  10920
acggaggctt gtagatgttt tccttaatga ttcgagcttt gacccatatg atgtgataat  10980
gtatgttgta agtggagctt acctccatga ccctgagttc aacctgtctt acagcctgaa  11040
agaaaaggag atcaaggaaa caggtagact tttgctaaa atgacttaca aaatgagggc  11100
atgccaagtg attgctgaaa atctaatctc aaacgggatt ggcaaatatt ttaaggacaa  11160
tgggatggcc aaggatgagc acgatttgac taaggcactc cacactctag ctgtctcagg  11220
agtccccaaa gatctcaaag aaagtcacag gggggggcca gtcttaaaaa cctactcccg  11280
aagcccagtc cacacaagta ccaggaacgt gagagcagca aaagggttta tagggttccc  11340
tcaagtaatt cggcaggacc aagacactga tcatccggag aatatggaag cttacgagac  11400
agtcagtgca tttatcacga ctgatctcaa gaagtactgc cttaattgga gatatgagac  11460
catcagcttg tttgcacaga ggctaaatga gatttacgga ttgccctcat tttccagtg  11520
gctgcataag aggcttgaga cctctgtcct gtatgtaagt gaccctcatt gcccccccga  11580
ccttgacgcc catatcccgt tatataaagt ccccaatgat caaatcttca ttaagtaccc  11640
tatgggaggt atagaagggt attgtcagaa gctgtggacc atcagcacca ttccctatct  11700
atacctggct gcttatgaga gcggagtaag gattgcttcg ttagtgcaag gggacaatca  11760
gaccatagcc gtaacaaaaa gggtacccag cacatggccc tacaacctta agaaacggga  11820
agctgctaga gtaactagag attactttgt aattcttagg caaaggctac atgatattgg  11880
ccatcacctc aaggcaaatg agacaattgt ttcatcacat ttttttgtct attcaaaagg  11940
aatatattat gatgggctac ttgtgtccca atcactcaag agcatcgcaa gatgtgtatt  12000
ctggtcagag actatagttg atgaaacaag ggcagcatgc agtaatattg ctacaacaat  12060
ggctaaaagc atcgagagag gttatgaccg ttaccttgca tattccctga acgtcctaaa  12120
agtgatacag caaattctga tctctcttgg cttcacaatc aattcaacca tgacccggga  12180
tgtagtcata cccctcctca caaacaacga cctcttaata aggatggcac tgttgcccgc  12240
tcctattggg ggatgaatt atctgaatat gagcaggctg tttgtcagaa acatcggtga  12300
tccagtaaca tcatcaattg ctgatctcaa gagaatgatt ctcgcctcac taatgcctga  12360
agagaccctc catcaagtaa tgacacaaca accgggggac tcttcattcc tagactgggc  12420
tagcgaccct tactcagcaa atcttgtatg tgtccagagc atcactagac tcctcaagaa  12480
cataactgca aggtttgtcc tgatccatag tccaaaccca atgttaaaag gattattcca  12540
tgatgacagt aaagaagagg acgagggact ggcggcattc ctcatggaca ggcatattat  12600
agtacctagg gcagctcatg aaatcctgga tcatagtgtc acaggggcaa gagagtctat  12660
tgcaggcatg ctggatacca caaaaggctt gattcgagcc agcatgagga aggggggtt  12720
aacctctcga gtgataacca gattgtccaa ttatgactat gaacaattca gagcagggat  12780
ggtgctattg acaggaagaa agagaaatgt cctcattgac aaagagtcat gttcagtgca  12840
gctggcgaga gctctaagaa gccatatgtg ggcgaggcta gctcgaggac ggcctattta  12900
```

```
cggccttgag gtccctgatg tactagaatc tatgcgaggc caccttattc ggcgtcatga  12960
gacatgtgtc atctgcgagt gtggatcagt caactacgga tggtttttg tcccctcggg   13020
ttgccaactg gatgatattg acaaggaaac atcatccttg agagtcccat atattggttc  13080
taccactgat gagagaacag acatgaagct tgccttcgta agagccccaa gtcgatcctt  13140
gcgatctgct gttagaatag caacagtgta ctcatgggct tacggtgatg atgatagctc  13200
ttggaacgaa gcctggttgt tggctaggca aagggccaat gtgagcctgg aggagctaag  13260
ggtgatcact cccatctcaa cttcgactaa tttagcgcat aggttgaggg atcgtagcac  13320
tcaagtgaaa tactcaggta catcccttgt ccgagtggcg aggtatacca caatctccaa  13380
cgacaatctc tcatttgtca tatcagataa gaaggttgat actaacttta tataccaaca  13440
aggaatgctt ctagggttgg gtgttttaga aacattgttt cgactcgaga aagataccgg  13500
atcatctaac acggtattac atcttcacgt cgaaacagat tgttgcgtga tcccgatgat  13560
agatcatccc aggataccca gctcccgcaa gctagagctg agggcagagc tatgtaccaa  13620
cccattgata tatgataatg cacctttaat tgacagagat gcaacaaggc tatacaccca  13680
gagccatagg aggcaccttg tggaatttgt tacatggtcc acaccccaac tatatcacat  13740
tttagctaag tccacagcac tatctatgat tgacctggta acaaaatttg agaaggacca  13800
tatgaatgaa atttcagctc tcatagggga tgacgatatc aatagtttca taactgagtt  13860
tctgctcata gagccaagat tattcactat ctacttgggc cagtgtgcgg ccatcaattg  13920
ggcatttgat gtacattatc atagaccatc agggaaatat cagatgggtg agctgttgtc  13980
atcgttcctt tctagaatga gcaaaggagt gtttaaggtg cttgtcaatg ctctaagcca  14040
cccaaagatc tacaagaaat tctggcattg tggtattata gagcctatcc atggtccttc  14100
acttgatgct caaaacttgc acacaactgt gtgcaacatg gtttacacat gctatatgac  14160
ctacctcgac ctgttgttga atgaagagtt agaagagttc acatttctct tgtgtgaaag  14220
cgacgaggat gtagtaccgg acagattcga caacatccag gcaaaacact tatgtgttct  14280
ggcagatttg tactgtcaac cagggacctg cccaccaatt cgaggtctaa gaccggtaga  14340
gaaatgtgca gttctaaccg accatatcaa ggcagaggct atgttatctc cagcaggatc  14400
ttcgtggaac ataaatccaa ttattgtaga ccattactca tgctctctga cttatctccg  14460
gcgaggatcg atcaaacaga taagattgag agttgatcca ggattcattt tcgacgccct  14520
cgctgaggta aatgtcagtc agccaaagat cggcagcaac aacatctcaa atatgagcat  14580
caaggctttc agacccccac acgatgatgt tgcaaaattg ctcaaagata tcaacacaag  14640
caagcacaat cttcccattt caggggcaa tctcgccaat tatgaaatcc atgctttccg   14700
cagaatcggg ttgaactcat ctgcttgcta caaagctgtt gagatatcaa cattaattag  14760
gagatgcctt gagccagggg aggacggctt gttcttgggt gagggatcgg gttctatgtt  14820
gatcacttat aaagagatac ttaaactaaa caagtgcttc tataatagtg gggtttccgc  14880
caattctaga tctggtcaaa gggaattagc accctatccc tccgaagttg gccttgtcga  14940
acacagaatg ggagtaggta atattgtcaa agtgctcttt aacgggaggc ccgaagtcac  15000
gtgggtaggc agtgtagatt gcttcaattt catagttagt aatatcccta cctctagtgt  15060
ggggtttatc cattcagata tagagacctt gcctgacaaa gatactatag agaagctaga  15120
ggaattggca gccatcttat cgatggctct gctcctgggc aaaataggat caatactggt  15180
gattaagctt atgcctttca gcggggattt tgttcaggga tttataagtt atgtagggtc  15240
```

```
tcattataga gaagtgaacc ttgtataccc tagatacagc aacttcatct ctactgaatc  15300
ttatttggtt atgacagatc tcaaggctaa ccggctaatg aatcctgaaa agattaagca  15360
gcagataatt gaatcatctg tgaggacttc acctggactt ataggtcaca tcctatccat  15420
taagcaacta agctgcatac aagcaattgt gggagacgca gttagtagag gtgatatcaa  15480
tcctactctg aaaaaactta cacctataga gcaggtgctg atcaattgcg ggttggcaat  15540
taacggacct aagctgtgca aagaattgat ccaccatgat gttgcctcag ggcaagatgg  15600
attgcttaat tctatactca tcctctacag ggagttggca agattcaaag acaaccaaag  15660
aagtcaacaa gggatgttcc acgcttaccc cgtattggta agtagcaggc aacgagaact  15720
tatatctagg atcacccgca aattctgggg gcacattctt ctttactccg ggaacaaaaa  15780
gttgataaat aagtttatcc agaatctcaa gtccggctat ctgatactag acttacacca  15840
gaatatcttc gttaagaatc tatccaagtc agagaaacag attattatga cgggggggttt  15900
gaaacgtgag tgggttttta aggtaacagt caaggagacc aaagaatggt ataagttagt  15960
cggatacagt gccctgatta aggactaatt ggttgaactc cggaacccta atcctgccct  16020
aggtggttag gcattatttg caatatatta aagaaaactt tgaaaatacg aagtttctat  16080
tcccagcttt gtctggtggc cggcatggtc ccagcctcct cgctggcgcc ggctgggcaa  16140
cattccgagg ggaccgtccc ctcggtaatg gcgaatggga cgcggccgat ccggctgcta  16200
acaaagcccg aaaggaagct gagttggctg ctgccaccgc tgagcaataa ctagcataac  16260
cccttggggc ctctaaacgg gtcttgaggg gttttttgct gaaaggagga actatatccg  16320
gatgcggccg cgggccctat ggtacccagc ttttgttccc tttagtgagg gttaattccg  16380
agcttggcgt aatcatggtc atagctgttt cctgtgtgaa attgttatcc gctcacaatt  16440
ccacacaaca taggagccgg aagcataaag tgtaaagcct ggggtgccta atgagtgagg  16500
taactcacat taattgcgtt gcgctcactg cccgctttcc agtcgggaaa cctgtcgtgc  16560
cagctgcatt aatgaatcgg ccaacgcgcg gggagaggcg gtttgcgtat tgggcgctct  16620
tccgcttcct cgctcactga ctcgctgcgc tcggtcgttc ggctgcggcg agcggtatca  16680
gctcactcaa aggcggtaat acggttatcc acagaatcag gggataacgc aggaaagaac  16740
atgtgagcaa aaggccagca aaaggccagg aaccgtaaaa aggccgcgtt gctggcgttt  16800
ttccataggc tcggcccccc tgacgagcat cacaaaaatc gacgctcaag tcagaggtgg  16860
cgaaacccga caggactata aagataccag gcgtttcccc ctggaagctc cctcgtgcgc  16920
tctcctgttc cgaccctgcc gcttaccgga tacctgtccg cctttctccc ttcgggaagc  16980
gtggcgcttt ctcaatgctc acgctgtagg tatctcagtt cggtgtaggt cgttcgctcc  17040
aagctgggct gtgtgcacga accccccgtt cagcccgacc gctgcgcctt atccggtaac  17100
tatcgtcttg agtccaaccc ggtaagacac gacttatcgc cactggcagc agccactggt  17160
aacaggatta gcagagcgag gtatgtaggc ggtgctacag agttcttgaa gtggtggcct  17220
aactacggct acactagaag gacagtattt ggtatctgcg ctctgctgaa gccagttacc  17280
ttcggaaaaa gagttggtag ctcttgatcc ggcaaacaaa ccaccgctgg tagcggtggt  17340
ttttttgttt gcaagcagca gattacgcgc agaaaaaaag gatctcaaga agatcctttg  17400
atcttttcta cggggtctga cgctcagtgg aacgaaaact cacgttaagg gattttggtc  17460
atgagattat caaaaaggat cttcacctag atcctttttaa attaaaaatg aagttttaaa  17520
tcaatctaaa gtatatatga gtaaacttgg tctgacagtt accaatgctt aatcagtgag  17580
gcacctatct cagcgatctg tctatttcgt tcatccatag ttgcctgact gcccgtcgtg  17640
```

tagataacta cgatacggga gggcttacca tctggcccca gtgctgcaat gataccgcga 17700
gacccacgct caccggctcc agatttatca gcaataaacc agccagccgg aagggccgag 17760
cgcagaagtg gtcctgcaac tttatccgcc tccatccagt ctattaattg ttgccgggaa 17820
gctagagtaa gtagttcgcc agttaatagt ttgcgcaacg ttgttgccat tgctacaggc 17880
atcgtggtgt cacgctcgtc gtttggtatg gcttcattca gctccggttc ccaacgatca 17940
aggcgagtta catgatcccc catgttgtga aaaaaagcgg ttagctcctt cggtcctccg 18000
atcgttgtca gaagtaagtt ggccgcagtg ttatcactca tgcttatggc agcactgcat 18060
aattctctta ctgtcatgcc atccgtaaga tgcttttctg tgactggtga gtactcaacc 18120
aagtcattct gagaatagtg tatgcggcga ccgagttgct cttgcccggc gtcaatacgg 18180
gataataccg cgccacatag cagaacttta aaagtgctca tcattggaaa acgttcttcg 18240
gggcgaaaac tctcaaggat cttaccgctg ttgagatcca gttcgatgta acccactcgt 18300
gcacccaact gatcttcagc atcttttact ttcaccagcg tttctgggtg agcaaaaaca 18360
ggaaggcaaa atgccgcaaa aaagggaata agggcgacac ggaaatgttg aatactcata 18420
ctcttccttt ttcaatatta ttgaagcatt tatcagggtt attgtctcat gagcggatac 18480
atatttgaat gtatttagaa aaataaacaa ataggggttc cgcgcacatt tccccgaaaa 18540
gtgccacctg aaattgtaaa cgttaatatt ttgttaaaat tcgcgttaaa tttttgttaa 18600
atcagctcat tttttaacca ataggccgaa atcggcaaaa tcccttataa atcaaaagaa 18660
tagaccgaga tagggttgag tgttgttcca gtttggaaca agagtccact attaaagaac 18720
gtggactcca acgtcaaagg gcgaaaaacc gtctatcagg gcgatggccc actacgtgaa 18780
ccatcaccct aatcaagttt tttggggtcg aggtgccgta aagcactaaa tcggaaccct 18840
aaagggagcc cccgatttag agcttgacgg ggaaagccgg cgaacgtggc gagaaaggaa 18900
gggaagaaag cgaaaggagc gggcgctagg gcgctggcaa gtgtagcggt cacgctgcgc 18960
gtaaccacca cacccgccgc gcttaatgcg ccgctacagg gcgcgtccca ttcgccattc 19020
aggctgcgca actgttggga agggcgatcg gtgcgggcct cttcgctatt acgccagcca 19080
ccgcggtgat ccttataaag ctagatg 19107

<210> SEQ ID NO 5
<211> LENGTH: 20896
<212> TYPE: DNA
<213> ORGANISM: artificial sequence
<220> FEATURE:
<223> OTHER INFORMATION: MV Zika sE codon optimization (human)

<400> SEQUENCE: 5
tcatgaacgc ggccgctaat acgactcact atagggccaa ctttgtttgg tctgatgagt 60
ccgtgaggac gaaacccgga gtcccgggtc accaaacaaa gttgggtaag gatagttcaa 120
tcaatgatca tcttctagtg cacttaggat tcaagatcct attatcaggg acaagagcag 180
gattagggat atccgagatg gccacacttt taaggagctt agcattgttc aaaagaaaca 240
aggacaaacc acccattaca tcaggatccg gtggagccat cagaggaatc aaacacatta 300
ttatagtacc aatccctgga gattcctcaa ttaccactcg atccagactt ctggaccggt 360
tggtgaggtt aattggaaac ccggatgtga gcgggcccaa actaacaggg gcactaatag 420
gtatattatc cttatttgtg gagtctccag gtcaattgat tcagaggatc accgatgacc 480
ctgacgttag cataaggctg ttagaggttg tccagagtga ccagtcacaa tctggcctta 540

```
ccttcgcatc aagaggtacc aacatggagg atgaggcgga ccaatacttt tcacatgatg    600
atccaattag tagtgatcaa tccaggttcg gatggttcgg gaacaaggaa atctcagata    660
ttgaagtgca agaccctgag ggattcaaca tgattctggg taccatccta gcccaaattt    720
gggtcttgct cgcaaaggcg gttacggccc cagacacggc agctgattcg gagctaagaa    780
ggtggataaa gtacacccaa caaagaaggg tagttggtga atttagattg gagagaaaat    840
ggttggatgt ggtgaggaac aggattgccg aggacctctc cttacgccga ttcatggtcg    900
ctctaatcct ggatatcaag agaacacccg gaaacaaacc caggattgct gaaatgatat    960
gtgacattga tacatatatc gtagaggcag gattagccag ttttatcctg actattaagt   1020
ttgggataga aactatgtat cctgctcttg gactgcatga atttgctggt gagttatcca   1080
cacttgagtc cttgatgaac ctttaccagc aaatggggga aactgcaccc tacatggtaa   1140
tcctggagaa ctcaattcag aacaagttca gtgcaggatc ataccctctg ctctggagct   1200
atgccatggg agtaggagtg gaacttgaaa actccatggg aggtttgaac tttggccgat   1260
cttactttga tccagcatat tttagattag ggcaagagat ggtaaggagg tcagctggaa   1320
aggtcagttc cacattggca tctgaactcg gtatcactgc cgaggatgca aggcttgttt   1380
cagagattgc aatgcatact actgaggaca agatcagtag agcggttgga cccagacaag   1440
cccaagtatc atttctacac ggtgatcaaa gtgagaatga gctaccgaga ttgggggggca   1500
aggaagatag gagggtcaaa cagagtcgag gagaagccag ggagagctac agagaaaccg   1560
ggcccagcag agcaagtgat gcgagagctg cccatcttcc aaccggcaca ccccctagaca   1620
ttgacactgc aacggagtcc agccaagatc cgcaggacag tcgaaggtca gctgacgccc   1680
tgcttaggct gcaagccatg gcaggaatct cggaagaaca aggctcagac acggacaccc   1740
ctatagtgta caatgacaga aatcttctag actaggtgcg agaggccgag ggccagaaca   1800
acatccgcct accatccatc attgttataa aaaacttagg aaccaggtcc acacagccgc   1860
cagcccatca accatccact cccacgattg gagccaatgg cagaagagca ggcacgccat   1920
gtcaaaaacg gactggaatg catccgggct ctcaaggccg agcccatcgg ctcactggcc   1980
atcgaggaag ctatggcagc atggtcagaa atatcagaca acccaggaca ggagcgagcc   2040
acctgcaggg aagagaaggc aggcagttcg ggtctcagca aaccatgcct ctcagcaatt   2100
ggatcaactg aaggcggtgc acctcgcatc cgcggtcagg gacctggaga gagcgatgac   2160
gacgctgaaa ctttgggaat ccccccaaga aatctccagg catcaagcac tgggttacag   2220
tgttattacg tttatgatca cagcggtgaa gcggttaagg gaatccaaga tgctgactct   2280
atcatggttc aatcaggcct tgatggtgat agcaccctct caggaggaga caatgaatct   2340
gaaaacagcg atgtggatat tggcgaacct gataccgagg gatatgctat cactgaccgg   2400
ggatctgctc ccatctctat ggggttcagg gcttctgatg ttgaaactgc agaaggaggg   2460
gagatccacg agctcctgag actccaatcc agaggcaaca actttccgaa gcttgggaaa   2520
actctcaatg ttcctccgcc cccggacccc ggtagggcca gcacttccgg gacacccatt   2580
aaaaagggca cagacgcgag attagcctca tttggaacgg agatcgcgtc tttattgaca   2640
ggtggtgcaa cccaatgtgc tcgaaagtca ccctcggaac catcagggcc aggtgcacct   2700
gcggggaatg tccccgagtg tgtgagcaat gccgcactga tacaggagtg gacacccgaa   2760
tctggtacca caatctcccc gagatcccag aataatgaag aagggggaga ctattatgat   2820
gatgagctgt tctctgatgt ccaagatatt aaaacagcct tggccaaaat acacgaggat   2880
aatcagaaga taatctccaa gctagaatca ctgctgttat tgaagggaga agttgagtca   2940
```

```
attaagaagc agatcaacag gcaaaatatc agcatatcca ccctggaagg acacctctca   3000
agcatcatga tcgccattcc tggacttggg aaggatccca acgaccccac tgcagatgtc   3060
gaaatcaatc ccgacttgaa acccatcata ggcagagatt caggccgagc actggccgaa   3120
gttctcaaga aacccgttgc cagccgacaa ctccaaggaa tgacaaatgg acggaccagt   3180
tccagaggac agctgctgaa ggaatttcag ctaaagccga tcgggaaaaa gatgagctca   3240
gccgtcgggt ttgttcctga caccggccct gcatcacgca gtgtaatccg ctccattata   3300
aaatccagcc ggctagagga ggatcggaag cgttacctga tgactctcct tgatgatatc   3360
aaaggagcca atgatcttgc caagttccac cagatgctga tgaagataat aatgaagtag   3420
ctacagctca acttacctgc caaccccatg ccagtcgacc caactagcct accctccatc   3480
attgttataa aaaacttagg aaccaggtcc acacagccgc cagcccatca acgcgtacgg   3540
ccaccatggc acgcagagga gcggatacgt cagttggcat tgtgggcttg ctcctcacca   3600
ccgctatggc cgcagaagtt acaagaagag ggtctgccta ctacatgtat ctggacagga   3660
acgatgctgg cgaagccatc tcctttccca caaccctggg gatgaacaag tgctacattc   3720
agatcatgga tcttggtcac atgtgcgatg ccacaatgtc ctatgagtgt cccatgctcg   3780
atgagggcgt cgagcctgac gacgttgatt gctggtgtaa caccaccagc acctgggtgg   3840
tctatggcac ttgccatcac aagaagggtg aagcacggag gtcacgacgg gcagtgacat   3900
tgccaagtca tagcactagg aaactgcaga ctcgctccca gacctggctt gaatcccgag   3960
agtacacgaa acacctcatt cgtgtggaga actggatctt ccggaatccc gggtttgccc   4020
tggctgctgc cgctattgcc tggttgctcg gctctagcac atcacagaaa gtcatctacc   4080
tggtgatgat cttgctcatt gctccagcct actctatcag atgcatcgga gtttccaatc   4140
gtgactttgt cgaagggatg tccggaggca cctgggttga cgtggtgctt gagcatggtg   4200
gctgcgtaac ggtaatggct caggacaaac ccacggttga catagaactg gtgaccacga   4260
ctgtcagtaa tatggccgaa gtgcgaagct actgctatga ggcctctatc tctgacatgg   4320
catcagacag ccggtgtcca actcaaggcg aagcttatct ggacaagcaa tccgatacac   4380
agtacgtgtg caagcggact ctcgtggata gaggttgggg caatgggtgt ggtctgtttg   4440
ggaaaggcag tctggtaaca tgcgcaaagt tcgcatgttc caagaaaatg acaggaaaga   4500
gcattcagcc ggaaaatctg gagtatagga ttatgctcag cgtgcatggg agccagcaca   4560
gtggcatgat tgtcaatgat acaggccacg aaaccgacga gaacagagcg aaggttgaga   4620
tcactcccaa ttcacctcgc gcagaggcca ctctgggagg gtttggaagt ctcggtctgg   4680
actgtgaacc tcgcactggc ctggacttca gcgatctgta ttacctgacg atgaacaaca   4740
agcattggct ggtccataag gagtggttcc atgatattcc gcttccttgg catgccggag   4800
ccgataccgg aacaccccac tggaacaaca aagaggcttt ggtggagttc aaagatgcac   4860
acgctaagcg ccaaaccgtc gtggtcctgg gtagccaaga aggagcggtt cacactgcgc   4920
ttgccggagc cctggaggcg gaaatggatg gggccaaagg gcgcctttcc agtggacacc   4980
tgaagtgtcg gctgaaaatg gacaagctga gactgaaagg tgtgtcttac agcctgtgca   5040
ccgcagcctt cactttcacc aaaatccctg ctgaaacctt gcacggaaca gtgacagtag   5100
aggtgcagta tgcaggcaca gatggcccat gtaaggtgcc agctcagatg gcagtggaca   5160
tgcagaccct gactccagtg ggaaggctca taactgccaa tccggtcatc acagagtcta   5220
ccgagaactc aaagatgatg ctggagctgg accctccctt tggggactct tacatagtca   5280
```

-continued

```
taggggtagg cgagaagaaa atcacccatc actggcacag gagctaatga taagcgcgca   5340
gcgcttagac gtctcgcgat cgatactagt acaacctaaa tccattataa aaaacttagg   5400
agcaaagtga ttgcctccca aggtccacaa tgacagagac ctacgacttc gacaagtcgg   5460
catgggacat caaagggtcg atcgctccga tacaacccac cacctacagt gatggcaggc   5520
tggtgcccca ggtcagagtc atagatcctg gtctaggcga caggaaggat gaatgcttta   5580
tgtacatgtt tctgctgggg gttgttgagg acagcgattc cctagggcct ccaatcgggc   5640
gagcatttgg gttcctgccc ttaggtgttg gcagatccac agcaaagccc gaaaaactcc   5700
tcaaagaggc cactgagctt gacatagttg ttagacgtac agcagggctc aatgaaaaac   5760
tggtgttcta caacaacacc ccactaactc tcctcacacc ttggagaaag gtcctaacaa   5820
cagggagtgt cttcaacgca aaccaagtgt gcaatgcggt taatctgata ccgctcgata   5880
ccccgcagag gttccgtgtt gtttatatga gcatcacccg tctttcggat aacgggtatt   5940
acaccgttcc tagaagaatg ctggaattca gatcggtcaa tgcagtggcc ttcaacctgc   6000
tggtgaccct taggattgac aaggcgatag gccctgggaa gatcatcgac aatacagagc   6060
aacttcctga ggcaacattt atggtccaca tcgggaactt caggagaaag aagagtgaag   6120
tctactctgc cgattattgc aaaatgaaaa tcgaaaagat gggcctggtt tttgcacttg   6180
gtgggatagg gggcaccagt cttcacatta gaagcacagg caaaatgagc aagactctcc   6240
atgcacaact cgggttcaag aagaccttat gttacccgct gatggatatc aatgaagacc   6300
ttaatcgatt actctggagg agcagatgca agatagtaag aatccaggca gttttgcagc   6360
catcagttcc tcaagaattc cgcatttacg acgacgtgat cataaatgat gaccaaggac   6420
tattcaaagt tctgtagacc gtagtgccca gcaatgcccg aaaacgaccc ccctcacaat   6480
gacagccaga aggcccggac aaaaaagccc cctccgaaag actccacgga ccaagcgaga   6540
ggccagccag cagccgacgg caagcgcgaa caccaggcgg ccccagcaca gaacagccct   6600
gacacaaggc caccaccagc caccccaatc tgcatcctcc tcgtgggacc cccgaggacc   6660
aacccccaag gctgcccccg atccaaacca ccaaccgcat ccccaccacc cccgggaaag   6720
aaacccccag caattggaag gcccctcccc ctcttcctca acacaagaac tccacaaccg   6780
aaccgcacaa gcgaccgagg tgacccaacc gcaggcatcc gactccctag acagatcctc   6840
tctccccggc aaactaaaca aaacttaggg ccaaggaaca tacacaccca acagaaccca   6900
gaccccggcc cacggcgccg cgcccccaac ccccgacaac cagagggagc cccccaaccaa   6960
tcccgccggc tcccccggtg cccacaggca gggacaccaa cccccgaaca gacccagcac   7020
ccaaccatcg acaatccaag acggggggc cccccaaaa aaaggccccc aggggccgac   7080
agccagcacc gcgaggaagc ccacccaccc cacacacgac cacggcaacc aaaccagaac   7140
ccagaccacc ctgggccacc agctcccaga ctcggccatc accccgcaga aaggaaaggc   7200
cacaacccgc gcaccccagc cccgatccgg cggggagcca cccaacccga accagcaccc   7260
aagagcgatc cccgaaggac ccccgaaccg caaaggacat cagtatccca cagcctctcc   7320
aagtcccccg gtctcctcct cttctcgaag ggaccaaaag atcaatccac cacacccgac   7380
gacactcaac tccccacccc taaaggagac accgggaatc ccagaatcaa gactcatcca   7440
atgtccatca tgggtctcaa ggtgaacgtc tctgccatat tcatggcagt actgttaact   7500
ctccaaacac ccaccggtca aatccattgg ggcaatctct ctaagatagg ggtggtagga   7560
ataggaagtg caagctacaa agttatgact cgttccagcc atcaatcatt agtcataaaa   7620
ttaatgccca atataactct cctcaataac tgcacgaggg tagagattgc agaatacagg   7680
```

```
agactactga gaacagtttt ggaaccaatt agagatgcac ttaatgcaat gacccagaat   7740
ataagaccgg ttcagagtgt agcttcaagt aggagacaca agagatttgc gggagtagtc   7800
ctggcaggtg cggccctagg cgttgccaca gctgctcaga taacagccgg cattgcactt   7860
caccagtcca tgctgaactc tcaagccatc gacaatctga gagcgagcct ggaaactact   7920
aatcaggcaa ttgagacaat cagacaagca gggcaggaga tgatattggc tgttcagggt   7980
gtccaagact acatcaataa tgagctgata ccgtctatga accaactatc ttgtgattta   8040
atcggccaga agctcgggct caaattgctc agatactata cagaaatcct gtcattattt   8100
ggccccagtt tacgggaccc catatctgcg gagatatcta tccaggcttt gagctatgcg   8160
cttggaggag acatcaataa ggtgttagaa aagctcggat acagtggagg tgatttactg   8220
ggcatcttag agagcggagg aataaaggcc cggataactc acgtcgacac agagtcctac   8280
ttcattgtcc tcagtatagc ctatccgacg ctgtccgaga ttaagggggt gattgtccac   8340
cggctagagg gggtctcgta caacataggc tctcaagagt ggtataccac tgtgcccaag   8400
tatgttgcaa cccaagggta ccttatctcg aattttgatg agtcatcgtg tactttcatg   8460
ccagagggga ctgtgtgcag ccaaaatgcc ttgtacccga tgagtcctct gctccaagaa   8520
tgcctccggg ggtacaccaa gtcctgtgct cgtacactcg tatccgggtc ttttgggaac   8580
cggttcattt tatcacaagg gaacctaata gccaattgtg catcaatcct ttgcaagtgt   8640
tacacaacag gaacgatcat taatcaagac cctgacaaga tcctaacata cattgctgcc   8700
gatcactgcc cggtagtcga ggtgaacggc gtgaccatcc aagtcgggag caggaggtat   8760
ccagacgctg tgtacttgca cagaattgac ctcggtcctc ccatatcatt ggagaggttg   8820
gacgtaggga caaatctggg gaatgcaatt gctaagttgg aggatgccaa ggaattgttg   8880
gagtcatcgg accagatatt gaggagtatg aaaggtttat cgagcactag catagtctac   8940
atcctgattg cagtgtgtct tggagggttg atagggatcc ccgctttaat atgttgctgc   9000
agggggcgtt gtaacaaaaa gggagaacaa gttggtatgt caagaccagg cctaaagcct   9060
gatcttacgg gaacatcaaa atcctatgta aggtcgctct gatcctctac aactcttgaa   9120
acacaaatgt cccacaagtc tcctcttcgt catcaagcaa ccaccgcacc cagcatcaag   9180
cccacctgaa attatctccg gcttccctct ggccgaacaa tatcggtagt taatcaaaac   9240
ttagggtgca agatcatcca caatgtcacc acaacgagac cggataaatg ccttctacaa   9300
agataacccc catcccaagg gaagtaggat agtcattaac agagaacatc ttatgattga   9360
tagaccttat gttttgctgg ctgttctgtt tgtcatgttt ctgagcttga tcgggttgct   9420
agccattgca ggcattagac ttcatcgggc agccatctac accgcagaga tccataaaag   9480
cctcagcacc aatctagatg taactaactc aatcgagcat caggtcaagg acgtgctgac   9540
accactcttc aaaatcatcg gtgatgaagt gggcctgagg acacctcaga gattcactga   9600
cctagtgaaa ttaatctctg acaagattaa attccttaat ccggataggg agtacgactt   9660
cagagatctc acttggtgta tcaacccgcc agagagaatc aaattggatt atgatcaata   9720
ctgtgcagat gtggctgctg aagagctcat gaatgcattg gtgaactcaa ctctactgga   9780
gaccagaaca accaatcagt tcctagctgt ctcaaaggga aactgctcag ggcccactac   9840
aatcagaggt caattctcaa acatgtcgct gtccctgtta gacttgtatt taggtcgagg   9900
ttacaatgtg tcatctatag tcactatgac atcccaggga atgtatgggg gaacttacct   9960
agtggaaaag cctaatctga gcagcaaaag gtcagagttg tcacaactga gcatgtaccg  10020
```

-continued

```
agtgtttgaa gtaggtgtta tcagaaatcc gggtttgggg gctccggtgt tccatatgac  10080
aaactatctt gagcaaccag tcagtaatga tctcagcaac tgtatggtgg ctttgggggga  10140
gctcaaactc gcagcccttt gtcacgggga agattctatc acaattccct atcagggatc  10200
agggaaaggt gtcagcttcc agctcgtcaa gctaggtgtc tggaaatccc caaccgacat  10260
gcaatcctgg gtccccttat caacggatga tccagtgata gacaggcttt acctctcatc  10320
tcacagaggt gttatcgctg acaatcaagc aaaatgggct gtcccgacaa cacgaacaga  10380
tgacaagttg cgaatggaga catgcttcca acaggcgtgt aagggtaaaa tccaagcact  10440
ctgcgagaat cccgagtggg caccattgaa ggataacagg attccttcat acggggtctt  10500
gtctgttgat ctgagtctga cagttgagct taaaatcaaa attgcttcgg gattcgggcc  10560
attgatcaca cacggttcag ggatggacct atacaaatcc aaccacaaca atgtgtattg  10620
gctgactatc ccgccaatga agaacctagc cttaggtgta atcaacacat tggagtggat  10680
accgagattc aaggttagtc cctacctctt cactgtccca attaaggaag caggcgaaga  10740
ctgccatgcc ccaacatacc tacctgcgga ggtggatggt gatgtcaaac tcagttccaa  10800
tctggtgatt ctacctggtc aagatctcca atatgttttg gcaacctacg atacttccag  10860
ggttgaacat gctgtggttt attacgttta cagcccaagc cgctcatttt cttactttta  10920
tccttttagg ttgcctataa agggggtccc catcgaatta caagtggaat gcttcacatg  10980
ggaccaaaaa ctctggtgcc gtcacttctg tgtgcttgcg gactcagaat ctggtggaca  11040
tatcactcac tctgggatgg tgggcatggg agtcagctgc acagtcaccc gggaagatgg  11100
aaccaatcgc agatagggct gctagtgaac caatcacatg atgtcaccca gacatcaggc  11160
atacccacta gtgtgaaata gacatcagaa ttaagaaaaa cgtagggtcc aagtggttcc  11220
ccgttatgga ctcgctatct gtcaaccaga tcttataccc tgaagttcac ctagatagcc  11280
cgatagttac caataagata gtagccatcc tggagtatgc tcgagtccct cacgcttaca  11340
gcctggagga ccctacactg tgtcagaaca tcaagcaccg cctaaaaaac ggattttcca  11400
accaaatgat tataaacaat gtggaagttg ggaatgtcat caagtccaag cttaggagtt  11460
atccggccca ctctcatatt ccatatccaa attgtaatca ggatttattt aacatagaag  11520
acaaagagtc aacgaggaag atccgtgaac tcctcaaaaa ggggaattcg ctgtactcca  11580
aagtcagtga taaggttttc caatgcttaa gggacactaa ctcacggctt ggcctaggct  11640
ccgaattgag ggaggacatc aaggagaaag ttattaactt gggagtttac atgcacagct  11700
cccagtggtt tgagcccttt ctgttttggt ttacagtcaa gactgagatg aggtcagtga  11760
ttaaatcaca aacccatact tgccatagga ggagacacac acctgtattc ttcactggta  11820
gttcagttga gttgctaatc tctcgtgacc ttgttgctat aatcagtaaa gagtctcaac  11880
atgtatatta cctgacattt gaactggttt tgatgtattg tgatgtcata gaggggaggt  11940
taatgacaga gaccgctatg actattgatg ctaggtatac agagcttcta ggaagagtca  12000
gatacatgtg gaaactgata gatggtttct tccctgcact cgggaatcca acttatcaaa  12060
ttgtagccat gctggagcct ctttcacttg cttacctgca gctgagggat ataacagtag  12120
aactcagagg tgctttcctt aaccactgct ttactgaaat acatgatgtt cttgaccaaa  12180
acgggttttc tgatgaaggt acttatcatg agttaactga agctctagat tacattttca  12240
taactgatga catacatctg acaggggaga ttttctcatt tttcagaagt ttcggccacc  12300
ccagacttga agcagtaacg gctgctgaaa atgttaggaa atacatgaat cagcctaaag  12360
tcattgtgta tgagactctg atgaaaggtc atgccatatt ttgtggaatc ataatcaacg  12420
```

```
gctatcgtga caggcacgga ggcagttggc caccgctgac cctccccctg catgctgcag  12480
acacaatccg gaatgctcaa gcttcaggtg aagggttaac acatgagcag tgcgttgata  12540
actggaaatc ttttgctgga gtgaaatttg gctgctttat gcctcttagc ctggatagtg  12600
atctgacaat gtacctaaag gacaaggcac ttgctgctct ccaaagggaa tgggattcag  12660
tttacccgaa agagttcctg cgttacgacc ctcccaaggg aaccgggtca cggaggcttg  12720
tagatgtttt ccttaatgat tcgagctttg acccatatga tgtgataatg tatgttgtaa  12780
gtggagctta cctccatgac cctgagttca acctgtctta cagcctgaaa gaaaaggaga  12840
tcaaggaaac aggtagactt tttgctaaaa tgacttacaa aatgagggca tgccaagtga  12900
ttgctgaaaa tctaatctca aacgggattg gcaaatattt taaggacaat gggatggcca  12960
aggatgagca cgatttgact aaggcactcc acactctagc tgtctcagga gtccccaaag  13020
atctcaaaga aagtcacagg ggggggccag tcttaaaaac ctactcccga agcccagtcc  13080
acacaagtac caggaacgtg agagcagcaa aagggtttat agggttccct caagtaattc  13140
ggcaggacca agacactgat catccggaga atatggaagc ttacgagaca gtcagtgcat  13200
ttatcacgac tgatctcaag aagtactgcc ttaattggag atatgagacc atcagcttgt  13260
ttgcacagag gctaaatgag atttacggat tgccctcatt tttccagtgg ctgcataaga  13320
ggcttgagac ctctgtcctg tatgtaagtg accctcattg cccccccgac cttgacgccc  13380
atatcccgtt atataaagtc cccaatgatc aaatcttcat taagtaccct atgggaggta  13440
tagaagggta ttgtcagaag ctgtggacca tcagcaccat tccctatcta tacctggctg  13500
cttatgagag cggagtaagg attgcttcgt tagtgcaagg ggacaatcag accatagccg  13560
taacaaaaag ggtacccagc acatggccct acaaccttaa gaaacgggaa gctgctagag  13620
taactagaga ttactttgta attcttaggc aaaggctaca tgatattggc catcacctca  13680
aggcaaatga gacaattgtt tcatcacatt tttttgtcta ttcaaaagga atatattatg  13740
atgggctact tgtgtcccaa tcactcaaga gcatcgcaag atgtgtattc tggtcagaga  13800
ctatagttga tgaaacaagg gcagcatgca gtaatattgc tacaacaatg gctaaaagca  13860
tcgagagagg ttatgaccgt taccttgcat attccctgaa cgtcctaaaa gtgatacagc  13920
aaattctgat ctctcttggc ttcacaatca attcaaccat gacccgggat gtagtcatac  13980
ccctcctcac aaacaacgac ctcttaataa ggatggcact gttgcccgct cctattgggg  14040
ggatgaatta tctgaatatg agcaggctgt ttgtcagaaa catcggtgat ccagtaacat  14100
catcaattgc tgatctcaag agaatgattc tcgcctcact aatgcctgaa gagaccctcc  14160
atcaagtaat gacacaacaa ccgggggact cttcattcct agactgggct agcgaccctt  14220
actcagcaaa tcttgtatgt gtccagagca tcactagact cctcaagaac ataactgcaa  14280
ggtttgtcct gatccatagt ccaaacccaa tgttaaaagg attattccat gatgacagta  14340
aagaagagga cgagggactg gcggcattcc tcatggacag gcatattata gtacctaggg  14400
cagctcatga aatcctggat catagtgtca caggggcaag agagtctatt gcaggcatgc  14460
tggataccac aaaaggcttg attcgagcca gcatgaggaa ggggggggtta acctctcgag  14520
tgataaccag attgtccaat tatgactatg aacaattcag agcagggatg gtgctattga  14580
caggaagaaa gagaaatgtc ctcattgaca aagagtcatg ttcagtgcag ctggcgagag  14640
ctctaagaag ccatatgtgg gcgaggctag ctcgaggacg gcctatttac ggccttgagg  14700
tccctgatgt actagaatct atgcgaggcc accttattcg gcgtcatgag acatgtgtca  14760
```

```
tctgcgagtg tggatcagtc aactacggat ggttttttgt cccctcgggt tgccaactgg  14820

atgatattga caaggaaaca tcatccttga gagtcccata tattggttct accactgatg  14880

agagaacaga catgaagctt gccttcgtaa gagccccaag tcgatccttg cgatctgctg  14940

ttagaatagc aacagtgtac tcatgggctt acggtgatga tgatagctct tggaacgaag  15000

cctggttgtt ggctaggcaa agggccaatg tgagcctgga ggagctaagg gtgatcactc  15060

ccatctcaac ttcgactaat ttagcgcata ggttgaggga tcgtagcact caagtgaaat  15120

actcaggtac atcccttgtc cgagtggcga ggtataccac aatctccaac gacaatctct  15180

catttgtcat atcagataag aaggttgata ctaactttat ataccaacaa ggaatgcttc  15240

tagggttggg tgttttagaa acattgtttc gactcgagaa agataccgga tcatctaaca  15300

cggtattaca tcttcacgtc gaaacagatt gttgcgtgat cccgatgata gatcatccca  15360

ggatacccag ctcccgcaag ctagagctga gggcagagct atgtaccaac ccattgatat  15420

atgataatgc acctttaatt gacagagatg caacaaggct atacacccag agccatagga  15480

ggcaccttgt ggaatttgtt acatggtcca caccccaact atatcacatt ttagctaagt  15540

ccacagcact atctatgatt gacctggtaa caaaatttga gaaggaccat atgaatgaaa  15600

tttcagctct catagggat gacgatatca atagtttcat aactgagttt ctgctcatag  15660

agccaagatt attcactatc tacttgggcc agtgtgcggc catcaattgg gcatttgatg  15720

tacattatca tagaccatca gggaaatatc agatgggtga gctgttgtca tcgttccttt  15780

ctagaatgag caaaggagtg tttaaggtgc ttgtcaatgc tctaagccac ccaaagatct  15840

acaagaaatt ctggcattgt ggtattatag agcctatcca tggtccttca cttgatgctc  15900

aaaacttgca cacaactgtg tgcaacatgg tttacacatg ctatatgacc tacctcgacc  15960

tgttgttgaa tgaagagtta gaagagttca catttctctt gtgtgaaagc gacgaggatg  16020

tagtaccgga cagattcgac aacatccagg caaaacactt atgtgttctg gcagatttgt  16080

actgtcaacc agggacctgc ccaccaattc gaggtctaag accggtagag aaatgtgcag  16140

ttctaaccga ccatatcaag gcagaggcta tgttatctcc agcaggatct tcgtggaaca  16200

taaatccaat tattgtagac cattactcat gctctctgac ttatctccgg cgaggatcga  16260

tcaaacagat aagattgaga gttgatccag gattcatttt cgacgccctc gctgaggtaa  16320

atgtcagtca gccaaagatc ggcagcaaca acatctcaaa tatgagcatc aaggctttca  16380

gacccccaca cgatgatgtt gcaaaattgc tcaaagatat caacacaagc aagcacaatc  16440

ttcccatttc agggggcaat ctcgccaatt atgaaatcca tgctttccgc agaatcgggt  16500

tgaactcatc tgcttgctac aaagctgttg agatatcaac attaattagg agatgccttg  16560

agccagggga ggacggcttg ttcttgggtg agggatcggg ttctatgttg atcacttata  16620

aagagatact taaactaaac aagtgcttct ataatagtgg ggtttccgcc aattctagat  16680

ctggtcaaag ggaattagca ccctatccct ccgaagttgg ccttgtcgaa cacagaatgg  16740

gagtaggtaa tattgtcaaa gtgctcttta acgggaggcc cgaagtcacg tgggtaggca  16800

gtgtagattg cttcaatttc atagttagta atatccctac ctctagtgtg gggtttatcc  16860

attcagatat agagaccttg cctgacaaag atactataga gaagctagag gaattggcag  16920

ccatcttatc gatggctctg ctcctgggca aaataggatc aatactggtg attaagctta  16980

tgcctttcag cggggatttt gttcagggat ttataagtta tgtagggtct cattatagag  17040

aagtgaacct tgtataccct agatacagca acttcatctc tactgaatct tatttggtta  17100

tgacagatct caaggctaac cggctaatga atcctgaaaa gattaagcag cagataattg  17160
```

```
aatcatctgt gaggacttca cctggactta taggtcacat cctatccatt aagcaactaa  17220
gctgcataca agcaattgtg ggagacgcag ttagtagagg tgatatcaat cctactctga  17280
aaaaacttac acctatagag caggtgctga tcaattgcgg gttggcaatt aacggaccta  17340
agctgtgcaa agaattgatc caccatgatg ttgcctcagg gcaagatgga ttgcttaatt  17400
ctatactcat cctctacagg gagttggcaa gattcaaaga caaccaaaga agtcaacaag  17460
ggatgttcca cgcttacccc gtattggtaa gtagcaggca acgagaactt atatctagga  17520
tcacccgcaa attctggggg cacattcttc tttactccgg gaacaaaaag ttgataaata  17580
agtttatcca gaatctcaag tccggctatc tgatactaga cttacaccag aatatcttcg  17640
ttaagaatct atccaagtca gagaaacaga ttattatgac gggggggtttg aaacgtgagt  17700
gggtttttaa ggtaacagtc aaggagacca aagaatggta taagttagtc ggatacagtg  17760
ccctgattaa ggactaattg gttgaactcc ggaaccctaa tcctgcccta ggtggttagg  17820
cattatttgc aatatattaa agaaaacttt gaaaatacga agtttctatt cccagctttg  17880
tctggtggcc ggcatggtcc cagcctcctc gctggcgccg gctgggcaac attccgaggg  17940
gaccgtcccc tcggtaatgg cgaatgggac gcggccgatc cggctgctaa caaagcccga  18000
aaggaagctg agttggctgc tgccaccgct gagcaataac tagcataacc ccttggggcc  18060
tctaaacggg tcttgagggg ttttttgctg aaaggaggaa ctatatccgg atgcggccgc  18120
gggccctatg gtacccagct tttgttccct ttagtgaggg ttaattccga gcttggcgta  18180
atcatggtca tagctgtttc ctgtgtgaaa ttgttatccg ctcacaattc cacacaacat  18240
aggagccgga agcataaagt gtaaagcctg gggtgcctaa tgagtgaggt aactcacatt  18300
aattgcgttg cgctcactgc ccgctttcca gtcgggaaac ctgtcgtgcc agctgcatta  18360
atgaatcggc caacgcgcgg ggagaggcgg tttgcgtatt gggcgctctt ccgcttcctc  18420
gctcactgac tcgctgcgct cggtcgttcg gctgcggcga gcggtatcag ctcactcaaa  18480
ggcggtaata cggttatcca cagaatcagg ggataacgca ggaaagaaca tgtgagcaaa  18540
aggccagcaa aaggccagga accgtaaaaa ggccgcgttg ctggcgtttt tccataggct  18600
cggccccct gacgagcatc acaaaaatcg acgctcaagt cagaggtggc gaaacccgac  18660
aggactataa agataccagg cgtttccccc tggaagctcc ctcgtgcgct ctcctgttcc  18720
gaccctgccg cttaccggat acctgtccgc ctttctccct tcgggaagcg tggcgctttc  18780
tcaatgctca cgctgtaggt atctcagttc ggtgtaggtc gttcgctcca agctgggctg  18840
tgtgcacgaa ccccccgttc agcccgaccg ctgcgcctta tccggtaact atcgtcttga  18900
gtccaacccg gtaagacacg acttatcgcc actggcagca gccactggta acaggattag  18960
cagagcgagg tatgtaggcg gtgctacaga gttcttgaag tggtggccta actacggcta  19020
cactagaagg acagtatttg gtatctgcgc tctgctgaag ccagttacct tcggaaaaag  19080
agttggtagc tcttgatccg gcaaacaaac caccgctggt agcggtggtt tttttgtttg  19140
caagcagcag attacgcgca gaaaaaaagg atctcaagaa gatcctttga tcttttctac  19200
ggggtctgac gctcagtgga acgaaaactc acgttaaggg attttggtca tgagattatc  19260
aaaaaggatc ttcacctaga tccttttaaa ttaaaaatga agttttaaat caatctaaag  19320
tatatatgag taaacttggt ctgacagtta ccaatgctta atcagtgagg cacctatctc  19380
agcgatctgt ctatttcgtt catccatagt tgcctgactg ccccgtcgtgt agataactac  19440
gatacgggag ggcttaccat ctggccccag tgctgcaatg ataccgcgag acccacgctc  19500
```

accggctcca gatttatcag caataaacca gccagccgga agggccgagc gcagaagtgg 19560
tcctgcaact ttatccgcct ccatccagtc tattaattgt tgccgggaag ctagagtaag 19620
tagttcgcca gttaatagtt tgcgcaacgt tgttgccatt gctacaggca tcgtggtgtc 19680
acgctcgtcg tttggtatgg cttcattcag ctccggttcc caacgatcaa ggcgagttac 19740
atgatccccc atgttgtgaa aaaaagcggt tagctccttc ggtcctccga tcgttgtcag 19800
aagtaagttg gccgcagtgt tatcactcat gcttatggca gcactgcata attctcttac 19860
tgtcatgcca tccgtaagat gcttttctgt gactggtgag tactcaacca agtcattctg 19920
agaatagtgt atgcggcgac cgagttgctc ttgcccggcg tcaatacggg ataataccgc 19980
gccacatagc agaactttaa aagtgctcat cattggaaaa cgttcttcgg ggcgaaaact 20040
ctcaaggatc ttaccgctgt tgagatccag ttcgatgtaa cccactcgtg cacccaactg 20100
atcttcagca tcttttactt tcaccagcgt ttctgggtga gcaaaaacag gaaggcaaaa 20160
tgccgcaaaa aagggaataa gggcgacacg gaaatgttga atactcatac tcttcctttt 20220
tcaatattat tgaagcattt atcagggtta ttgtctcatg agcggataca tatttgaatg 20280
tatttagaaa aataaacaaa taggggttcc gcgcacattt ccccgaaaag tgccacctga 20340
aattgtaaac gttaatattt tgttaaaatt cgcgttaaat ttttgttaaa tcagctcatt 20400
ttttaaccaa taggccgaaa tcggcaaaat cccttataaa tcaaaagaat agaccgagat 20460
agggttgagt gttgttccag tttggaacaa gagtccacta ttaaagaacg tggactccaa 20520
cgtcaaaggg cgaaaaaccg tctatcaggg cgatggccca ctacgtgaac catcacccta 20580
atcaagtttt ttggggtcga ggtgccgtaa agcactaaat cggaacccta aagggagccc 20640
ccgatttaga gcttgacggg gaaagccggc gaacgtggcg agaaaggaag ggaagaaagc 20700
gaaaggagcg ggcgctaggg cgctggcaag tgtagcggtc acgctgcgcg taaccaccac 20760
acccgccgcg cttaatgcgc cgctacaggg cgcgtcccat tcgccattca ggctgcgcaa 20820
ctgttgggaa gggcgatcgg tgcgggcctc ttcgctatta cgccagccac cgcggtgatc 20880
cttataaagc tagatg 20896

<210> SEQ ID NO 6
<211> LENGTH: 21196
<212> TYPE: DNA
<213> ORGANISM: artificial sequence
<220> FEATURE:
<223> OTHER INFORMATION: MV Zika RSP codon optimization (human) L107D

<400> SEQUENCE: 6
tcatgaacgc ggccgctaat acgactcact atagggccaa ctttgtttgg tctgatgagt 60
ccgtgaggac gaaacccgga gtcccgggtc accaaacaaa gttgggtaag gatagttcaa 120
tcaatgatca tcttctagtg cacttaggat tcaagatcct attatcaggg acaagagcag 180
gattagggat atccgagatg gccacacttt taaggagctt agcattgttc aaaagaaaca 240
aggacaaacc acccattaca tcaggatccg gtggagccat cagaggaatc aaacacatta 300
ttatagtacc aatccctgga gattcctcaa ttaccactcg atccagactt ctggaccggt 360
tggtgaggtt aattggaaac ccggatgtga gcgggcccaa actaacaggg gcactaatag 420
gtatattatc cttatttgtg gagtctccag gtcaattgat tcagaggatc accgatgacc 480
ctgacgttag cataaggctg ttagaggttg tccagagtga ccagtcacaa tctggcctta 540
ccttcgcatc aagaggtacc aacatggagg atgaggcgga ccaatacttt tcacatgatg 600
atccaattag tagtgatcaa tccaggttcg gatggttcgg gaacaaggaa atctcagata 660

```
ttgaagtgca agaccctgag ggattcaaca tgattctggg taccatccta gcccaaattt    720
gggtcttgct cgcaaaggcg gttacggccc cagacacggc agctgattcg gagctaagaa    780
ggtggataaa gtacacccaa caaagaaggg tagttggtga atttagattg gagagaaaat    840
ggttggatgt ggtgaggaac aggattgccg aggacctctc cttacgccga ttcatggtcg    900
ctctaatcct ggatatcaag agaacacccg gaaacaaacc caggattgct gaaatgatat    960
gtgacattga tacatatatc gtagaggcag gattagccag ttttatcctg actattaagt   1020
ttgggataga aactatgtat cctgctcttg gactgcatga atttgctggt gagttatcca   1080
cacttgagtc cttgatgaac ctttaccagc aaatggggga aactgcaccc tacatggtaa   1140
tcctggagaa ctcaattcag aacaagttca gtgcaggatc ataccctctg ctctggagct   1200
atgccatggg agtaggagtg gaacttgaaa actccatggg aggtttgaac tttggccgat   1260
cttactttga tccagcatat tttagattag ggcaagagat ggtaaggagg tcagctggaa   1320
aggtcagttc cacattggca tctgaactcg gtatcactgc cgaggatgca aggcttgttt   1380
cagagattgc aatgcatact actgaggaca agatcagtag agcggttgga cccagacaag   1440
cccaagtatc atttctacac ggtgatcaaa gtgagaatga gctaccgaga ttgggggggca   1500
aggaagatag gagggtcaaa cagagtcgag gagaagccag ggagagctac agagaaaccg   1560
ggcccagcag agcaagtgat gcgagagctg cccatcttcc aaccggcaca cccctagaca   1620
ttgacactgc aacggagtcc agccaagatc cgcaggacag tcgaaggtca gctgacgccc   1680
tgcttaggct gcaagccatg gcaggaatct cggaagaaca aggctcagac acggacaccc   1740
ctatagtgta caatgacaga aatcttctag actaggtgcg agaggccgag ggccagaaca   1800
acatccgcct accatccatc attgttataa aaaacttagg aaccaggtcc acacagccgc   1860
cagcccatca accatccact cccacgattg gagccaatgg cagaagagca ggcacgccat   1920
gtcaaaaacg gactggaatg catccgggct ctcaaggccg agcccatcgg ctcactggcc   1980
atcgaggaag ctatggcagc atggtcagaa atatcagaca acccaggaca ggagcgagcc   2040
acctgcaggg aagagaaggc aggcagttcg ggtctcagca aaccatgcct ctcagcaatt   2100
ggatcaactg aaggcggtgc acctcgcatc cgcggtcagg gacctggaga gagcgatgac   2160
gacgctgaaa ctttgggaat ccccccaaga aatctccagg catcaagcac tgggttacag   2220
tgttattacg tttatgatca cagcggtgaa gcggttaagg gaatccaaga tgctgactct   2280
atcatggttc aatcaggcct tgatggtgat agcaccctct caggaggaga caatgaatct   2340
gaaaacagcg atgtggatat tggcgaacct gataccgagg gatatgctat cactgaccgg   2400
ggatctgctc ccatctctat ggggttcagg gcttctgatg ttgaaactgc agaaggaggg   2460
gagatccacg agctcctgag actccaatcc agaggcaaca actttccgaa gcttgggaaa   2520
actctcaatg ttcctccgcc cccggacccc ggtagggcca gcacttccgg gacacccatt   2580
aaaaagggca cagacgcgag attagcctca tttggaacgg agatcgcgtc tttattgaca   2640
ggtggtgcaa cccaatgtgc tcgaaagtca ccctcggaac catcagggcc aggtgcacct   2700
gcggggaatg tccccgagtg tgtgagcaat gccgcactga tacaggagtg gacacccgaa   2760
tctggtacca caatctcccc gagatcccag aataatgaag aagggggaga ctattatgat   2820
gatgagctgt tctctgatgt ccaagatatt aaaacagcct tggccaaaat acacgaggat   2880
aatcagaaga taatctccaa gctagaatca ctgctgttat tgaagggaga agttgagtca   2940
attaagaagc agatcaacag gcaaaatatc agcatatcca ccctggaagg acacctctca   3000
```

```
agcatcatga tcgccattcc tggacttggg aaggatccca acgaccccac tgcagatgtc   3060
gaaatcaatc ccgacttgaa acccatcata ggcagagatt caggccgagc actggccgaa   3120
gttctcaaga aacccgttgc cagccgacaa ctccaaggaa tgacaaatgg acggaccagt   3180
tccagaggac agctgctgaa ggaatttcag ctaaagccga tcgggaaaaa gatgagctca   3240
gccgtcgggt ttgttcctga caccggccct gcatcacgca gtgtaatccg ctccattata   3300
aaatccagcc ggctagagga ggatcggaag cgttacctga tgactctcct tgatgatatc   3360
aaaggagcca atgatcttgc caagttccac cagatgctga tgaagataat aatgaagtag   3420
ctacagctca acttacctgc caaccccatg ccagtcgacc caactagcct accctccatc   3480
attgttataa aaaacttagg aaccaggtcc acacagccgc cagcccatca acgcgtacgg   3540
ccaccatggc acgcagaggc gctgatacct cagttggtat agtgggattg ctgttgacaa   3600
ccgccatggc cgcagaagtg acgagaaggg gttctgccta ctatatgtac cttgatcgga   3660
atgacgctgg agaggcaatc tcattcccga ccaccttggg catgaacaaa tgctacatcc   3720
agattatgga cctgggacat atgtgcgatg ccactatgag ctatgagtgc cccatgctgg   3780
atgagggagt agagcctgac gatgttgact gctggtgtaa caccactagt acatgggtgg   3840
tgtacggaac gtgccaccac aagaaaggag aagctcgaag atcccgtcgc gcggttactc   3900
ttccctccca ttccacaagg aaactccaaa cccgtagcca gacatggctt gaaagccgag   3960
aatacactaa acacttgata cggtagagaa actggatttt ccgcaatccc gggtttgctc   4020
ttgcagctgc ggcaattgct tggctcctcg ggtcaagcac atcccagaag gtgatctacc   4080
tggtgatgat cctgctgatt gcaccagcct attcaatccg gtgtatcggt gtctcaaatc   4140
gtgacttcgt cgaggggatg agtggcggga cctgggtgga tgtcgttctg gaacatggag   4200
gctgtgtaac ggtgatggct caagacaagc caaccgttga catcgaactg gtaacgacga   4260
cagtcagcaa tatggccgaa gtccgctctt actgctatga agccagcatc agcgatatgg   4320
ccagcgatag tcgatgtccg actcaaggcg aagcctatct cgacaaacag tctgacaccc   4380
agtacgtgtg caagaggact ctcgtggata gagggtgggg caatggttgt ggggatttcg   4440
gcaaggggtc actggtaacc tgtgcaaagt tcgcctgctc taagaagatg actgggaaga   4500
gtatccagcc cgagaatctg gagtatagga tcatgctgag cgttcatgga tcccagcata   4560
gcgggatgat cgtgaatgat acgggtcacg aaacagacga gaaccgcgca aaggtcgaga   4620
ttactcccaa ttcccctagg gccgaagcca cactcggagg ctttggcagt ctcggcctgg   4680
attgcgagcc tcgcactgga ctggatttct ccgacctgta ctacctgact atgaacaaca   4740
aacattggct ggtgcacaag gaatggtttc acgacattcc cctgccttgg cacgctgggg   4800
ctgacactgg tacacctcat tggaacaaca aagaggctct ggtggagttc aaagatgcac   4860
atgccaagag acaaaccgtg gtggttctgg gatcacagga aggcgccgtg cataccgcgc   4920
ttgccggagc actggaagca gagatggacg gtgctaaagg ccggttgagc tctggccacc   4980
ttaagtgtcg gctgaagatg gacaagctga gattgaaagg agtctcctat agtctgtgta   5040
cagccgcgtt tacctttacg aaaatccccg ctgagacact gcacggaaca gtgaccgtgg   5100
aggtgcaata tgcagggact gatggcccat gtaaggtgcc agcacagatg gctgttgaca   5160
tgcagactct caccccagtc ggcaggctta ttactgccaa tccggtcata accgagagta   5220
cagagaatag caagatgatg ctggagcttg accctccatt cggagactcc tacattgtca   5280
ttggcgtcgg tgagaagaag attacccacc actggcacag gtctggctcc acaatcggta   5340
aagccttcga agcgacagtg agaggagcca aacggatggc ggtactcgga gacacagcct   5400
```

```
gggatttcgg gagcgttggt ggcgctctga actctctcgg gaaaggtatc caccagatat   5460
ttggggcagc ctttaaatca ctctttggcg gcatgagctg gttttctcag atcctgattg   5520
ggaccctcct gatgtggctg gggctgaaca ccaagaacgg ctctataagc ctgatgtgct   5580
tggccctggg cggggtgttg attttcctgt ccaccgctgt gagtgcctaa tgagcgcgca   5640
gcgcttagac gtctcgcgat cgatactagt acaacctaaa tccattataa aaaacttagg   5700
agcaaagtga ttgcctccca aggtccacaa tgacagagac ctacgacttc gacaagtcgg   5760
catgggacat caaagggtcg atcgctccga tacaacccac cacctacagt gatggcaggc   5820
tggtgcccca ggtcagagtc atagatcctg gtctaggcga caggaaggat gaatgcttta   5880
tgtacatgtt tctgctgggg gttgttgagg acagcgattc cctagggcct ccaatcgggc   5940
gagcatttgg gttcctgccc ttaggtgttg gcagatccac agcaaagccc gaaaaactcc   6000
tcaaagaggc cactgagctt gacatagttg ttagacgtac agcagggctc aatgaaaaac   6060
tggtgttcta caacaacacc ccactaactc tcctcacacc ttggagaaag gtcctaacaa   6120
cagggagtgt cttcaacgca aaccaagtgt gcaatgcggt taatctgata ccgctcgata   6180
ccccgcagag gttccgtgtt gtttatatga gcatcacccg tctttcggat aacgggtatt   6240
acaccgttcc tagaagaatg ctggaattca gatcggtcaa tgcagtggcc ttcaacctgc   6300
tggtgaccct taggattgac aaggcgatag gccctgggaa gatcatcgac aatacagagc   6360
aacttcctga ggcaacattt atggtccaca tcgggaactt caggagaaag aagagtgaag   6420
tctactctgc cgattattgc aaaatgaaaa tcgaaaagat gggcctggtt tttgcacttg   6480
gtgggatagg gggcaccagt cttcacatta gaagcacagg caaaatgagc aagactctcc   6540
atgcacaact cgggttcaag aagaccttat gttacccgct gatggatatc aatgaagacc   6600
ttaatcgatt actctggagg agcagatgca agatagtaag aatccaggca gttttgcagc   6660
catcagttcc tcaagaattc cgcatttacg acgacgtgat cataaatgat gaccaaggac   6720
tattcaaagt tctgtagacc gtagtgccca gcaatgcccg aaaacgaccc ccctcacaat   6780
gacagccaga aggcccggac aaaaaagccc cctccgaaag actccacgga ccaagcgaga   6840
ggccagccag cagccgacgg caagcgcgaa caccaggcgg ccccagcaca gaacagccct   6900
gacacaaggc caccaccagc caccccaatc tgcatcctcc tcgtgggacc cccgaggacc   6960
aacccccaag gctgccccccg atccaaacca ccaaccgcat ccccaccacc cccgggaaag   7020
aaacccccag caattggaag gcccctcccc ctcttcctca acacaagaac tccacaaccg   7080
aaccgcacaa gcgaccgagg tgacccaacc gcaggcatcc gactccctag acagatcctc   7140
tctccccggc aaactaaaca aaacttaggg ccaaggaaca tacacaccca acagaaccca   7200
gaccccggcc cacggcgccg cgcccccaac ccccgacaac cagagggagc cccccaaccaa   7260
tcccgccggc tcccccggtg cccacaggca gggacaccaa cccccgaaca gacccagcac   7320
ccaaccatcg acaatccaag acgggggggc ccccccaaaa aaaggccccc aggggccgac   7380
agccagcacc gcgaggaagc ccacccaccc cacacacgac cacggcaacc aaaccagaac   7440
ccagaccacc ctgggccacc agctcccaga ctcggccatc accccgcaga aaggaaaggc   7500
cacaacccgc gcaccccagc cccgatccgg cggggagcca cccaacccga accagcaccc   7560
aagagcgatc cccgaaggac ccccgaaccg caaaggacat cagtatccca cagcctctcc   7620
aagtcccccg gtctcctcct cttctcgaag ggaccaaaag atcaatccac cacacccgac   7680
gacactcaac tccccacccc taaaggagac accgggaatc ccagaatcaa gactcatcca   7740
```

```
atgtccatca tgggtctcaa ggtgaacgtc tctgccatat tcatggcagt actgttaact   7800
ctccaaacac ccaccggtca aatccattgg ggcaatctct ctaagatagg ggtggtagga   7860
ataggaagtg caagctacaa agttatgact cgttccagcc atcaatcatt agtcataaaa   7920
ttaatgccca atataactct cctcaataac tgcacgaggg tagagattgc agaatacagg   7980
agactactga gaacagtttt ggaaccaatt agagatgcac ttaatgcaat gacccagaat   8040
ataagaccgg ttcagagtgt agcttcaagt aggagacaca agagatttgc gggagtagtc   8100
ctggcaggtg cggccctagg cgttgccaca gctgctcaga taacagccgg cattgcactt   8160
caccagtcca tgctgaactc tcaagccatc gacaatctga gagcgagcct ggaaactact   8220
aatcaggcaa ttgagacaat cagacaagca gggcaggaga tgatattggc tgttcagggt   8280
gtccaagact acatcaataa tgagctgata ccgtctatga accaactatc ttgtgattta   8340
atcggccaga agctcgggct caaattgctc agatactata cagaaatcct gtcattattt   8400
ggccccagtt tacgggaccc catatctgcg gagatatcta tccaggcttt gagctatgcg   8460
cttggaggag acatcaataa ggtgttagaa aagctcggat acagtggagg tgatttactg   8520
ggcatcttag agagcggagg aataaaggcc cggataactc acgtcgacac agagtcctac   8580
ttcattgtcc tcagtatagc ctatccgacg ctgtccgaga ttaaggggt gattgtccac   8640
cggctagagg gggtctcgta caacataggc tctcaagagt ggtataccac tgtgcccaag   8700
tatgttgcaa cccaagggta ccttatctcg aattttgatg agtcatcgtg tactttcatg   8760
ccagagggga ctgtgtgcag ccaaaatgcc ttgtacccga tgagtcctct gctccaagaa   8820
tgcctccggg ggtacaccaa gtcctgtgct cgtacactcg tatccgggtc ttttgggaac   8880
cggttcattt tatcacaagg gaacctaata gccaattgtg catcaatcct ttgcaagtgt   8940
tacacaacag gaacgatcat taatcaagac cctgacaaga tcctaacata cattgctgcc   9000
gatcactgcc cggtagtcga ggtgaacggc gtgaccatcc aagtcgggag caggaggtat   9060
ccagacgctg tgtacttgca cagaattgac ctcggtcctc ccatatcatt ggagaggttg   9120
gacgtaggga caaatctggg gaatgcaatt gctaagttgg aggatgccaa ggaattgttg   9180
gagtcatcgg accagatatt gaggagtatg aaaggtttat cgagcactag catagtctac   9240
atcctgattg cagtgtgtct tggagggttg atagggatcc ccgctttaat atgttgctgc   9300
agggggcgtt gtaacaaaaa gggagaacaa gttggtatgt caagaccagg cctaaagcct   9360
gatcttacgg gaacatcaaa atcctatgta aggtcgctct gatcctctac aactcttgaa   9420
acacaaatgt cccacaagtc tcctcttcgt catcaagcaa ccaccgcacc cagcatcaag   9480
cccacctgaa attatctccg gcttccctct ggccgaacaa tatcggtagt taatcaaaac   9540
ttagggtgca agatcatcca caatgtcacc acaacgagac cggataaatg ccttctacaa   9600
agataacccc catcccaagg gaagtaggat agtcattaac agagaacatc ttatgattga   9660
tagaccttat gttttgctgg ctgttctgtt tgtcatgttt ctgagcttga tcgggttgct   9720
agccattgca ggcattagac ttcatcgggc agccatctac accgcagaga tccataaaag   9780
cctcagcacc aatctagatg taactaactc aatcgagcat caggtcaagg acgtgctgac   9840
accactcttc aaaatcatcg gtgatgaagt gggcctgagg acacctcaga gattcactga   9900
cctagtgaaa ttaatctctg acaagattaa attccttaat ccggataggg agtacgactt   9960
cagagatctc acttggtgta tcaacccgcc agagagaatc aaattggatt atgatcaata  10020
ctgtgcagat gtggctgctg aagagctcat gaatgcattg gtgaactcaa ctctactgga  10080
gaccagaaca accaatcagt tcctagctgt ctcaaaggga aactgctcag ggcccactac  10140
```

aatcagaggt caattctcaa acatgtcgct gtccctgtta gacttgtatt taggtcgagg 10200
ttacaatgtg tcatctatag tcactatgac atcccaggga atgtatgggg gaacttacct 10260
agtggaaaag cctaatctga gcagcaaaag gtcagagttg tcacaactga gcatgtaccg 10320
agtgtttgaa gtaggtgtta tcagaaatcc gggtttgggg gctccggtgt tccatatgac 10380
aaactatctt gagcaaccag tcagtaatga tctcagcaac tgtatggtgg ctttgggggga 10440
gctcaaactc gcagcccttt gtcacgggga agattctatc acaattccct atcagggatc 10500
agggaaaggt gtcagcttcc agctcgtcaa gctaggtgtc tggaaatccc caaccgacat 10560
gcaatcctgg gtccccttat caacggatga tccagtgata gacaggcttt acctctcatc 10620
tcacagaggt gttatcgctg acaatcaagc aaaatgggct gtcccgacaa cacgaacaga 10680
tgacaagttg cgaatggaga catgcttcca acaggcgtgt aagggtaaaa tccaagcact 10740
ctgcgagaat cccgagtggg caccattgaa ggataacagg attccttcat acggggtctt 10800
gtctgttgat ctgagtctga cagttgagct taaaatcaaa attgcttcgg gattcgggcc 10860
attgatcaca cacggttcag ggatggacct atacaaatcc aaccacaaca atgtgtattg 10920
gctgactatc ccgccaatga agaacctagc cttaggtgta atcaacacat tggagtggat 10980
accgagattc aaggttagtc cctacctctt cactgtccca attaaggaag caggcgaaga 11040
ctgccatgcc ccaacatacc tacctgcgga ggtggatggt gatgtcaaac tcagttccaa 11100
tctggtgatt ctacctggtc aagatctcca atatgttttg gcaacctacg atacttccag 11160
ggttgaacat gctgtggttt attacgttta cagcccaagc cgctcatttt cttactttta 11220
tcctttttagg ttgcctataa agggggtccc catcgaatta caagtggaat gcttcacatg 11280
ggaccaaaaa ctctggtgcc gtcacttctg tgtgcttgcg gactcagaat ctggtggaca 11340
tatcactcac tctgggatgg tgggcatggg agtcagctgc acagtcaccc gggaagatgg 11400
aaccaatcgc agatagggct gctagtgaac caatcacatg atgtcaccca gacatcaggc 11460
atacccacta gtgtgaaata gacatcagaa ttaagaaaaa cgtagggtcc aagtggttcc 11520
ccgttatgga ctcgctatct gtcaaccaga tcttataccc tgaagttcac ctagatagcc 11580
cgatagttac caataagata gtagccatcc tggagtatgc tcgagtccct cacgcttaca 11640
gcctggagga ccctacactg tgtcagaaca tcaagcaccg cctaaaaaac ggattttcca 11700
accaaatgat tataaacaat gtggaagttg ggaatgtcat caagtccaag cttaggagtt 11760
atccggccca ctctcatatt ccatatccaa attgtaatca ggatttattt aacatagaag 11820
acaaagagtc aacgaggaag atccgtgaac tcctcaaaaa ggggaattcg ctgtactcca 11880
aagtcagtga taaggttttc caatgcttaa gggacactaa ctcacggctt ggcctaggct 11940
ccgaattgag ggaggacatc aaggagaaag ttattaactt gggagtttac atgcacagct 12000
cccagtggtt tgagcccttt ctgttttggt ttacagtcaa gactgagatg aggtcagtga 12060
ttaaatcaca aacccatact tgccatagga ggagacacac acctgtattc ttcactggta 12120
gttcagttga gttgctaatc tctcgtgacc ttgttgctat aatcagtaaa gagtctcaac 12180
atgtatatta cctgacattt gaactggttt tgatgtattg tgatgtcata gaggggaggt 12240
taatgacaga gaccgctatg actattgatg ctaggtatac agagcttcta ggaagagtca 12300
gatacatgtg gaaactgata gatggtttct tccctgcact cgggaatcca acttatcaaa 12360
ttgtagccat gctggagcct ctttcacttg cttacctgca gctgagggat ataacagtag 12420
aactcagagg tgctttcctt aaccactgct ttactgaaat acatgatgtt cttgaccaaa 12480

```
acgggttttc tgatgaaggt acttatcatg agttaactga agctctagat tacattttca  12540
taactgatga catacatctg acaggggaga ttttctcatt tttcagaagt ttcggccacc  12600
ccagacttga agcagtaacg gctgctgaaa atgttaggaa atacatgaat cagcctaaag  12660
tcattgtgta tgagactctg atgaaaggtc atgccatatt ttgtggaatc ataatcaacg  12720
gctatcgtga caggcacgga ggcagttggc caccgctgac cctccccctg catgctgcag  12780
acacaatccg gaatgctcaa gcttcaggtg aagggttaac acatgagcag tgcgttgata  12840
actggaaatc ttttgctgga gtgaaatttg gctgctttat gcctcttagc ctggatagtg  12900
atctgacaat gtacctaaag gacaaggcac ttgctgctct ccaaagggaa tgggattcag  12960
tttacccgaa agagttcctg cgttacgacc ctcccaaggg aaccgggtca cggaggcttg  13020
tagatgtttt ccttaatgat tcgagctttg acccatatga tgtgataatg tatgttgtaa  13080
gtggagctta cctccatgac cctgagttca acctgtctta cagcctgaaa gaaaaggaga  13140
tcaaggaaac aggtagactt tttgctaaaa tgacttacaa aatgagggca tgccaagtga  13200
ttgctgaaaa tctaatctca aacgggattg gcaaatattt taaggacaat gggatggcca  13260
aggatgagca cgatttgact aaggcactcc acactctagc tgtctcagga gtccccaaag  13320
atctcaaaga aagtcacagg ggggggccag tcttaaaaac ctactcccga agcccagtcc  13380
acacaagtac caggaacgtg agagcagcaa aagggtttat agggttccct caagtaattc  13440
ggcaggacca agacactgat catccggaga atatggaagc ttacgagaca gtcagtgcat  13500
ttatcacgac tgatctcaag aagtactgcc ttaattggag atatgagacc atcagcttgt  13560
ttgcacagag gctaaatgag atttacggat tgccctcatt tttccagtgg ctgcataaga  13620
ggcttgagac ctctgtcctg tatgtaagtg accctcattg cccccccgac cttgacgccc  13680
atatcccgtt atataaagtc cccaatgatc aaatcttcat taagtaccct atgggaggta  13740
tagaagggta ttgtcagaag ctgtggacca tcagcaccat tccctatcta tacctggctg  13800
cttatgagag cggagtaagg attgcttcgt tagtgcaagg ggacaatcag accatagccg  13860
taacaaaaag ggtacccagc acatggccct acaaccttaa gaaacgggaa gctgctagag  13920
taactagaga ttactttgta attcttaggc aaaggctaca tgatattggc catcacctca  13980
aggcaaatga gacaattgtt tcatcacatt tttttgtcta ttcaaaagga atatattatg  14040
atgggctact tgtgtcccaa tcactcaaga gcatcgcaag atgtgtattc tggtcagaga  14100
ctatagttga tgaaacaagg gcagcatgca gtaatattgc tacaacaatg gctaaaagca  14160
tcgagagagg ttatgaccgt taccttgcat attccctgaa cgtcctaaaa gtgatacagc  14220
aaattctgat ctctcttggc ttcacaatca attcaaccat gacccgggat gtagtcatac  14280
ccctcctcac aaacaacgac ctcttaataa ggatggcact gttgcccgct cctattgggg  14340
ggatgaatta tctgaatatg agcaggctgt ttgtcagaaa catcggtgat ccagtaacat  14400
catcaattgc tgatctcaag agaatgattc tcgcctcact aatgcctgaa gagaccctcc  14460
atcaagtaat gacacaacaa ccgggggact cttcattcct agactgggct agcgaccctt  14520
actcagcaaa tcttgtatgt gtccagagca tcactagact cctcaagaac ataactgcaa  14580
ggtttgtcct gatccatagt ccaaacccaa tgttaaaagg attattccat gatgacagta  14640
aagaagagga cgagggactg gcggcattcc tcatggacag gcatattata gtacctaggg  14700
cagctcatga aatcctggat catagtgtca caggggcaag agagtctatt gcaggcatgc  14760
tggataccac aaaaggcttg attcgagcca gcatgaggaa ggggggggtta acctctcgag  14820
tgataaccag attgtccaat tatgactatg aacaattcag agcagggatg gtgctattga  14880
```

caggaagaaa gagaaatgtc ctcattgaca aagagtcatg ttcagtgcag ctggcgagag 14940
ctctaagaag ccatatgtgg gcgaggctag ctcgaggacg gcctatttac ggccttgagg 15000
tccctgatgt actagaatct atgcgaggcc accttattcg gcgtcatgag acatgtgtca 15060
tctgcgagtg tggatcagtc aactacggat ggttttttgt cccctcgggt tgccaactgg 15120
atgatattga caaggaaaca tcatccttga gagtcccata tattggttct accactgatg 15180
agagaacaga catgaagctt gccttcgtaa gagccccaag tcgatccttg cgatctgctg 15240
ttagaatagc aacagtgtac tcatgggctt acggtgatga tgatagctct tggaacgaag 15300
cctggttgtt ggctaggcaa agggccaatg tgagcctgga ggagctaagg gtgatcactc 15360
ccatctcaac ttcgactaat ttagcgcata ggttgaggga tcgtagcact caagtgaaat 15420
actcaggtac atcccttgtc cgagtggcga ggtataccac aatctccaac gacaatctct 15480
catttgtcat atcagataag aaggttgata ctaactttat ataccaacaa ggaatgcttc 15540
tagggttggg tgttttagaa acattgtttc gactcgagaa agataccgga tcatctaaca 15600
cggtattaca tcttcacgtc gaaacagatt gttgcgtgat cccgatgata gatcatccca 15660
ggatacccag ctcccgcaag ctagagctga gggcagagct atgtaccaac ccattgatat 15720
atgataatgc acctttaatt gacagagatg caacaaggct atacacccag agccatagga 15780
ggcaccttgt ggaatttgtt acatggtcca caccccaact atatcacatt ttagctaagt 15840
ccacagcact atctatgatt gacctggtaa caaaatttga gaaggaccat atgaatgaaa 15900
tttcagctct catagggat gacgatatca atagtttcat aactgagttt ctgctcatag 15960
agccaagatt attcactatc tacttgggcc agtgtgcggc catcaattgg gcatttgatg 16020
tacattatca tagaccatca gggaaatatc agatgggtga gctgttgtca tcgttccttt 16080
ctagaatgag caaaggagtg tttaaggtgc ttgtcaatgc tctaagccac ccaaagatct 16140
acaagaaatt ctggcattgt ggtattatag agcctatcca tggtccttca cttgatgctc 16200
aaaacttgca cacaactgtg tgcaacatgg tttacacatg ctatatgacc tacctcgacc 16260
tgttgttgaa tgaagagtta gaagagttca catttctctt gtgtgaaagc gacgaggatg 16320
tagtaccgga cagattcgac aacatccagg caaaacactt atgtgttctg gcagatttgt 16380
actgtcaacc agggacctgc ccaccaattc gaggtctaag accggtagag aaatgtgcag 16440
ttctaaccga ccatatcaag gcagaggcta tgttatctcc agcaggatct tcgtggaaca 16500
taaatccaat tattgtagac cattactcat gctctctgac ttatctccgg cgaggatcga 16560
tcaaacagat aagattgaga gttgatccag gattcatttt cgacgccctc gctgaggtaa 16620
atgtcagtca gccaaagatc ggcagcaaca acatctcaaa tatgagcatc aaggctttca 16680
gacccccaca cgatgatgtt gcaaaattgc tcaaagatat caacacaagc aagcacaatc 16740
ttcccatttc agggggcaat ctcgccaatt atgaaatcca tgctttccgc agaatcgggt 16800
tgaactcatc tgcttgctac aaagctgttg agatatcaac attaattagg agatgccttg 16860
agccagggga ggacggcttg ttcttgggtg agggatcggg ttctatgttg atcacttata 16920
aagagatact taaactaaac aagtgcttct ataatagtgg ggtttccgcc aattctagat 16980
ctggtcaaag ggaattagca ccctatccct ccgaagttgg ccttgtcgaa cacagaatgg 17040
gagtaggtaa tattgtcaaa gtgctcttta acgggaggcc cgaagtcacg tgggtaggca 17100
gtgtagattg cttcaatttc atagttagta atatccctac ctctagtgtg gggtttatcc 17160
attcagatat agagaccttg cctgacaaag atactataga gaagctagag gaattggcag 17220

```
ccatcttatc gatggctctg ctcctgggca aaataggatc aatactggtg attaagctta  17280
tgcctttcag cggggatttt gttcagggat ttataagtta tgtagggtct cattatagag  17340
aagtgaacct tgtataccct agatacagca acttcatctc tactgaatct tatttggtta  17400
tgacagatct caaggctaac cggctaatga atcctgaaaa gattaagcag cagataattg  17460
aatcatctgt gaggacttca cctggactta taggtcacat cctatccatt aagcaactaa  17520
gctgcataca agcaattgtg ggagacgcag ttagtagagg tgatatcaat cctactctga  17580
aaaaacttac acctatagag caggtgctga tcaattgcgg gttggcaatt aacggaccta  17640
agctgtgcaa agaattgatc caccatgatg ttgcctcagg gcaagatgga ttgcttaatt  17700
ctatactcat cctctacagg gagttggcaa gattcaaaga caaccaaaga agtcaacaag  17760
ggatgttcca cgcttacccc gtattggtaa gtagcaggca acgagaactt atatctagga  17820
tcacccgcaa attctggggg cacattcttc tttactccgg gaacaaaaag ttgataaata  17880
agtttatcca gaatctcaag tccggctatc tgatactaga cttacaccag aatatcttcg  17940
ttaagaatct atccaagtca gagaaacaga ttattatgac ggggggtttg aaacgtgagt  18000
gggtttttaa ggtaacagtc aaggagacca aagaatggta taagttagtc ggatacagtg  18060
ccctgattaa ggactaattg gttgaactcc ggaaccctaa tcctgcccta ggtggttagg  18120
cattatttgc aatatattaa agaaaacttt gaaaatacga agtttctatt cccagctttg  18180
tctggtggcc ggcatggtcc cagcctcctc gctggcgccg gctgggcaac attccgaggg  18240
gaccgtcccc tcggtaatgg cgaatgggac gcggccgatc cggctgctaa caaagcccga  18300
aaggaagctg agttggctgc tgccaccgct gagcaataac tagcataacc ccttggggcc  18360
tctaaacggg tcttgagggg ttttttgctg aaaggaggaa ctatatccgg atgcggccgc  18420
gggccctatg gtacccagct tttgttccct ttagtgaggg ttaattccga gcttggcgta  18480
atcatggtca tagctgtttc ctgtgtgaaa ttgttatccg ctcacaattc cacacaacat  18540
aggagccgga agcataaagt gtaaagcctg gggtgcctaa tgagtgaggt aactcacatt  18600
aattgcgttg cgctcactgc ccgctttcca gtcgggaaac ctgtcgtgcc agctgcatta  18660
atgaatcggc caacgcgcgg ggagaggcgg tttgcgtatt gggcgctctt ccgcttcctc  18720
gctcactgac tcgctgcgct cggtcgttcg gctgcggcga gcggtatcag ctcactcaaa  18780
ggcggtaata cggttatcca cagaatcagg ggataacgca ggaaagaaca tgtgagcaaa  18840
aggccagcaa aaggccagga accgtaaaaa ggccgcgttg ctggcgtttt tccataggct  18900
cggcccccct gacgagcatc acaaaaatcg acgctcaagt cagaggtggc gaaacccgac  18960
aggactataa agataccagg cgttcccccc tggaagctcc ctcgtgcgct ctcctgttcc  19020
gaccctgccg cttaccggat acctgtccgc ctttctccct tcgggaagcg tggcgctttc  19080
tcaatgctca cgctgtaggt atctcagttc ggtgtaggtc gttcgctcca agctgggctg  19140
tgtgcacgaa ccccccgttc agcccgaccg ctgcgcctta tccggtaact atcgtcttga  19200
gtccaacccg gtaagacacg acttatcgcc actggcagca gccactggta acaggattag  19260
cagagcgagg tatgtaggcg gtgctacaga gttcttgaag tggtggccta actacggcta  19320
cactagaagg acagtatttg gtatctgcgc tctgctgaag ccagttacct tcggaaaaag  19380
agttggtagc tcttgatccg gcaaacaaac caccgctggt agcggtggtt tttttgtttg  19440
caagcagcag attacgcgca gaaaaaaagg atctcaagaa gatcctttga tcttttctac  19500
ggggtctgac gctcagtgga acgaaaactc acgttaaggg attttggtca tgagattatc  19560
aaaaaggatc ttcacctaga tccttttaaa ttaaaaatga agttttaaat caatctaaag  19620
```

tatatatgag taaacttggt ctgacagtta ccaatgctta atcagtgagg cacctatctc 19680
agcgatctgt ctatttcgtt catccatagt tgcctgactg cccgtcgtgt agataactac 19740
gatacgggag ggcttaccat ctggccccag tgctgcaatg ataccgcgag acccacgctc 19800
accggctcca gatttatcag caataaacca gccagccgga agggccgagc gcagaagtgg 19860
tcctgcaact ttatccgcct ccatccagtc tattaattgt tgccgggaag ctagagtaag 19920
tagttcgcca gttaatagtt tgcgcaacgt tgttgccatt gctacaggca tcgtggtgtc 19980
acgctcgtcg tttggtatgg cttcattcag ctccggttcc caacgatcaa ggcgagttac 20040
atgatccccc atgttgtgaa aaaaagcggt tagctccttc ggtcctccga tcgttgtcag 20100
aagtaagttg gccgcagtgt tatcactcat gcttatggca gcactgcata attctcttac 20160
tgtcatgcca tccgtaagat gcttttctgt gactggtgag tactcaacca agtcattctg 20220
agaatagtgt atgcggcgac cgagttgctc ttgcccggcg tcaatacggg ataataccgc 20280
gccacatagc agaactttaa aagtgctcat cattggaaaa cgttcttcgg ggcgaaaact 20340
ctcaaggatc ttaccgctgt tgagatccag ttcgatgtaa cccactcgtg cacccaactg 20400
atcttcagca tcttttactt tcaccagcgt ttctgggtga gcaaaaacag gaaggcaaaa 20460
tgccgcaaaa aagggaataa gggcgacacg gaaatgttga atactcatac tcttcctttt 20520
tcaatattat tgaagcattt atcagggtta ttgtctcatg agcggataca tatttgaatg 20580
tatttagaaa aataaacaaa taggggttcc gcgcacattt ccccgaaaag tgccacctga 20640
aattgtaaac gttaatattt tgttaaaatt cgcgttaaat ttttgttaaa tcagctcatt 20700
ttttaaccaa taggccgaaa tcggcaaaat cccttataaa tcaaaagaat agaccgagat 20760
agggttgagt gttgttccag tttggaacaa gagtccacta ttaaagaacg tggactccaa 20820
cgtcaaaggg cgaaaaaccg tctatcaggg cgatggccca ctacgtgaac catcacccta 20880
atcaagtttt ttggggtcga ggtgccgtaa agcactaaat cggaacccta aagggagccc 20940
ccgatttaga gcttgacggg gaaagccggc gaacgtggcg agaaaggaag ggaagaaagc 21000
gaaaggagcg ggcgctaggg cgctggcaag tgtagcggtc acgctgcgcg taaccaccac 21060
acccgccgcg cttaatgcgc cgctacaggg cgcgtcccat tcgccattca ggctgcgcaa 21120
ctgttgggaa gggcgatcgg tgcgggcctc ttcgctatta cgccagccac cgcggtgatc 21180
cttataaagc tagatg 21196

<210> SEQ ID NO 7
<211> LENGTH: 19075
<212> TYPE: DNA
<213> ORGANISM: artificial sequence
<220> FEATURE:
<223> OTHER INFORMATION: pTM 2ATU MV Schw short - Measles virus scaffold with ATU

<400> SEQUENCE: 7
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag gggcactaat aggtatatta 420

```
tccttatttg tggagtctcc aggtcaattg attcagagga tcaccgatga ccctgacgtt    480
agcataaggc tgttagaggt tgtccagagt gaccagtcac aatctggcct taccttcgca    540
tcaagaggta ccaacatgga ggatgaggcg gaccaatact tttcacatga tgatccaatt    600
agtagtgatc aatccaggtt cggatggttc gggaacaagg aaatctcaga tattgaagtg    660
caagaccctg agggattcaa catgattctg ggtaccatcc tagcccaaat ttgggtcttg    720
ctcgcaaagg cggttacggc cccagacacg gcagctgatt cggagctaag aaggtggata    780
aagtacaccc aacaaagaag ggtagttggt gaatttagat tggagagaaa atggttggat    840
gtggtgagga acaggattgc cgaggacctc tccttacgcc gattcatggt cgctctaatc    900
ctggatatca agagaacacc cggaaacaaa cccaggattg ctgaaatgat atgtgacatt    960
gatacatata tcgtagaggc aggattagcc agttttatcc tgactattaa gtttgggata   1020
gaaactatgt atcctgctct tggactgcat gaatttgctg gtgagttatc cacacttgag   1080
tccttgatga acctttacca gcaaatgggg gaaactgcac cctacatggt aatcctggag   1140
aactcaattc agaacaagtt cagtgcagga tcataccctc tgctctggag ctatgccatg   1200
ggagtaggag tggaacttga aaactccatg ggaggtttga actttggccg atcttacttt   1260
gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg gacccagaca agcccaagta   1440
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccccctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
```

```
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac ggcgcgcagc   3540
gcttagacgt ctcgcgatcg atactagtac aacctaaatc cattataaaa aacttaggag   3600
caaagtgatt gcctcccaag gtccacaatg acagagacct acgacttcga caagtcggca   3660
tgggacatca aagggtcgat cgctccgata caacccacca cctacagtga tggcaggctg   3720
gtgccccagg tcagagtcat agatcctggt ctaggcgaca ggaaggatga atgctttatg   3780
tacatgtttc tgctgggggt tgttgaggac agcgattccc tagggcctcc aatcgggcga   3840
gcatttgggt tcctgccctt aggtgttggc agatccacag caaagcccga aaaactcctc   3900
aaagaggcca ctgagcttga catagttgtt agacgtacag cagggctcaa tgaaaaactg   3960
gtgttctaca acaacacccc actaactctc ctcacacctt ggagaaaggt cctaacaaca   4020
gggagtgtct tcaacgcaaa ccaagtgtgc aatgcggtta atctgatacc gctcgatacc   4080
ccgcagaggt tccgtgttgt ttatatgagc atcacccgtc tttcggataa cgggtattac   4140
accgttccta gaagaatgct ggaattcaga tcggtcaatg cagtggcctt caacctgctg   4200
gtgaccctta ggattgacaa ggcgataggc cctgggaaga tcatcgacaa tacagagcaa   4260
cttcctgagg caacatttat ggtccacatc gggaacttca ggagaaagaa gagtgaagtc   4320
tactctgccg attattgcaa aatgaaaatc gaaaagatgg gcctggtttt tgcacttggt   4380
gggatagggg gcaccagtct tcacattaga agcacaggca aaatgagcaa gactctccat   4440
gcacaactcg ggttcaagaa gaccttatgt tacccgctga tggatatcaa tgaagacctt   4500
aatcgattac tctggaggag cagatgcaag atagtaagaa tccaggcagt tttgcagcca   4560
tcagttcctc aagaattccg catttacgac gacgtgatca taaatgatga ccaaggacta   4620
ttcaaagttc tgtagaccgt agtgcccagc aatgcccgaa aacgaccccc ctcacaatga   4680
cagccagaag gcccggacaa aaaagccccc tccgaaagac tccacggacc aagcgagagg   4740
ccagccagca gccgacggca agcgcgaaca ccaggcggcc ccagcacaga acagccctga   4800
cacaaggcca ccaccagcca ccccaatctg catcctcctc gtgggacccc cgaggaccaa   4860
cccccaaggc tgcccccgat ccaaaccacc aaccgcatcc ccaccacccc cgggaaagaa   4920
acccccagca attggaaggc ccctccccct cttcctcaac acaagaactc cacaaccgaa   4980
ccgcacaagc gaccgaggtg acccaaccgc aggcatccga ctccctagac agatcctctc   5040
tccccggcaa actaaacaaa acttagggcc aaggaacata cacacccaac agaacccaga   5100
ccccggccca cggcgccgcg cccccaaccc ccgacaacca gagggagccc ccaaccaatc   5160
```

```
ccgccggctc ccccggtgcc cacaggcagg gacaccaacc cccgaacaga cccagcaccc   5220
aaccatcgac aatccaagac gggggggccc ccccaaaaaa aggcccccag gggccgacag   5280
ccagcaccgc gaggaagccc acccacccca cacacgacca cggcaaccaa accagaaccc   5340
agaccaccct gggccaccag ctcccagact cggccatcac cccgcagaaa ggaaaggcca   5400
caacccgcgc accccagccc cgatccggcg gggagccacc caacccgaac cagcacccaa   5460
gagcgatccc cgaaggaccc ccgaaccgca aaggacatca gtatcccaca gcctctccaa   5520
gtcccccggt ctcctcctct tctcgaaggg accaaaagat caatccacca cacccgacga   5580
cactcaactc cccaccccta aaggagacac cgggaatccc agaatcaaga ctcatccaat   5640
gtccatcatg ggtctcaagg tgaacgtctc tgccatattc atggcagtac tgttaactct   5700
ccaaacaccc accggtcaaa tccattgggg caatctctct aagatagggg tggtaggaat   5760
aggaagtgca agctacaaag ttatgactcg ttccagccat caatcattag tcataaaatt   5820
aatgcccaat ataactctcc tcaataactg cacgagggta gagattgcag aatacaggag   5880
actactgaga acagttttgg aaccaattag agatgcactt aatgcaatga cccagaatat   5940
aagaccggtt cagagtgtag cttcaagtag gagacacaag agatttgcgg gagtagtcct   6000
ggcaggtgcg gccctaggcg ttgccacagc tgctcagata acagccggca ttgcacttca   6060
ccagtccatg ctgaactctc aagccatcga caatctgaga gcgagcctgg aaactactaa   6120
tcaggcaatt gagacaatca gacaagcagg gcaggagatg atattggctg ttcagggtgt   6180
ccaagactac atcaataatg agctgatacc gtctatgaac caactatctt gtgatttaat   6240
cggccagaag ctcgggctca aattgctcag atactataca gaaatcctgt cattatttgg   6300
ccccagttta cgggacccca tatctgcgga gatatctatc caggctttga gctatgcgct   6360
tggaggagac atcaataagg tgttagaaaa gctcggatac agtggaggtg atttactggg   6420
catcttagag agcggaggaa taaaggcccg gataactcac gtcgacacag agtcctactt   6480
cattgtcctc agtatagcct atccgacgct gtccgagatt aagggggtga ttgtccaccg   6540
gctagagggg gtctcgtaca acataggctc tcaagagtgg tataccactg tgcccaagta   6600
tgttgcaacc caagggtacc ttatctcgaa ttttgatgag tcatcgtgta ctttcatgcc   6660
agaggggact gtgtgcagcc aaaatgcctt gtacccgatg agtcctctgc tccaagaatg   6720
cctccggggg tacaccaagt cctgtgctcg tacactcgta tccgggtctt ttgggaaccg   6780
gttcatttta tcacaaggga acctaatagc caattgtgca tcaatccttt gcaagtgtta   6840
cacaacagga acgatcatta atcaagaccc tgacaagatc ctaacataca ttgctgccga   6900
tcactgcccg gtagtcgagg tgaacggcgt gaccatccaa gtcgggagca ggaggtatcc   6960
agacgctgtg tacttgcaca gaattgacct cggtcctccc atatcattgg agaggttgga   7020
cgtagggaca aatctgggga atgcaattgc taagttggag gatgccaagg aattgttgga   7080
gtcatcggac cagatattga ggagtatgaa aggtttatcg agcactagca tagtctacat   7140
cctgattgca gtgtgtcttg gagggttgat agggatcccc gctttaatat gttgctgcag   7200
ggggcgttgt aacaaaaagg gagaacaagt tggtatgtca agaccaggcc taaagcctga   7260
tcttacggga acatcaaaat cctatgtaag gtcgctctga tcctctacaa ctcttgaaac   7320
acaaatgtcc cacaagtctc ctcttcgtca tcaagcaacc accgcaccca gcatcaagcc   7380
cacctgaaat tatctccggc ttccctctgg ccgaacaata tcggtagtta atcaaaactt   7440
agggtgcaag atcatccaca atgtcaccac aacgagaccg gataaatgcc ttctacaaag   7500
```

```
ataaccccca tcccaaggga agtaggatag tcattaacag agaacatctt atgattgata   7560
gaccttatgt tttgctggct gttctgtttg tcatgtttct gagcttgatc gggttgctag   7620
ccattgcagg cattagactt catcgggcag ccatctacac cgcagagatc cataaaagcc   7680
tcagcaccaa tctagatgta actaactcaa tcgagcatca ggtcaaggac gtgctgacac   7740
cactcttcaa aatcatcggt gatgaagtgg gcctgaggac acctcagaga ttcactgacc   7800
tagtgaaatt aatctctgac aagattaaat tccttaatcc ggatagggag tacgacttca   7860
gagatctcac ttggtgtatc aacccgccag agagaatcaa attggattat gatcaatact   7920
gtgcagatgt ggctgctgaa gagctcatga atgcattggt gaactcaact ctactggaga   7980
ccagaacaac caatcagttc ctagctgtct caaagggaaa ctgctcaggg cccactacaa   8040
tcagaggtca attctcaaac atgtcgctgt ccctgttaga cttgtattta ggtcgaggtt   8100
acaatgtgtc atctatagtc actatgacat cccagggaat gtatggggga acttacctag   8160
tggaaaagcc taatctgagc agcaaaaggt cagagttgtc acaactgagc atgtaccgag   8220
tgtttgaagt aggtgttatc agaaatccgg gtttgggggc tccggtgttc catatgacaa   8280
actatcttga gcaaccagtc agtaatgatc tcagcaactg tatggtggct ttgggggagc   8340
tcaaactcgc agccctttgt cacggggaag attctatcac aattccctat cagggatcag   8400
ggaaaggtgt cagcttccag ctcgtcaagc taggtgtctg gaaatcccca accgacatgc   8460
aatcctgggt ccccttatca acggatgatc cagtgataga caggctttac ctctcatctc   8520
acagaggtgt tatcgctgac aatcaagcaa aatgggctgt cccgacaaca cgaacagatg   8580
acaagttgcg aatggagaca tgcttccaac aggcgtgtaa gggtaaaatc caagcactct   8640
gcgagaatcc cgagtgggca ccattgaagg ataacaggat tccttcatac ggggtcttgt   8700
ctgttgatct gagtctgaca gttgagctta aaatcaaaat tgcttcggga ttcgggccat   8760
tgatcacaca cggttcaggg atggacctat acaaatccaa ccacaacaat gtgtattggc   8820
tgactatccc gccaatgaag aacctagcct taggtgtaat caacacattg gagtggatac   8880
cgagattcaa ggttagtccc tacctcttca ctgtcccaat taaggaagca ggcgaagact   8940
gccatgcccc aacataccta cctgcggagg tggatggtga tgtcaaactc agttccaatc   9000
tggtgattct acctggtcaa gatctccaat atgttttggc aacctacgat acttccaggg   9060
ttgaacatgc tgtggtttat tacgtttaca gcccaagccg ctcattttct tacttttatc   9120
cttttaggtt gcctataaag ggggtcccca tcgaattaca agtggaatgc ttcacatggg   9180
accaaaaact ctggtgccgt cacttctgtg tgcttgcgga ctcagaatct ggtggacata   9240
tcactcactc tgggatggtg ggcatgggag tcagctgcac agtcacccgg gaagatggaa   9300
ccaatcgcag atagggctgc tagtgaacca atcacatgat gtcacccaga catcaggcat   9360
acccactagt gtgaaataga catcagaatt aagaaaaacg tagggtccaa gtggttcccc   9420
gttatggact cgctatctgt caaccagatc ttataccctg aagttcacct agatagcccg   9480
atagttacca ataagatagt agccatcctg gagtatgctc gagtccctca cgcttacagc   9540
ctggaggacc ctacactgtg tcagaacatc aagcaccgcc taaaaaacgg attttccaac   9600
caaatgatta taaacaatgt ggaagttggg aatgtcatca agtccaagct taggagttat   9660
ccggcccact ctcatattcc atatccaaat tgtaatcagg atttatttaa catagaagac   9720
aaagagtcaa cgaggaagat ccgtgaactc ctcaaaaagg ggaattcgct gtactccaaa   9780
gtcagtgata aggttttcca atgcttaagg gacactaact cacggcttgg cctaggctcc   9840
gaattgaggg aggacatcaa ggagaaagtt attaacttgg gagtttacat gcacagctcc   9900
```

```
cagtggtttg agccctttct gttttggttt acagtcaaga ctgagatgag gtcagtgatt    9960
aaatcacaaa cccatacttg ccataggagg agacacacac ctgtattctt cactggtagt   10020
tcagttgagt tgctaatctc tcgtgacctt gttgctataa tcagtaaaga gtctcaacat   10080
gtatattacc tgacatttga actggttttg atgtattgtg atgtcataga ggggaggtta   10140
atgacagaga ccgctatgac tattgatgct aggtatacag agcttctagg aagagtcaga   10200
tacatgtgga aactgataga tggtttcttc cctgcactcg ggaatccaac ttatcaaatt   10260
gtagccatgc tggagcctct ttcacttgct tacctgcagc tgagggatat aacagtagaa   10320
ctcagaggtg ctttccttaa ccactgcttt actgaaatac atgatgttct tgaccaaaac   10380
gggttttctg atgaaggtac ttatcatgag ttaactgaag ctctagatta cattttcata   10440
actgatgaca tacatctgac aggggagatt ttctcatttt tcagaagttt cggccacccc   10500
agacttgaag cagtaacggc tgctgaaaat gttaggaaat acatgaatca gcctaaagtc   10560
attgtgtatg agactctgat gaaaggtcat gccatatttt gtggaatcat aatcaacggc   10620
tatcgtgaca ggcacggagg cagttggcca ccgctgaccc tcccccctgca tgctgcagac   10680
acaatccgga atgctcaagc ttcaggtgaa gggttaacac atgagcagtg cgttgataac   10740
tggaaatctt ttgctggagt gaaatttggc tgctttatgc ctcttagcct ggatagtgat   10800
ctgacaatgt acctaaagga caaggcactt gctgctctcc aaagggaatg ggattcagtt   10860
tacccgaaag agttcctgcg ttacgaccct cccaagggaa ccgggtcacg gaggcttgta   10920
gatgttttcc ttaatgattc gagctttgac ccatatgatg tgataatgta tgttgtaagt   10980
ggagcttacc tccatgaccc tgagttcaac ctgtcttaca gcctgaaaga aaaggagatc   11040
aaggaaacag gtagactttt tgctaaaatg acttacaaaa tgagggcatg ccaagtgatt   11100
gctgaaaatc taatctcaaa cgggattggc aaatatttta aggacaatgg gatggccaag   11160
gatgagcacg atttgactaa ggcactccac actctagctg tctcaggagt ccccaaagat   11220
ctcaaagaaa gtcacagggg ggggccagtc ttaaaaacct actcccgaag cccagtccac   11280
acaagtacca ggaacgtgag agcagcaaaa gggtttatag ggttccctca agtaattcgg   11340
caggaccaag acactgatca tccggagaat atggaagctt acgagacagt cagtgcattt   11400
atcacgactg atctcaagaa gtactgcctt aattggagat atgagaccat cagcttgttt   11460
gcacagaggc taaatgagat ttacggattg ccctcatttt tccagtggct gcataagagg   11520
cttgagacct ctgtcctgta tgtaagtgac cctcattgcc cccccgacct tgacgcccat   11580
atcccgttat ataaagtccc caatgatcaa atcttcatta agtaccctat gggaggtata   11640
gaagggtatt gtcagaagct gtggaccatc agcaccattc cctatctata cctggctgct   11700
tatgagagcg gagtaaggat tgcttcgtta gtgcaagggg acaatcagac catagccgta   11760
acaaaaaggg tacccagcac atggccctac aaccttaaga aacgggaagc tgctagagta   11820
actagagatt actttgtaat tcttaggcaa aggctacatg atattggcca tcacctcaag   11880
gcaaatgaga caattgtttc atcacatttt tttgtctatt caaaaggaat atattatgat   11940
gggctacttg tgtcccaatc actcaagagc atcgcaagat gtgtattctg gtcagagact   12000
atagttgatg aaacaagggc agcatgcagt aatattgcta caacaatggc taaaagcatc   12060
gagagaggtt atgaccgtta ccttgcatat tccctgaacg tcctaaaagt gatacagcaa   12120
attctgatct ctcttggctt cacaatcaat tcaaccatga cccgggatgt agtcataccc   12180
ctcctcacaa acaacgacct cttaataagg atggcactgt tgcccgctcc tattgggggg   12240
```

```
atgaattatc tgaatatgag caggctgttt gtcagaaaca tcggtgatcc agtaacatca  12300
tcaattgctg atctcaagag aatgattctc gcctcactaa tgcctgaaga gaccctccat  12360
caagtaatga cacaacaacc gggggactct tcattcctag actgggctag cgacccttac  12420
tcagcaaatc ttgtatgtgt ccagagcatc actagactcc tcaagaacat aactgcaagg  12480
tttgtcctga tccatagtcc aaacccaatg ttaaaaggat tattccatga tgacagtaaa  12540
gaagaggacg agggactggc ggcattcctc atggacaggc atattatagt acctagggca  12600
gctcatgaaa tcctggatca tagtgtcaca ggggcaagag agtctattgc aggcatgctg  12660
gataccacaa aaggcttgat tcgagccagc atgaggaagg gggggttaac ctctcgagtg  12720
ataaccagat tgtccaatta tgactatgaa caattcagag cagggatggt gctattgaca  12780
ggaagaaaga gaaatgtcct cattgacaaa gagtcatgtt cagtgcagct ggcgagagct  12840
ctaagaagcc atatgtgggc gaggctagct cgaggacggc ctatttacgg ccttgaggtc  12900
cctgatgtac tagaatctat gcgaggccac cttattcggc gtcatgagac atgtgtcatc  12960
tgcgagtgtg gatcagtcaa ctacggatgg ttttttgtcc cctcgggttg ccaactggat  13020
gatattgaca aggaaacatc atccttgaga gtcccatata ttggttctac cactgatgag  13080
agaacagaca tgaagcttgc cttcgtaaga gccccaagtc gatccttgcg atctgctgtt  13140
agaatagcaa cagtgtactc atgggcttac ggtgatgatg atagctcttg gaacgaagcc  13200
tggttgttgg ctaggcaaag ggccaatgtg agcctggagg agctaagggt gatcactccc  13260
atctcaactt cgactaattt agcgcatagg ttgagggatc gtagcactca agtgaaatac  13320
tcaggtacat cccttgtccg agtggcgagg tataccacaa tctccaacga caatctctca  13380
tttgtcatat cagataagaa ggttgatact aactttatat accaacaagg aatgcttcta  13440
gggttgggtg ttttagaaac attgtttcga ctcgagaaag ataccggatc atctaacacg  13500
gtattacatc ttcacgtcga aacagattgt tgcgtgatcc cgatgataga tcatcccagg  13560
atacccagct cccgcaagct agagctgagg gcagagctat gtaccaaccc attgatatat  13620
gataatgcac ctttaattga cagagatgca acaaggctat acacccagag ccataggagg  13680
caccttgtgg aatttgttac atggtccaca ccccaactat atcacatttt agctaagtcc  13740
acagcactat ctatgattga cctggtaaca aaatttgaga aggaccatat gaatgaaatt  13800
tcagctctca taggggatga cgatatcaat agtttcataa ctgagtttct gctcatagag  13860
ccaagattat tcactatcta cttgggccag tgtgcggcca tcaattgggc atttgatgta  13920
cattatcata gaccatcagg gaaatatcag atgggtgagc tgttgtcatc gttcctttct  13980
agaatgagca aaggagtgtt taaggtgctt gtcaatgctc taagccaccc aaagatctac  14040
aagaaattct ggcattgtgg tattatagag cctatccatg gtccttcact tgatgctcaa  14100
aacttgcaca caactgtgtg caacatggtt tacacatgct atatgaccta cctcgacctg  14160
ttgttgaatg aagagttaga agagttcaca tttctcttgt gtgaaagcga cgaggatgta  14220
gtaccggaca gattcgacaa catccaggca aaacacttat gtgttctggc agatttgtac  14280
tgtcaaccag ggacctgccc accaattcga ggtctaagac cggtagagaa atgtgcagtt  14340
ctaaccgacc atatcaaggc agaggctatg ttatctccag caggatcttc gtggaacata  14400
aatccaatta ttgtagacca ttactcatgc tctctgactt atctccggcg aggatcgatc  14460
aaacagataa gattgagagt tgatccagga ttcattttcg acgccctcgc tgaggtaaat  14520
gtcagtcagc caaagatcgg cagcaacaac atctcaaata tgagcatcaa ggctttcaga  14580
cccccacacg atgatgttgc aaaattgctc aaagatatca acacaagcaa gcacaatctt  14640
```

```
cccatttcag ggggcaatct cgccaattat gaaatccatg ctttccgcag aatcgggttg  14700
aactcatctg cttgctacaa agctgttgag atatcaacat taattaggag atgccttgag  14760
ccaggggagg acggcttgtt cttgggtgag ggatcgggtt ctatgttgat cacttataaa  14820
gagatactta aactaaacaa gtgcttctat aatagtgggg tttccgccaa ttctagatct  14880
ggtcaaaggg aattagcacc ctatccctcc gaagttggcc ttgtcgaaca cagaatggga  14940
gtaggtaata ttgtcaaagt gctctttaac gggaggcccg aagtcacgtg ggtaggcagt  15000
gtagattgct tcaatttcat agttagtaat atccctacct ctagtgtggg gtttatccat  15060
tcagatatag agaccttgcc tgacaaagat actatagaga agctagagga attggcagcc  15120
atcttatcga tggctctgct cctgggcaaa ataggatcaa tactggtgat taagcttatg  15180
cctttcagcg gggattttgt tcagggattt ataagttatg tagggtctca ttatagagaa  15240
gtgaaccttg tataccctag atacagcaac ttcatctcta ctgaatctta tttggttatg  15300
acagatctca aggctaaccg gctaatgaat cctgaaaaga ttaagcagca gataattgaa  15360
tcatctgtga ggacttcacc tggacttata ggtcacatcc tatccattaa gcaactaagc  15420
tgcatacaag caattgtggg agacgcagtt agtagaggtg atatcaatcc tactctgaaa  15480
aaacttacac ctatagagca ggtgctgatc aattgcgggt tggcaattaa cggacctaag  15540
ctgtgcaaag aattgatcca ccatgatgtt gcctcagggc aagatggatt gcttaattct  15600
atactcatcc tctacaggga gttggcaaga ttcaaagaca accaaagaag tcaacaaggg  15660
atgttccacg cttaccccgt attggtaagt agcaggcaac gagaacttat atctaggatc  15720
acccgcaaat tctgggggca cattcttctt tactccggga acaaaaagtt gataaataag  15780
tttatccaga atctcaagtc cggctatctg atactagact tacaccagaa tatcttcgtt  15840
aagaatctat ccaagtcaga gaaacagatt attatgacgg ggggtttgaa acgtgagtgg  15900
gtttttaagg taacagtcaa ggagaccaaa gaatggtata agttagtcgg atacagtgcc  15960
ctgattaagg actaattggt tgaactccgg aaccctaatc ctgccctagg tggttaggca  16020
ttatttgcaa tatattaaag aaaactttga aaatacgaag tttctattcc cagctttgtc  16080
tggtggccgg catggtccca gcctcctcgc tggcgccggc tgggcaacat tccgagggga  16140
ccgtcccctc ggtaatggcg aatgggacgc ggccgatccg gctgctaaca aagcccgaaa  16200
ggaagctgag ttggctgctg ccaccgctga gcaataacta gcataacccc ttggggcctc  16260
taaacgggtc ttgaggggtt ttttgctgaa aggaggaact atatccggat gcggccgcgg  16320
gccctatggt acccagcttt tgttcccttt agtgagggtt aattccgagc ttggcgtaat  16380
catggtcata gctgtttcct gtgtgaaatt gttatccgct cacaattcca cacaacatag  16440
gagccggaag cataaagtgt aaagcctggg gtgcctaatg agtgaggtaa ctcacattaa  16500
ttgcgttgcg ctcactgccc gctttccagt cgggaaacct gtcgtgccag ctgcattaat  16560
gaatcggcca acgcgcgggg agaggcggtt tgcgtattgg gcgctcttcc gcttcctcgc  16620
tcactgactc gctgcgctcg gtcgttcggc tgcggcgagc ggtatcagct cactcaaagg  16680
cggtaatacg gttatccaca gaatcagggg ataacgcagg aaagaacatg tgagcaaaag  16740
gccagcaaaa ggccaggaac cgtaaaaagg ccgcgttgct ggcgtttttc cataggctcg  16800
gcccccctga cgagcatcac aaaaatcgac gctcaagtca gaggtggcga aacccgacag  16860
gactataaag ataccaggcg tttccccctg gaagctccct cgtgcgctct cctgttccga  16920
ccctgccgct taccggatac ctgtccgcct ttctcccttc gggaagcgtg gcgctttctc  16980
```

```
aatgctcacg ctgtaggtat ctcagttcgg tgtaggtcgt tcgctccaag ctgggctgtg  17040
tgcacgaacc ccccgttcag cccgaccgct gcgccttatc cggtaactat cgtcttgagt  17100
ccaacccggt aagacacgac ttatcgccac tggcagcagc cactggtaac aggattagca  17160
gagcgaggta tgtaggcggt gctacagagt tcttgaagtg gtggcctaac tacggctaca  17220
ctagaaggac agtatttggt atctgcgctc tgctgaagcc agttaccttc ggaaaaagag  17280
ttggtagctc ttgatccggc aaacaaacca ccgctggtag cggtggtttt tttgtttgca  17340
agcagcagat tacgcgcaga aaaaaaggat ctcaagaaga tcctttgatc ttttctacgg  17400
ggtctgacgc tcagtggaac gaaaactcac gttaagggat tttggtcatg agattatcaa  17460
aaaggatctt cacctagatc cttttaaatt aaaaatgaag ttttaaatca atctaaagta  17520
tatatgagta aacttggtct gacagttacc aatgcttaat cagtgaggca cctatctcag  17580
cgatctgtct atttcgttca tccatagttg cctgactgcc cgtcgtgtag ataactacga  17640
tacgggaggg cttaccatct ggccccagtg ctgcaatgat accgcgagac ccacgctcac  17700
cggctccaga tttatcagca ataaaccagc cagccggaag ggccgagcgc agaagtggtc  17760
ctgcaacttt atccgcctcc atccagtcta ttaattgttg ccgggaagct agagtaagta  17820
gttcgccagt taatagtttg cgcaacgttg ttgccattgc tacaggcatc gtggtgtcac  17880
gctcgtcgtt tggtatggct tcattcagct ccggttccca acgatcaagg cgagttacat  17940
gatcccccat gttgtgaaaa aaagcggtta gctccttcgg tcctccgatc gttgtcagaa  18000
gtaagttggc cgcagtgtta tcactcatgc ttatggcagc actgcataat tctcttactg  18060
tcatgccatc cgtaagatgc ttttctgtga ctggtgagta ctcaaccaag tcattctgag  18120
aatagtgtat gcggcgaccg agttgctctt gcccggcgtc aatacgggat aataccgcgc  18180
cacatagcag aactttaaaa gtgctcatca ttggaaaacg ttcttcgggg cgaaaactct  18240
caaggatctt accgctgttg agatccagtt cgatgtaacc cactcgtgca cccaactgat  18300
cttcagcatc ttttactttc accagcgttt ctgggtgagc aaaaacagga aggcaaaatg  18360
ccgcaaaaaa gggaataagg gcgacacgga aatgttgaat actcatactc ttcctttttc  18420
aatattattg aagcatttat cagggttatt gtctcatgag cggatacata tttgaatgta  18480
tttagaaaaa taaacaaata ggggttccgc gcacatttcc ccgaaaagtg ccacctgaaa  18540
ttgtaaacgt taatattttg ttaaaattcg cgttaaattt ttgttaaatc agctcatttt  18600
ttaaccaata ggccgaaatc ggcaaaatcc cttataaatc aaaagaatag accgagatag  18660
ggttgagtgt tgttccagtt tggaacaaga gtccactatt aaagaacgtg gactccaacg  18720
tcaaagggcg aaaaaccgtc tatcagggcg atggcccact acgtgaacca tcaccctaat  18780
caagtttttt ggggtcgagg tgccgtaaag cactaaatcg gaaccctaaa gggagccccc  18840
gatttagagc ttgacgggga aagccggcga acgtggcgag aaaggaaggg aagaaagcga  18900
aaggagcggg cgctagggcg ctggcaagtg tagcggtcac gctgcgcgta accaccacac  18960
ccgccgcgct taatgcgccg ctacagggcg cgtcccattc gccattcagg ctgcgcaact  19020
gttgggaagg gcgatcggtg cgggcctctt cgctattacg ccagccaccg cggtg       19075
```

<210> SEQ ID NO 8
<211> LENGTH: 22825
<212> TYPE: DNA
<213> ORGANISM: artificial sequence
<220> FEATURE:
<223> OTHER INFORMATION: pTM 2ATU MV CHIK short

<400> SEQUENCE: 8

```
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag ggacaagagc aggattaggg     180
atatccgaga tggccacact tttaaggagc ttagcattgt tcaaaagaaa caaggacaaa     240
ccacccatta catcaggatc cggtggagcc atcagaggaa tcaaacacat tattatagta     300
ccaatccctg gagattcctc aattaccact cgatccagac ttctggaccg gttggtgagg     360
ttaattggaa acccggatgt gagcgggccc aaactaacag gggcactaat aggtatatta     420
tccttatttg tggagtctcc aggtcaattg attcagagga tcaccgatga ccctgacgtt     480
agcataaggc tgttagaggt tgtccagagt gaccagtcac aatctggcct taccttcgca     540
tcaagaggta ccaacatgga ggatgaggcg gaccaatact tttcacatga tgatccaatt     600
agtagtgatc aatccaggtt cggatggttc gggaacaagg aaatctcaga tattgaagtg     660
caagaccctg agggattcaa catgattctg ggtaccatcc tagcccaaat ttgggtcttg     720
ctcgcaaagg cggttacggc cccagacacg gcagctgatt cggagctaag aaggtggata     780
aagtacaccc aacaaagaag ggtagttggt gaatttagat tggagagaaa atggttggat     840
gtggtgagga acaggattgc cgaggacctc tccttacgcc gattcatggt cgctctaatc     900
ctggatatca agagaacacc cggaaacaaa cccaggattg ctgaaatgat atgtgacatt     960
gatacatata tcgtagaggc aggattagcc agttttatcc tgactattaa gtttgggata    1020
gaaactatgt atcctgctct tggactgcat gaatttgctg gtgagttatc cacacttgag    1080
tccttgatga acctttacca gcaaatgggg gaaactgcac cctacatggt aatcctggag    1140
aactcaattc agaacaagtt cagtgcagga tcataccctc tgctctggag ctatgccatg    1200
ggagtaggag tggaacttga aaactccatg ggaggtttga actttggccg atcttacttt    1260
gatccagcat attttagatt agggcaagag atggtaagga ggtcagctgg aaaggtcagt    1320
tccacattgg catctgaact cggtatcact gccgaggatg caaggcttgt ttcagagatt    1380
gcaatgcata ctactgagga caagatcagt agagcggttg gacccagaca agcccaagta    1440
tcatttctac acggtgatca aagtgagaat gagctaccga gattgggggg caaggaagat    1500
aggagggtca aacagagtcg aggagaagcc agggagagct acagagaaac cgggcccagc    1560
agagcaagtg atgcgagagc tgcccatctt ccaaccggca caccccctaga cattgacact    1620
gcaacggagt ccagccaaga tccgcaggac agtcgaaggt cagctgacgc cctgcttagg    1680
ctgcaagcca tggcaggaat ctcggaagaa caaggctcag acacggacac ccctatagtg    1740
tacaatgaca gaaatcttct agactaggtg cgagaggccg agggccagaa caacatccgc    1800
ctaccatcca tcattgttat aaaaaactta ggaaccaggt ccacacagcc gccagcccat    1860
caaccatcca ctcccacgat tggagccaat ggcagaagag caggcacgcc atgtcaaaaa    1920
cggactggaa tgcatccggg ctctcaaggc cgagcccatc ggctcactgg ccatcgagga    1980
agctatggca gcatggtcag aaatatcaga caacccagga caggagcgag ccacctgcag    2040
ggaagagaag gcaggcagtt cgggtctcag caaaccatgc ctctcagcaa ttggatcaac    2100
tgaaggcggt gcacctcgca tccgcggtca gggacctgga gagagcgatg acgacgctga    2160
aactttggga atccccccaa gaaatctcca ggcatcaagc actgggttac agtgttatta    2220
cgtttatgat cacagcggtg aagcggttaa gggaatccaa gatgctgact ctatcatggt    2280
tcaatcaggc cttgatggtg atagcaccct ctcaggagga gacaatgaat ctgaaaacag    2340
```

```
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac gatggagttc   3540
atcccaaccc aaacttttta caataggagg taccagcctc gaccctggac tccgcgccct   3600
actatccaag tcatcaggcc cagaccgcgc cctcagaggc aagctgggca acttgcccag   3660
ctgatctcag cagttaataa actgacaatg agagcggtac cccaacagaa gccacgcagg   3720
aatcggaaga ataagaagca aaagcaaaaa caacaggcgc cacaaaacaa cacaaatcaa   3780
aagaagcagc cacctaaaaa gaaaccggct caaaagaaaa agaagccggg ccgcagagag   3840
aggatgtgca tgaaaatcga aaatgattgt attttcgaag tcaagcacga aggtaaggta   3900
acaggttacg cgtgcctggt gggggacaaa gtaatgaaac cagcacacgt caagggcacc   3960
atcgataacg cggacctggc caaactggcc tttaagcggt catctaagta tgaccttgaa   4020
tgcgctcaga tacccgtgca catgaagtcc gacgcttcga agttcaccca tgagaaaccg   4080
gaggggtact acaactggca ccacggagca gtacagtact caggaggccg gttcaccatc   4140
cctacaggtg ctggcaaacc aggggacagc ggcagaccga tcttcgacaa caagggacgc   4200
gtggtggcca tagtcttagg aggagctaat gaaggagccc gtacagccct ctcggtggtg   4260
acctggaata aagacattgt cactaaaatc acccccgagg gggccgaaga gtggagtctt   4320
gccatcccag ttatgtgcct gttggcaaac accacgttcc catgctccca gccaccttgc   4380
acgccctgct gctacgagaa ggaaccggag gaaaccctac gcatgcttga ggacaacgtc   4440
atgagacctg ggtactatca gctgctacaa gcatccttaa catgttctcc ccaccgccag   4500
cgacgcagca ccaaggacaa cttcaatgtc tataaagcca caagaccata cttagctcac   4560
tgtcccgact gtggagaagg gcactcgtgc catagtcccg tagcactaga acgcatcaga   4620
aatgaagcga cagacgggac gctgaaaatc caggtctcct tgcaaatcgg aataaagacg   4680
gatgacagcc acgattggac caagctgcgt tatatggaca accacatgcc agcagacgca   4740
```

gagagggcgg ggctatttgt aagaacatca gcaccgtgta cgattactgg aacaatggga 4800
cacttcatcc tggcccgatg tcctaaaggc gaaactctga cggtgggatt cactgacagt 4860
aggaagatta gtcactcatg tacgcaccca tttcaccacg accctcctgt gataggtcgg 4920
gagaaattcc attcccgacc gcagcacggt aaagagctac cttgcagcac ctacgtgcag 4980
agcaccgccg caactaccga ggagatagag gtacacatgc ccccagacac ccctgatcgc 5040
acattaatgt cacaacagtc cggcaacgta aagatcacag tcaatggcca gacggtgcgg 5100
tacaagtgta attgcggtgg ctcaaatgaa ggactaacaa ctacagacaa agtgattaat 5160
aactgcaagg ttgatcaatg tcatgccgcg gtcaccaatc acaaaaagtg gcagtataac 5220
tcccctctgg tcccgcgtaa tgctgaactt ggggaccgga aaggaaaaat tcacatcccg 5280
tttccgctgg caaatgtaac atgcagggtg cctaaagcaa ggaaccccac cgtgacgtat 5340
ggcaaaaacc aagtcatcat gctactgtat cctgaccacc caacactcct gtcctaccgg 5400
aatatgggag aagaaccaaa ctatcaagaa gagtgggtga tgcataagaa ggaagtcgtg 5460
ctaaccgtgc cgactgaagg gctcgaggtc acgtggggca acaacgagcc gtataagtat 5520
tggccgcagt tatctacaaa cggtacagcc catggccacc cgcacgagat aattctgtat 5580
tattatgagc tgtaccccac tatgactgta gtagttgtgt cagtggccac gttcatactc 5640
ctgtcgatgg tgggtatggc agcggggatg tgcatgtgtg cacgacgcag atgcatcaca 5700
ccgtatgaac tgacaccagg agctaccgtc ccattcctgc ttagcctaat atgctgcatc 5760
agaacagcta aagcggccac ataccaagag gctgcgatat acctgtggaa cgagcagcaa 5820
cctttgtttt ggctacaagc ccttattccg ctggcagccc tgattgttct atgcaactgt 5880
ctgagactct taccatgctg ctgtaaaacg ttggcttttt tagccgtaat gagcgtcggt 5940
gcccacactg tgagcgctta cgaacacgta acagtgatcc cgaacacggt gggagtaccg 6000
tataagactc tagtcaatag acctggctac agccccatgg tattggagat ggaactactg 6060
tcagtcactt tggagccaac actatcgctt gattacatca cgtgcgagta caaaaccgtc 6120
atcccgtctc cttacgtgaa gtgctgcggt acagcagagt gcaaggacaa aaacctacct 6180
gactacagct gtaaggtctt caccggcgtc tacccattta tgtggggcgg cgcctactgc 6240
ttctgcgacg ctgaaaacac gcagttgagc gaagcacacg tggagaagtc cgaatcatgc 6300
aaaacagaat ttgcatcagc atacagggct cataccgcat ctgcatcagc taagctccgc 6360
gtcctttacc aaggaaataa catcactgta actgcctatg caaacggcga ccatgccgtc 6420
acagttaagg acgccaaatt cattgtgggg ccaatgtctt cagcctggac acctttcgac 6480
aacaaaattg tggtgtacaa aggtgacgtc tataacatgg actacccgcc cttcggcgca 6540
ggaagaccag gacaatttgg cgatatccaa agtcgcacac ctgagagtaa agacgtctat 6600
gctaatacac aactggtact gcagagaccg gctgtgggta cggtacacgt gccatactct 6660
caggcaccat ctggctttaa gtattggcta aaagaacgcg gggcgtcgct gcagcacaca 6720
gcaccatttg gctgccaaat agcaacaaac ccggtaagag cggtgaactg cgccgtaggg 6780
aacatgccca tctccatcga cataccggaa gcggccttca ctagggtcgt cgacgcgccc 6840
tctttaacgg acatgtcgtg cgaggtacca gcctgcaccc attcctcaga ctttgggggc 6900
gtcgccatta ttaaatatgc agccagcaag aaaggcaagt gtgcggtgca ttcgatgact 6960
aacgccgtca ctattcggga agctgagata gaagttgaag ggaattctca gctgcaaatc 7020
tctttctcga cggccttagc cagcgccgaa ttccgcgtac aagtctgttc tacacaagta 7080

```
cactgtgcag ccgagtgcca ccccccgaag gaccacatag tcaactaccc ggcgtcacat   7140
accaccctcg gggtccagga catctccgct acggcgatgt catgggtgca gaagatcacg   7200
ggaggtgtgg gactggttgt tgctgttgcc gcactgattc taatcgtggt gctatgcgtg   7260
tcgttcagca ggcactaata ggcgcgcagc gcttagacgt ctcgcgatcg atactagtac   7320
aacctaaatc cattataaaa aacttaggag caaagtgatt gcctcccaag gtccacaatg   7380
acagagacct acgacttcga caagtcggca tgggacatca aagggtcgat cgctccgata   7440
caacccacca cctacagtga tggcaggctg gtgccccagg tcagagtcat agatcctggt   7500
ctaggcgaca ggaaggatga atgctttatg tacatgtttc tgctgggggt tgttgaggac   7560
agcgattccc tagggcctcc aatcgggcga gcatttgggt tcctgccctt aggtgttggc   7620
agatccacag caaagcccga aaaactcctc aaagaggcca ctgagcttga catagttgtt   7680
agacgtacag cagggctcaa tgaaaaactg gtgttctaca acaacacccc actaactctc   7740
ctcacacctt ggagaaaggt cctaacaaca gggagtgtct tcaacgcaaa ccaagtgtgc   7800
aatgcggtta atctgatacc gctcgatacc ccgcagaggt tccgtgttgt ttatatgagc   7860
atcacccgtc tttcggataa cgggtattac accgttccta gaagaatgct ggaattcaga   7920
tcggtcaatg cagtggcctt caacctgctg gtgaccctta ggattgacaa ggcgataggc   7980
cctgggaaga tcatcgacaa tacagagcaa cttcctgagg caacatttat ggtccacatc   8040
gggaacttca ggagaaagaa gagtgaagtc tactctgccg attattgcaa aatgaaaatc   8100
gaaaagatgg gcctggtttt tgcacttggt gggatagggg gcaccagtct tcacattaga   8160
agcacaggca aaatgagcaa gactctccat gcacaactcg ggttcaagaa gaccttatgt   8220
tacccgctga tggatatcaa tgaagacctt aatcgattac tctggaggag cagatgcaag   8280
atagtaagaa tccaggcagt tttgcagcca tcagttcctc aagaattccg catttacgac   8340
gacgtgatca taaatgatga ccaaggacta ttcaaagttc tgtagaccgt agtgcccagc   8400
aatgcccgaa aacgaccccc ctcacaatga cagccagaag gcccggacaa aaaagccccc   8460
tccgaaagac tccacggacc aagcgagagg ccagccagca gccgacggca agcgcgaaca   8520
ccaggcggcc ccagcacaga acagccctga cacaaggcca ccaccagcca ccccaatctg   8580
catcctcctc gtgggacccc cgaggaccaa cccccaaggc tgcccccgat ccaaaccacc   8640
aaccgcatcc ccaccacccc cgggaaagaa acccccagca attggaaggc ccctccccct   8700
cttcctcaac acaagaactc cacaaccgaa ccgcacaagc gaccgaggtg acccaaccgc   8760
aggcatccga ctccctagac agatcctctc tccccggcaa actaaacaaa acttagggcc   8820
aaggaacata cacacccaac agaacccaga ccccggccca cggcgccgcg cccccaaccc   8880
ccgacaacca gagggagccc ccaaccaatc ccgccggctc cccggtgcc cacaggcagg   8940
gacaccaacc cccgaacaga cccagcaccc aaccatcgac aatccaagac ggggggggccc   9000
ccccaaaaaa aggcccccag gggccgacag ccagcaccgc gaggaagccc acccacccca   9060
cacacgacca cggcaaccaa accagaaccc agaccaccct gggccaccag ctcccagact   9120
cggccatcac cccgcagaaa ggaaaggcca caacccgcgc accccagccc cgatccggcg   9180
gggagccacc caacccgaac cagcacccaa gagcgatccc cgaaggaccc ccgaaccgca   9240
aaggacatca gtatcccaca gcctctccaa gtcccccggt ctcctcctct tctcgaaggg   9300
accaaaagat caatccacca cacccgacga cactcaactc cccaccccta aaggagacac   9360
cgggaatccc agaatcaaga ctcatccaat gtccatcatg ggtctcaagg tgaacgtctc   9420
tgccatattc atggcagtac tgttaactct ccaaacaccc accggtcaaa tccattgggg   9480
```

-continued

```
caatctctct aagatagggg tggtaggaat aggaagtgca agctacaaag ttatgactcg   9540
ttccagccat caatcattag tcataaaatt aatgcccaat ataactctcc tcaataactg   9600
cacgagggta gagattgcag aatacaggag actactgaga acagttttgg aaccaattag   9660
agatgcactt aatgcaatga cccagaatat aagaccggtt cagagtgtag cttcaagtag   9720
gagacacaag agatttgcgg gagtagtcct ggcaggtgcg gccctaggcg ttgccacagc   9780
tgctcagata acagccggca ttgcacttca ccagtccatg ctgaactctc aagccatcga   9840
caatctgaga gcgagcctgg aaactactaa tcaggcaatt gagacaatca gacaagcagg   9900
gcaggagatg atattggctg ttcagggtgt ccaagactac atcaataatg agctgatacc   9960
gtctatgaac caactatctt gtgatttaat cggccagaag ctcgggctca aattgctcag  10020
atactataca gaaatcctgt cattatttgg ccccagttta cgggacccca tatctgcgga  10080
gatatctatc caggctttga gctatgcgct tggaggagac atcaataagg tgttagaaaa  10140
gctcggatac agtggaggtg atttactggg catcttagag agcggaggaa taaaggcccg  10200
gataactcac gtcgacacag agtcctactt cattgtcctc agtatagcct atccgacgct  10260
gtccgagatt aagggggtga ttgtccaccg gctagagggg gtctcgtaca acataggctc  10320
tcaagagtgg tataccactg tgcccaagta tgttgcaacc caagggtacc ttatctcgaa  10380
ttttgatgag tcatcgtgta ctttcatgcc agaggggact gtgtgcagcc aaaatgcctt  10440
gtacccgatg agtcctctgc tccaagaatg cctccggggg tacaccaagt cctgtgctcg  10500
tacactcgta tccgggtctt ttgggaaccg gttcatttta tcacaaggga acctaatagc  10560
caattgtgca tcaatccttt gcaagtgtta cacaacagga acgatcatta atcaagaccc  10620
tgacaagatc ctaacataca ttgctgccga tcactgcccg gtagtcgagg tgaacggcgt  10680
gaccatccaa gtcgggagca ggaggtatcc agacgctgtg tacttgcaca gaattgacct  10740
cggtcctccc atatcattgg agaggttgga cgtagggaca aatctgggga atgcaattgc  10800
taagttggag gatgccaagg aattgttgga gtcatcggac cagatattga ggagtatgaa  10860
aggtttatcg agcactagca tagtctacat cctgattgca gtgtgtcttg gagggttgat  10920
agggatcccc gctttaatat gttgctgcag ggggcgttgt aacaaaaagg gagaacaagt  10980
tggtatgtca agaccaggcc taaagcctga tcttacggga acatcaaaat cctatgtaag  11040
gtcgctctga tcctctacaa ctcttgaaac acaaatgtcc cacaagtctc ctcttcgtca  11100
tcaagcaacc accgcaccca gcatcaagcc cacctgaaat tatctccggc ttccctctgg  11160
ccgaacaata tcggtagtta atcaaaactt agggtgcaag atcatccaca atgtcaccac  11220
aacgagaccg gataaatgcc ttctacaaag ataaccccca tcccaaggga agtaggatag  11280
tcattaacag agaacatctt atgattgata gaccttatgt tttgctggct gttctgtttg  11340
tcatgtttct gagcttgatc gggttgctag ccattgcagg cattagactt catcgggcag  11400
ccatctacac cgcagagatc cataaaagcc tcagcaccaa tctagatgta actaactcaa  11460
tcgagcatca ggtcaaggac gtgctgacac cactcttcaa aatcatcggt gatgaagtgg  11520
gcctgaggac acctcagaga ttcactgacc tagtgaaatt aatctctgac aagattaaat  11580
tccttaatcc ggatagggag tacgacttca gagatctcac ttggtgtatc aacccgccag  11640
agagaatcaa attggattat gatcaatact gtgcagatgt ggctgctgaa gagctcatga  11700
atgcattggt gaactcaact ctactggaga ccagaacaac caatcagttc ctagctgtct  11760
caaagggaaa ctgctcaggg cccactacaa tcagaggtca attctcaaac atgtcgctgt  11820
```

```
ccctgttaga cttgtattta ggtcgaggtt acaatgtgtc atctatagtc actatgacat  11880
cccagggaat gtatggggga acttacctag tggaaaagcc taatctgagc agcaaaaggt  11940
cagagttgtc acaactgagc atgtaccgag tgtttgaagt aggtgttatc agaaatccgg  12000
gtttgggggc tccggtgttc catatgacaa actatcttga gcaaccagtc agtaatgatc  12060
tcagcaactg tatggtggct ttgggggagc tcaaactcgc agccctttgt cacggggaag  12120
attctatcac aattccctat cagggatcag ggaaaggtgt cagcttccag ctcgtcaagc  12180
taggtgtctg gaaatcccca accgacatgc aatcctgggt ccccttatca acggatgatc  12240
cagtgataga caggctttac ctctcatctc acagaggtgt tatcgctgac aatcaagcaa  12300
aatgggctgt cccgacaaca cgaacagatg acaagttgcg aatggagaca tgcttccaac  12360
aggcgtgtaa gggtaaaatc caagcactct gcgagaatcc cgagtgggca ccattgaagg  12420
ataacaggat tccttcatac ggggtcttgt ctgttgatct gagtctgaca gttgagctta  12480
aaatcaaaat tgcttcggga ttcgggccat tgatcacaca cggttcaggg atggacctat  12540
acaaatccaa ccacaacaat gtgtattggc tgactatccc gccaatgaag aacctagcct  12600
taggtgtaat caacacattg gagtggatac cgagattcaa ggttagtccc tacctcttca  12660
ctgtcccaat taaggaagca ggcgaagact gccatgcccc aacataccta cctgcggagg  12720
tggatggtga tgtcaaactc agttccaatc tggtgattct acctggtcaa gatctccaat  12780
atgttttggc aacctacgat acttccaggg ttgaacatgc tgtggtttat tacgtttaca  12840
gcccaagccg ctcattttct tacttttatc cttttaggtt gcctataaag ggggtcccca  12900
tcgaattaca agtggaatgc ttcacatggg accaaaaact ctggtgccgt cacttctgtg  12960
tgcttgcgga ctcagaatct ggtggacata tcactcactc tgggatggtg ggcatgggag  13020
tcagctgcac agtcacccgg gaagatggaa ccaatcgcag atagggctgc tagtgaacca  13080
atcacatgat gtcacccaga catcaggcat acccactagt gtgaaataga catcagaatt  13140
aagaaaaacg tagggtccaa gtggttcccc gttatggact cgctatctgt caaccagatc  13200
ttataccctg aagttcacct agatagcccg atagttacca ataagatagt agccatcctg  13260
gagtatgctc gagtccctca cgcttacagc ctggaggacc ctacactgtg tcagaacatc  13320
aagcaccgcc taaaaaacgg attttccaac caaatgatta taaacaatgt ggaagttggg  13380
aatgtcatca agtccaagct taggagttat ccggcccact ctcatattcc atatccaaat  13440
tgtaatcagg atttatttaa catagaagac aaagagtcaa cgaggaagat ccgtgaactc  13500
ctcaaaaagg ggaattcgct gtactccaaa gtcagtgata aggttttcca atgcttaagg  13560
gacactaact cacggcttgg cctaggctcc gaattgaggg aggacatcaa ggagaaagtt  13620
attaacttgg gagtttacat gcacagctcc cagtggtttg agccctttct gttttggttt  13680
acagtcaaga ctgagatgag gtcagtgatt aaatcacaaa cccatacttg ccataggagg  13740
agacacacac ctgtattctt cactggtagt tcagttgagt tgctaatctc tcgtgacctt  13800
gttgctataa tcagtaaaga gtctcaacat gtatattacc tgacatttga actggttttg  13860
atgtattgtg atgtcataga ggggaggtta atgacagaga ccgctatgac tattgatgct  13920
aggtatacag agcttctagg aagagtcaga tacatgtgga aactgataga tggtttcttc  13980
cctgcactcg ggaatccaac ttatcaaatt gtagccatgc tggagcctct ttcacttgct  14040
tacctgcagc tgagggatat aacagtagaa ctcagaggtg ctttccttaa ccactgcttt  14100
actgaaatac atgatgttct tgaccaaaac gggttttctg atgaaggtac ttatcatgag  14160
ttaactgaag ctctagatta cattttcata actgatgaca tacatctgac aggggagatt  14220
```

```
ttctcatttt tcagaagttt cggccacccc agacttgaag cagtaacggc tgctgaaaat  14280
gttaggaaat acatgaatca gcctaaagtc attgtgtatg agactctgat gaaaggtcat  14340
gccatatttt gtggaatcat aatcaacggc tatcgtgaca ggcacggagg cagttggcca  14400
ccgctgaccc tccccctgca tgctgcagac acaatccgga atgctcaagc ttcaggtgaa  14460
gggttaacac atgagcagtg cgttgataac tggaaatctt ttgctggagt gaaatttggc  14520
tgctttatgc ctcttagcct ggatagtgat ctgacaatgt acctaaagga caaggcactt  14580
gctgctctcc aaagggaatg ggattcagtt tacccgaaag agttcctgcg ttacgaccct  14640
cccaagggaa ccgggtcacg gaggcttgta gatgttttcc ttaatgattc gagctttgac  14700
ccatatgatg tgataatgta tgttgtaagt ggagcttacc tccatgaccc tgagttcaac  14760
ctgtcttaca gcctgaaaga aaaggagatc aaggaaacag gtagactttt tgctaaaatg  14820
acttacaaaa tgagggcatg ccaagtgatt gctgaaaatc taatctcaaa cgggattggc  14880
aaatatttta aggacaatgg gatggccaag gatgagcacg atttgactaa ggcactccac  14940
actctagctg tctcaggagt ccccaaagat ctcaaagaaa gtcacagggg ggggccagtc  15000
ttaaaaacct actcccgaag cccagtccac acaagtacca ggaacgtgag agcagcaaaa  15060
gggtttatag ggttccctca agtaattcgg caggaccaag acactgatca tccggagaat  15120
atggaagctt acgagacagt cagtgcattt atcacgactg atctcaagaa gtactgcctt  15180
aattggagat atgagaccat cagcttgttt gcacagaggc taaatgagat ttacggattg  15240
ccctcatttt tccagtggct gcataagagg cttgagacct ctgtcctgta tgtaagtgac  15300
cctcattgcc cccccgacct tgacgcccat atcccgttat ataaagtccc caatgatcaa  15360
atcttcatta agtaccctat gggaggtata gaagggtatt gtcagaagct gtggaccatc  15420
agcaccattc cctatctata cctggctgct tatgagagcg gagtaaggat tgcttcgtta  15480
gtgcaagggg acaatcagac catagccgta acaaaaaggg tacccagcac atggccctac  15540
aaccttaaga aacgggaagc tgctagagta actagagatt actttgtaat tcttaggcaa  15600
aggctacatg atattggcca tcacctcaag gcaaatgaga caattgtttc atcacatttt  15660
tttgtctatt caaaaggaat atattatgat gggctacttg tgtcccaatc actcaagagc  15720
atcgcaagat gtgtattctg gtcagagact atagttgatg aaacaagggc agcatgcagt  15780
aatattgcta caacaatggc taaaagcatc gagagaggtt atgaccgtta ccttgcatat  15840
tccctgaacg tcctaaaagt gatacagcaa attctgatct ctcttggctt cacaatcaat  15900
tcaaccatga cccgggatgt agtcataccc ctcctcacaa acaacgacct cttaataagg  15960
atggcactgt tgcccgctcc tattgggggg atgaattatc tgaatatgag caggctgttt  16020
gtcagaaaca tcggtgatcc agtaacatca tcaattgctg atctcaagag aatgattctc  16080
gcctcactaa tgcctgaaga gaccctccat caagtaatga cacaacaacc gggggactct  16140
tcattcctag actgggctag cgacccttac tcagcaaatc ttgtatgtgt ccagagcatc  16200
actagactcc tcaagaacat aactgcaagg tttgtcctga tccatagtcc aaacccaatg  16260
ttaaaaggat tattccatga tgacagtaaa gaagaggacg agggactggc ggcattcctc  16320
atggacaggc atattatagt acctagggca gctcatgaaa tcctggatca tagtgtcaca  16380
ggggcaagag agtctattgc aggcatgctg gataccacaa aaggcttgat tcgagccagc  16440
atgaggaagg gggggttaac ctctcgagtg ataaccagat tgtccaatta tgactatgaa  16500
caattcagag cagggatggt gctattgaca ggaagaaaga gaaatgtcct cattgacaaa  16560
```

```
gagtcatgtt cagtgcagct ggcgagagct ctaagaagcc atatgtgggc gaggctagct  16620
cgaggacggc ctatttacgg ccttgaggtc cctgatgtac tagaatctat gcgaggccac  16680
cttattcggc gtcatgagac atgtgtcatc tgcgagtgtg gatcagtcaa ctacggatgg  16740
ttttttgtcc cctcgggttg ccaactggat gatattgaca aggaaacatc atccttgaga  16800
gtcccatata ttggttctac cactgatgag agaacagaca tgaagcttgc cttcgtaaga  16860
gccccaagtc gatccttgcg atctgctgtt agaatagcaa cagtgtactc atgggcttac  16920
ggtgatgatg atagctcttg gaacgaagcc tggttgttgg ctaggcaaag ggccaatgtg  16980
agcctggagg agctaagggt gatcactccc atctcaactt cgactaattt agcgcatagg  17040
ttgagggatc gtagcactca agtgaaatac tcaggtacat cccttgtccg agtggcgagg  17100
tataccacaa tctccaacga caatctctca tttgtcatat cagataagaa ggttgatact  17160
aactttatat accaacaagg aatgcttcta gggttgggtg ttttagaaac attgtttcga  17220
ctcgagaaag ataccggatc atctaacacg gtattacatc ttcacgtcga aacagattgt  17280
tgcgtgatcc cgatgataga tcatcccagg atacccagct cccgcaagct agagctgagg  17340
gcagagctat gtaccaaccc attgatatat gataatgcac ctttaattga cagagatgca  17400
acaaggctat acacccagag ccataggagg caccttgtgg aatttgttac atggtccaca  17460
ccccaactat atcacatttt agctaagtcc acagcactat ctatgattga cctggtaaca  17520
aaatttgaga aggaccatat gaatgaaatt tcagctctca taggggatga cgatatcaat  17580
agtttcataa ctgagtttct gctcatagag ccaagattat tcactatcta cttgggccag  17640
tgtgcggcca tcaattgggc atttgatgta cattatcata gaccatcagg gaaatatcag  17700
atgggtgagc tgttgtcatc gttcctttct agaatgagca aaggagtgtt taaggtgctt  17760
gtcaatgctc taagccaccc aaagatctac aagaaattct ggcattgtgg tattatagag  17820
cctatccatg gtccttcact tgatgctcaa aacttgcaca caactgtgtg caacatggtt  17880
tacacatgct atatgaccta cctcgacctg ttgttgaatg aagagttaga agagttcaca  17940
tttctcttgt gtgaaagcga cgaggatgta gtaccggaca gattcgacaa catccaggca  18000
aaacacttat gtgttctggc agatttgtac tgtcaaccag ggacctgccc accaattcga  18060
ggtctaagac cggtagagaa atgtgcagtt ctaaccgacc atatcaaggc agaggctatg  18120
ttatctccag caggatcttc gtggaacata aatccaatta ttgtagacca ttactcatgc  18180
tctctgactt atctccggcg aggatcgatc aaacagataa gattgagagt tgatccagga  18240
ttcattttcg acgccctcgc tgaggtaaat gtcagtcagc caaagatcgg cagcaacaac  18300
atctcaaata tgagcatcaa ggctttcaga cccccacacg atgatgttgc aaaattgctc  18360
aaagatatca acacaagcaa gcacaatctt cccatttcag gggcaatct cgccaattat  18420
gaaatccatg ctttccgcag aatcgggttg aactcatctg cttgctacaa agctgttgag  18480
atatcaacat taattaggag atgccttgag ccaggggagg acggcttgtt cttgggtgag  18540
ggatcgggtt ctatgttgat cacttataaa gagatactta aactaaacaa gtgcttctat  18600
aatagtgggg tttccgccaa ttctagatct ggtcaaaggg aattagcacc ctatccctcc  18660
gaagttggcc ttgtcgaaca cagaatggga gtaggtaata ttgtcaaagt gctctttaac  18720
gggaggcccg aagtcacgtg ggtaggcagt gtagattgct tcaatttcat agttagtaat  18780
atccctacct ctagtgtggg gtttatccat tcagatatag agaccttgcc tgacaaagat  18840
actatagaga agctagagga attggcagcc atcttatcga tggctctgct cctgggcaaa  18900
ataggatcaa tactggtgat taagcttatg cctttcagcg gggattttgt tcagggattt  18960
```

```
ataagttatg tagggtctca ttatagagaa gtgaaccttg tataccctag atacagcaac  19020
ttcatctcta ctgaatctta tttggttatg acagatctca aggctaaccg gctaatgaat  19080
cctgaaaaga ttaagcagca gataattgaa tcatctgtga ggacttcacc tggacttata  19140
ggtcacatcc tatccattaa gcaactaagc tgcatacaag caattgtggg agacgcagtt  19200
agtagaggtg atatcaatcc tactctgaaa aaacttacac ctatagagca ggtgctgatc  19260
aattgcgggt tggcaattaa cggacctaag ctgtgcaaag aattgatcca ccatgatgtt  19320
gcctcagggc aagatggatt gcttaattct atactcatcc tctacaggga gttggcaaga  19380
ttcaaagaca accaaagaag tcaacaaggg atgttccacg cttaccccgt attggtaagt  19440
agcaggcaac gagaacttat atctaggatc acccgcaaat tctgggggca cattcttctt  19500
tactccggga acaaaaagtt gataaataag tttatccaga atctcaagtc cggctatctg  19560
atactagact tacaccagaa tatcttcgtt aagaatctat ccaagtcaga gaaacagatt  19620
attatgacgg ggggtttgaa acgtgagtgg gtttttaagg taacagtcaa ggagaccaaa  19680
gaatggtata agttagtcgg atacagtgcc ctgattaagg actaattggt tgaactccgg  19740
aaccctaatc ctgccctagg tggttaggca ttatttgcaa tatattaaag aaaactttga  19800
aaatacgaag tttctattcc cagctttgtc tggtggccgg catggtccca gcctcctcgc  19860
tggcgccggc tgggcaacat tccgagggga ccgtcccctc ggtaatggcg aatgggacgc  19920
ggccgatccg gctgctaaca aagcccgaaa ggaagctgag ttggctgctg ccaccgctga  19980
gcaataacta gcataacccc ttggggcctc taaacgggtc ttgaggggtt ttttgctgaa  20040
aggaggaact atatccggat gcggccgcgg gccctatggt acccagcttt tgttcccttt  20100
agtgagggtt aattccgagc ttggcgtaat catggtcata gctgtttcct gtgtgaaatt  20160
gttatccgct cacaattcca cacaacatag gagccggaag cataaagtgt aaagcctggg  20220
gtgcctaatg agtgaggtaa ctcacattaa ttgcgttgcg ctcactgccc gctttccagt  20280
cgggaaacct gtcgtgccag ctgcattaat gaatcggcca acgcgcgggg agaggcggtt  20340
tgcgtattgg gcgctcttcc gcttcctcgc tcactgactc gctgcgctcg gtcgttcggc  20400
tgcggcgagc ggtatcagct cactcaaagg cggtaatacg gttatccaca gaatcagggg  20460
ataacgcagg aaagaacatg tgagcaaaag gccagcaaaa ggccaggaac cgtaaaaagg  20520
ccgcgttgct ggcgtttttc cataggctcg gcccccctga cgagcatcac aaaaatcgac  20580
gctcaagtca gaggtggcga aacccgacag gactataaag ataccaggcg tttccccctg  20640
gaagctccct cgtgcgctct cctgttccga ccctgccgct taccggatac ctgtccgcct  20700
ttctcccttc gggaagcgtg gcgctttctc aatgctcacg ctgtaggtat ctcagttcgg  20760
tgtaggtcgt tcgctccaag ctgggctgtg tgcacgaacc ccccgttcag cccgaccgct  20820
gcgccttatc cggtaactat cgtcttgagt ccaacccggt aagacacgac ttatcgccac  20880
tggcagcagc cactggtaac aggattagca gagcgaggta tgtaggcggt gctacagagt  20940
tcttgaagtg gtggcctaac tacggctaca ctagaaggac agtatttggt atctgcgctc  21000
tgctgaagcc agttaccttc ggaaaaagag ttggtagctc ttgatccggc aaacaaacca  21060
ccgctggtag cggtggtttt tttgtttgca agcagcagat tacgcgcaga aaaaaaggat  21120
ctcaagaaga tcctttgatc ttttctacgg ggtctgacgc tcagtggaac gaaaactcac  21180
gttaagggat tttggtcatg agattatcaa aaaggatctt cacctagatc cttttaaatt  21240
aaaaatgaag ttttaaatca atctaaagta tatatgagta aacttggtct gacagttacc  21300
```

```
aatgcttaat cagtgaggca cctatctcag cgatctgtct atttcgttca tccatagttg  21360
cctgactgcc cgtcgtgtag ataactacga tacgggaggg cttaccatct ggccccagtg  21420
ctgcaatgat accgcgagac ccacgctcac cggctccaga tttatcagca ataaaccagc  21480
cagccggaag ggccgagcgc agaagtggtc ctgcaacttt atccgcctcc atccagtcta  21540
ttaattgttg ccgggaagct agagtaagta gttcgccagt taatagtttg cgcaacgttg  21600
ttgccattgc tacaggcatc gtggtgtcac gctcgtcgtt tggtatggct tcattcagct  21660
ccggttccca acgatcaagg cgagttacat gatcccccat gttgtgaaaa aaagcggtta  21720
gctccttcgg tcctccgatc gttgtcagaa gtaagttggc cgcagtgtta tcactcatgc  21780
ttatggcagc actgcataat tctcttactg tcatgccatc cgtaagatgc ttttctgtga  21840
ctggtgagta ctcaaccaag tcattctgag aatagtgtat gcggcgaccg agttgctctt  21900
gcccggcgtc aatacgggat aataccgcgc cacatagcag aactttaaaa gtgctcatca  21960
ttggaaaacg ttcttcgggg cgaaaactct caaggatctt accgctgttg agatccagtt  22020
cgatgtaacc cactcgtgca cccaactgat cttcagcatc ttttactttc accagcgttt  22080
ctgggtgagc aaaaacagga aggcaaaatg ccgcaaaaaa gggaataagg gcgacacgga  22140
aatgttgaat actcatactc ttcctttttc aatattattg aagcatttat cagggttatt  22200
gtctcatgag cggatacata tttgaatgta tttagaaaaa taaacaaata ggggttccgc  22260
gcacatttcc ccgaaaagtg ccacctgaaa ttgtaaacgt taatattttg ttaaaattcg  22320
cgttaaattt ttgttaaatc agctcatttt ttaaccaata ggccgaaatc ggcaaaatcc  22380
cttataaatc aaaagaatag accgagatag ggttgagtgt tgttccagtt tggaacaaga  22440
gtccactatt aaagaacgtg gactccaacg tcaaagggcg aaaaaccgtc tatcagggcg  22500
atggcccact acgtgaacca tcaccctaat caagtttttt ggggtcgagg tgccgtaaag  22560
cactaaatcg gaaccctaaa gggagccccc gatttagagc ttgacgggga aagccggcga  22620
acgtggcgag aaaggaaggg aagaaagcga aaggagcggg cgctagggcg ctggcaagtg  22680
tagcggtcac gctgcgcgta accaccacac ccgccgcgct taatgcgccg ctacagggcg  22740
cgtcccattc gccattcagg ctgcgcaact gttgggaagg gcgatcggtg cgggcctctt  22800
cgctattacg ccagccaccg cggtg                                         22825
```

<210> SEQ ID NO 9
<211> LENGTH: 20661
<212> TYPE: DNA
<213> ORGANISM: artificial sequence
<220> FEATURE:
<223> OTHER INFORMATION: pTM 2ATU MV DVAX1 long

<400> SEQUENCE: 9

```
tccaaccgcg cgcgcggccg ctaatacgac tcactatagg gccaactttg tttggtctga     60
tgagtccgtg aggacgaaac ccggagtccc gggtcaccaa acaaagttgg gtaaggatag    120
ttcaatcaat gatcatcttc tagtgcactt aggattcaag atcctattat cagggacaag    180
agcaggatta gggatatccg agatggccac acttttaagg agcttagcat tgttcaaaag    240
aaacaaggac aaaccaccca ttacatcagg atccggtgga gccatcagag gaatcaaaca    300
cattattata gtaccaatcc ctggagattc ctcaattacc actcgatcca gacttctgga    360
ccggttggtg aggttaattg gaaacccgga tgtgagcggg cccaaactaa caggggcact    420
aataggtata ttatccttat ttgtggagtc tccaggtcaa ttgattcaga ggatcaccga    480
tgaccctgac gttagcataa ggctgttaga ggttgtccag agtgaccagt cacaatctgg    540
```

```
ccttaccttc gcatcaagag gtaccaacat ggaggatgag gcggaccaat acttttcaca    600
tgatgatcca attagtagtg atcaatccag gttcggatgg ttcgggaaca aggaaatctc    660
agatattgaa gtgcaagacc ctgagggatt caacatgatt ctgggtacca tcctagccca    720
aatttgggtc ttgctcgcaa aggcggttac ggccccagac acggcagctg attcggagct    780
aagaaggtgg ataaagtaca cccaacaaag aagggtagtt ggtgaattta gattggagag    840
aaaatggttg gatgtggtga ggaacaggat tgccgaggac ctctccttac gccgattcat    900
ggtcgctcta atcctggata tcaagagaac acccggaaac aaacccagga ttgctgaaat    960
gatatgtgac attgatacat atatcgtaga ggcaggatta gccagtttta tcctgactat   1020
taagtttggg atagaaacta tgtatcctgc tcttggactg catgaatttg ctggtgagtt   1080
atccacactt gagtccttga tgaaccttta ccagcaaatg ggggaaactg caccctacat   1140
ggtaatcctg gagaactcaa ttcagaacaa gttcagtgca ggatcatacc ctctgctctg   1200
gagctatgcc atgggagtag gagtggaact tgaaaactcc atgggaggtt tgaactttgg   1260
ccgatcttac tttgatccag catattttag attagggcaa gagatggtaa ggaggtcagc   1320
tggaaaggtc agttccacat tggcatctga actcggtatc actgccgagg atgcaaggct   1380
tgtttcagag attgcaatgc atactactga ggacaagatc agtagagcgg ttggacccag   1440
acaagcccaa gtatcatttc tacacggtga tcaaagtgag aatgagctac cgagattggg   1500
gggcaaggaa gataggaggg tcaaacagag tcgaggagaa gccagggaga gctacagaga   1560
aaccgggccc agcagagcaa gtgatgcgag agctgcccat cttccaaccg gcacacccct   1620
agacattgac actgcaacgg agtccagcca agatccgcag gacagtcgaa ggtcagctga   1680
cgccctgctt aggctgcaag ccatggcagg aatctcggaa gaacaaggct cagacacgga   1740
cacccctata gtgtacaatg acagaaatct tctagactag gtgcgagagg ccgagggcca   1800
gaacaacatc cgcctaccat ccatcattgt tataaaaaac ttaggaacca ggtccacaca   1860
gccgccagcc catcaaccat ccactcccac gattggagcc aatggcagaa gagcaggcac   1920
gccatgtcaa aaacggactg gaatgcatcc gggctctcaa ggccgagccc atcggctcac   1980
tggccatcga ggaagctatg gcagcatggt cagaaatatc agacaaccca ggacaggagc   2040
gagccacctg cagggaagag aaggcaggca gttcgggtct cagcaaacca tgcctctcag   2100
caattggatc aactgaaggc ggtgcacctc gcatccgcgg tcagggacct ggagagagcg   2160
atgacgacgc tgaaactttg ggaatccccc caagaaatct ccaggcatca agcactgggt   2220
tacagtgtta ttacgtttat gatcacagcg gtgaagcggt taagggaatc caagatgctg   2280
actctatcat ggttcaatca ggccttgatg gtgatagcac cctctcagga ggagacaatg   2340
aatctgaaaa cagcgatgtg gatattggcg aacctgatac cgagggatat gctatcactg   2400
accggggatc tgctcccatc tctatggggt tcagggcttc tgatgttgaa actgcagaag   2460
gaggggagat ccacgagctc ctgagactcc aatccagagg caacaacttt ccgaagcttg   2520
ggaaaactct caatgttcct ccgcccccgg accccggtag ggccagcact tccgggacac   2580
ccattaaaaa gggcacagac gcgagattag cctcatttgg aacggagatc gcgtctttat   2640
tgacaggtgg tgcaacccaa tgtgctcgaa agtcaccctc ggaaccatca gggccaggtg   2700
cacctgcggg gaatgtcccc gagtgtgtga gcaatgccgc actgatacag gagtggacac   2760
ccgaatctgg taccacaatc tccccgagat cccagaataa tgaagaaggg ggagactatt   2820
atgatgatga gctgttctct gatgtccaag atattaaaac agccttggcc aaaatacacg   2880
```

-continued

```
aggataatca gaagataatc tccaagctag aatcactgct gttattgaag ggagaagttg   2940
agtcaattaa gaagcagatc aacaggcaaa atatcagcat atccaccctg gaaggacacc   3000
tctcaagcat catgatcgcc attcctggac ttgggaagga tcccaacgac cccactgcag   3060
atgtcgaaat caatcccgac ttgaaaccca tcataggcag agattcaggc cgagcactgg   3120
ccgaagttct caagaaaccc gttgccagcc gacaactcca aggaatgaca aatggacgga   3180
ccagttccag aggacagctg ctgaaggaat ttcagctaaa gccgatcggg aaaaagatga   3240
gctcagccgt cgggtttgtt cctgacaccg gccctgcatc acgcagtgta atccgctcca   3300
ttataaaatc cagccggcta gaggaggatc ggaagcgtta cctgatgact ctccttgatg   3360
atatcaaagg agccaatgat cttgccaagt tccaccagat gctgatgaag ataataatga   3420
agtagctaca gctcaactta cctgccaacc ccatgccagt cgacccaact agcctaccct   3480
ccatcattgt tataaaaaac ttaggaacca ggtccacaca gccgccagcc catcaacgcg   3540
tacgatgggc atcatattca ttcttcttat gctggttaca ccgtctatgg cggagaaact   3600
tcgaatcaaa ggtatgagct atacgatgtg cagcggcaag ttcaagatcg agaaggaaat   3660
ggctgaaacc cagcacggta caactgtggt caaagtcaaa tatgaggggg ctggcgctcc   3720
ctgtaaagta cccattgaga ttagggacgt caataaagag aaggtggtag gtcgcatcat   3780
ctccagtaca cctttggccg agaacacgaa ctccgtcaca aacatagagt tggaaccccc   3840
gttcggagac tcatacattg tgatcggggt gggcaactct gcactcacac tgcattggtt   3900
caagaaggga agcagtatcg gccgcaggga taagagagac aaactgaaat tgaaaggtat   3960
gtcctatgcc atgtgcacga atactttcgt tctcaagaaa gaagtatctg agactcagca   4020
cggaaccatc ctgatcaaag tcgagtacaa aggagaagac gtgccctgta agatcccatt   4080
cagtaccgag gatggacagg gcaaggccca taacggcagg ctgataaccg ccaaccctgt   4140
ggttacaaag aaggaagagc cagtcaatat cgaagctgag ccaccgttcg gggagagcaa   4200
catagtaatt ggcatagggg ataatgcttt gaagatcaac tggtacaaga aaggaagctc   4260
cattggccga agagataagc gcgacaaact ccagctgaaa ggaatgagct actccatgtg   4320
tactgggaag ttcaagattg tcaaggaaat cgccgaaact cagcatggca ctattgtgat   4380
ccgcgtgcag tatgaaggcg atggtagccc ctgcaagata ccatttgaaa tcaccgattt   4440
ggagaaacgg cacgtcctgg gtcggctcat taccgtgaac ccaatcgtga ccgagaagga   4500
cagtccagtt aatatcgagg ccgagcctcc tttcggcgac agttacatca ttgtaggggt   4560
ggaaccaggg caactgaagc tgaactggtt caagaaaggc agcagtatag gacggcggga   4620
taaacgggac aaactcacac tgaaaggcat gtcatacgtt atgtgcaccg gctcattcaa   4680
actggagaag gaagttgcag agacacagca tgggaccgtg ctcgtgcagg tcaaatacga   4740
gggcaccgac gctccttgca agattccgtt cagtacacag gacgagaaag gcgtgactca   4800
gaacggcaga ttgattacag cgaaccctat cgtgactgac aaggagaagc cagttaacat   4860
cgagactgag ccgcctttcg gagaatcata cattatcgtg ggagccggcg agaaggcact   4920
gaaactcagc tggttcaaga agggcagctc aatcggtcgg agagacaagc ggtctgtcgc   4980
cctcgcaccg cacgtgggcc tgggtctgga aacgaggacc gagacgtgga tgagttccga   5040
aggcgcatgg aagcaaatcc agaaagtgga gacgtgggcc ctcaggcatc cgtaatgagc   5100
gcgcagcgct tagacgtctc gcgatcgata ctagtacaac ctaaatccat tataaaaaac   5160
ttaggagcaa agtgattgcc tcccaaggtc cacaatgaca gagacctacg acttcgacaa   5220
gtcggcatgg gacatcaaag ggtcgatcgc tccgatacaa cccaccacct acagtgatgg   5280
```

```
caggctggtg ccccaggtca gagtcataga tcctggtcta ggcgacagga aggatgaatg   5340
ctttatgtac atgtttctgc tgggggttgt tgaggacagc gattccctag ggcctccaat   5400
cgggcgagca tttgggttcc tgcccttagg tgttggcaga tccacagcaa agcccgaaaa   5460
actcctcaaa gaggccactg agcttgacat agttgttaga cgtacagcag ggctcaatga   5520
aaaactggtg ttctacaaca acaccccact aactctcctc acaccttgga gaaaggtcct   5580
aacaacaggg agtgtcttca acgcaaacca agtgtgcaat gcggttaatc tgataccgct   5640
cgatacccg cagaggttcc gtgttgttta tatgagcatc acccgtcttt cggataacgg   5700
gtattacacc gttcctagaa gaatgctgga attcagatcg gtcaatgcag tggccttcaa   5760
cctgctggtg acccttagga ttgacaaggc gataggccct gggaagatca tcgacaatac   5820
agagcaactt cctgaggcaa catttatggt ccacatcggg aacttcagga gaaagaagag   5880
tgaagtctac tctgccgatt attgcaaaat gaaaatcgaa aagatgggcc tggtttttgc   5940
acttggtggg atagggggca ccagtcttca cattagaagc acaggcaaaa tgagcaagac   6000
tctccatgca caactcgggt tcaagaagac cttatgttac ccgctgatgg atatcaatga   6060
agaccttaat cgattactct ggaggagcag atgcaagata gtaagaatcc aggcagtttt   6120
gcagccatca gttcctcaag aattccgcat ttacgacgac gtgatcataa atgatgacca   6180
aggactattc aaagttctgt agaccgtagt gcccagcaat gcccgaaaac gaccccccctc   6240
acaatgacag ccagaaggcc cggacaaaaa agccccctcc gaaagactcc acggaccaag   6300
cgagaggcca gccagcagcc gacggcaagc gcgaacacca ggcggcccca gcacagaaca   6360
gccctgacac aaggccacca ccagccaccc caatctgcat cctcctcgtg ggacccccga   6420
ggaccaaccc ccaaggctgc ccccgatcca aaccaccaac cgcatcccca ccacccccgg   6480
gaaagaaacc cccagcaatt ggaaggcccc tccccctctt cctcaacaca agaactccac   6540
aaccgaaccg cacaagcgac cgaggtgacc caaccgcagg catccgactc cctagacaga   6600
tcctctctcc ccggcaaact aaacaaaact tagggccaag gaacatacac acccaacaga   6660
acccagaccc cggcccacgg cgccgcgccc ccaacccccg acaaccagag ggagccccca   6720
accaatcccg ccggctcccc cggtgcccac aggcagggac accaaccccc gaacagaccc   6780
agcacccaac catcgacaat ccaagacggg ggggcccccc caaaaaaagg cccccagggg   6840
ccgacagcca gcaccgcgag gaagcccacc caccccacac acgaccacgg caaccaaacc   6900
agaacccaga ccaccctggg ccaccagctc ccagactcgg ccatcacccc gcagaaagga   6960
aaggccacaa cccgcgcacc ccagccccga tccggcgggg agccacccaa cccgaaccag   7020
cacccaagag cgatccccga aggacccccg aaccgcaaag gacatcagta tcccacagcc   7080
tctccaagtc cccggtctc ctcctcttct cgaagggacc aaaagatcaa tccaccacac   7140
ccgacgacac tcaactcccc accctaaag gagacaccgg gaatcccaga atcaagactc   7200
atccaatgtc catcatgggt ctcaaggtga acgtctctgc catattcatg gcagtactgt   7260
taactctcca aacacccacc ggtcaaatcc attggggcaa tctctctaag atagggtgg   7320
taggaatagg aagtgcaagc tacaaagtta tgactcgttc cagccatcaa tcattagtca   7380
taaaattaat gcccaatata actctcctca ataactgcac gagggtagag attgcagaat   7440
acaggagact actgagaaca gttttggaac caattagaga tgcacttaat gcaatgaccc   7500
agaatataag accggttcag agtgtagctt caagtaggag acacaagaga tttgcgggag   7560
tagtcctggc aggtgcggcc ctaggcgttg ccacagctgc tcagataaca gccggcattg   7620
```

-continued

```
cacttcacca gtccatgctg aactctcaag ccatcgacaa tctgagagcg agcctggaaa   7680
ctactaatca ggcaattgag acaatcagac aagcagggca ggagatgata ttggctgttc   7740
agggtgtcca agactacatc aataatgagc tgataccgtc tatgaaccaa ctatcttgtg   7800
atttaatcgg ccagaagctc gggctcaaat tgctcagata ctatacagaa atcctgtcat   7860
tatttggccc cagtttacgg gaccccatat ctgcggagat atctatccag gctttgagct   7920
atgcgcttgg aggagacatc aataaggtgt tagaaaagct cggatacagt ggaggtgatt   7980
tactgggcat cttagagagc ggaggaataa aggcccggat aactcacgtc gacacagagt   8040
cctacttcat tgtcctcagt atagcctatc cgacgctgtc cgagattaag gggtgattg    8100
tccaccggct agagggggtc tcgtacaaca taggctctca agagtggtat accactgtgc   8160
ccaagtatgt tgcaacccaa gggtacctta tctcgaattt tgatgagtca tcgtgtactt   8220
tcatgccaga ggggactgtg tgcagccaaa atgccttgta cccgatgagt cctctgctcc   8280
aagaatgcct ccgggggtac accaagtcct gtgctcgtac actcgtatcc gggtcttttg   8340
ggaaccggtt cattttatca caagggaacc taatagccaa ttgtgcatca atcctttgca   8400
agtgttacac aacaggaacg atcattaatc aagaccctga caagatccta acatacattg   8460
ctgccgatca ctgcccggta gtcgaggtga acggcgtgac catccaagtc gggagcagga   8520
ggtatccaga cgctgtgtac ttgcacagaa ttgacctcgg tcctcccata tcattggaga   8580
ggttggacgt agggacaaat ctggggaatg caattgctaa gttggaggat gccaaggaat   8640
tgttggagtc atcggaccag atattgagga gtatgaaagg tttatcgagc actagcatag   8700
tctacatcct gattgcagtg tgtcttggag ggttgatagg gatccccgct ttaatatgtt   8760
gctgcagggg gcgttgtaac aaaaagggag aacaagttgg tatgtcaaga ccaggcctaa   8820
agcctgatct tacgggaaca tcaaaatcct atgtaaggtc gctctgatcc tctacaactc   8880
ttgaaacaca aatgtcccac aagtctcctc ttcgtcatca agcaaccacc gcacccagca   8940
tcaagcccac ctgaaattat ctccggcttc cctctggccg aacaatatcg gtagttaatc   9000
aaaacttagg gtgcaagatc atccacaatg tcaccacaac gagaccggat aaatgccttc   9060
tacaaagata acccccatcc caagggaagt aggatagtca ttaacagaga acatcttatg   9120
attgatagac cttatgtttt gctggctgtt ctgtttgtca tgtttctgag cttgatcggg   9180
ttgctagcca ttgcaggcat tagacttcat cgggcagcca tctacaccgc agagatccat   9240
aaaagcctca gcaccaatct agatgtaact aactcaatcg agcatcaggt caaggacgtg   9300
ctgacaccac tcttcaaaat catcggtgat gaagtgggcc tgaggacacc tcagagattc   9360
actgacctag tgaaattaat ctctgacaag attaaattcc ttaatccgga tagggagtac   9420
gacttcagag atctcacttg gtgtatcaac ccgccagaga gaatcaaatt ggattatgat   9480
caatactgtg cagatgtggc tgctgaagag ctcatgaatg cattggtgaa ctcaactcta   9540
ctggagacca gaacaaccaa tcagttccta gctgtctcaa agggaaactg ctcagggccc   9600
actacaatca gaggtcaatt ctcaaacatg tcgctgtccc tgttagactt gtatttaggt   9660
cgaggttaca atgtgtcatc tatagtcact atgacatccc agggaatgta tgggggaact   9720
tacctagtgg aaaagcctaa tctgagcagc aaaaggtcag agttgtcaca actgagcatg   9780
taccgagtgt ttgaagtagg tgttatcaga aatccgggtt tgggggctcc ggtgttccat   9840
atgacaaact atcttgagca accagtcagt aatgatctca gcaactgtat ggtggctttg   9900
ggggagctca aactcgcagc cctttgtcac ggggaagatt ctatcacaat tccctatcag   9960
ggatcaggga aaggtgtcag cttccagctc gtcaagctag gtgtctggaa atccccaacc  10020
```

```
gacatgcaat cctgggtccc cttatcaacg gatgatccag tgatagacag gctttacctc  10080
tcatctcaca gaggtgttat cgctgacaat caagcaaaat gggctgtccc gacaacacga  10140
acagatgaca agttgcgaat ggagacatgc ttccaacagg cgtgtaaggg taaaatccaa  10200
gcactctgcg agaatcccga gtgggcacca ttgaaggata acaggattcc ttcatacggg  10260
gtcttgtctg ttgatctgag tctgacagtt gagcttaaaa tcaaaattgc ttcgggattc  10320
gggccattga tcacacacgg ttcagggatg gacctataca aatccaacca caacaatgtg  10380
tattggctga ctatcccgcc aatgaagaac ctagccttag gtgtaatcaa cacattggag  10440
tggataccga gattcaaggt tagtccctac ctcttcactg tcccaattaa ggaagcaggc  10500
gaagactgcc atgccccaac atacctacct gcggaggtgg atggtgatgt caaactcagt  10560
tccaatctgg tgattctacc tggtcaagat ctccaatatg ttttggcaac ctacgatact  10620
tccagggttg aacatgctgt ggtttattac gtttacagcc caagccgctc attttcttac  10680
ttttatcctt ttaggttgcc tataaagggg gtccccatcg aattacaagt ggaatgcttc  10740
acatgggacc aaaaactctg gtgccgtcac ttctgtgtgc ttgcggactc agaatctggt  10800
ggacatatca ctcactctgg gatggtgggc atgggagtca gctgcacagt cacccgggaa  10860
gatggaacca atcgcagata gggctgctag tgaaccaatc acatgatgtc acccagacat  10920
caggcatacc cactagtgtg aaatagacat cagaattaag aaaaacgtag ggtccaagtg  10980
gttccccgtt atggactcgc tatctgtcaa ccagatctta taccctgaag ttcacctaga  11040
tagcccgata gttaccaata agatagtagc catcctggag tatgctcgag tccctcacgc  11100
ttacagcctg gaggacccta cactgtgtca gaacatcaag caccgcctaa aaaacggatt  11160
ttccaaccaa atgattataa acaatgtgga agttgggaat gtcatcaagt ccaagcttag  11220
gagttatccg gcccactctc atattccata tccaaattgt aatcaggatt tatttaacat  11280
agaagacaaa gagtcaacga ggaagatccg tgaactcctc aaaaagggga attcgctgta  11340
ctccaaagtc agtgataagg ttttccaatg cttaagggac actaactcac ggcttggcct  11400
aggctccgaa ttgagggagg acatcaagga gaaagttatt aacttgggag tttacatgca  11460
cagctcccag tggtttgagc cctttctgtt ttggtttaca gtcaagactg agatgaggtc  11520
agtgattaaa tcacaaaccc atacttgcca taggaggaga cacacacctg tattcttcac  11580
tggtagttca gttgagttgc taatctctcg tgaccttgtt gctataatca gtaaagagtc  11640
tcaacatgta tattacctga catttgaact ggttttgatg tattgtgatg tcatagaggg  11700
gaggttaatg acagagaccg ctatgactat tgatgctagg tatacagagc ttctaggaag  11760
agtcagatac atgtggaaac tgatagatgg tttcttccct gcactcggga atccaactta  11820
tcaaattgta gccatgctgg agcctctttc acttgcttac ctgcagctga gggatataac  11880
agtagaactc agaggtgctt tccttaacca ctgctttact gaaatacatg atgttcttga  11940
ccaaaacggg ttttctgatg aaggtactta tcatgagtta actgaagctc tagattacat  12000
tttcataact gatgacatac atctgacagg ggagattttc tcatttttca gaagtttcgg  12060
ccaccccaga cttgaagcag taacggctgc tgaaaatgtt aggaaataca tgaatcagcc  12120
taaagtcatt gtgtatgaga ctctgatgaa aggtcatgcc atattttgtg gaatcataat  12180
caacggctat cgtgacaggc acggaggcag ttggccaccg ctgaccctcc ccctgcatgc  12240
tgcagacaca atccggaatg ctcaagcttc aggtgaaggg ttaacacatg agcagtgcgt  12300
tgataactgg aaatcttttg ctggagtgaa atttggctgc tttatgcctc ttagcctgga  12360
```

```
tagtgatctg acaatgtacc taaaggacaa ggcacttgct gctctccaaa gggaatggga  12420
ttcagtttac ccgaaagagt tcctgcgtta cgaccctccc aagggaaccg ggtcacggag  12480
gcttgtagat gttttcctta atgattcgag ctttgaccca tatgatgtga taatgtatgt  12540
tgtaagtgga gcttacctcc atgaccctga gttcaacctg tcttacagcc tgaaagaaaa  12600
ggagatcaag gaaacaggta gactttttgc taaaatgact tacaaaatga gggcatgcca  12660
agtgattgct gaaaatctaa tctcaaacgg gattggcaaa tattttaagg acaatgggat  12720
ggccaaggat gagcacgatt tgactaaggc actccacact ctagctgtct caggagtccc  12780
caaagatctc aaagaaagtc acaggggggg gccagtctta aaaacctact cccgaagccc  12840
agtccacaca agtaccagga acgtgagagc agcaaaaggg tttatagggt tccctcaagt  12900
aattcggcag gaccaagaca ctgatcatcc ggagaatatg gaagcttacg agacagtcag  12960
tgcatttatc acgactgatc tcaagaagta ctgccttaat tggagatatg agaccatcag  13020
cttgtttgca cagaggctaa atgagattta cggattgccc tcatttttcc agtggctgca  13080
taagaggctt gagacctctg tcctgtatgt aagtgaccct cattgccccc ccgaccttga  13140
cgcccatatc ccgttatata aagtccccaa tgatcaaatc ttcattaagt accctatggg  13200
aggtatagaa gggtattgtc agaagctgtg gaccatcagc accattccct atctatacct  13260
ggctgcttat gagagcggag taaggattgc ttcgttagtg caaggggaca atcagaccat  13320
agccgtaaca aaaagggtac ccagcacatg gccctacaac cttaagaaac gggaagctgc  13380
tagagtaact agagattact ttgtaattct taggcaaagg ctacatgata ttggccatca  13440
cctcaaggca aatgagacaa ttgtttcatc acattttttt gtctattcaa aaggaatata  13500
ttatgatggg ctacttgtgt cccaatcact caagagcatc gcaagatgtg tattctggtc  13560
agagactata gttgatgaaa caagggcagc atgcagtaat attgctacaa caatggctaa  13620
aagcatcgag agaggttatg accgttacct tgcatattcc ctgaacgtcc taaaagtgat  13680
acagcaaatt ctgatctctc ttggcttcac aatcaattca accatgaccc gggatgtagt  13740
catacccctc ctcacaaaca acgacctctt aataaggatg gcactgttgc ccgctcctat  13800
tggggggatg aattatctga atatgagcag gctgtttgtc agaaacatcg gtgatccagt  13860
aacatcatca attgctgatc tcaagagaat gattctcgcc tcactaatgc ctgaagagac  13920
cctccatcaa gtaatgacac aacaaccggg ggactcttca ttcctagact gggctagcga  13980
cccttactca gcaaatcttg tatgtgtcca gagcatcact agactcctca agaacataac  14040
tgcaaggttt gtcctgatcc atagtccaaa cccaatgtta aaaggattat tccatgatga  14100
cagtaaagaa gaggacgagg gactggcggc attcctcatg gacaggcata ttatagtacc  14160
tagggcagct catgaaatcc tggatcatag tgtcacaggg gcaagagagt ctattgcagg  14220
catgctggat accacaaaag gcttgattcg agccagcatg aggaaggggg ggttaacctc  14280
tcgagtgata accagattgt ccaattatga ctatgaacaa ttcagagcag ggatggtgct  14340
attgacagga agaaagagaa atgtcctcat tgacaaagag tcatgttcag tgcagctggc  14400
gagagctcta agaagccata tgtgggcgag gctagctcga ggacggccta tttacggcct  14460
tgaggtccct gatgtactag aatctatgcg aggccacctt attcggcgtc atgagacatg  14520
tgtcatctgc gagtgtggat cagtcaacta cggatggttt tttgtcccct cgggttgcca  14580
actggatgat attgacaagg aaacatcatc cttgagagtc ccatatattg gttctaccac  14640
tgatgagaga acagacatga agcttgcctt cgtaagagcc ccaagtcgat ccttgcgatc  14700
tgctgttaga atagcaacag tgtactcatg ggcttacggt gatgatgata gctcttggaa  14760
```

```
cgaagcctgg ttgttggcta ggcaaagggc caatgtgagc ctggaggagc taagggtgat  14820
cactcccatc tcaacttcga ctaatttagc gcataggttg agggatcgta gcactcaagt  14880
gaaatactca ggtacatccc ttgtccgagt ggcgaggtat accacaatct ccaacgacaa  14940
tctctcattt gtcatatcag ataagaaggt tgatactaac tttatatacc aacaaggaat  15000
gcttctaggg ttgggtgttt tagaaacatt gtttcgactc gagaaagata ccggatcatc  15060
taacacggta ttacatcttc acgtcgaaac agattgttgc gtgatcccga tgatagatca  15120
tcccaggata cccagctccc gcaagctaga gctgagggca gagctatgta ccaacccatt  15180
gatatatgat aatgcacctt taattgacag agatgcaaca aggctataca cccagagcca  15240
taggaggcac cttgtggaat ttgttacatg gtccacaccc caactatatc acattttagc  15300
taagtccaca gcactatcta tgattgacct ggtaacaaaa tttgagaagg accatatgaa  15360
tgaaatttca gctctcatag gggatgacga tatcaatagt ttcataactg agtttctgct  15420
catagagcca agattattca ctatctactt gggccagtgt gcggccatca attgggcatt  15480
tgatgtacat tatcatagac catcagggaa atatcagatg ggtgagctgt tgtcatcgtt  15540
cctttctaga atgagcaaag gagtgtttaa ggtgcttgtc aatgctctaa gccacccaaa  15600
gatctacaag aaattctggc attgtggtat tatagagcct atccatggtc cttcacttga  15660
tgctcaaaac ttgcacacaa ctgtgtgcaa catggtttac acatgctata tgacctacct  15720
cgacctgttg ttgaatgaag agttagaaga gttcacattt ctcttgtgtg aaagcgacga  15780
ggatgtagta ccggacagat tcgacaacat ccaggcaaaa cacttatgtg ttctggcaga  15840
tttgtactgt caaccaggga cctgcccacc aattcgaggt ctaagaccgg tagagaaatg  15900
tgcagttcta accgaccata tcaaggcaga ggctatgtta tctccagcag gatcttcgtg  15960
gaacataaat ccaattattg tagaccatta ctcatgctct ctgacttatc tccggcgagg  16020
atcgatcaaa cagataagat tgagagttga tccaggattc attttcgacg ccctcgctga  16080
ggtaaatgtc agtcagccaa agatcggcag caacaacatc tcaaatatga gcatcaaggc  16140
tttcagaccc ccacacgatg atgttgcaaa attgctcaaa gatatcaaca caagcaagca  16200
caatcttccc atttcagggg gcaatctcgc caattatgaa atccatgctt tccgcagaat  16260
cgggttgaac tcatctgctt gctacaaagc tgttgagata tcaacattaa ttaggagatg  16320
ccttgagcca ggggaggacg gcttgttctt gggtgaggga tcgggttcta tgttgatcac  16380
ttataaagag atacttaaac taaacaagtg cttctataat agtggggttt ccgccaattc  16440
tagatctggt caaagggaat tagcacccta tccctccgaa gttggccttg tcgaacacag  16500
aatgggagta ggtaatattg tcaaagtgct ctttaacggg aggcccgaag tcacgtgggt  16560
aggcagtgta gattgcttca atttcatagt tagtaatatc cctacctcta gtgtggggtt  16620
tatccattca gatatagaga ccttgcctga caaagatact atagagaagc tagaggaatt  16680
ggcagccatc ttatcgatgg ctctgctcct gggcaaaata ggatcaatac tggtgattaa  16740
gcttatgcct ttcagcgggg attttgttca gggatttata agttatgtag ggtctcatta  16800
tagagaagtg aaccttgtat accctagata cagcaacttc atctctactg aatcttattt  16860
ggttatgaca gatctcaagg ctaaccggct aatgaatcct gaaaagatta agcagcagat  16920
aattgaatca tctgtgagga cttcacctgg acttataggt cacatcctat ccattaagca  16980
actaagctgc atacaagcaa ttgtgggaga cgcagttagt agaggtgata tcaatcctac  17040
tctgaaaaaa cttacaccta tagagcaggt gctgatcaat tgcgggttgg caattaacgg  17100
```

```
acctaagctg tgcaaagaat tgatccacca tgatgttgcc tcagggcaag atggattgct  17160
taattctata ctcatcctct acagggagtt ggcaagattc aaagacaacc aaagaagtca  17220
acaagggatg ttccacgctt accccgtatt ggtaagtagc aggcaacgag aacttatatc  17280
taggatcacc cgcaaattct gggggcacat tcttctttac tccgggaaca aaaagttgat  17340
aaataagttt atccagaatc tcaagtccgg ctatctgata ctagacttac accagaatat  17400
cttcgttaag aatctatcca agtcagagaa acagattatt atgacggggg gtttgaaacg  17460
tgagtgggtt tttaaggtaa cagtcaagga gaccaaagaa tggtataagt tagtcggata  17520
cagtgccctg attaaggact aattggttga actccggaac cctaatcctg ccctaggtgg  17580
ttaggcatta tttgcaatat attaaagaaa actttgaaaa tacgaagttt ctattcccag  17640
ctttgtctgg tggccggcat ggtcccagcc tcctcgctgg cgccggctgg gcaacattcc  17700
gaggggaccg tcccctcggt aatggcgaat gggacgcggc cgatccggct gctaacaaag  17760
cccgaaagga agctgagttg gctgctgcca ccgctgagca ataactagca taaccccttg  17820
gggcctctaa acgggtcttg aggggttttt tgctgaaagg aggaactata tccggatgcg  17880
gccgcgggcc ctatggtacc cagcttttgt tccctttagt gagggttaat tccgagcttg  17940
gcgtaatcat ggtcatagct gtttcctgtg tgaaattgtt atccgctcac aattccacac  18000
aacataggag ccggaagcat aaagtgtaaa gcctggggtg cctaatgagt gaggtaactc  18060
acattaattg cgttgcgctc actgcccgct ttccagtcgg gaaacctgtc gtgccagctg  18120
cattaatgaa tcggccaacg cgcggggaga ggcggtttgc gtattgggcg ctcttccgct  18180
tcctcgctca ctgactcgct gcgctcggtc gttcggctgc ggcgagcggt atcagctcac  18240
tcaaaggcgg taatacggtt atccacagaa tcaggggata acgcaggaaa gaacatgtga  18300
gcaaaaggcc agcaaaaggc caggaaccgt aaaaaggccg cgttgctggc gtttttccat  18360
aggctcggcc cccctgacga gcatcacaaa aatcgacgct caagtcagag gtggcgaaac  18420
ccgacaggac tataaagata ccaggcgttc ccccctggaa gctccctcgt gcgctctcct  18480
gttccgaccc tgccgcttac cggatacctg tccgcctttc tcccttcggg aagcgtggcg  18540
ctttctcaat gctcacgctg taggtatctc agttcggtgt aggtcgttcg ctccaagctg  18600
ggctgtgtgc acgaaccccc cgttcagccc gaccgctgcg ccttatccgg taactatcgt  18660
cttgagtcca acccggtaag acacgactta tcgccactgg cagcagccac tggtaacagg  18720
attagcagag cgaggtatgt aggcggtgct acagagttct tgaagtggtg gcctaactac  18780
ggctacacta gaaggacagt atttggtatc tgcgctctgc tgaagccagt taccttcgga  18840
aaaagagttg gtagctcttg atccggcaaa caaaccaccg ctggtagcgg tggttttttt  18900
gtttgcaagc agcagattac gcgcagaaaa aaaggatctc aagaagatcc tttgatcttt  18960
tctacggggt ctgacgctca gtggaacgaa aactcacgtt aagggatttt ggtcatgaga  19020
ttatcaaaaa ggatcttcac ctagatcctt ttaaattaaa aatgaagttt taaatcaatc  19080
taaagtatat atgagtaaac ttggtctgac agttaccaat gcttaatcag tgaggcacct  19140
atctcagcga tctgtctatt tcgttcatcc atagttgcct gactgcccgt cgtgtagata  19200
actacgatac gggagggctt accatctggc cccagtgctg caatgatacc gcgagaccca  19260
cgctcaccgg ctccagattt atcagcaata aaccagccag ccggaagggc cgagcgcaga  19320
agtggtcctg caactttatc cgcctccatc cagtctatta attgttgccg ggaagctaga  19380
gtaagtagtt cgccagttaa tagtttgcgc aacgttgttg ccattgctac aggcatcgtg  19440
gtgtcacgct cgtcgtttgg tatggcttca ttcagctccg gttcccaacg atcaaggcga  19500
```

-continued

```
gttacatgat cccccatgtt gtgaaaaaaa gcggttagct ccttcggtcc tccgatcgtt  19560

gtcagaagta agttggccgc agtgttatca ctcatgctta tggcagcact gcataattct  19620

cttactgtca tgccatccgt aagatgcttt tctgtgactg gtgagtactc aaccaagtca  19680

ttctgagaat agtgtatgcg gcgaccgagt tgctcttgcc cggcgtcaat acgggataat  19740

accgcgccac atagcagaac tttaaaagtg ctcatcattg gaaaacgttc ttcggggcga  19800

aaactctcaa ggatcttacc gctgttgaga tccagttcga tgtaacccac tcgtgcaccc  19860

aactgatctt cagcatcttt tactttcacc agcgtttctg ggtgagcaaa aacaggaagg  19920

caaaatgccg caaaaaaggg aataagggcg acacggaaat gttgaatact catactcttc  19980

cttttcaat attattgaag catttatcag ggttattgtc tcatgagcgg atacatattt  20040

gaatgtattt agaaaaataa acaaataggg gttccgcgca catttccccg aaaagtgcca  20100

cctgaaattg taaacgttaa tattttgtta aaattcgcgt taaatttttg ttaaatcagc  20160

tcatttttta accaataggc cgaaatcggc aaaatccctt ataaatcaaa agaatagacc  20220

gagatagggt tgagtgttgt tccagtttgg aacaagagtc cactattaaa gaacgtggac  20280

tccaacgtca aagggcgaaa aaccgtctat cagggcgatg gcccactacg tgaaccatca  20340

ccctaatcaa gtttttggg gtcgaggtgc cgtaaagcac taaatcggaa ccctaaaggg  20400

agcccccgat ttagagcttg acggggaaag ccggcgaacg tggcgagaaa ggaagggaag  20460

aaagcgaaag gagcgggcgc tagggcgctg gcaagtgtag cggtcacgct gcgcgtaacc  20520

accacacccg ccgcgcttaa tgcgccgcta cagggcgcgt cccattcgcc attcaggctg  20580

cgcaactgtt gggaagggcg atcggtgcgg gcctcttcgc tattacgcca gccaccgcgg  20640

tgatccttat aaagctagat g                                           20661
```

CHROMATOGRAPHY BASED PURIFICATION STRATEGIES FOR VIRUSES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 900259_402USPC_SEQUENCE_LISTING.txt. The text file is 238 KB, was created on Jun. 14, 2018, and is being submitted electronically via EFS-Web.

TECHNICAL FIELD

The present invention generally relates to the field of virology and specifically relates to the provision of purification strategies for sterically demanding, i.e. large and pleomorphic, infectious virus particles or VLPs derived therefrom, particularly for viruses having a measles virus scaffold to yield fractions or compositions comprising infectious virus particles with a significantly reduced content of contaminating host cell DNA and a reduced content of further process-related impurities. Furthermore, the present invention relates to methods of propagating and purifying infectious virus particles, preferably for viruses having a measles virus scaffold suitable to provide a preparation having a strongly reduced content of contaminating host cell DNA and a reduced content of further process-related impurities. In addition, immunogenic and vaccine compositions based on the above methods are provided. Finally, there are provided immunogenic or vaccine compositions produced by the disclosed methods, which are suitable for use in immunogenic or prophylactic vaccination treatment of a subject in need thereof.

BACKGROUND OF THE INVENTION

Emerging and re-emerging infectious diseases represent an ongoing threat for public health despite all global vaccination efforts. Especially phenomena like the ongoing climate change, the increased mobility of human populations, environmental modification and the widespread and injudicious use of antimicrobials are factors contributing to the problem of eradicating viral, microbial and other pathogenic infections. Concerning viral infections, measles virus has recently gained a lot of intention in Europe and the USA, as there are frequently Measles cases and outbreaks despite the WHO's strong efforts to eradicate the disease with the help of vaccination programs large outbreaks of measles are jeopardizing this ultimate goal. At the same time measles caused deaths are declining, but from a global perspective, still large populations remain unprotected. Therefore, there exists an ongoing need to provide suitable vaccines having an acceptable immunogenicity, safety and tolerability profile for world-wide application in nationwide vaccination.

Concerning safety issues of viral vaccines, especially life attenuated viruses (LAVs) have been used for a long time as efficient vaccines for humans and animals. As LAVs are derived from the disease-causing pathogen, but have been attenuated in a purposive manner under laboratory conditions, they are suitable to stimulate a good immune response. They will grow in a vaccinated individual, but because they are attenuated, they will cause no or very mild disease, however, still being infectious. Currently, there are several LAVs approved by the WHO including an oral polio vaccine, a measles vaccine, a rotavirus and a yellow fever vaccine. Still, several safety and stability issues remain in the context of LAVs, which still contain potentially infectious material, inter alia concerning issues like reversion, purity and potential contaminations in the viral preparation used as vaccine and the like.

Concerning LAVs, EP 1 939 214 B1 discloses that live attenuated RNA viruses especially the measles vaccine, has been used in hundreds of millions of children and has been proven to be effective and safe. This vaccine induces life-long immunity after one or two injections. It is easily produced on a large scale at low cost in most countries. These advantages make measles virus, especially attenuated vaccine strains, a good candidate vector to immunize children. Measles virus (MV) belongs to the genus *Morbillivirus* in the family Paramyxoviridae. It is an enveloped virus with a non-segmented RNA genome of negative polarity (15,894 bp). Measles can only be contracted once as the immune system mounts a strong specific response and establishes life-long memory protecting against re-infection. Such protection is based on both the production of antibodies and memory cytotoxic CD8+ T lymphocytes (CTL). Pathogenic strains strongly disrupt haematopoiesis (Arneborn et al., 1983; Kim et al., 2002; Okada et al., 2000) thus resulting in transitory immunosuppression responsible for most deaths due to measles infection in developing countries. In contrast to primary strains, attenuated strains do not induce immunosuppression (Okada et al., 2001). The Edmonston strain of measles virus was isolated in 1954 by culture in primary human cells (Enders et al., 1954). Adaptation to chicken embryonic fibroblasts produced vaccine seeds that were furthermore attenuated by subsequent passages in chicken embryonic fibroblasts (Schwarz et al., 1962). The Schwarz and Moraten strains that possess identical nucleotide sequences (Parks et al., 2001a; Parks et al., 2001 b) constitute the most frequently used measles vaccine. Vaccination with one or two injections induces life-long immunity (Griffin et al., 2001; Hilleman et al., 2002). The inventors of EP 1 939 214 B1 have developed a vector using the Schwarz MV, the most commonly used measles vaccine in the world (Combredet et al., 2003). This vector can stably express a variety of genes or combination of large genes for more than 12 passages. Recombinant MV vectors containing 4,000-5,000 additional nucleotides were produced, representing an additional 30% of genome. These viruses were produced in cell culture at titers comparable to standard MV.

To optimize the output of the reverse genetics system, the antigenomic viral cDNA was placed under the control of the T7 phage RNA polymerase promoter with an additional GGG motif required for optimal efficacy. To allow exact cleavage of the viral RNA, a hammerhead ribozyme was inserted between the GGG motif and the first viral nucleotide, and the ribozyme from hepatitis delta virus was placed downstream of the last viral nucleotide. The resulting pTM-MVSchw plasmid enabled the production of the corresponding virus using a previously described reverse genetics system based on the transfection of human helper cells (Radecke et al., 1995). Furthermore, EP 1 939 214 B1 discloses that pTM-MVSchw plasmid was modified for the expression of foreign genes by the introduction of additional transcriptional units (ATU) at different positions of the genome. These ATUs are multi-cloning site cassettes inserted in a copy of the intergenic N-P region of the viral genome (containing the cis acting sequences required for transcription).

This basis recombinant and infectious measles vector allows the design of combined vaccines based on a live attenuated approved vaccine strain that is currently globally in use, i.e. a vaccine against another virus other than a certain strain of the measles virus so that the recombinant measles virus vector is used as a scaffold for the introduction, production and purification of infectious virus particles expressing epitopes other than those derived from a measles virus strain.

As one example for the use of the above described measles virus scaffold for providing vaccines for another infectious viral disease is described in WO 2014/049094 A1. WO 2014/049094 A1 discloses the production of vaccines based on recombinant infectious replicative measles virus recombined with polynucleotides encoding Chikungunya virus (CHIK or CHIKV) antigens, which are recovered when the recombinant virus replicates in particular in the host after administration. The nucleic acid construct of this WO application is suitable and intended for the preparation of recombinant infectious replicative measles—Chikungunya virus (MV-CHIKV or MV-CHIK) and accordingly said nucleic acid construct is intended for insertion in a transfer genome vector that as a result comprises the cDNA molecule of the measles virus, especially of the Schwarz strain, for the production of said MV-CHIKV virus and yield of CHIKV structural protein(s), in particular CHIKV virus-like particles (VLPs). This application thus relates to a live CHIK virus vaccine based on the widely used Schwarz measles pediatric vaccine. Chikungunya virus (CHIKV) is a positive-strand RNA virus of the genus *Alphavirus* within the family of Togaviridae, first isolated in Tanzania in 1952. Infection by this virus causes human disease that is characterized by symptoms similar to dengue fever, with an acute febrile phase during two to five days, followed by a prolonged arthralgic disease that affects the joints of the extremities. CHIKV is endemic in Africa, India and South-East Asia and is transmitted by *Aedes* mosquitoes through an urban or sylvatic transmission cycle. In 2006, an outbreak of CHIKV fever occurred in numerous islands of the Indian Ocean, e.g. the Comoros, Mauritius, Seychelles, Madagascar and Reunion island, before jumping to India where an estimated 1.4 million cases have been reported. More recently, imported infections have been described in Europe, and around 200 endemic cases have been reported in Italy (Jose, J. et al, A structural and functional perspective of alphavirus replication and assembly. Future Microbiol., 2009. 4(7): p. 837-56). Clinically, this CHIKV epidemic was accompanied by more severe symptoms than previous outbreaks, with reports of severe polyarthralgia and myalgia, complications and deaths. Currently, there is no specific antiviral drug treatment for Chikungunya infection. Treatment is directed primarily at relieving the symptoms, including the joint pain using anti-pyretics, optimal analgesics and fluids. Furthermore, there is no commercial Chikungunya vaccine, which would be approved by the relevant authorities on the market yet.

EP 1 599 495 B9 discloses another example for a recombinant virus based on a defective or live attenuated measles virus. The patent discloses a recombinant virus comprising and thus being able to express antigens from a West-Nile virus or a Dengue virus antigen.

Brandler et al. (Vaccine, 31, pp. 3718-3725, 2013) discloses a recombinant measles vaccine expressing Chikungunya virus-like particle and its immunogenic and protective potential. As evident from FIG. 1E of Brandler et al., said publication focuses on Chikungunya virus-like particles secreted in the supernatants of host cells, rather than focusing on an infectious replicating measles virus-Chikungunya fusion. Furthermore, Brandler et al. does not teach or suggest that any purification of the virus-like particles would be feasible.

Vicente et al. (Journal of Invertebrate Pathology, 107, S42-S48, 2011) discloses methods suitable for the production and purification of VLP-based vaccines. To this end, Vicente et al. exclusively focuses on techniques for VLP purification, but does not disclose any method which would be suitable to purify vaccines or viruses having a huge particle size and being pleomorphic, which can be derived from the particle sizes as shown in Table 1 or the introduction of Vicente et al. teaching size ranges of viruses from 22-200 nm. There is, however, no guidance of how to purify, via chromatographic methods, a virus having a particle size of up to 1 μm as applicable for measles virus.

Nestola et al. (Biotechnology and Bioengineering, Vol. 112, No. 5, May, 2015) discloses improved virus purification processes for vaccination. Nestola et al. mentions the use of monolithic columns for the purification of viruses, yet exclusively mentions that inter alia lentiviruses, baculoviruses, rubella, enterovirus 71 and adenovirus could be purified via monoliths due to the problem of clogging mediated by host cell DNA. Notably, Nestola et al. is completely silent as to purification schemes for sterically demanding huge viruses, e.g. measles virus. In contrast, the generally prevailing problem that viruses have sizes from 30 nm to 300 nm or even larger, and, as such, cannot diffuse into the pores of commercially adsorbent resins available is emphasized in Nestola, but also for the monolithic columns having a radial geometric design no enabling example is presented which show the successful purification of a large virus particle.

Jungbauer and Hahn (Journal of Separation Science, Vol. 27, No. 10/11, pp. 767-778, 2004) discloses that monolithic columns could be used for the purification of biomaterials. This publication, however, is completely silent as to a successful example of virus purification and rather discloses examples of small (amino acid-based) biomolecules like lysozyme, BSA, or immunoglobulins, not teaching or suggesting any enabling example for the purification of a whole virus, let alone a huge virus particle.

Branovic et al. (J. Virol. Meth., 110, 163-171, 2003) discloses monolithic chromatography media as novel generation of stationary phases for chromatographic applications. The enrichment of virus RNA on short monolithic columns prior to molecular detection of viruses is described. Measles and mumps viruses were chosen as model viruses. The results presented show that it is possible to bind viral RNA on monoliths and to concentrate viral nucleic acids from a fairly diluted sample. There is, however, no technical teaching on a monolithic column and a corresponding method which would be suitable to purify a whole intact virus which is by far more demanding than purifying single components of a virus. Branovic et al. rather teaches that total RNA is extracted from measles or mumps viruses and partially purified before it is applied to a monolithic column.

Rajamanickam et al. (Chromatography, 2, 195-212, 2015) discloses monolithic columns and their use in bioprocess technology. With respect to virus purification, Rajamanickam et al., however, exclusively discloses viruses like bacteriophage T4 enterovirus, adenovirus, mycobacteriophage D29, potato virus Y or VLPs and does not provide any example of a huge virus having a particle size in the high nm range.

None of the above cited prior art, however, discloses an efficient purification scheme for the respective virus particles or virus-like particles, which would not only be suitable for the purification of viruses with a small particle size or non replicating VLPs, but which would be suitable for huge viruses or VLPs for which presently no efficient chromatography based purification strategies are available, or for the differential separation of viral preparations comprising both, a fraction comprising infectious virus particles, and a corresponding VLP fraction.

In general, it is a common hurdle in the field of virology and vaccination that viruses and also virus-like particles possess highly different and divergent biological and biochemical properties and therefore purification schemes must be established specifically for each virus or virus-(like) particle. Virus genomes generally show a high degree of variability. In general, they can be composed of DNA, single or doublestranded, or RNA, as plus or minus strand or ambisense, the genome can be linear, circular or segmented and there can be an envelope (composed of lipids and proteins) or not. Besides that, the genome size can vary a lot from about 1.7 kilobase (kb) (e.g. Circoviridae or Hepatitis delta virus) to about 2.5 megabase (Mb) (e.g. *Pandoravirus salinus*). With respect to purification, especially the size, diameter and chemical reactivity the exposed surface of a virus particle, especially of the envelope, if present, are factors to be taken into consideration.

To finally bring a measles virus scaffold based vaccine preparation to the market, especially when the viral vector encodes at least one antigen of a viral pathogen not yet approved for therapy it is not only required to provide recombinant infectious virus particles suitable to elicit a desired immune response, it is also mandatory to provide sufficient amounts, stable preparations and in a dosage form, which contains no residual contaminants of host cell DNA and proteins as remnants of the production of the infectious virus particles in a host cell and the subsequent isolation therefrom and optional treatment with enzymes like DNAses. The WHO and the responsible national and regional approval authorities, like the FDA in the USA and the EMEA in Europe, understandably impose high requirements to a composition used as vaccine comprising clinical trials and labeling to achieve the provision of safe biological products. The important hallmarks to be fulfilled by a vaccine candidate are its safety, purity and potency. Concerning product- or process related impurities, in 1986, a WHO Study Group was convened in Geneva to discuss the safety concerns with the use of continuous cell lines for the production of biologicals. The conclusions from the discussions with respect to DNA was that for biologic products manufactured in continuous cell lines, the amount of DNA per parenteral dose should be 100 pg or less, a value that was considered to represent an insignificant risk. This was a conservative decision and was based predominantly on the results of studies on the oncogenic activity of polyoma virus DNA (see FDA: FDA Briefing Document Vaccines and Related Biological Products Advisory Committee Meeting Sep. 19, 2012). The value of 100 pg of host cell DNA per vaccine dose remained the recommended standard for a decade. However, the issue was revisited in 1997 for several reasons. First, vaccine manufacturers could not always meet this level of residual cell-substrate DNA for some viral vaccines, such as with certain enveloped viruses, e.g. the Measles virus. Second, more information was available as to the oncogenic events in human cancers, where it has been established that multiple events, both genetic and epigenetic, are required (for secondary literature, see FDA Briefing Document Vaccines and Related Biological Products Advisory Committee Meeting Sep. 19, 2012). Third, for continuous non-tumorigenic cell lines such as Vero, the major cell substrate that was being considered at the time, the presence of activated dominant oncogenes in these cells was unlikely. This last problem associated with Vero cells is nowadays studied in more detail and the recombinant cell lines available are well characterized and there are plenty of studies, e.g., concerning the number of passages suitable to use these specific cell lines under sustainably controlled conditions. The outcome of the 1997 WHO meeting was that the amount of residual cell-substrate DNA allowed per dose in a vaccine produced in a continuous cell line and one administered by the parenteral route was raised from 100 pg to 10 ng per dosis (Brown, F., E. Griffiths, F. Horaud, and J. C. Petricciani (ed.). 1998. Safety of Biological Products Prepared from Mammalian Cell Culture, vol. 93. Karger, Basel). As there are still concerns regarding DNA impurities in viral vaccines, there is an ongoing need in establishing purification schemes suitable for the industrial production of viral vaccines, especially for enveloped virus particles like the measles virus and measles virus scaffold based products to achieve a higher degree of purity, e.g. with regard to contaminating host cell DNA, and thus a better safety of the resulting product.

Especially regarding purity considerations, all of the above described vaccine candidates based on a measles virus scaffold suffer from the drawback that current purification strategies exclusively rely on the clarification, including filtration, of the infectious virus particles and optional treatments, e.g. with DNAses. Besides the removal of cells and cell-debris, and an optional DNAse treatment there is thus no further purification step, before the infectious virus particles are aliquotted, optionally stabilized, and stored. Process-related impurities arising from the measles vaccine bulk manufacturing processes, for example, are classified as cell substrate- or cell culture-derived by the EMEA and can thus, as also meant herein, refer to cells, cell debris, protein contaminants, either resulting from cell culture additives or from enzymes added during cultivation and processing, a microcarrier used for host-cell cultivation, or foreign nucleic acids neither belonging to the host cell nor the recombinant infectious virus or particles thereof of interest.

As the measles virus scaffold based vaccines are propagated in a comparable way as conventional measles virus, e.g. using a rescue system as described in EP 1 375 512 B1, process-related impurities are likewise relevant for measles virus scaffold based products, e.g. contaminations by the inherently necessary cultivation in a suitable eukaryotic cell necessitating the addition of supplements, including serum or proteinases. As the current isolation procedure does not comprise strategies like chromatography, as the measles virus as well as the recombinant infectious particles based on a measles virus scaffold are large (around 100 to 300 nm) and pleomorphic in size hampering classical filtration and chromatographic approaches and increasing the need for aseptic GMP manufacturing throughout the whole process. Recently, deep sequencing revealed that certain commercially available and approved LAV-based vaccines contained sequences endogenous retroviral sequences from the producer avian and primate cells. For one vaccine, the presence of a porcine circovirus as contaminant was detected (Victoria et al., "Viral Nucleic Acids in Live-Attenuated Vaccines: Detection of Minority Variants and an Adventitious Virus", *J. Virol*. June 2010 vol. 84 no. 12 6033-6040). Even though many of these impurities might not be critical to human health, as e.g. the porcine circovirus will not be critical for human subjects and some contaminations might even have a positive adjuvants effect on the immune system, these findings provoked a discussion on the safety and purity levels of already approved vaccines in use for many years exemplifying the ongoing need for immunogenic and vaccine compositions of a higher degree of purity.

Therefore, there is still a considerable amount of product-related impurities including DNA, proteins and other substances remaining in the preparation comprising a measles virus scaffold based infectious virus particle, either coming from the host cell needed for propagating the virus, or from culture additives, e.g. bovine serum albumin, if no serum-free approach is chosen, or from further additives like added DNAses.

Said impurities, however, can have an impact on the immune system of a subject to be treated and thus are highly considerable in the context of vaccine safety. Many vaccines currently at the market have been approved by the relevant authorities when methods like deep sequencing and RT-PCR, but also enzyme based methods were not yet that sophisticated. Consequently, nowadays there is also an ongoing need in improving vaccine compositions already on the market to obtain higher purity levels and thus a better safety of the product. Furthermore, the removal of process related impurities can further improve the acceptance of vaccine products and thus potentially contribute to a higher coverage in the rate of vaccinated individuals to provide nationwide immunity against selected dangerous viral pathogens.

Due to the high diversity of different viruses and consequently the different molecular, biological and biochemical properties thereof, it is mandatory to define a specific scheme of purification for each virus or virus-(like) particle, as the purified sample still has to contain a sufficient amount of the desired infectious virus particle, so that suitable purification schemes have to be found, which do not significantly reduce the yield of a virus particle preparation to be purified. At the same time, the purification scheme must be suitable to generate a viral preparation with preserved infectivity and in sufficient yields, preferably without any additional concentration steps.

Therefore, despite the availability of first vaccine candidates based on a measles virus scaffold, there exists an ongoing need to provide suitable measles virus scaffold based vaccines providing high safety and thus purity, which can be manufactured in a cost sensitive way to allow the provision of a safer vaccine finding more acceptance and being faced with less concerns due to their impurities.

There is thus a need to provide purification schemes for removing product-related impurities from virus preparations intended for vaccination purposes, particularly if derived from sterically demanding large viruses, for example, from the order Mononegavirales, particularly the family Paramyxoviridae, for example measles virus scaffold based infectious virus particles, simultaneously allowing the provision of an infectious and immunogenic virus population without the need of further concentration, which can be conducted under GMP conditions. It is another aim to provide purification schemes, which are suitable to differentially purify infectious and replicative virus particles from non-replicative VLPs in an efficient manner. Likewise it is an aim to enable the provision of measles based vaccines, which are cost-effective in production and stable to provide them to human beings, especially children, in economically less developed countries, where measles are still widespread. Finally, there is still an ongoing need to define new vaccine candidates and vaccines for severe viral diseases, where currently a prophylactic treatment is not at hand.

SUMMARY OF THE INVENTION

The object of the present invention was thus the provision of method for purifying recombinant infectious virus particles yielding purified infectious virus particles containing less than 33.33 ng/mL of contaminating host cell DNA and preferably also a reduced content of other process related impurities. It was another object to provide a method for propagating and purifying recombinant infectious virus particles, preferably derived from a measles virus scaffold, to yield purified infectious virus particles containing less than 33.33 ng/mL of contaminating host cell DNA and preferably also a reduced content of other process related impurities. Finally, it was an object to provide immunogenic or vaccine compositions produced by the aforementioned methods, containing less than 100 pg/dosis of contaminating host-cell DNA, preferably containing less than 1.1 pg/dosis of contaminating host-cell DNA, wherein the immunogenic or vaccine compositions are suitable for use in a method of eliciting an immune response or in the prophylactic treatment of a subject for protecting the subject from infection with a virus.

These objects have been achieved by providing, in a first aspect, a method for purifying recombinant infectious virus particles, wherein the method comprises the following steps: (i) providing at least one clarified virus sample comprising at least one recombinant infectious virus particle, preferably derived from a measles virus scaffold, obtained from at least one host cell infected with a virus stock comprising the at least one recombinant infectious virus particle; (ii) purifying the at least one recombinant infectious virus particle by means of chromatography; (iii) obtaining purified recombinant infectious virus particles within at least one fraction from the chromatography of step (ii), wherein the purified infectious virus particles contain less than 33.33 ng/mL of contaminating host cell DNA with respect to 1 mL of the at least one fraction and in one embodiment also a reduced content of other process related impurities.

The object was further achieved by providing in a second aspect a method for purifying recombinant infectious virus particles according to the first aspect, wherein the method comprises the following further steps: (a) providing at least one host cell; (b) providing a virus stock comprising at least one recombinant infectious virus particle, wherein the at least one recombinant infectious virus particle is encoded by at least one nucleic acid sequence, wherein the nucleic acid sequence comprises a first nucleic acid sequence encoding a virus scaffold and at least one second nucleic acid sequence operably linked to the first nucleic acid sequence, wherein the at least one second nucleic acid sequence encodes at least one antigen, preferably at least one virus antigen; (c) infecting the at least one host cell of step (a) with the virus stock provided in step (b); (d) incubating the infected at least one host cell at a temperature in the range of 32.0° C.+/−4° C., preferably at a temperature in the range of 32.0° C.+/−1° C.; (e) obtaining at least one virus sample from the at least one infected host cell comprising the at least one recombinant infectious virus particle; (f) clarifying the at least one virus sample of step (e).

In another embodiment, the methods disclosed herein can be used to purify viral scaffolds for tumor vaccination. According to these embodiments, the at least one second nucleic acid according to the present invention does not encode a viral antigen, but can encode a protein or a regulatory RNA, for example a micro RNA (miRNA), assisting tumor treatment, preferably in a mammalian, or more particularly in a human subject, wherein the protein or RNA encoded by the second nucleic acid can mediate the interaction or uptake of the measles virus scaffold and a tumor cell, or wherein the second nucleic acid sequence encodes a gene toxic for a tumor cell of interest, e.g. a suicide gene comprising a fusion of a cytosine deaminase, particularly yeast cytosine deaminase, and a uracil phosphoribosyltransferase, particularly yeast uracil phosphoribosyltransferase, or wherein the second nucleic acid sequence encodes a protein/RNA that enhances antitumor cytotoxicity and immunity. Furthermore, the second non-viral nucleic acid can be configured to promote a strong anti-tumor immune response, e.g. by activating antigen presenting cells, preferably dendritic cells, for example plasmacytoid dendritic cells, by activating their ability to produce high quantities of IFN-$\alpha$ and/or to cross-present tumor antigens from infected to tumor cells to tumor-specific CD8+ T lymphocytes to achieve a strong cellular immune response against the tumor cells or tissue. "Cross-presentation" or "cross-presenting" in this context means the ability of certain antigen-presenting cells to take up, process and present extracellular antigens with MHC class I molecules to CD8+ T cells (cytotoxic T cells). Cross-priming, the result of this process, describes the stimulation of the naïve cytotoxic $CD8^+$ T cell. This process is necessary for immunity against most tumors and against viruses that do not readily infect antigen-presenting cells, or impair dendritic cell normal function. It is also required for induction of cytotoxic immunity by vaccination with protein antigens, for example, tumor vaccination.

For these embodiments relying on at least one non-viral second nucleic acid sequence, an infectious recombinant virus scaffold may be additionally attenuated, for example by deleting certain genes, for example a viral accessory protein of the scaffold virus.

As oncolytic therapy is based on a virus scaffold, for example, a measles virus scaffold and primarily uses the inherent virotherapeutic capacity of the respective virus, i.e. (onco)lysis as primary effect, the present invention is particularly suitable to purify recombinant infectious virus particles based on a measles virus backbone, as the methods disclosed herein provide detailed guidance for achieving high purity of those viruses whilst maintaining their capacity to interact with a host cell of interest, to mediate oncolysis and antitumor immune activation.

In one embodiment of all aspects according to the present invention, the purification methods and the resulting products also have a reduced content of other process related impurities.

In a further embodiment there is provided a method, wherein the at least one host cell consists of cells selected from the group consisting of Vero cells, chicken embryo fibroblast cells, HEK293 cells, HeLa cells or MRC5 cells.

In yet a further embodiment there is provided a method, wherein the at least one recombinant infectious virus particle is encoded by the at least one nucleic acid sequence, wherein the at least one nucleic acid sequence comprises at least one first nucleic acid sequence encoding a virus scaffold and at least one second nucleic acid sequence operably linked to the first nucleic acid sequence, wherein the at least one second nucleic acid sequence encodes at least one antigen of at least one virus, wherein the nucleic acid sequence encoding the at least one antigen is selected from the group consisting of a nucleic acid sequence derived from a virus belonging to the family of Flaviviridae, including a nucleic acid sequence derived from a West-Nile virus, a tick-borne encephalitis virus, a Japanese encephalitis virus, a yellow fever virus, a Zika virus, or a Dengue virus, a Chikungunya virus, a norovirus, a virus belonging to the family of Paramyxoviridae, including a nucleic acid sequence derived from a human respiratory syncytical virus, a measles virus or a metapneumovirus, a parvovirus, a coronavirus, including a nucleic acid sequence derived from a Middle East respiratory syndrome antigen or a severe acute respiratory syndrome antigen, a human enterovirus 71, a cytomegalovirus, a poliovirus, an Epstein-Barr virus, a hepatitis E virus, a human papilloma virus, preferably a human papilloma virus 16, a human papilloma virus 5, a human papilloma virus 4, a human papilloma virus 1 or a human papilloma virus 41, or a varicella zoster virus.

Another embodiment of the methods of the present invention is provided, wherein the infectious measles virus scaffold is derived from an attenuated virus strain, preferably being selected from the group consisting of the Schwarz strain, the Zagreb strain, the AIK-C strain and the Moraten strain.

In a further embodiment, there is provided a method, wherein the purification by means of chromatography is performed using a stationary phase, preferably a stationary phase having a monolithic arrangement, wherein the stationary phase has a pore size of at least 5 μm, preferably a pore size of at least 6 μm, and more preferably a pore size of at least 7 μm, or wherein the purification by means of chromatography is performed using a stationary phase having a monolithic arrangement, wherein the mode of adsorption is hydrophobic interaction.

In still another embodiment, there is provided a method, wherein the at least one virus sample is treated with a DNAse, preferably with a benzonase, before or after the clarification.

Further, there is provided an embodiment according to the methods of the present invention, wherein the clarification is performed by a method other than centrifugation, preferably, wherein clarification is performed by a filtration method, or wherein clarification is performed by treating the at least one virus sample from at least one infected host cell with a DNAse, preferably with a benzonase, or by directly transferring a supernatant from at least one infected host cell to a chromatography resin.

In another embodiment, there is provided a method, wherein the purified recombinant infectious virus particles contain less than 30 ng/mL, preferably less than 20 ng/mL, more preferably less than 10 ng/mL even more preferably less than 1 ng/mL, even more preferably less than 100 pg/mL, even more preferably less than 10 pg/mL and most preferably less than 1.1 pg/mL of contaminating host cell DNA per one mL of the recombinant infectious virus particles as directly obtained within at least one fraction after chromatographic purification with respect to 1 mL of the at least one fraction.

In still a further embodiment, there is provided a method, additionally comprising a further purification step (iv) according to the method of the first or second aspect disclosed herein, comprising: further purifying the purified recombinant infectious virus particles by means of filtration, centrifugation, tangential flow filtration, membrane filtration, purification with grafted media, aqueous two phase extraction, precipitation, buffer exchange, dialysis or chromatography, including size exclusion chromatography for separating the purified recombinant infectious virus particles into a fraction containing virions and another fraction containing virus-like particles.

Finally, in a further aspect there are provided immunogenic and/or vaccine compositions produced by the aforementioned methods according to the first and the second aspect, wherein the immunogenic and/or the vaccine compositions are further suitable for use in a method of eliciting an immune response or in a method of prophylactic treatment of a subject for protecting the subject from infection with a virus, wherein protection is achieved by exposing the subject to the recombinant infectious virus particles comprised by the immunogenic composition or the vaccine composition, wherein the recombinant infectious virus particles are preferably derived from a measles virus scaffold, the scaffold being encoded by at least one nucleic acid sequence, wherein the nucleic acid sequence comprises at least one first nucleic acid sequence encoding the virus scaffold and at least one second nucleic acid sequence operably linked to the first nucleic acid sequence, wherein the at least one second nucleic acid sequence encodes at least one polypeptide, wherein the polypeptide is an antigen of at least one virus, or wherein the second nucleic acid encodes a polypeptide or a RNA other than a viral antigen and suitable for oncolytic tumor therapy based on an infectious recombinant measles virus scaffold encoded by the first nucleic acid sequence, wherein the measles virus scaffold encodes an attenuated measles virus.

In one embodiment, there is provided a composition, wherein the immunogenic or the vaccine composition additionally comprises at least one pharmaceutically and/or veterinary acceptable carrier and/or excipient.

In a further embodiment, there is provided a composition, wherein the immunogenic or the vaccine composition is characterized by a content of contaminating host cell DNA of less than 100 pg/dosis, preferably of less than 75 pg/dosis, more preferably of less than 50 pg/dosis, even more preferably less than 25 pg/dosis and most preferably of less than 10 pg/dosis, wherein one dosis represents one dosis comprising the immunogenic or the vaccine composition to be administered to a subject as a single dose.

In a further aspect, there is provided a method of treating, preferably prophylactically treating, a subject for protecting the subject from infection with a virus, wherein protection is achieved by exposing the subject to the at least one purified recombinant infectious virus particles comprised by the immunogenic composition or the vaccine composition disclosed herein, wherein the at least one purified recombinant infectious virus particle is encoded by at least one nucleic acid sequence, wherein the at least nucleic acid sequence comprises at least one first nucleic acid sequence encoding a virus scaffold and at least one second nucleic acid sequence operably linked to the first nucleic acid sequence, wherein the at least one second nucleic acid sequence encodes at least one antigen, preferably but not limited to an antigen of at least one virus.

As the various embodiments and aspects encompassed by the present disclosure all relate to possible variations of the methods of the present invention, they can be used alone or in combination with each other all forming individual embodiments according to the various aspects according to the present disclosure, where reasonable for the skilled person having knowledge of the present disclosure. Especially, all embodiments disclosed for the first aspect according to the present invention likewise apply for the second aspect of the present application, as both methods described by said aspects are built on each other.

Further aspects and embodiments of the present invention can be derived from the subsequent detailed description, the Sequence Listing, the deposited biological material as well as the attached set of claims.

DEFINITIONS

A "viral particle" or "virus particle" or "recombinant infectious virus particle" as used herein refers to a single particle derived from a viral nucleic acid, which is located outside a cell. The viral particle thus represents the mature and infectious form of a virus. As the viral particle contains genetic information, it is able to replicate and/or it can be propagated in a susceptible host cell. Depending on the complexity of a virus, the viral particle comprises nucleic acid and polypeptide sequences and, optionally lipids, preferably in the form of a lipid membrane derived from the host cell.

A "virion" as used herein refers to a single particle derived from a viral nucleic acid, which is located outside a cell containing nucleic acids and thus being able to replicate or to be transcribed in a suitable host cell.

A "virus-like particle" or "VLP" as used herein refers to at least one virus particle, which does not contain any nucleic acid. VLPs can thus be used to for vaccination or for inducing an immunogenic reaction in a subject, due to the absence of nucleic acids they will, however, not be able to replicate in a host cell and are thus non-replicative.

A "virus sample", "virus material" or the like thus refers to a material comprising at least one of a (recombinant infectious) virus particle and/or a virion and/or a VLP.

The term "viral vaccine" or "vaccine composition" as used herein refers to a virus particle, which is able to induce a protective immune response in a subject.

An "immunogenic composition" as used herein refers to a composition which is able to induce an immune response in a subject. An immunogenic composition according to the present disclosure comprises at least one vaccine composition based on the measles virus backbone platform comprising at least one antigen. A vaccine per se also is an immunological composition. However, it is well known to the skilled person that for being suitable to administration to an animal, an immunogenic composition can additionally comprise suitable pharmaceutically and/or veterinary acceptable carriers.

As used herein, the term "immune response" refers to an adaptive immune response, e.g. the T cell response or the increased serum levels of antibodies to an antigen due to a B-cell response, or presence of neutralizing antibodies to an antigen, such as an antigen, or it refers to an innate immune response, e.g. mediated by the complement system and cells of the innate immune system like macrophages or dendritic cells. It also refers to an allergic response, inter alia including mast-cell, eosinophil or NK-cell action, T-cells, B-cell secreted antibodies. The term immune response is to be understood as including a humoral response and/or a cellular response and/or an inflammatory response.

The term "antigen" as used herein and as commonly used in the field of immunology refers to an "antibody generating" molecule, i.e. a substance, which can elicit an adaptive immune response. An antigen is thus a molecule binding to an antigen-specific receptor, either a T-cell or a B-cell receptor. An antigen is usually a (poly)peptide, but it can also be a polysaccharide or a lipid, possibly combined with a protein or polysaccharide carrier molecule. For the purpose of the various aspects and embodiments of the present invention, the antigen is a (poly)peptide, i.e. an amino acid sequence. In the case of binding to a T-cell receptor, the antigen is presented to the respective T-cell receptor via an antigen-presenting cell as an antigenic peptide bound to a histocompatibility molecule on the surface of the antigen presenting cell, wherein the antigenic peptide has been processed in advance by the antigen presenting cell. Thus, an "antigen" as used herein refers to a molecule, such as a protein or a polypeptide, containing one or more epitopes that will stimulate a host's immune system to make a humoral and/or cellular antigen-specific response. The term is also used interchangeably with the term “immunogen” and concerning the effect “immunogenic”.

The term “protection” or “protective immunity” or “protective immune response” refers herein to the ability of the serum antibodies and cellular response induced during immunization to protect (partially or totally) against a virus of interest. Thus, an animal immunized by the compositions or vaccines of the invention will afterwards experience limited growth and spread if infected with the respective naturally occurring virus.

An “adjuvant” in the field of immunology and as used herein refers to a substance or composition enhancing antigenicity of another substance. This is achieved by specifically stimulating and balancing mainly the Th1 and Th2 subsets of T-cells and thus their effector molecules. Usually, immunogenic compositions based on live-attenuated or killed viruses are highly immunogenic per se and thus there might not be the need for an additional adjuvant, whereas an additional adjuvant might still be favourable to balance the provoked immune response. Th1 cells secrete IFN-γ, which activates macrophages and thus induces the production of opsonizing antibodies by B cells. The Th1 response therefore leads mainly to a cell-mediated immunity. Th2 cells mainly secrete cytokines, including IL-4, which induces B cells to make neutralizing antibodies. Th2 cells generally to induce a humoral (antibody) response critical in the defense against extracellular pathogens (helminths, extracellular microbes and toxins).

The terms “genetically modified” or “recombinant” or “genetical engineering”/“genetically engineered” as used herein refer to a nucleic acid molecule or an amino acid molecule or a host cell implying a targeted and purposive manipulation and/or modification achieved by means of molecular biology or protein engineering, e.g. by introducing a heterologous sequence into another host cell, by modifying a naturally occurring nucleic acid sequences and the like. Further modifications include, but are not limited to, one or more point mutation(s), one or more point mutation(s), e.g. for targeted protein engineering or for codon optimization, deletion(s), and one or more insertion(s) of at least one nucleic acid or amino acid molecule, modification of an amino acid sequence, or a combination thereof. The terms can also imply a sequence, which per se occurs in nature, but has been purposively treated by means of molecular biology isolated from its natural environment in vitro.

A “cell population” as used herein refers to at least one but preferably more than one host cell. The term host cell comprises non-recombinant cells, i.e. cells that were not immortalized or transformed or manipulated in a purposive manner. The term host cell also comprises host cells. To be suitable for the purposes of the present invention, the host cell(s) of the cell population must be able to support the measles virus replication cycle, i.e. the cell(s) must be susceptible to measles virus or measles virus scaffold infection and the cell(s) must suitable for the subsequent propagation or replication cycle, including replication, translation encapsidation of the RNA of the virus and budding from the host cell to be released as virus particle. Several eukaryotic host cells are fulfilling this purpose are cited herein or known to the skilled person.

The terms “derived”, “derived from”, “derivative” or “descendant” or “progenitor” as used herein in the context of either a host cell, a cell population or an infectious virus particle according to the present application relates to the descendants of such a host cell or infectious virus particle which results from natural reproductive propagation including sexual and asexual propagation and, in the context of virus nucleic acids, the propagation of the virus genetic material by the host cell machinery. It is well known to the person having skill in the art that said propagation can lead to the introduction of mutations into the genome of an organism resulting from natural phenomena which results in a descendant or progeny, which is genomically different to the parental host cell, however, still belongs to the same genus/species and possesses the same characteristics as the parental host cell. In the context of a virus, derivative or descendant or progenitor can thus naturally possess one or more mutations. Such derivatives or descendants resulting from natural phenomena during reproduction or propagation are thus comprised by the term host cell or cell population according to the present disclosure and the skilled person can easily define, by means of molecular biology, microscopy or the like, that the derivative or descendant is indeed derived from a parental host cell of the same genus. These terms, therefore, do not refer to any arbitrary derivative, descendant or progenitor, but rather to a derivative, or descendant or progenitor phylogenetically associated with, i.e. based on, a parent cell or virus or a molecule thereof, whereas this relationship between the derivative, descendant or progenitor and the “parent” is clearly inferable by a person skilled in the art.

The terms “attenuation” or “attenuated” as used herein in connection with a virus stain or a material derived therefrom refers to a virus weakened under laboratory conditions which is less vigorous than the respective wild-type virus. An attenuated virus may be used to make a vaccine that is capable of stimulating an immune response and creating immunity, but not of causing illness.

The term “vector” or “plasmid vector” as used herein defines a system comprising at least one vector suitable for transformation, transfection or transduction of a host cell. A vector per se thus denotes a cargo for the delivery of a biomolecule into a host cell of interest, wherein the biomolecule includes a nucleic acid molecule, including DNA, RNA and cDNA, or, in the case of a transfection system as vector, an amino acid molecule, or a combination thereof. A preferred vector according to the present invention is a plasmid or expression vector. An expression vector can comprise one vector encoding at least one target molecule, preferably a nucleic acid molecule, to be introduced into a host cell. A vector of the vector system can also comprise more than one target molecules to be introduced. Alternatively, the vector system can be built from several individual vectors carrying at least one target molecule to be introduced. An expression vector additionally comprises all elements necessary for driving transcription and/or translation of a sequence of interest in a host cell, the expression vector is designed for. These elements comprise, inter alia, regulatory elements, which are involved in the regulation of transcription, including promoters and the like functional in the host cell of interest. Furthermore, an expression vector comprises an origin of replication and optionally depending on the type of vector and the intended use a selectable marker gene, a multiple cloning site, a tag to be attached to a sequence of interest, a chromosomal integration cassette and the like. The choice and possible modification of a suitable expression vector for use with a respective host cell and sequence of interest to be inserted into the expression vector is well within the capabilities of the person skilled in the art.

The term “cDNA” stands for a complementary DNA and refers to a nucleic acid sequence/molecule obtained by reverse transcription from an RNA molecule. As it is a standard method for the person skilled in the art to obtain cDNAs from a given sequence and to further use this cDNA or to clone said cDNA into a vector, preferably a plasmid vector, of interest.

The term “regulatory sequence” as used herein refers to a nucleic acid sequence which can direct and/or influence the transcription and/or translation of a target nucleic acid sequence of interest. The term thus refers to promoter and terminator sequences or to polyadenylation signals and the like.

The terms “amino acid molecule/sequence”, “protein”, or “peptide” or “polypeptide” are used interchangeably herein. The term “amino acid” or “amino acid sequence” or “amino acid molecule” comprises any natural or chemically synthesized protein, peptide, or polypeptide or a modified protein, peptide, polypeptide and enzyme, wherein the term “modified” comprises any chemical or enzymatic modification of the protein, peptide, polypeptide and enzyme.

The terms “sequence(s)” and “molecule(s)” are used interchangeably herein when referring to nucleic acid or amino acid sequences/molecules.

As used herein, the term “pharmaceutically acceptable” refers to those compounds, materials, compositions, and/or dosage forms which are, within the scope of medical judgment or within the definition of any regulatory medical authority, suitable for contact with the cells, tissues, or components of a subject, i.e. human beings and animals, including contact with malignant cells or tissues of a subject, without excessive toxicity, irritation, allergic response, or other complications or side-effects commensurate with a reasonable benefit/risk ratio for a subject/patient.

Whenever the present disclosure relates to the percentage of the homology or identity of nucleic acid or amino acid sequences these values define those as obtained by using the EMBOSS Water Pairwise Sequence Alignments (nucleotide) programme (www.ebi.ac.uk) nucleic acids or the EMBOSS Water Pairwise Sequence Alignments (protein) programme (www.ebi.ac.uk) for amino acid sequences. Those tools provided by the European Molecular Biology Laboratory (EMBL) European Bioinformatics Institute (EBI) for local sequence alignments use a modified Smith-Waterman algorithm (see www.ebi.ac.uk and Smith, T. F. & Waterman, M. S. “Identification of common molecular subsequences” Journal of Molecular Biology, 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5.

The term “purifying” or “purify” as used herein in the context of purifying a biological material implies that the material of interest, i.e. recombinant infectious virus particles and/or VLPs are separated from further constituents including any product- or process related impurities as present due to the cultivation in a host cell or additives used during cell-culture or cell harvest/digest.

The term “polishing” as used herein in the context of a biological material implies that an already purified material is again subject to a further step of purification so that the resulting material of interest is made better than before in view of its purity. From a technical point of view, the means for purifying or polishing a material of interest can be the same or different.

DETAILED DESCRIPTION

According to a first aspect of the present invention, there is provided a method for purifying recombinant infectious virus particles, wherein the method comprises the following steps: (i) providing at least one clarified virus sample comprising at least one recombinant infectious virus particle, preferably derived from a measles virus scaffold, obtained from at least one host cell infected with a virus stock comprising the at least one recombinant infectious virus particle; (ii) purifying the at least one recombinant infectious virus particle by means of chromatography; (iii) obtaining purified recombinant infectious virus particles within at least one fraction from the chromatography of step (ii), wherein the purified infectious virus particles contain less than 33.33 ng/mL of contaminating host cell DNA with respect to 1 mL of the at least one fraction.

Due to the fact that the present invention inter alia provides methods for purifying at least one recombinant infectious virus particle for providing said particles as vaccines, it is a huge advantage to have a replication-competent vector, i.e. the recombinant infectious virus particles, optionally together with VLPs, in the such purified fraction, as this yields a vaccine with continuously expressed antigens even after immunization to provide a powerful, antigen-focused immune response, optionally also assisted by VLPs, to confer long-term immunity, as shown for other Paramyxoviridae-based, particularly measles-based, vaccines tested and/or approved.

The challenges in the production process thus not only imply the provision of a suitable vaccine vector and propagation strategies, but further demand the provision of improved methods for downstream processing, including purifying, the vaccine virus material of interest to achieve a significant increase in purity of the resulting material without a loss in functional, i.e. immunogenic, recombinant infectious virus particles and/or VLPs.

According to the methods of the present invention, the infectious virus particles purified according to the present disclosure contain less than 33.33 ng/mL of contaminating host cell DNA with respect to 1 mL. As further detailed in Example 10 below, host cell protein (HCP) levels for the material as obtainable according to Brandler et al. (supra) or for material as obtainable according to the disclosure of WO 2014/049094 A1, where HCP values of between 316.28 μg/mL to 861.31 μg/mL were obtained, the methods of the present invention thus on average provide significantly better purities inter alia regarding the HCP values over the prior art.

Therefore, according to the present disclosure, infectious virus particles and/or VLPs co-produced from the same scaffold can be directly obtained in a high degree of purity after at least one chromatographic step.

“Obtained” or “obtaining” in the context of obtaining purified virus particles this means that the respective particles can be directly obtained from a chromatographic step without any further processing, purification or polishing steps, whereas such further downstream steps are not excluded according to the methods of the present invention. Said further downstream processing to can comprise additional purification, chromatographic or by filtration, polishing, buffer exchange and the like to achieve either differential fractionation of desired compounds, to yield even higher purities, or to provide the such purified product in a suitable buffer system.

In a second aspect according to the present invention there is provided a method for purifying recombinant infectious virus particles according to the first aspect, wherein the method comprises the following further steps: (a) providing at least one host cell, preferably comprising at least one eukaryotic cell; (b) providing a virus stock comprising at least one recombinant infectious virus particle, wherein the at least one recombinant infectious virus particle is encoded by at least one nucleic acid sequence, wherein the nucleic acid sequence comprises at least one first nucleic acid sequence encoding a virus scaffold and at least one second nucleic acid sequence operably linked to the first nucleic acid sequence, wherein the at least one second nucleic acid sequence encodes at least one antigen, preferably an antigen of at least one virus, or a non-viral antigen suitable to render the infectious recombinant virus scaffold, per se being oncolytic, further anti-tumor capacities; (c) infecting the at least one host cell of step (a) with the virus stock provided in step (b); (d) incubating the at least one infected host cell at a temperature in the range of 32.0° C.+/−4° C., preferably at a temperature in the range of 32.0° C.+/−1° C.; (e) obtaining at least one virus sample from the at least one infected host cell comprising at least one recombinant infectious virus particle; (f) clarifying the at least one virus sample of step (e), wherein purifying the clarified virus sample by means of chromatography according to the first aspect of the present invention yield purified infectious virus particles containing less than 33.33 ng/mL of contaminating host cell DNA with respect to 1 mL of the at least one fraction.

The term "infectious" according to the present disclosure implies that the infectious virus particles after production in a host cell, preferably a host cell, or cell population comprising more than one host cells of interest carry all necessary molecules and are assembled in a way so that they are able to reinfect another cell population, host cell or subject of interest, i.e. the term implies the possibility of an infectious particle to enter and to replicate in a host cell and to potentially spread to further cells or tissues. Preferably, the infectious virus particles, optionally comprising virions and/or non-infectious virus-like particles (VLPs), or a mixture thereof, as obtained by the methods according to the present invention are suitable as immunogenic or as vaccine compositions as directly obtained by the methods disclosed herein. VLPs according to the present invention are understood to represent particles lacking genetic information and are thus non-replicative. VLPs per se are thus non-infectious in the sense that they cannot replicate in a cell to give rise to new viral particles and thus to spread to further cells after a replicative cycle. Still, VLPs, after their assembly and based on the molecules exposed on their surface, can interact with a host cell and/or host cell molecules, e.g. surface receptors, or, after uptake and/or processing by an immune cell, e.g. an antigen-representing cell, epitopes or antigens comprised by a VLP can be presented or to cross-presented by the immune cell to effector cells. By means of this interaction, VLPs can induce an immune response in an organism. This ability makes VLPs suitable structures for the provision of safe immunogenic or vaccine compositions.

The term encoding in connection with a nucleic acid sequence encoding a recombinant infectious virus particles derived from a measles virus scaffold according to the present invention means that the nucleic acid sequence provides the genetic information for the transcription and for polypeptides also the translation of the virus genome. Naturally, the recombinant infectious virus particles can contain further material, e.g. in their envelop as being released from a host cell after budding from the cell membrane.

In one embodiment of all aspects according to the present invention, the purification methods and the resulting products also have a reduced content of other process related impurities. Such process related purities comprise, but are not limited to host cells, cell debris, protein contaminants, either resulting from cell culture additives or from enzymes added during cultivation and processing, a microcarrier used for host-cell cultivation, or foreign nucleic acids neither belonging to the host cell nor the recombinant infectious virus or particles thereof of interest.

According to the above aspects, the purified recombinant infectious virus particles derived from a measles virus scaffold are obtained in one or more fractions corresponding to the product peak of the chromatography elution step. The concentration of contaminating DNA thus refers to the concentration of DNA detected within 1 mL of a fraction comprising the purified recombinant infectious virus particles derived from a measles virus scaffold. In case, there is more than one product peak of the chromatography elution step comprising the purified recombinant infectious virus particles derived from a measles virus scaffold, the concentration of less than 33.33 ng/mL, or preferably less, of contaminating host cell DNA can be achieved either in each of these individual fractions or in selected fractions thereof.

The terms "clarified" or "clarification" according to the present disclosure refers to a step for removing large product or process related impurities from a bulk product to be clarified. For the purpose of the present invention, the bulk product consists of the infectious virus particles and/or the VLPs produced in and released from a cell population or from a host cell. Clarification thus only aims at removing cells and cell-debris from the host cells infected with and producing a virus. Clarification usually does not imply, but can imply for certain host cells and viruses/VLPs, a specific separation of the analyte, i.e. the virus or virus particle or virus-like particle, with the aim of achieving high purity to eliminate further product- and process related impurities. Common methods for clarification are centrifugation and microfiltration, including tangential flow filtration, ultracentrifugation, filtering by filter cartridges and the like, which are both familiar to the skilled person in the relevant field. In the context of clarifying a bulk product comprising recombinant infectious virus particles derived from a measles virus scaffold is has to be noted that centrifugation should be avoided, as centrifugation processes are not easily scalable under GMP conditions or there is an increased risk of contamination of the desired product. Therefore, according to one embodiment, there is provided a method, wherein the clarification is performed by a method other than centrifugation, preferably, wherein clarification is performed by a filtration method, including inter alia depth filtrations or membrane filtration. Using filtration or any clarification technique relying on adsorption as separating principle a filter material should be chosen, which does not show unspecific binding or modification of the infectious measles virus particles. Suitable filter materials are disclosed in the Examples Section below.

In another embodiment, there is provided a method, wherein the clarification is achieved by harvesting a supernatant from a cell culture having been infected with at least one infectious virus particle and comprising infectious virus particles and/or VLPs according to the present disclosure and the supernatant is transferred to a chromatographic system. "Clarification" in this context thus means the separation of the host cell infected with and producing the virus material from the bulk product, i.e. the supernatant containing virus material, wherein the supernatant can then be directly transferred to a chromatographic system including a suitable chromatography medium, or the supernatant comprising the at least one infectious recombinant virus particle and optionally VLPs can be subjected to further means of removing product- or process-related impurities before chromatography.

For example, in case certain core bead technologies are used during chromatography, said chromatography medium or chromatography resin might tolerate that a supernatant from an infected cell culture is directly applied to the chromatography medium and clarification in this context thus means the transfer of the supernatant comprising the infectious virus particles and/or VLPs, only optionally including further steps in the context of clarification like filtration, DNAse treatment, centrifugation, concentration and the like. The direct transfer of virus material in the form of supernatant to a chromatographic system to interact with a chromatographic material or resin for purification might additionally comprise a subsequent concentration step to provide the virus material of interest in a suitably concentrated form.

In the field of purifying biomolecules of medical interest, downstream processing of a material produced by a host-cell of interest usually comprises a series of steps, comprising at least one capture step, e.g. for concentration and/or clarification, at least one purification step and optionally at least one polishing step. Said overall processing is comprised by the methods of the present invention.

In a further embodiment of the methods disclosed herein, the clarification can be accomplished in the form of a capture step, wherein the biological material to be subsequently purified, e.g. a virus sample comprising recombinant infectious virus particles and/or VLPs, is initially gathered and/or concentrated by means of filtration, centrifugation and the like. There is no specific limitation concerning the capture mode, i.e. either impurities may be captured, i.e. retained, on a capture material and thus separated from a virus sample passing through and being collectable in the flow through to be further used, or the virus sample may be retained on a material of interest, whilst any impurities pass through a capture or clarification system and the virus sample of interest can then be eluted and further processed subsequently.

In yet a further embodiment, the supernatant comprising infectious virus particles and/or VLPs according to the present disclosure is treated with a DNAse, preferably with a benzonase, either before or after harvesting, i.e. removing, the supernatant from a cell culture used for the production and/or propagation of an infectious virus particle of interest. In this embodiment, the clarification thus can be the treatment with a suitable DNAse. Any other method known to the skilled person and suitable to perform a crude separation of the host cellular material and the supernatant comprising the virus particles and/or VLPs of interest thus are also comprised by the term "clarifying" or "clarification".

In a further embodiment according to the methods of the present invention, an additional or alternative preparation or capture step prior to the provision of the clarified virus sample comprising recombinant infectious virus particles obtained from at least one host cell infected with a virus stock can be envisaged, comprising, inter alia, subjecting the virus sample to a filtration step, preferably tangential flow filtration, a concentration step, a centrifugation step, bead- and chromatography based capture techniques, or a combination thereof, depending on the nature of the virus scaffold to be purified.

The term virus stock refers to a seed stock comprising at least one recombinant infectious virus particle derived from a measles virus scaffold suitable to infect a host cell of interest. Given the fact that a virus has to be provided in a certain amount to efficiently infect a host cell of interest, the term virus stock usually implies a stock comprising more than one infectious virus particle derived from a measles virus scaffold, as depending on the host cell of interest, the infectious virus particle of interest and the intended multiplicity of infection (MOI) used for infection. The MOI usually depends on the Tissue culture infective dose (TCID). Alternative methods for the TCID method are a plaque assay, an immune focus assay or quantitative PCR (qPCR). The $TCID_{50}$ as used herein refers to median tissue culture infective dose, i.e the amount of a pathogenic agent that will produce pathological change in 50% of cell cultures inoculated. An appropriate MOI/$TCID_{50}$ can be determined following common tests, e.g. the Kärber method or the Reed Muench method. A virus stock as used herein preferably refers to a recombinant virus stock. As the genetic material derived from a measles virus scaffold and encoding a recombinant infectious virus particle is suitable as an immunogenic or as a vaccine composition, the material is preferably prepared under GMP conditions. A virus sample as used herein refers to a sample obtainable from an infected host cell during the various steps of the methods according to the present application. The term can thus refer to a sample obtained from the supernatant, or a sample obtained from the lysate of a cell. A virus sample can be used for further clarification and/or purification as disclosed herein or for the purpose of analysis, e.g. for determining the correct sequence of a transcribed virus genome or for the analysis of virus virions and/or virus-like particles.

According to all aspects of the present disclosure, the at least one host cell can be selected from the group consisting of cells selected from the group consisting Vero cells, chicken embryo fibroblast cells, HEK293 cells, HeLa cells or MRC5 cells. The person skilled in the art can easily define further suitable host cells and the corresponding culture conditions for a selected infectious recombinant virus scaffold of interest.

According to all aspects and embodiments of the present disclosure, a measles virus scaffold refers to a nucleic acid molecule comprising all, parts of the antigenomic region of a measles virus, preferably including further recombinant enhancements. A suitable measles virus scaffold is disclosed in SEQ ID NOs:1 and 4 and in WO 2014/049094 A1 or EP 1 939 214 B1.

Notably, the present disclosure is not restricted to the purification of Paramyxoviridae or measles virus based scaffolds. The disclosure provided herein is rather suitable for the purification of further sterically demanding viruses and particularly also for enveloped viruses, i.e. for viruses having a viral envelop covering the capsid. Classed of enveloped viruses containing human pathogens, which can be purified according to the present disclosure, comprise, for example Herpesvirus, Poxvirus, Hepadnavirus, Flavivirus, Togavirus, Coronavirus, Hepatitis D virus, Orthomyxovirus, Rhabdovirus, Bunyavirus, Filovirus, or certain retroviruses.

According to any embodiment of the various aspects of the present disclosure, the nucleic acid construct encoding a recombinant infectious virus particles comprising an infectious measles virus (MV) scaffold for use according to the present invention thus comprises the following gene transcription units encompassing from 5' to 3': (a) a polynucleotide encoding the N protein of a MV, (b) a polynucleotide encoding the P protein of a MV, (c) the polynucleotide encoding at least one structural protein used as antigen, for example at least one Chikungunya structural protein, suitable as antigen (d) a polynucleotide encoding the M protein of a MV, (e) a polynucleotide encoding the F protein of a MV, (f) a polynucleotide encoding the H protein of a MV, and (g) a polynucleotide encoding the L protein of a MV, said polynucleotides and nucleic acid construct being operably linked and under the control of viral replication and transcription regulatory sequences such as MV leader and trailer sequences. The expressions "N protein", "P protein", "M protein", "F protein", "H protein" and "L protein" refer respectively to the nucleoprotein (N), the phosphoprotein (P), the matrix protein (M), the fusion protein (F), the hemagglutinin protein (H) and the RNA polymerase large protein (L) of a Measles virus. These components have been identified in the prior art and are especially disclosed in Fields, Virology (Knipe & Howley, 2001). Hemagglutinin (H) and fusion protein (F) are components of the viral envelope of MV which are responsible to mediate fusion with the host cells. H binds to CD46 and CD150 on the surface of a host cell. Especially H is very immunogenic in the host cell or organism and during a natural infection it is responsible for (life)long immunity that follows said infection. Said immunity is due to the establishing of cell-mediated memory and the production of neutralizing antibodies against H protein. During the replication cycle, synthesis of measles virus or measles virus scaffold mRNA, translation, and replication all take place in the cytoplasm of a host cell. The expression "operably linked" thus refers to the functional link existing between the at least one antigen encoding nucleic acid sequence according to the methods of the invention such that said at least one nucleic acid sequence within the measles virus scaffold is efficiently transcribed and translated, in particular in cells or cell lines, especially in cells or cell lines used as cell bank according to the present invention so that an antigenic epitope can be presented after. It is well within the capability of the person having skill in the art to clone a nucleic acid of interest into a measles virus scaffold as disclosed herein.

A particular cDNA nucleic acid molecule suitable for use in the embodiments according to all aspects of the present invention is the one obtained using the Schwarz strain of measles virus. Accordingly, the cDNA used within the present invention may be obtained as disclosed in WO 2004/000876 A1. The sequence of this plasmid without ATUs is disclosed herein as SEQ ID NO:1. The plasmid pTM-MVSchw has been obtained from a Bluescript plasmid and comprises the polynucleotide coding for the full-length measles virus (+) RNA strand of the Schwarz strain placed under the control of the promoter of the T7 RNA polymerase. It has 18994 nucleotides and a sequence represented as SEQ ID NO:1 cDNA molecules (also designated cDNA of the measles virus or MV cDNA for convenience) from other MV strains may be similarly obtained starting from the nucleic acid purified from viral particles of attenuated MV such as those described herein. SEQ ID NOs:4 and 7 then discloses the measles virus scaffold including ATUs (Additional Transcription Units). SEQ ID NOs: 4 and 7 have a different lengths, as the both sequences comprise varying remaining sequences of the pBluescript plasmid, said sequences are derived from.

In another embodiment according to the present invention a cDNA nucleic acid molecule suitable for use in the methods according to the present invention comprises at least one antigen, which is derived from a virus other than a measles virus. The sequence according to SEQ ID NOs:1 or 4 or 7, which contains an infectious MV cDNA corresponding to the anti-genome of the Schwarz MV vaccine strain, has been described elsewhere (Combredet, C, et al., A molecularly cloned Schwarz strain of measles virus vaccine induces strong immune responses in macaques and transgenic mice. J Virol, 2003. 77(21): 1546-54). For example, the cDNA encoding for the structural antigens of the Chikungunya virus can be generated by chemical synthesis (GenScript, USA). It can contain the sequence for viral structural proteins C-E3-E2-6K-E1 from CHIKV strain 06-49 (WO 2014/049094 A1). The complete sequence respects the "rule of six", which stipulates that the number of nucleotides into the MV genome must be a multiple of 6, and contains BsiWI restriction site at the 5' end, and BssHII at the 3' end. The sequence was codon optimized for measles virus expression in mammalian cells. This cDNA was inserted into BsiWI/BssHII-digested pTM-MVSchw-ATU2, which contains an additional transcription unit (ATU) between the phosphoprotein (P) and the matrix (M) genes of the Schwarz MV genome (Combredet, C, et al., A molecularly cloned Schwarz strain of measles virus vaccine induces strong immune responses in macaques and transgenic mice. J Virol, 2003. 77(21): 1546-54). The resulting nucleic acid sequence is represented in SEQ ID NOs:2 and 8 (pTM 2ATU MV CHIK long (SEQ ID NO:2) and short (SEQ ID NO:8), respectively, said sequences only differing in the length of remaining pBluescript material and otherwise being identical). Rescue of a recombinant infectious virus particles derived from a measles virus scaffold can then be performed as previously described using a rescue system previously described (Radecke, F., et al., Rescue of measles viruses from cloned DNA. EMBO J, 1995. 14(23): p. 5773-84; WO 2008/078198 A2). Viral titers can be determined by endpoint limit dilution assay, e.g. on Vero cells, and $TCID_{50}$ can be calculated by using the Kärber method known to the person skilled in the art or an alternative method as disclosed above.

Another example for a nucleic acid sequence encoding a recombinant infectious virus particle derived from a measles virus scaffold according to disclosure of the present invention, which can be purified according to the methods of the present invention is shown in SEQ ID NOs:3 and 9 (pTM 2ATU MV DVAX1 short (SEQ ID NO:3) and long (SEQ ID NO:9), respectively, said sequences only differing in the number of remaining pBluescript sequences and otherwise being identical), which comprises antigens derived from the Dengue virus cloned into an ATU of the measles virus scaffold.

The person having skill in the art provided with the information of the present disclosure can easily determine the unique restriction sites present in SEQ ID NO:1 for the purpose of cloning, i.e. creating an operably linkage, between the recombinant infectious measles virus scaffold and a nucleic acid sequence encoding an antigen of a virus operably linked to said measles virus scaffold. As the measles virus scaffold as disclosed on SEQ ID NO:1 is well characterized, the skilled person can define a suitable cloning strategy to introduce a nucleic acid sequence of interest into a measles virus scaffold at different positions to allow a functional insertion. A functional insertion or the term operably linked in this context is thus intended to mean an introduction, which will allow the transcription and translation of all amino acid sequences encoded by the measles virus scaffold, i.e. the insertion may not disrupt a regulatory sequence, including a promoter and the like, or a amino acid coding sequence, including the structurally and functionally relevant proteins of the measles virus, i.e. the "N protein", "P protein", "M protein", "F protein", "H protein" and "L protein", or the antigen sequence of interest introduced into the measles virus scaffold.

In one embodiment according to the aspects of the present invention the operable linkage refers to the insertion of a nucleic acid molecule encoding at least one antigen of at least one virus into the measles virus scaffold. As detailed above and as evident from SEQ ID NOs:1, 4 and 7 in comparison to SEQ ID NOs:2/8 and 3/9, the measles virus scaffold, from a structural point of view, will always represent the majority of the material to be transcribed/translated into a recombinant infectious virus particle. It will thus also predominantly influence the functional and biological characteristics of the envelope of the purified infectious virus particles and, in certain embodiments, the functional and biological characteristics of virus-like particles (VLPs). In certain embodiments of the methods disclosed herein, replication of the measles virus scaffold comprising at least one nucleic acid sequence encoding at least one polypeptide, wherein the polypeptide is an antigen of at least one virus, allows the co-purification of measles virus scaffold derived virions and the VLPs.

In one embodiment according to the various aspects of the present invention there is further provided a method, wherein the recombinant infectious virus particles are encoded by at least one first nucleic acid sequence encoding the virus scaffold and further comprising at least one second nucleic acid sequence operably linked to the first nucleic acid sequence, wherein the second nucleic acid sequence encodes at least one antigen, preferably of at least one virus for immunization purposes, or a non-viral antigen in case of oncolytic tumor treatment purposes, wherein the nucleic acid sequence encoding at least one antigen is selected from the group consisting of a nucleic acid sequence derived from a virus belonging to the family of Flaviviridae, including a nucleic acid sequence derived from a West-Nile virus (cf. NCBI reference sequence NC_009942.1), a tick-borne encephalitis virus (NCBI reference sequence NC_001672.1), a Japanese encephalitis virus (NCBI reference sequence NC_001437.1), a yellow fever virus (NCBI reference sequence NC_002031.1), a Zika virus (NCBI reference sequence NC_012532.1), or a Dengue virus (e.g. NCBI Dengue virus 1/strain Nauru/West Pac/1974: NC_001477.1), a Chikungunya virus, a norovirus (e.g. Norwalk virus, NCBI NC_001959.2), a virus belonging to the family of Paramyxoviridae, including a nucleic acid sequence derived from a human respiratory syncytical virus (RSV) (e.g. NCBI: NC_001781.1), a measles virus or a metapneumovirus (e.g. human: NCBI Gene ID: 2830349; avian: NCBI Gene ID: 5130032), a parvovirus (e.g. human parvovirus B19, NCBI: NC_001348.1), a coronavirus, including a nucleic acid sequence derived from a Middle East respiratory syndrome antigen (see e.g. NCBI: NC_019843.3), or a severe acute respiratory syndrome antigen (e.g. NCBI: NC_004718.3), a human enterovirus 71 (e.g. enterovirus A, NCBI: NC_001612.1), a cytomegalovirus (e.g. human herpesvirus 5, NCBI: NC_006273.2), a poliovirus (e.g. human enterovirus C serotype PV-1, NCBI: NC_002058.3, an Epstein-Barr virus (e.g. human herpesvirus 4, NCBI: NC_009334.1 or NC_007605.1, respectively), a hepatitis E virus (e.g. NCBI: NC_001434.1), a human papilloma virus, preferably a human papilloma virus 16, a human papilloma virus 5, a human papilloma virus 4, a human papilloma virus 1 or a human papilloma virus 41 (see e.g. NCBI: HPV-16: NC_001526.2; HPV-5: NC_001531.1; HPV-4: NC_001457.1; HPV-1: NC_001356.1; HPV-41: NC_001354.1), or a varicella zoster virus (e.g. human herpesvirus 3, NCBI: NC_001348.1). As the purification methods according to the present invention insofar as they rely to the measles virus scaffold rely on the physic-chemical properties of the measles virus scaffold from which the recombinant infectious virus particles are derived, any of the above antigens can be inserted and operably linked to the measles virus scaffold and the resulting recombinant construct encoding a virus can be purified according to the methods of the present invention, even if the design of the specific at least one antigen to be inserted of at least one virus might, due to the very nature of the matter in the field of virology and immunology, require a specific design and several tests and research efforts, still resulting in a recombinant infectious virus particle derived from a measles virus scaffold, which can be purified according to the methods of the present invention.

The broad applicability of the methods according to the present invention are elucidated by the fact that very different virus particles as a common feature all being derived from a measles virus scaffold (e.g. SEQ ID NOs:2 to 9 as disclosed herein) could be efficiently purified according to the methods disclosed and claimed herein and all resulting in a high pure and functional product having less than 33.33 ng/mL of contaminating host cell DNA in the virus fraction as obtained after chromatography. In certain embodiments, even a purity of below 1.1 pg/mL (1.1 fg/μl) and thus below the detection limit of the assay described in the Examples could be achieved after the purification of construct according to SEQ ID NOs:2/8 and 3/9 as well as SEQ ID NOs:5 and 6 as to the first and second aspect of the present invention.

In one embodiment according to different aspects of the present invention the infectious virus scaffold is derived from an attenuated virus strain, preferably from an attenuated measles virus strain being selected from the group consisting of the Schwarz strain, the Zagreb strain, the AIK-C strain and the Moraten strain.

In one embodiment according to the various aspects of the present invention there is further provided a method additionally comprising a further purification step (iv), comprising: further purifying the purified recombinant infectious virus particles derived from a virus scaffold by means of filtration, centrifugation, tangential flow filtration, membrane filtration, purification with grafted media, aqueous two phase extraction, precipitation, buffer exchange, dialysis or chromatography, including size exclusion chromatography for separating the purified recombinant infectious virus particles derived from a virus scaffold into a fraction containing virions and another fraction containing virus-like particles. Said embodiment is especially useful in case the antigenic region inserted as nucleic acid sequence into the virus scaffold has to be further separated into at least one fraction containing the replication competent virions of the virus containing genetic material and into at least one fraction containing the VLPs self-assembled from the antigens of at least one virus, wherein the VLPs are devoid of genetic material. Therefore, they posses relevant surface antigens, but cannot further be propagated in a host cell, which makes VLPs an interesting target for several applications in immunology. Thus, the skilled person having knowledge of the present disclosure can easily apply the disclosed purification strategies for any measles virus scaffold related infectious virus particle having a sequence derived from SEQ ID NOs:1 to 9 or a homologous sequence having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology thereto provided that the homologous sequence after transcription and optionally translation in a cell population or host cell still results in a measles virus scaffold optionally operably linked to at least one antigen of at least one virus, which is infectious and immunogenic, but does not comprise a mutation in a region of the measles virus genome, which would disturb its natural replication cycle, or which would revert the attenuated measles virus scaffold back into a non-attenuated virus form. Said sequence homology range is thus caused by the fact that a measles virus scaffold can, by means of recombinant technology, comprise codon optimized positions, further regulatory or antigen positions and the like. Said modifications, however, would still lead to a recombinant infectious virus particles derived from a measles virus scaffold, which can be purified according to the methods of the present invention, as the disclosed purification principles would still apply for such a modified virus scaffold.

In another embodiment according to the various aspects of the present invention there is further provided a method additionally comprising a further polishing or buffer-exchange step, comprising: further purifying or polishing a recombinant infectious virus particles, or subjecting a recombinant infectious virus particles to a buffer-exchange by means of filtration, centrifugation, tangential flow filtration, membrane filtration, purification with grafted media, aqueous two phase extraction, precipitation, buffer exchange, dialysis or chromatography, including size exclusion chromatography for further polishing the virus particles or for providing a suitable buffer exchange possibly necessary for the downstream manufacture of a desired product. Such an additional step of polishing or buffer-exchange is furthermore especially suitable to further decrease the amount of process-related DNAses or serum proteins used during the manufacturing process of the virus particles according to the present invention and thus to achieve a higher degree of purity in terms of protein contaminants in the purified recombinant infectious virus particles and in an immunogenic or a vaccine composition obtainable therefrom. Additionally, said step can be applied to further separate VLPs from the recombinant infectious virus particles.

All nucleic acid molecules according to the present disclosure can optionally be codon optimized. This implies that the codon usage of a given nucleic acid sequence can be modified to be compatible with the codon usage of a host cell of interest to allow better transcription rates and the expression of functional amino acid sequences in a host cell of interest. The person having skill in the art in the knowledge of the genetic code and the codon usage of a target host cell can easily adapt a nucleic acid molecule according to the present disclosure without effecting a change in the resulting amino acid sequence after translation. Therefore, codon optimized sequences of the nucleic acid molecules according to the present invention are also comprised by the present disclosure.

In a particular embodiment of the methods of the present invention, the construct is prepared by cloning a polynucleotide sequence encoding one structural protein or a plurality of structural proteins of a virus other than a measles virus in the cDNA encoding the full-length antigenomic (+) RNA of the measles virus. Alternatively, a nucleic acid construct of the invention may be prepared to using steps of synthesis of nucleic acid fragments or polymerization from a template, including by PCR. It is further disclosed that the polynucleotide encoding the at least one protein of the virus other than a measles virus, or each of these polynucleotides, is cloned into an ATU (Additional Transcription Unit) inserted in the cDNA of the measles virus. Usually, there is one ATU per construct. ATU sequences usually comprise three potential regions of inserting a nucleic acid and further comprise, for use in steps of cloning into cDNA of MV, cis-acting sequences necessary for MV-dependent expression of a recombinant transgene, such as a promoter preceding a gene of interest, in MV cDNA, the insert represented by the polynucleotide encoding the viral protein(s) inserted into a multiple cloning sites cassette. The ATU is advantageously located in the N-terminal sequence of the cDNA molecule encoding the full-length (+)RNA strand of the antigenome of the MV and is especially located between the P and M genes of this virus or between the H and L genes. It has been observed that the transcription of the viral RNA of MV follows a gradient from the 5' to the 3' end. This explains that, when inserted in the 5' end of the coding sequence of the cDNA, the ATU will enable a more efficient expression of the heterologous recombinant nucleic acid DNA sequence. The ATU sequence can, however, be located at any position of SEQ ID NO:1 provided that it does not disrupt a coding sequence or a regulatory sequence thereof.

Furthermore, according to any aspect of the present invention, the disclosed nucleic acid molecules can be further modified by means of molecular biology to introduce a new or a modified regulatory sequence, restriction enzyme binding/cutting site as well as various nucleic acid sequences encoding an antigenic region of interest, preferably respecting the above identified "rule of six". This rule was established for certain viruses belonging to the Paramyxoviridae family where the measles virus scaffold of the present disclosure phylogenetically is derived from/belongs to. This rule is thus derived from the fact that in order for the entire process of RNA synthesis, genome replication and encapsidation which the measles virus proceeds through in a host cell to be efficient at generating full-length genomic and antigenomic molecules it is necessary that the viral genome is enclosed within its protein coat, specifically the N proteins. Without this, the virus replication machinery will find problems to begin replication. Each N molecule associates with exactly 6 nucleotides, which explains the reason as to why these viruses require their genomes to be a multiple of six. It is thus evident that a variety of modifications of the measles virus scaffold can be undertaken with the proviso that it still results in a measles virus scaffold able to infect a host cell. Therefore, means like codon optimization and the like can be applied as long as no mutation introduced which would change the functional properties of a regulatory sequence or a structural protein of the measles virus. Furthermore, in the case of virions comprising genetic material, it has to be ensured by sequencing that the resulting purified recombinant infectious virus particles derived from a measles virus scaffold do not comprise a mutation rendering the attenuated virus virulent again. Such methods of nucleic acid sequencing, including deep sequencing, for means of sequence confirmation belong to the common general knowledge of the skilled person in the field of molecular biology and virology and can be applied at any stage of the methods according to the present disclosure.

The same holds true for virus-like particles which may not comprise potentially harmful mutations in the sequences encoding for their structural proteins. VLP production can inter alia be monitored by means of electron microscopy. To this end, for example, supernatants from infected cells, e.g. Vero cells, can be collected after 36 h of infection with an MOI of 0.0001 to 1, preferably with an MOI of 0.0001 to 0.1, after infection with a construct as detailed in SEQ ID NO:2/8. The supernatants are then clarified by centrifugation at 3,000 rpm for 30 min, layered on 20% sucrose cushion in PBS and centrifuged at 41,000 rpm for 2 h in a SW41 rotor. Pellets are next resuspended in PBS with 1%

BSA and analysed by electron microscopy. Negative staining is conducted by 2% uranyl acetate on copper grids coated with carbon and glow discharged just before use. The samples can be observed at 80 kV with a Jeol JEM1200 (Tokyo, Japan) transmission electron microscope. Images were recorded using an Eloise Keenview camera and the Analysis Pro-software version 3.1 (Eloise SARL, Roissy, France).

Therefore, any recombinant infectious virus particle, particularly derived from a measles virus scaffold, can be purified according to the methods of the present invention, as the methods are specifically optimized taking into consideration the peculiar chemical and physical properties of the huge and pleomorphic measles virus, wherein said properties are mainly influenced by the measles virus envelope/capsid making up the majority of the surface accessible are of the recombinant infectious virus particle derived from a measles virus scaffold and thus the criteria decisive for a column-based purification strategy according to the present invention so that also any huge or sterically demanding virus, or any enveloped virus can likewise be subjected to the purification schemes disclosed and claimed herein.

In one embodiment according to the various aspects of the present invention, the at least one virus sample is treated with a DNAse, preferably with a benzonase, a DNAse endonuclease genetically engineered originally being from *Serratia*, either before or after the clarification. In one embodiment, the DNAse treatment is performed before the clarification step. In another embodiment, the DNAse treatment is performed with a clarified virus sample comprising recombinant infectious virus particles. Said step fulfills two functions: first of all, unwanted nucleic acids in the form of DNA can be cleaved to allow a more efficient removal of DNA during the further purification. Secondly, the virus sample which can be obtained from this treatment reduces the viscosity of the resulting material. Said lower viscosity results in an enhanced performance of the material in chromatography, as the material otherwise would easily clog a column comprising the stationary phase of interest.

In one embodiment according to the various aspects of the present invention, no DNAse treatment is conducted. The choice of a DNAse treatment or omitting said step will depend on the chromatographic resin to be used during the subsequent purification, the type of host cell, the culture conditions and the degree of lysis of the host cells and the like.

According to any embodiment according to the various aspects of the present disclosure the recombinant infectious virus particles derived from a measles virus scaffold by means of chromatography, preferably liquid chromatography. Chromatography refers to a separating principle or a procedure in which a biological or chemical mixture of substances comprising an analyte carried by a liquid or a gas is separated into its components as a result of differential distribution of the solutes between a stationary and a mobile phase, as they flow around or over a stationary liquid, gel or solid phase as stationary phase. Passing of the analyte containing mixture through the stationary phase leads to a retention of the analyte depending inter alia on the interaction between the analyte and the stationary phase and its diffusion characteristics as dictated by the chemical and physical properties of the analyte. For the purpose of the present invention, the analyte is represented by the recombinant infectious virus particles derived from a measles virus scaffold and/or VLPs thereof. Given the above outlined genome size of the measles virus scaffold and the resulting huge particle size of 100 to up to 1,000 nm for the enveloped virus and the physico-chemical properties of the infectious virus particles or the virus-like particles derived from the measles virus scaffold, so far no efficient chromatography based approach exists for purifying the measles virus derived infectious virus particles. Attempts to purify the measles virus or a measles virus scaffold derived virus particle were accompanied by huge loss of the material to be purified so far and could not be conducted at an industry grade under GMP conditions.

Not only for vaccination, but even more for oncolytic virus-based cancer treatment GMP purification protocols are urgently needed to safely use those viruses having pleotropic modes of action, which include, besides viral tumor cell lysis, activation of antitumor immunity. Parvovirus, adenovirus, herpes simplex virus (HSV), vaccinia virus, reovirus, and measles virus have been suggested as oncolytic viruses. Besides measles virus (MV), also HSV and vaccinia virus, for example, represent huge viruses for which new GMP approved purification strategies are thus needed, which can be implemented according to the methods of the present invention. In contrast to using MV as a vaccine, oncolytic activity as an advanced therapy medicinal product depends on high concentration of infectious particles. While the size range of pleomorphic MV particles is often quoted as 100-300 nm, in practice, MV must be treated as >1 μm particles that are extremely shear sensitive, to maximize recoveries and retain infectivity. Therefore, the entire production and purification process has to be done under gentle and aseptic GMP conditions.

MV vaccine strains are oncolytic by preferentially entering tumor cells through CD46, a membrane protein that is typically overexpressed in malignant cells. For the commercially produced MV vaccine, the WHO recommends values ≤100 pg per dose (i.e., 1,000 ip) for residual host cell DNA. But for the use of high doses of MV in cancer therapies (e.g., $10^9$ ip for intratumoral injections), the limit for expectedly higher amounts of residual host DNA in the final product has to be coordinated with the regulating authorities (for a review, see Ungerechts et al., Mol. Ther.—Methods and Clinical Development (2016), 3, 16018). Therefore, the methods disclosed herein are particularly suitable for providing highly purified virus material for oncolytic cancer therapy, particularly if based on an attenuated infectious measles virus scaffold, as very high purities of 1.1 pg/mL of contaminating host cell DNA per one mL of the recombinant infectious virus particles as directly obtained within at least one fraction after chromatographic purification with respect to 1 mL of the at least one fraction can be achieved for measles virus based scaffolds using the purification schemes according to the present invention. Therefore, the present invention is not restricted to methods using at least one second nucleic acid sequence being selected from a virus as origin for this second sequence for immunization purposes, but is rather suitable for the purification of oncolytic viruses for cancer therapy.

In one embodiment according to the various aspects of the present disclosure, the purification by means of chromatography is performed using a stationary phase, preferably a stationary phase having a monolithic arrangement, wherein the stationary phase has a pore size of at least 5 μm, preferably a pore size of at least 6 μm, and more preferably a pore size of at least 7 μm, or wherein the purification by means of chromatography is performed using a stationary phase having a monolithic arrangement, wherein the mode of adsorption is hydrophobic interaction. The methods according to the present invention can be conducted with a variety of stationary phase arrangements, including a monolithic arrangement or an arrangement of irregularly or spherically shaped particles, including porous particles, or with an arrangement of a porous membrane. The stationary phase is preferably packed into a suitable carrier device, e.g. a column, of interest. Suitable columns and column formats are readily available to the skilled person.

In the field of chromatography, it is known to the skilled person that the stationary phases, especially in the context of the purification of a virus, will preferably consist of pre-packed porous beds, a matrix consisting of membrane adsorbers or that the stationary phase can have a monolithic arrangement. The column material can also consist of a hydrogel, or bio- or nano-fibres, optionally functionalized. Hydrogels, and particularly polymeric hydrogels, may be provided in the form of a flexible porous support matrix to make them suitable for chromatography-based approaches and to achieve a high binding capacity and high flow rates. For all different kinds of stationary phases, several separation modes or modes of adsorption exist being classified according to their principle of interaction and/or separation of the analyte to be separated/purified. Said modes include affinity chromatography, ion exchange chromatography, including cation and anion exchange chromatography, hydrophobic interaction, size exclusion, or a combination thereof. For example, a dual functionality, size exclusion, and binding chromatography in one chromatography medium can be used. In another embodiment, membrane adsorbers may be used combining the advantages of using a convective media for ion or anion exchange chromatography for virus or VLP capture and thus purification.

Concerning the methods according to the present invention, membrane adsorbers and even more preferably monolithic stationary phases are especially advantageous, as the show a high binding capacity as well as a high possible flow rate. In addition, low pressure has to be applied. This makes the methods according to the present application especially suitable for large and/or enveloped viruses.

In one embodiment according to the present invention, the chromatography is based on convective chromatography techniques, including a monolithically arranged stationary phase or a membrane adsorber as stationary phase. This allows the purification of recombinant infectious virus particles, optionally comprising virions and/or virus-like particles, even for sterically demanding particles of huge viruses having a large diameter, or for particles having peculiar surface characteristics. Furthermore, said specific stationary phases provide improved characteristics regarding their capacity, resolution, the yield of the virus product to be purified and the high possible flow rates. In one embodiment according to the present invention, the step of purifying the recombinant infectious virus particles, preferably comprising an infectious measles virus scaffold by means of chromatography after clarification is performed by using a hydrophobic interaction approach. Said strategy for purifying the crude virus sample obtained after clarification is especially suitable for particles derived from the measles virus scaffold, as other modes of separation like ion exchange, might not be suitable or might require a tedious process optimization for measles virus scaffold based infectious virus particles, as the huge measles virus derived virus particles, the virions and/or the virus-like particles derived therefrom and their isoelectric point as well as the huge surface area of a virus reactive groups associated therewith is prone to lead to unspecific interactions in case a ion exchange mode is used for interaction hampering an efficient purification, wherein the loss of virus material has to be as low as possible. One exemplary suitable monolithic stationary phase is provided in a CIMmultus™ column (BIA separations) with an optimized pore size of at least 4 μm, preferably of at least 5 μm, and more preferably of at least 6 μm. One possible ligand defining the purification mode and thus the surface chemistry of the monolithic stationary phase is a OH-ligand, whereas the resulting OH-monoliths are very hydrophilic due to the highly density of the hydroxyl groups, which makes them suitable in an hydrophobic interaction purification approach of the infectious virus particles derived from a measles virus scaffold according to the methods of the present invention.

In another embodiment, a hydrogel-based column material may be used.

In a further embodiment, fibre-based technologies, or hollow fibre field-flow fractionation may be used as chromatographic purification and/or polishing steps. For hollow fibre field-flow fractionation, a liquid flow comprising a virus sample to be purified is thus pumped through the opening (inflow end) of a fibre bundle having porous walls. A portion of the stream can exit through the walls and forms a cross-flow relative to the main flow direction, wherein the main flow direction corresponds to the orientation of the fibres from the inflow to the outflow end of a cartridge. As the cross flow will superimpose with the parabolic flow profile of the longitudinal flow, there is a separation and thus purification/polishing of material of interest due to the inherently different diffusion coefficients of the components within the material to be purified/polished and in turn the depending on the hydrodynamic radius and/or the molecular mass of the components to be purified/polished.

In another embodiment according to the present invention ion exchange chromatography can, however, be used to purify virus-like particles obtainable from a virus stock according to the present invention. Due to the smaller overall size of the measles virus scaffold derived virus-like particles and their defined surface characteristics, ion exchange chromatography and also size exclusion chromatography, and a combination or mixture thereof in the form of several chromatographic steps, can be used to purify virus-like particles according to the present invention.

In another embodiment of the present invention, size exclusion chromatography as mode of interaction is used to separate the clarified virus stock, wherein the pore size of the stationary phase material is at least 5 μm, preferably at least 6 μm, and more preferably a pore size of at least 7 μm.

In another embodiment of the present invention directed to the further purification of VLPs, size exclusion chromatography as mode of interaction is used to separate the clarified virus stock, wherein the pore size of the stationary phase material is less than 5 μm, less than 4 μm, or less than 3 μm in view of the fact that the VLPs have smaller dimensions than the infectious measles virus particles.

In a further embodiment according to the present invention, size exclusion, ion exchange or hydrophobic interaction chromatography is used to further purify the recombinant infectious virus particles, preferably derived from a measles virus scaffold after a first chromatographic purification. Other purification methods like tangential flow filtration, purification with grafted media, aqueous two phase extraction or precipitation are also possible. Said modes of purification are especially suitable to further decrease the amount of process-related DNAses or serum proteins used during the manufacturing process of the virus particles, preferably derived from a measles virus scaffold according to the present invention and thus to achieve a higher degree of purity in terms of protein contaminants in the purified recombinant infectious virus particles and in an immunogenic or a vaccine, or an anti-tumor composition obtainable therefrom. Alternatively, according to another embodiment of the present invention, the second purification step to further remove process-related protein contaminants from the purified recombinant infectious virus particles is conducted by tangential flow filtration. Preferably, the level of contaminating process-related total protein contaminants in the purification in the sample, i.e. in the at least one fraction comprising the infectious virus particles, directly obtained from the first chromatographic step according to the present invention is below 1 ng/mL, more preferably it is below 100 pg/mL, even more preferably, it is below 10 pg/mL, and most preferably, it is below 1.1 pg/mL.

Preferably, the level of contaminating process-related protein contaminants in the purification in the sample, i.e. in the at least one fraction comprising the infectious virus particles, directly obtained from the second chromatographic or the subsequent purification step after conducting the first chromatographic step according to the present invention is below 5 μg/mL, preferably below 1 μg/mL, more preferably it is below 100 pg/mL and even more preferably, it is below 10 pg/mL.

In yet another embodiment according to the present invention, affinity chromatography is used to purify the recombinant infectious virus particles, preferably derived from a measles virus scaffold as second chromatography step. Said embodiment is especially suitable in case an antibody binding an antigen expressed and presented on the recombinant infectious virus particles is present, or where a tag has been fused and thus operably linked to the nucleic acid sequence encoding surface exposed parts of the recombinant infectious virus particles.

The person skilled in the art is aware that several columns and chromatography systems exist which are suitable to conduct the methods using the separation techniques and stationary phases as detailed herein.

In one embodiment according to the various aspects according to the present invention, the purified recombinant infectious virus particles contain less than 30 ng/mL, preferably less than 20 ng/mL, more preferably less than 10 ng/mL, even more preferably less than 1 ng/mL, even more preferably less than 100 pg/mL, even more preferably less than 10 pg/mL and most preferably less than 1.1 pg/mL of contaminating host cell DNA per one mL of the recombinant infectious virus particles as directly obtained within at least one fraction after chromatographic purification with respect to 1 mL of the at least one fraction. The term directly obtained after chromatographic purification implies the degree of purity obtained in the sample as directly obtained without any further concentration or filtration steps after collecting the product peak from the chromatography step.

Methods to determine the concentration of contaminating host cell DNA are known to the person having skill in the art. Said methods rapidly advance and thus the limit of quantification (LOQ: amount of target DNA that maximizes the sum of sensitivity and specificity) and the limit of detection (LOD: lowest amount of target DNA which can be amplified with a false-negative rate below a given threshold) for a sample of interest are getting improved rapidly. Therefore, nowadays much more precise quantification of process- and product related impurities/contaminants are possible than 20 years ago. A standard method for detecting small amounts of contaminating DNA in a sample is quantitative real-time PCR (qPCR or qRT PCR) (e.g. PicoGreen® assay (Life Technologies)). Another method for detecting contaminating DNA or proteins in a sample of interest are threshold DNA assays (e.g. Threshold® Immunoligand Assay (ILA) or Threshold® Total DNA Assay Molecular Devices). Said methods both show a high sensitivity and a good detection limit in the pictogram range and are readily available to the skilled person. Likewise, methods for performing quantification of total protein, or of specific proteins contained as contaminants in a sample or in an immunogenic or a vaccine composition comprising the purified infectious virus particles derived from the measles virus scaffold can be quantified by methods readily available to the skilled person. Said methods, inter alia, include a BCA (bicinchoninic acid) assay or a Vero cell host cell protein (HCP) ELISA assay (Cygnus Technologies, current detection limit as declared by the manufacturer: 700 pg/mL) or other enzyme and/or fluorescence based methods. Said methods are readily available to the skilled person.

The methods according to the present invention thus for the first time provides a chromatography based approach for purifying infectious virus particles derived from a measles virus scaffold. These methods are designed so that they can be conducted under GMP conditions in a large scale which represents a prerequisite for the use of said methods for the production of virus material to be used as immunogenic or as vaccine composition in a subject. For example, density gradient centrifugation is both expensive and laborious in scaling up so that it is not suitable for large scale measles virus and measles virus scaffold based purification. Furthermore, the inventive methods for the first time allow the preparation of infectious virus particles derived from the measles virus scaffold characterized in a significantly reduced level of contaminating host cell DNA in the preparation directly obtained from the chromatography and thus a significantly reduced level of contaminating host cell DNA in the final dosis to be administered to a subject in need thereof. Furthermore, it is an advantage of the methods according to the present invention and the products which can be obtained therefrom that in principle no further processing or concentration is necessary after the chromatography step which is advantageous as every further step would intrinsically be prone to a loss of virus material and would have to be performed under GMP conditions. Moreover, the methods according to the present invention and the products which can be obtained therefrom are provided in a high yield and in active form from the chromatography step allowing, if intended, a further purification step, for example, in case a further separation of infectious virions and virus-like particles, if present, from the pool of purified infectious virus particles, or a further decrease of product- and process-related impurities is desired, for example during an additional purification, polishing or buffer-exchange step. The use of additional polishing steps according to the methods of the present invention after initial purification are thus envisaged and can, for example, comprise at least one step selected from the group consisting of tangential-flow filtration, dia-filtration, dialysis, buffer exchange, a further chromatographic purification step, membrane filtration or the like to achieve a greater purity and/or a differential separation of virus and VLP material, a concentration without losing the biological activity, i.e. its immunogenic potential, of the purified virus and/or VLP material, a stabilization by means of transfer to a suitable buffer system, the system being pharmaceutically acceptable for administration to a subject, or any combination thereof.

According to one embodiment of the present invention, all nucleic acid or amino acid sequences used according to the methods of the present invention or disclosure can additionally comprise a tag sequence. A tag sequence is a nucleic acid or amino acid sequence portion which can be located in front, in the middle or at the end of a sequence of interest, encoding or representing a sequence allowing the better analysis of a sequence of interest, wherein the analysis includes, but is not restricted to the purification, visualisation or further processing of a sequence of interest. Suitable tags can be selected from the group consisting of a polyhistidin(His)-tag, a glutathione-S-transferase (GST)-tag, a thioredoxin-tag, a FLAG-tag, a tag having fluorescent properties, selected from (E)GFP ((enhanced) green fluorescent protein) tag, a DsRed-tag, a mCherry-tag and the like or, a streptavidin or strep-tag, a maltose-binding protein (MBP) tag, a transit peptide allowing the targeting to a subcellular compartment, including mitochondria or the nucleus, a snap-tag and/or a secretion tag allowing the secretion of an amino acid sequence attached thereto, a non-naturally amino acid not normally occurring in nature, or a combination of the aforementioned tags.

In one embodiment, an antigen of a virus comprised by the recombinant infectious virus particles derived from a measles virus scaffold can carry at least one tag enabling purification via affinity chromatography either as first chromatographic purification step or as an additional purification step.

In another embodiment of the different aspects of the present invention, there is provided at least one host cell, comprising at least on eukaryotic cell or host cell suitable for propagating a recombinant infectious virus particles derived from a measles virus scaffold according to the present disclosure. The term propagating in this context implies that the host cell or the cell population comprising at least one host cell, preferably a host cell, can support a full replicative cycle of the measles virus scaffold derived infectious virus particles, including infection, transcription, replication and for protein sequences of the virus translation as well as encapsidation of the virus particles, or the assembly of virus-like particles, and preferably also their release. The at least on eukaryotic cell or host cell is preferably a recombinant cell, as the use of an established recombinant cell line allows the establishment of standardized GMP protocols.

In one embodiment according to the various aspects of the present disclosure the cell population or the host cell, the cell population or the host cell consists of cells selected from the group consisting of Vero cells (African green monkey kidney cells), e.g. the WHO reference cell line Vero RCB 10-87 established in 1987 and subjected to a broad range of tests to establish its suitability for vaccine production or ATCC-CRL-1587™, chicken embryo fibroblast cells, e.g. ATCC® CRL-12203™, HEK293 cells, e.g. ATCC® CCL-1573™, HeLa cells, e.g. ATCC® CCL-2™ or ATCC® CCL-2™, or MRC5 cells, e.g. ATCC® CCL-171™. As detailed above, any cell line is suitable for the purpose of the present invention as long as it can be infected with a virus scaffold, preferably a measles virus scaffold, derived infectious virus particle and as long as it supports a replication cycle thereof. The skilled person can thus define a suitable and compatible host cell-virus system for the intended infectious virus scaffold to be produced. Preferably, the cell population comprising at least one cell or the at least one host cell are recombinant, as a host cell represents a standardized and well characterized material which are indispensable prerequisites for certain GMP approaches and concerning safety issues. It is further known to the skilled person that certain cell lines require permission to release, e.g. from the WHO, if they are intended for the production of a vaccine or a biological, or for the development of new candidate vaccines or biologicals following the FDA requirements. Said permission can be obtained by the relevant authorities as it is known to the skilled person. The cell population or the at least one host cell used for the purpose of the present invention, for example as master cell bank, will only be used until a certain number of passages is achieved to avoid the risk of a cell line to accumulate mutations which renders it potentially tumorigenic. Preferably, the number of cell passages will thus not exceed 170, preferably not exceed 160, more preferably not exceed 155, and most preferably not exceed 150 passages.

Methods and means for cultivating a host cell according to the present disclosure which allow the viability of the respective host cell and which allow the introduction, maintenance and transcription, translation and possibly secretion of the vectors, nucleic acid and amino acid molecules disclosed herein are well known to the person having skill in the art.

Suitable reaction conditions as referred to herein, including inter alia buffers, including buffer composition and pH, additives, temperature- and pH-conditions, reaction times and the like can be readily determined by the skilled person in knowledge of the disclosure provided herein. Said conditions may naturally vary depending on the host cells of the cell population chosen for infection with recombinant infectious virus particles derived from a measles virus scaffold, whereas the disclosure provided herein provides guidance for setting and determining said reaction conditions.

Another aspect of the present invention provides an immunogenic composition comprising purified recombinant infectious virus particles preferably comprising an infectious measles virus scaffold obtained by a method as detailed above for various above described aspects and embodiments. An immunogenic composition in this context is any composition eliciting an immune response in a subject.

In one embodiment of this aspect, the immunogenic composition additionally comprises at least one pharmaceutically and/or veterinary acceptable carrier and/or excipient.

Another aspect of the present invention provides a vaccine composition comprising a purified recombinant infectious virus particle preferably comprising an infectious measles virus scaffold obtained by a method as detailed above for various above described aspects and embodiments, optionally wherein the vaccine composition additionally comprises at least one pharmaceutically and/or veterinary acceptable carrier and/or excipient. As defined above, a vaccine composition according to the present invention is suitable to elicit a protective immune response in a subject after administration thereof as detailed above, i.e. protection is achieved by exposing the subject to the at least one purified recombinant infectious virus particles comprised by the immunogenic composition or the vaccine composition, wherein the at least one purified recombinant infectious virus particle is encoded by at least one nucleic acid sequence, wherein the at least nucleic acid sequence comprises at least one first nucleic acid sequence encoding a virus scaffold and at least one second nucleic acid sequence operably linked to the first nucleic acid sequence, wherein the at least one second nucleic acid sequence encodes at least one antigen of at least one virus for, e.g. for prophylactic immunization purposes, or wherein the at least one second nucleic acid sequence encodes at least one non-viral antigen, e.g. for curative oncolytic cancer therapy. Notably, the at least one second nucleic acid sequence can also be a viral molecule suitable for oncolytic cancer therapy purposes in certain cases.

There is thus provided a therapeutic method of treating a subject comprising administering to the subject in need thereof at least one immunogenic composition or at least one vaccine composition according to the present invention to prevent a disease and/or to cure the symptoms associated with a disease, wherein the disease is associated with infection by a virus capable of infecting a mammal, and wherein the at least one immunogenic composition or at least one vaccine composition according to the present invention comprises at least one antigen derived from this virus and thus specifically eliciting an immune response in a subject, preferably a mammal, and more preferably a human, wherein the immune response comprises antibody mediated B-cell responses as well as cellular responses mediated by T-cells, or mediated by any cell of the innate or adaptive immune system of a subject.

Furthermore, there is provided a therapeutic method of treating a subject suffering from a tumor/cancer, comprising administering to the subject in need thereof at least one oncolytic composition according to the present invention based on an infectious recombinant virus scaffold to cure the symptoms associated with a tumor/cancer disease in a subject, preferably a mammalian subject, and more preferably a human.

A carrier according to the present disclosure is a substance that aims at improving the delivery and effectiveness of a drug composition. Carrier materials may depend on the physical state of a drug composition to be administered. Typically, immunogenic or vaccine compositions are administered as liquid solution. Suitable substances are well known to those in the art and include, large, slowly metabolized macromolecules, such as proteins, polysaccharides, polylactic acids, polyglycolic acids, polymeric amino acids, amino acid copolymers, and inactive virus particles. Pharmaceutically and veterinary acceptable salts can also be used in the immunological composition, for example, mineral salts such as hydrochlorides, hydrobromides, phosphates, or sulfates, as well as the salts of organic acids such as acetates, propionates, malonates, or benzoates. Immunological compositions can also contain liquids, such as water, saline, glycerol, and ethanol, as well as substances such as wetting agents, emulsifying agents, or pH buffering agents. Furthermore, nanocarriers, including liposomes, also can be used as carriers. Depending on the nature of the at least one immunogenic or the vaccine composition used and dependent on the immune response, which is intended to be provoked, such a composition can additionally comprise an adjuvant and further pharmaceutically and/or veterinary acceptable carriers. Furthermore, an immunogenic or a vaccine composition according to the present disclosure can comprise more than one active ingredient in the form of an antigen.

An excipient is a substance included in a drug composition, including an immunological or a vaccine composition, which is added for the purpose of long-term stabilization, bulking up solid formulations that contain active ingredients, including, for example, infectious virus particles, or to confer a therapeutic enhancement on the active ingredient in the final dosage form, e.g. for improving the absorption, modifying the viscosity or for enhancing solubility.

In one embodiment of the present invention, the immunogenic composition or the vaccine composition is characterized by a content of contaminating host cell DNA of less than 100 pg/dosis, preferably of less than 50 pg/dosis, more preferably of less than 10 pg/dosis, even more preferably less than 10 pg/dosis and most preferably of less than 1.1 pg/dosis, wherein one dosis represents one dosis comprising the immunogenic or the vaccine composition to be administered to a subject in need thereof as a single dose. Several applications of a single dose of an immunogenic or a vaccine composition to be administered to a subject in need thereof can be needed depending on the reaction to be provoked. As detailed above for the various embodiments and aspects concerning the methods according to the present invention, the specific chromatography base purification scheme allows the provision of infectious virus particles based on or derived from a measles virus scaffold which show an improved purity in at least one fraction as directly obtained after a chromatography step following clarification of the crude bulk material. As a matter of course, the level of contaminating host cell DNA or the level of other process—pr product related impurities is even lower, at least by a factor of 1 to 10 depending inter alia on the efficiency of the production process and the final titer chosen for application, and, therefore, the level of contaminating DNA or proteins or other materials in an immunogenic or a vaccine composition is naturally even lower. As detailed in the Background of the Invention, currently, the WHO defines a limit of 10 ng/dosis of a drug vaccine composition to be administered to a subject, whereas the former limit of 100 pg/mL was increased to the 10 ng/dosis threshold, as many manufactures of virus compositions for use a viral vaccines, especially in the context of live attenuated viruses like measles, mumps and rubella could not consistently guarantee such a low level of contaminating host cell DNA. The immunogenic or vaccine composition as provided herein and as purified according to the methods of the present invention allows the provision of a drug composition, which even has a degree of contaminating host cell DNA of below 100 pg/dosis or even lower and, most preferably even below the current detection limit for DNA achievable by presently available detection methods, which currently is in the single-digit pictogram range depending on the material to be analyzed and the quantitative method used, including PCR; enzyme-based and luminescence based assays. For the purpose of the present invention given the detection system used herein at the date of this invention, said detection limit for DNA is 1.1 pg/mL (1.1 fg/μl).

In a further aspect according to the present invention there is provided a vaccine composition prepared according to the methods of the present invention for use in a method of prophylactic treatment of a subject for protecting the subject from infection with a virus, wherein protection is achieved by exposing the subject to the recombinant infectious virus particles comprised by the immunogenic composition or the vaccine composition, wherein the recombinant infectious virus particles derived from a measles virus scaffold are encoded by at least one nucleic acid sequence, wherein the nucleic acid sequence comprises at least one second nucleic acid sequence operably linked to the first nucleic acid sequence, wherein the at least one second nucleic acid sequence encodes at least one antigen of at least one virus.

A prophylactic treatment as referred to herein in the context of vaccine compositions means a treatment which mediated a protective immune response in a subject vaccinated so that there are no or less severe symptoms, when the subject after having been vaccinated and after having developed an immune response to the vaccine composition will encounter an infection with the non-attenuated wild-type strain of a virus antigens of which are present in the vaccine composition.

In accordance with the present disclosure, vaccines and/or immunogenic formulations of the present disclosure may be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. A third dose may be optionally administered when no or low levels of specific immunoglobulins are detected in the serum and/or urine or mucosal secretions of the subject after the second dose. In another embodiment, the compositions of the present disclosure can be administered as part of a combination therapy. For vaccine compositions according to the present invention derived from the measles virus scaffold, a single administration or one administration followed by one booster injection will usually suffice to establish a protective immune response even in the presence of pre-existing anti-vector immunity against the measles virus scaffold.

In one embodiment, the vaccine compositions according to the present application show significantly reduced acute side effects in comparison to a vaccine composition comprising the same infectious virus particle derived from a measles virus scaffold, yet not being purified. Acute side effects include local pain, tenderness, redness, swelling, itching, and induration which can be determined according to the respective guidance for industry from the US Food and Drug Administration and the guidance of the Brighton Collaboration (The Brighton Collaboration Foundation. https://brightoncollaboration.org/public (accessed Mar. 17, 2014) and WHO. Weekly epidemiological record. Jan. 19, 2007. http://www.who.int/wer/2007/wer8203.pdf (accessed Sep. 12, 2007)) as assessed before vaccination and 6 h post injection of a vaccine composition.

The present invention is further described with reference to the following non-limiting examples.

EXAMPLES

The present invention is further illustrated by the following non limiting examples.

Example 1: Master Cell Bank Production

First, a master cell bank (MCB) of Vero 10-87 cells, lot No 1416.01 MCB, P #145 was produced. The MCB is contained in cryovials, each containing 1 mL of cell suspension at a concentration of $1.0\times10^7$ cells/mL. The MCB was stored in a vapour phase liquid nitrogen cryogenic tank at different locations to assure continued disposability of the material. The same procedures likewise apply for the use of a different cell line as MCS, whereas the concentration of cells can in the range of $1.0\times10^3$ cells/mL to $1.0\times10^9$ cells/mL, depending on the cell type chosen. All procedures are conducted under GMP conditions. This results in the provision of the respective working cell bank (WCB).

Example 2: Measles Virus (MV) Master Virus Seed Stock (MVSS) Provision

Next, a master virus seed stock (MVSS) had to be provided. For the purpose of this example, a recombinant, Chikungunya protein expressing, live attenuate Measles virus (MV CHIK), lot number 1420.01 The MVSS used for this exemplary purification scheme can be obtained from the plasmid pTM 2ATU MV CHIK (SEQ ID NOs:2, 8; Chikungunya insert) or pTM 2ATU MV DVAX1 (SEQ ID NO:3, 9; Dengue insert). A representative plasmid for both inserts was deposited under the Budapest Treaty at the Leibniz-Institute DSMZ-German Collection of Microorganisms and Cell Cultures GmbH (Inhoffenstraße 7B, 38124 Braunschweig, Germany) under the accession number DSM 32235 (pTM 2ATU MV CHIK, Chikungunya insert) and DSM 32234 (pTM 2ATU MV DVAX1, Dengue insert), respectively, for the purpose of EP15202480.8 this application claims priority of. Specific reference is thus made to this material as deposited by the same applicant for the purpose of the priority founding application EP15202480.8. The material was deposited as plasmid DNA. *Escherichia coli* was indicated as suitable host for transformation and propagation of the respective plasmids. Both, the deposit DSM 32235 and DSM 32234 were deposited on 15 Dec. 2015 and the viability was confirmed by DSMZ in a viability statement under Rule 10.2 of the Budapest Treaty on 16 Dec. 2015. A MVSS can be easily obtained from the deposited material by performing the process for the preparation of recombinant infectious measles virus particles as disclosed in WO 2014/049094 A1, optionally under GMP conditions, by 1) transfecting helper cells with the invention with a transfer vector, wherein said helper cells are capable of expressing helper functions to express an RNA polymerase, and to express the N, P and L proteins of a MV virus; 2) co-cultivating said transfected helper cells of step 1) with passaged cells suitable for the passage of the MV attenuated strain from which the cDNA originates; 3) recovering the recombinant infectious MV CHIK virus expressing at least one structural protein of CHIK virus to provide a MVSS according to the disclosure of WO 2014/049094 A1. Likewise, MV-Zika material according to a plasmid shown in SEQ ID NOs: 5 and 6 and as further disclosed in EP16162688.2 was propagated and purified according to the methods of the present invention to demonstrate that the methods can also be used for any other measles- or Paramyxoviridae-based scaffold carrying a specifically designed insert of interest for vaccination.

The MVSS was contained in cryovials each containing 1 mL of unpurified viral suspension at a concentration of $5.75\times10^6$ tissue culture infective dose (TCID) $TCID_{50}$/mL. The MVSS is stored at −80±10° C. at two different locations. Logically, the $TCID_{50}$/mL value can vary depending on the vaccine insert provided together with the MV backbone. This results in the provision of a working viral seed stock (WVSS).

Example 3: MCB Revival and Expansion Under GMP Conditions

Two cryovials each containing 1.0 mL MCB or WCB were removed from storage in vapour phase liquid nitrogen and are transported to the cleanroom in a sanitised container which is in turn transported on dry ice. Once within the cleanroom, the MCB/WCB cryovials were thawed in hands/at ambient while gently swirling the content until all ice within the vials has melted. When the vials had thawed they were transferred to a biosafety cabinet. The thawed cell suspensions from each vial were transferred aseptically into 50 mL centrifuge tubes. 9 mL of pre-warmed Dulbecco's Modified Eagle Medium (DMEM)+10% fetal bovine serum (FBS) medium were added drop-wise to each 50 mL tube containing the thawed cells while gently swirling the tubes. The MCB/WCB cryovials were each rinsed with the homogeneous cell suspension from the centrifuge tube and the rinse was transferred back to the respective 50 mL tubes.

The cell suspensions were then centrifuged at 300×g±5% for 5 minutes at room temperature. The supernatants were discarded and the pellets were suspended in 10 mL DMEM+

10% FBS medium. The resuspended pellets were removed from the biosafety cabinet and centrifuged for a second time using the same parameters as before. The supernatant was again discarded and the pellets were resuspended in 10 mL DMEM+10% FBS medium. 0.5 mL from the prepared cell suspensions was removed and used to perform a cell count determining viable cells and viability. The remaining cell suspensions were passaged to one T225 cell culture flasks/suspension and medium was made up to 50 mL using pre-warmed DMEM+10% FBS medium. Thus, in total 2×T225 flasks were prepared (one per vial).

TABLE 1

Exemplary flask culture parameters: stage 1

| Stage | Parameter | Operating criteria (range) |
|---|---|---|
| Cell culture Stage 1 | Seeding density | From MCB revival |
| | Culture volume (T225) | 50 mL |
| | Culture medium | DMEM + 10% FBS |
| | Temperature | 36.5 ± 1° C. |
| | Duration | Approximately 3 ± 1 days |
| | $CO_2$ | 5.0% ± 2% |
| | Humidity | 80% ± 10% |
| | Final cell density | ≥80% confluent cells |
| | Final cell viability | ≥80% viability |

Following growth in flask culture, the supernatant from the 2×T225 flasks was removed, discarded and the cell monolayer was washed with pre-warmed D-PBS. Pre-warmed TrypLE Select was added to each flask and distributed evenly over the monolayer. Flasks were incubated to detach cells and then observed for cell detachment under the microscope. If necessary, the flasks were taped gently for cell detachment. If detachment was below 90%, flasks were further incubated until detachment of greater than 90% was reached. Parameters are described in Table 2 below.

Pre-warmed DMEM+10% FBS medium was added to each flask and the cell suspension was removed to sterile centrifuge tubes. The cell suspensions were then centrifuged as described in Table 2 (stage 2) below. After centrifugation, the supernatant was removed and discarded while the cell pellets were resuspended in DMEM+10% FBS medium by pipetting up and down. The cultures were fully suspended if no cell clumps were visible. Resuspended cell-solutions from 2×T225 flasks were each transferred into sterile containers (50 mL centrifugation tube) and mixed to obtain a homogenous solution of cells. 0.5 mL from the prepared cell suspensions were removed and used to perform a cell count determining viable cells and viability of each cell solution. The remaining cell suspensions were passaged to 5×T225 cell culture flasks/suspension and medium was made up to 50 mL using pre-warmed DMEM+10% FBS medium.

Thus, in total 10×T225 flasks were prepared in this exemplary setting, which might naturally depend of the nature of the product to be produced.

TABLE 2

Flask culture parameters: stage 2

| Stage | Parameter | Operating criteria (range) |
|---|---|---|
| Cell culture Stage 2 | Seeding density | 2.00 × $10^4$ cells/$cm^2$ |
| | Culture volume (T225) | 50 mL |
| | Culture media | DMEM + 10% FBS |
| | Incubation Temperature | 36.5 ± 1° C. |
| | Duration | Approximately 4 ± 1 days |
| | $CO_2$ | 5.0% ± 2% |
| | Humidity | 80% ± 10% |
| | Final cell density | ≥80% confluent cells |
| | Final cell viability | ≥80% viability |
| Cell harvest | PBS Cell wash volume (T225) | 10 mL |
| | TrypLE select volume (T225) | 5 mL |
| | Cell detachment incubation temperature | ambient |
| | Cell detachment incubation time | 5 min then until 90% detachment |
| | DMEM + 10% FBS added for centrifugation | 10 mL |
| | Centrifugation (g) | 300 × g ± 5% |
| | Centrifugation time | 5 minutes |
| | Centrifugation temperature | Room temperature |
| | Pellet resuspension media (DMEM + 10% FBS) volume | 10 mL |

Following growth in flask culture stage 2, the supernatant from the two T225 sets (5 T225 flasks per set; 10 T225 flasks in total) flasks was removed, discarded and the cell monolayer was washed with pre-warmed D-PBS. Pre-warmed TrypLE Select was then added to each flask and distributed evenly over the monolayer. Flasks were incubated to detach cells and then observed for cell detachment under the microscope. If necessary, the flasks were taped gently for cell detachment. If detachment was below 90%, flasks were further incubated until detachment of greater than 90% was reached. Parameters are described in Table 3 below.

Pre-warmed DMEM+10% FBS medium was added to each flask and the cell suspensions were removed to sterile centrifuge tubes. The cell suspensions were then centrifuged as described in Table 3 below. After centrifugation, the supernatant was removed and discarded while the cell pellets were resuspended in DMEM+10% FBS medium by pipetting up and down. The cultures were fully suspended if no cell clumps were visible. Resuspended cell-solutions from each set (5×T225 flasks) were transferred/pooled into one sterile container (50 mL centrifugation tube) and mixed to obtain a homogenous solution of cells. 0.5 mL from the prepared cell suspensions were removed and used to perform a cell count determining viable cells and viability of each cell solution. After analysis of viable cells and viability, the best performing set of T225 flasks was selected and passaged to 30×T225 cell culture flasks and medium was made up to 50 mL using pre-warmed DMEM+10% FBS medium.

TABLE 3

Flask culture parameters: stage 3

| Stage | Parameter | Operating criteria (range) |
|---|---|---|
| Cell culture Stage 3 | Seeding density | 2.00 × $10^4$ cells/$cm^2$ |
| | Culture volume (T225) | 50 mL |
| | Culture media | DMEM + 10% FBS |
| | Incubation Temperature | 36.5 ± 1° C. |
| | Duration | Approximately 4 ± 1 days |
| | $CO_2$ | 5.0% ± 2% |
| | Humidity | 80% ± 10% |
| | Final cell density | ≥80% confluent cells |
| | Final cell viability | ≥80% viability |
| Cell harvest | PBS Cell wash volume (T225) | 10 mL |
| | TrypLE select volume (T225) | 5 mL |
| | Cell detachment incubation temperature | ambient |

TABLE 3-continued

| Flask culture parameters: stage 3 | | |
|---|---|---|
| Stage | Parameter | Operating criteria (range) |
| | Cell detachment incubation time | 5 min then until 90% detachment |
| | DMEM + 10% FBS added for centrifugation | 10 mL |
| | Centrifugation (g) | 300 × g ± 5% |
| | Centrifugation time | 5 minutes |
| | Centrifugation temperature | Room temperature |
| | Pellet resuspension media (DMEM + 10% FBS) volume | 10 mL |

Following growth in flask culture stage 3, the supernatant from the 30×T225 flasks was removed, discarded and the cell monolayer was washed with pre-warmed D-PBS. Pre-warmed TrypLE Select was added to each flask and distributed evenly over the monolayer. Flasks were incubated to detach cells and observed for cell detachment under the microscope. If necessary, the flasks were taped gently for cell detachment. If detachment was below 90%, flasks were further incubated until detachment of greater than 90% was reached. Parameters are described in Table 4a below.

Pre-warmed DMEM+10% FBS medium was added to each flask and the cell suspension was removed to sterile centrifuge tubes. The cell suspension was then centrifuged as described in Table 4a below. After centrifugation, the supernatant was removed and discarded while the cell pellet was resuspended in DMEM+10% FBS medium by pipetting up and down. The culture was fully suspended if no cell clumps were visible. Resuspended cell-solutions from all 30×T225 flasks were transferred into one sterile container and mixed to obtain a homogenous solution of cells. 0.5 mL from the prepared cell suspension were removed and used to perform a cell count determining viable cells and viability.

TABLE 4a

| T Flask harvest parameters | | |
|---|---|---|
| Stage | Parameter | Operating criteria (range) |
| Cell harvest T-Flasks | PBS Cell wash volume (T225) | 10 mL |
| | TrypLE select volume (T225) | 5 mL |
| | Cell detachment incubation temperature | ambient |
| | Cell detachment incubation time | 5 min then until 90% detachment |
| | DMEM + 10% FBS added for centrifugation | 10 mL |
| | Centrifugation (g) | 300 × g ± 5% |
| | Centrifugation time | 5 minutes |
| | Centrifugation temperature | Room temperature |
| | Pellet resuspension media (DMEM + 10% FBS) volume | 10 mL |

Example 4: Spinner Flasks and Bioreactor Microcarrier Assisted Culture (Stage 4)

Per 1 L spinner flask, 10 g HillexII microcarrier were resuspended in 200 mL water-for-injection (WFI) and autoclaved under saturated steam for 20 minutes at 2 bar and 121° C. Any suitable microcarrier suitable as carrier material of a host cell of interest can be chosen for the purpose if the microcarrier assisted culture. Post sterilization, microcarrier were allowed to sediment, the WFI was removed carefully, discarded and microcarrier were washed with 200 mL PBS. Finally, PBS was replaced by 100 mL pre-warmed DEMEM+10% FCS medium without phenol red. Medium with phenol red can also be used for this step. The sterilized microcarrier was then transferred into the respective 1 L spinner flask by pipetting the medium/microcarrier suspension carefully.

The required amount of cells (as determined in Table 4b below) was transferred aseptically into each spinner flask. The medium was made up to 500 mL using DMEM+10% FBS medium without phenol red. In total, 6 spinner flasks were prepared and transferred into the incubator, containing magnetic stirrer plates; agitation is set to 35 rpm. Seeded spinner flasks were incubated over night and medium was made up to 1 L using DMEM+10% FBS medium without phenol red the next day.

TABLE 4b

| 1 L Spinner Flask inoculation parameters | | |
|---|---|---|
| Stage | Parameter | Operating criteria (range) |
| Cell culture Stage 4 | Seeding density | 2.50 × $10^4$ cells/$cm^2$ |
| | Culture flask type | 1 L Spinner flasks |
| | Surface area per g HillexII | 515 $cm^2$ |
| | Seeding culture volume | 500 mL |
| | Total culture volume | 1,000 mL |
| | Revolutions per minute | 35 |
| | Culture media | DMEM + 10% FBS; w/o Phenol Red |
| | Incubation Temperature | 36.5 ± 1° C. |
| | Duration | Approximately 5 ± 1 days |
| | $CO_2$ | 5.0% ± 2% |
| | Humidity | 80% ± 10% |
| | Final cell density | ≥80% confluent cells |
| | Final cell viability | ≥80% viability |

Spinner flasks were then removed from the incubator and transferred into a biosafety cabinet. Spinner flasks were allowed to stand for 5 minutes without agitation to enable cell-containing microcarrier to sediment. Supernatant from each spinner flask was removed carefully, discarded and the microcarriers were washed with pre-warmed D-PBS. The cell/microcarrier suspensions from each spinner flasks were then transferred into a sterile container (500 mL) and washed twice with D-PBS. Pre-warmed TrypLE Select was added to the container and mixed gently to obtain a homogenous solution. Microcarriers were incubated to detach cells and cell detachment was controlled under the microscope. When a cell detachment of greater than 90% was reached, pre-warmed DMEM+10% FBS medium without phenol red was added and a viable cell count as well determination of viability was performed.

TABLE 5

| 1 L spinner flask: harvest parameters | | |
|---|---|---|
| Stage | Parameter | Operating criteria (range) |
| Cell harvest 1 L spinner | Microcarrier sediment time | 5 minutes |
| | D-PBS transfer volume | 100 mL |
| | Expected microcarrier bed volume | 240 mL |
| | D-PBS cell wash volume | 300 mL |
| | TrypLE select concentration | 0.004 mL/$cm^2$ |
| | Cell detachment incubation temperature | 36.5 ± 1° C. |
| | Cell detachment incubation humidity | 80% ± 10% |
| | Cell detachment incubation $CO_2$ | 5.0% ± 2% |
| | Cell detachment incubation time | 5 min then until 90% detachment |

TABLE 5-continued

| 1 L spinner flask: harvest parameters | | |
|---|---|---|
| Stage | Parameter | Operating criteria (range) |
| | DMEM + 10% FBS added post detachment | 300 mL |

Per 10 L bioreactor, 100 g HillexII microcarrier were resuspended in 2000 mL WFI and autoclaved under saturated steam for 20 minutes at 2 bar and 121° C. Post sterilization, microcarrier were allowed to sediment, the WFI was removed carefully, discarded and microcarriers were washed with 2,000 mL PBS. The sterilized microcarriers were then transferred into the respective 10 L bioreactor by pumping the PBS/microcarrier suspension carefully using a peristaltic pump. Alternatively, microcarrier preparation can be performed together with the sterilization process of the bioreactor glass vessel: Fill the bioreactor with 100 g HillexII and add 20 ml WFI/g HillexII. Wash 1× with 20 ml fresh WFI/g HillexII and 1× with 20 mL PBS/g HillexII. When the bioreactor is completely assembled a pressure test will be performed to check if the bioreactor is closed. Then, autoclavation for 20 minutes at >121° C. was performed.

When the bioreactor was sterilized and connected to the control unit, all probes (dissolved oxygen (DO), temperature and pH) the heating jacket, stirrer and an extra sample pipe to extract medium 15 above settled microcarriers from the bioreactor were connected. When settings were stabilized for approximately 6 hours airflow over sparger with 75 RPM agitation and a temperature set point of 37° C. was started. When probe signals were stable a 100% DO calibration was performed. After the DO calibration airflow, heating and agitation was stopped and microcarriers were allowed to settle to the bottom of the bioreactor. Supernatant above settled carriers was removed using the extra sample pipe installed. The bioreactor was filled with 2.2 liter medium without phenol red (2 Liter medium+10% FBS). Finally, agitation at 75 RPM, airflow overlay 0.25 L/min, heating at 36.5° C. was started. A sample was taken to re-calibrate the pH by the offline measurement. The bioreactor was then ready for inoculation with cells.

The required amount of cells (as a suspension with the detached microcarrier from the previous step) was transferred aseptically into the reactor containing 100 g microcarrier and 2.2 L pre-warmed DMEM+10% FBS medium without phenol red. In general, the full content of two 1 L spinner flasks was transferred to one 10 L bioreactor. This represents a seeding density of 4 to $5\times10^4$ cells/cm$^2$ and a split ratio of 1:5. These parameters naturally can vary depending on the host cell and the MVSS chosen for each setting. After cell transfer, medium was filled up to 10 L working volume and pH control ($CO_2$ and sodium bicarbonate) as well as DO control ($O_2$ sparging) were started. Samples were regularly taken for microscopic observation and cell counts.

TABLE 6

| 10 L Bioreactor inoculation parameters | | |
|---|---|---|
| Stage | Parameter | Operating criteria (range) |
| Bioreactor Stage 5 | Seeding density | 4 to 5 × $10^4$ cells/cm$^2$ (this corresponds to the content of 2 × 1 L spinner flasks |

TABLE 6-continued

| 10 L Bioreactor inoculation parameters | | |
|---|---|---|
| Stage | Parameter | Operating criteria (range) |
| | Culture flask type | 10 L Bioreactor |
| | Surface area per 100 g HillexII | 51500 cm$^2$ |
| | Seeding culture volume | 2.2 L |
| | Total culture volume | 10 L |
| | Revolutions per minute | 75 |
| | Culture media | DMEM + 10% FBS; w/o Phenol Red |
| | Incubation Temperature | 36.5 ± 1° C. |
| | Duration | Approximately 7 ± 1 days |
| | Dissolved oxygen control by $O_2$ via sparger | >40% |
| | pH control by $CO_2$ via overlay (to decrease pH) and by sodium bicarbonate (to increase pH) | 7.1 ± 0.2 |
| | Temperature control | 36.5 ± 1° C. (during cell culture) 32.5 ± 1° C. (during virus production) |
| | Agitation control for sedimentation/homogeneous mixing by visual inspection | With 2 impellers. First impeller is placed at the bottom and the other is placed at a 20 cm distance |
| | Process Air | Air via overlay, 0.5 mL/min |
| | $CO_2$ | $CO_2$ via overlay with pH control |
| | $O_2$ | $O_2$ via sparger with DO control |
| | Final cell density | ≥80% confluent cells |
| | Final cell viability | ≥80% viability |

Throughout the cell expansion phase of the process, samples were taken for testing as described in Table 7 below:

TABLE 7

| Testing during cell expansion | | |
|---|---|---|
| Sample Stage | Testing | Acceptance criteria |
| Cell expansion | Macroscopic and microscopic observation | Adherent cuboidal cells |
| | Media Colour | Red/orange media; preferably none if w/o phenol red |
| | Evidence of contamination | No evidence of contamination |
| | Cell count | Report Result |
| | Cell viability | ≥80% viability |
| | Cell confluence | ≥80% confluence |

Example 5: Cell Culture Infection

Approximately 5 mL of the cell/microcarrier suspension within the bioreactor were removed to determine confluency of the microcarrier and a viable cell count was performed. Cells should be ≥80% viable and microcarrier ≥80% confluent. The cell count was used to determine the number of viral particles required to infect the culture at an MOI of 0.01 $TCID_{50}$/cell. This MOI may again vary depending on the host cell and the MVSS chosen, but can be easily determined after standard pretestings with the respective host cell and the respective virus. MOIs between 0.0001 and 0.1 are preferable. Notably, the time point for harvest will change depending on the chosen MOI, which can be determined by the skilled person.

After calculating the required amount of virus, an appropriate number of viral vials were removed from −80° C.

storage and they were transported to the cleanroom. The virus vials were thawed at ambient/in hands until all ice has melted. The virus volume required to infect the 10 L suspension at an MOI of 0.01 $TCID_{50}$/cell was calculated and is diluted in 5,000 mL VP-SFM w/o phenol red.

Agitation of the bioreactor, DO and pH control were stopped and the microcarrier/cells suspension within the bioreactor was allowed to stand for 10 minutes without agitation to enable cell-containing microcarrier to sediment. The spent medium was removed carefully, discarded and the microcarrier were washed twice with 2,500 mL pre-warmed D-PBS. 3,000 mL VP-SFM w/o phenol red was added, incubated for 5 minutes at 36.5±1° C./50 rpm, removed carefully and discarded. The previous prepared viral suspension was then added to the bioreactor and allowed to incubate for 4 to 6 hrs at 32.0° C.±2° C., preferably at 32° C.±1° C., pH at 7.2±0.2, DO>40% and 75 rpm. Viral adsorption proceeded in accordance with the parameters described in Table 8 below. After a viral adsorption period of 4-6 hrs, medium was filled up to 10 L using VP-SFM w/o phenol red.

TABLE 8

Viral Adsorption Parameters

| Stage | Parameter | Operating criteria (range) |
|---|---|---|
| Viral Adsorption | Viral stock | MV CHIK MVSS/WVSS |
| | Infection MOI | 0.01 $TCID_{50}$/cell |
| | Infection medium | VP-SFM w/o phenol red |
| | Virus thaw conditions | Ambient/in hands |
| | Virus thaw duration | Until ice has melted |
| | Volume of viral dilution media (VPSFM) | 5,000 mL |
| | Microcarrier sediment time | 10 min |
| | Volume of wash media (PBS) | 2,500 mL |
| | Volume of wash media (VPSFM) | 3,000 mL |
| | Volume of viral suspension to add to the reactor | 5,000 mL |
| | Total volume post viral adsorption | 10 L |
| | Incubation Temperature | 32° C. ± 2° C.<br>32° C. ± 1° C.<br>(for Vero Cells and MV CHIK MVSS grown on microcarrier) |
| | Duration | 4-6 hrs |
| | pH | 7.2 ± 0.2 |
| | DO | >40% |
| | Revolutions per minute | 75 rpm |

TABLE 9

Viral Propagation Parameters

| Stage | Parameter | Operating criteria (range) |
|---|---|---|
| Viral Propagation | Propagation medium | VP-SFM w/o phenol red |
| | Propagation volume | 10 L |
| | Incubation Temperature | 32° C. ± 1° C. |
| | Duration | 4-7 days |
| | pH | 7.2 ± 0.2 |
| | DO | >40% |
| | Revolutions per minute | 75 rpm |
| | Final cytopathic effect (CPE) target | ≥80% CPE |

The infected microcarrier/cell suspension was observed daily from the $4^{th}$ day of viral prorogation until ≥80% CPE was observed.

Testing was performed upon viral infection as described in Table 10 below.

TABLE 10

Testing during viral propagation

| Sample Stage | Testing | Acceptance criteria |
|---|---|---|
| Viral Propagation | Macroscopic and microscopic observation | Adherent cuboidal cells |
| | Media Colour | Red/orange media |
| | Evidence of contamination | No evidence of contamination |

Example 6: Benzonase Treatment

Additionally, the protocols disclosed herein can comprise a DNAse treatment step. This treatment can be performed before or after clarifying the virus suspension depending on the host cell and the recombinant infectious virus particle to be purified. A preferred DNAse is a benzonase, but any suitable DNAse having comparable activity, specificity and purity can be chosen for this purpose, whereas the choice of a suitable DNAse can easily be made by a person skilled in the art.

For the MV CHIK virus purification protocol, agitation, DO, pH control was stopped and the microcarrier/cells suspension within the bioreactor was allowed to stand for 10 minutes without agitation to enable cell-containing microcarrier to sediment. Virus-containing supernatant was transferred carefully from the bioreactor to one sterile 50 L flexboy bag using the aseptic transfer line by pressure and/or gravity.

The required amount of benzonase and magnesium chloride (the cofactor, concentration and required solution may vary depending on the DNAase chosen for the assay) to obtain final concentrations of 50 u/mL and 2 mM was calculated. Benzonase was removed from −20° C. storage, transported to the cleanroom on dry ice and thawed at ambient. Within the biosafety cabinet a stock solution of 200 mM magnesium chloride solution was prepared from 1 M magnesium chloride using WFI as diluent. Prior to addition, the calculated volumes of magnesium chloride and Benzonase were mixed together into a homogeneous solution and then added to the viral suspension and swirled gently. Magnesium chloride and Benzonase were added to such that the final concentration of the Benzonase within the solution was 50 u/mL and the final concentration of magnesium chloride is 2 mM. The 50 L bag was placed on an orbital shaker within an incubator and incubated at 37±1° C. for one hour under gentle agitation.

TABLE 11

Harvest and Benzonase Treatment Parameters

| Stage | Parameter | Operating criteria (range) |
|---|---|---|
| Benzonase Treatment | Microcarrier sediment time | 10 min |
| | Treatment vessel | 4 × 3 L spinner flasks |
| | Concentration of magnesium chloride required in each spinner | 2 mM |
| | Concentration of Benzonase required in each spinner | 50 U/mL |
| | Incubation shaker speed | 50 rpm |
| | Benzonase incubation temperature | 37° C. ± 1° C. |
| | Benzonase incubation time | 1 hour |

These parameters may vary depending on the DNAse used, but can easily be adapted by the person skilled in the art in the knowledge of the present disclosure.

The four 3 L spinner flasks containing the benzonase treated virus suspension were transferred to the downstream part directly (processing on one day) or stored at 4° C. over night (processing on two days). It should be avoided to store the benzonase treated pool longer than over night.

Testing performed prior to harvest is described in Table 12 below:

TABLE 12

| Testing immediately prior to harvest | | |
|---|---|---|
| Sample Stage | Testing | Acceptance criteria |
| Harvest | Macroscopic and microscopic observation | Adherent cells, showing sings of CPE |
| | Media Colour | Red/orange media; none in the case of medium w/o phenol red |
| | Evidence of contamination | No evidence of contamination |
| | CPE | ≥80% CPE |

Example 7: Unpurified Bulk Specification

Following harvest/benzonase treatment, the material was tested in accordance with the unpurified bulk specification as shown in Table 13 below. Kits and methods to perform said testing are readily available to the skilled person.

TABLE 13

| Unpurified Bulk Specification | | |
|---|---|---|
| Purity | Mycoplasma EP 2.6.7 | Negative |
| | In-vitro adventitious agents | Negative |
| | In-vivo adventitious agents | Negative |

Example 8: Downstream Manufacture—Clarification

For clarification of the optionally benzonase treated virus suspension, Sartorius Sartopore PP3 depth filtration units were used. Two filters are connected in parallel to allow a switch between filters in case of pressure increase. First, both filters were flushed with sterile PBS and a pressure hold test was performed at 20 psi for 5 minutes. The benzonase treated harvest was connected to the inlet tubing of the clarification filters whereas inlet of filter 1 was open and inlet and outlet of filter 2 were closed. Benzonase treated material was clarified by filtration through filter 1 using a maximum pressure of 20 psi. Pump speed may be adjusted to maintain pressure below 20 psi if required. In case pressure reaches 20 psi before the complete harvest is filtered switch to bypass filter (filter 2). Once the complete harvest was filtered, filter 1 (and 2) were emptied by pumping air to the filter trains. The clarified virus material was directly subjected to purification.

The clarification method chosen here can vary depending on material to be clarified and any suitable filtration method can be applied. It is important to consider the polymorphic large surface of the measles virus, which represents the scaffold structure to be clarified. Therefore, suitable filter materials have to be chosen, which do not show unspecific binding of the measles virus scaffold based preparation, which would result in a loss of yield or functionality. As detailed above, centrifugation should be avoided due to the limited scalability thereof under GMP conditions and/or the risk of contaminations associated with this procedure.

TABLE 14

| Clarification Parameters | | |
|---|---|---|
| Stage | Parameter | Operating criteria (range) |
| Virus Clarification | Clarification filter | Sartorius Sartopore PP3, 3 um, 0.42 m$^2$ |
| | Filter flush medium | PBS |
| | Pressure hold test | 20 psi, 5 minutes |
| | Maximum pressure | 20 psi |

Example 9: Column Chromatography Based Purification

CIM®-OH Column Preparation

1×80 mL CIM®-OH monolithic column (Bia Separations) with a pore size of 6 μm was removed from storage at 2-8° C. and was allowed to warm up for ≥2 hours prior to use. Any other suitable column can be used for purification provided that it allows specific retention of the measles virus scaffold based virus suspension comprising recombinant infectious virus particles in the respective dimensions and with the respective chemical properties of its surface structure. Preferably, a pore size of at least 4 μm, preferably more, should be chosen to avoid clogging of the column and unspecific binding due to the dimensions of the measles virus derived virus preparation to be purified. Any column based on hydrophobic interaction, affinity, size exclusion or ion exchange as separating principle can be used depending on the nature of the insert, which can, for example, comprise an affinity tag in a protein coding region or which can have specific characteristics to apply an ion exchange chromatography. An exemplary procedure using an ÄKTA Pilot chromatography system is set up as described below. Any suitable chromatography system can be chosen for the purpose of the present invention provided that it is compatible with the column chosen.

The pH electrode was calibrated according to respective standard operating procedures. Inlet tubings were connected to the ÄKTA Pilot system inlets A1, A2, B1, B2, B3 and sample inlets S1 and S2 and were tie wrapped. Using a sterile connective device (SCD), a two T-piece was connected to the inlet tubing on S1 to create a bypass on this line. Using the SCD, cleaning tubing was connected to the inlet tubing on A1, A2, B1, B2, B3, S2 and both lines of the T-piece on S1. Outlet tubing was connected to the ÄKTA Pilot system outlets F1, F3, F5 and F7 using and each connection was tie wrapped. Airvents were clamped off on the outlet tubing with Kocher clamps. Using the SCD a cleaning outlet tubing set was connected up to outlet tubing on F1, F3, F5 and F7 and to one 20 L waste bag. The CIM®-OH monolith column was connected in upflow direction to column position 2. The second column was placed to column position 3. Using the SCD, the 1.0 M NaOH solution (>6.5 L/column) was connected to the inlet cleaning tubing. All inlets, outlets and the system were flushed with 1.0 M NaOH. The monolith columns were conditioned with a minimum NaOH contact time of 120 minutes. Using the SCD the 1.0 M NaOH connected to the inlet cleaning tubing was replaced with 0.1 M NaOH (>4 L/column). All inlets, outlets and the system were flushed with 0.1 M NaOH (at this stage the columns can be stored connected to the system). Using the SCD the 0.1 M NaOH connected to the inlet cleaning tubing was replaced with WFI (>6.5 L/column). All inlets, outlets and the system were flushed with WFI. Using the SCD the equilibration buffer (>7 L/column)

was connected to A1, S1 and S2, the elution buffer (>3 L/column) to A2 and WFI (>4.5 L/column) to B2. 1.0 M NaOH was connected to B1. Using the cleaning tubing, equilibration buffer was connected to A1, S1 and S2. All inlets, outlets and the system were flushed with the respective buffers. When flush was complete, the outlet tubings are emptied by opening the attached air vent. Using the SCD the waste bag on F1 was replaced with a new waste bag. Using the SCD two sterile 20 L bags were connected to F3 to collect the flow through for each column. Bag 2 was clamped off. Using the SCD two sterile 5 L bags were connected to F5 to collect the wash fractions from each column. Using the SCD a sterile 1 L bag was connected to F7 to collected the elution fraction (elution from column 1 and 2 are pooled within one bag).

TABLE 15

CIM ® Column Preparation Parameters

| Stage | Parameter | Operating criteria (range) |
|---|---|---|
| Connections | Inlets - Buffer | A1, A2, B1, B2, B3 |
| | Inlets - Sample | S1 and S2 |
| | Outlets | F1, F3, F5 and F7 |
| NaOH flush (1M) | Buffer | 1M NaOH |
| | Volume | 6.5 L/column |
| | Flow rate | 300 mL/min |
| | Flow path | complete system |
| Conditioning of Column | Buffer | 1M NaOH |
| | Volume | NA |
| | Flow rate/ conditioning time | 160 mL/min; 120 minutes |
| | Flow path | B1 > column > F1 |
| NaOH flush (0.1M) | Buffer | 0.1M NaOH |
| | Volume | 4 L/column |
| | Flow rate | 300 mL/min |
| | Flow path | complete system |
| WFI flush (0.1M) | Buffer | WFI |
| | Volume | 6.5 L/column |
| | Flow rate | 300 mL/min |
| | Flow path | complete system |
| Buffer flush | Buffer | Equilibration buffer (A1, S1, S2), elution buffer (A2), NaOH (B1), WFI (B2) |
| | Volume | At least 8 column volumes |
| | Flow rate | 300 mL/min |
| | Flow path | Respective connections |

Sample Preparation

The benzonase treated material was connected to a sterile 50 L bag/bottle placed on an orbital shaker/stirring plate using the SCD. A peristaltic pump head was placed between virus suspension and the empty vessel. The unpurified bulk was pumped completely into the empty vessel. Using the SCD, the sample preparation buffer (>10 L) was connected to the 20 L vessel. A peristaltic pump head was placed between the buffer and the vessel already containing the 10 L virus suspension. An equal volume of sample preparation buffer has to be added to the virus pool to bring the Ammonium Sulphate concentration to 1.8 M. Pumping of buffer and stirring of the solution has to be performed in a very gentle way so that a vortex is seen but no foaming is observed.

Virus and Virus-Like Particle Purification

The diluted virus solution was connected to one of the bypass lines of inlet S1, using the SCD. The bypass on S1 is used to remove air from the line. It has to be ensured that no air will be introduced into inlet S1 later on. Otherwise only part of the virus material will be processed on the respective column. Purification was performed as outlined in Table 16. The virus peak is collected in F7 with UV monitoring (start >50 mAU, stop after 4 column volumes).

Depending on the resolution and the parameters chosen for column purification and depending on the column material, either one product peak will be obtained comprising the recombinant infectious virus particles derived from a measles virus scaffold including nucleic acid material packaged therein and optionally (if present) virus-like particles in one peak. Alternatively, two separate peaks can be obtained, one comprising the recombinant infectious virus particles derived from a measles virus scaffold including nucleic acid material packaged therein and the other one comprising virus-like particles devoid of nucleic acid material. In the case of co-elution, as exemplified in this example, the mixed population comprising both the recombinant infectious virus particles derived from a measles virus scaffold including nucleic acid material packaged therein and the virus-like particles can optionally further be purified, polished or subjected to a buffer -exchange as detailed above.

For the co-elution, the following parameters were chosen: Maximum pressure 5.0 bar. After completion of the run, all outlets were emptied by opening the air vent on the outlet. The outlet air vents and bags were clamped off and the bags were then disconnected from the outlets using the SCD

TABLE 16

Viral Purification Parameters

| Stage | Parameter | Operating criteria (range) |
|---|---|---|
| Final connection Setup | A1 | Equilibration Buffer |
| | A2 | Elution Buffer |
| | B1 | 1M NaOH |
| | B2 | WFI |
| | B3 | 20% EtOH |
| | S1 | Sample |
| | S2 | Equilibration Buffer |
| | F1 | Waste |
| | F3 | Collect Flow Through |
| | F5 | Collect Wash Fraction |
| | F7 | Collect Elution Fraction |
| Equilibration of column | Buffer | Equilibration Buffer |
| | Volume | >2,800 mL |
| | Flow rate | 250 mL/min |
| | Flow path | A1 > Column > F1 |
| | Column flow direction | Normal flow direction |
| Sample loading | Buffer | Sample |
| | Volume | 20 L |
| | Flow rate | 250 mL/min |
| | Flow path | S1 > Column > F3 |
| | Column flow direction | Normal flow direction |
| Wash | Buffer | Elution buffer |
| | Volume | 1,600 mL |
| | Flow rate | 250 mL/min |
| | Flow path | A1 > Column > F5 |
| | Column flow direction | Normal flow direction |
| Elution | Buffer | Equilibration Buffer |
| | Volume | At least 4 CV (320 mL) |
| | Flow rate | 80 mL/min |
| | Flow path | A2 > Column > F7 |
| | Column flow direction | Normal flow direction |
| Wash with WFI | Buffer | WFI |
| | Volume | Preferably at least 8 column volumes |
| | Flow rate | 250 mL/min |
| | Flow path | B2 > Column > F1 |
| | Column flow direction | Normal flow direction |
| Clean column with NaOH | Buffer | NaOH |
| | Volume | 1,200 mL |
| | Flow rate | 250 mL/min |
| | Flow path | B1 > Column > F1 |
| | Column flow direction | Normal flow direction |

TABLE 16-continued

| Viral Purification Parameters | | |
|---|---|---|
| Stage | Parameter | Operating criteria (range) |
| Clean column with WFI | Buffer | WFI |
| | Volume | 1,200 mL |
| | Flow rate | 250 mL/min |
| | Flow path | B2 > Column > F1 |
| | Column flow direction | Normal flow direction |

Product collection during elution was determined by $UV_{280}$ reading on the UV detector. The main peak collection was started when the $UV_{280}$ is >50 mAU and was stopped when a minimum of 4 CV's of Elution buffer had passed through the column. Peak collection parameters are tabulated in Table 17 below. At the end of the purification cycle, the exact volume of main peak fraction was noted and the bulk virus pool was snap frozen at −80° C.±10° C. directly or aliquot as required prior freezing. Alternatively, part of the virus pool can immediately be subjected to further analysis, including analysis for purity and infectivity and the like. The main peak fraction can additionally be subjected to a further round of purification, polishing or buffer-exchange to separate recombinant infectious virus particles containing genetic material from optionally present virus-like particles.

TABLE 17

| Peak Collection Parameters | | |
|---|---|---|
| Stage | Parameter | Operating criteria (range) |
| Main Peak Collection | Start | $A_{280}$ > 50 mAU |
| | End | Minimum of 4 CV |

Using the SCD, 20% EtOH was connected to buffer inlet B3. The system was flushed with 20% EtOH. Using the SCD, all buffers from the Äkta Pilot inlets were disconnected and discarded, the T-piece on inlet S1 was disconnected and discarded and a cleaning tubing was connected to inlets 51, S2, A1, A2, B1, B2 and B3. The cleaning inlet tubing was connected to 1 M NaOH. All inlets, outlets and the system were cleaned with 1 M NaOH. The 1 M NaOH connected to the cleaning tubing was replaced by WFI. Flush the system with WFI. Replace the WFI connected to the cleaning tubing by 20% EtOH. Store the Äkta Pilot in 20% EtOH.

Example 10: Testing

Following the purification of the recombinant infectious virus particles derived from a measles virus scaffold, the material was tested in accordance with the specification in Table 18 below.

TABLE 18

| Testing Specification | | |
|---|---|---|
| Test Category | Test Method | Acceptance Criteria |
| Potency | Titration of measles virus by TCID50 (Infectivity) | ≥$10^4$ $TCID_{50}$/mL |
| Identity | Determination of identity of MV-CHIK measles virus vaccine by PCR | Amplification product of 445 bp observed for PCR1 Amplification product of 497 bp observed for PCR2 |

TABLE 18-continued

| Testing Specification | | |
|---|---|---|
| Test Category | Test Method | Acceptance Criteria |
| Physico-chemical | Potentiometric determination of pH | 7.5 ± 0.5 |
| | Particulate contamination: visible particles | Clear to opaque colourless liquid (There may be product related particles visible) |
| Purity | Sterility | No growth |
| | Enzyme Immunoassay (EIA) for the detection and quantification of residual Benzonase in a test sample | below 100 ng/mL |
| | Detection and quantification of residual Vero DNA in biological samples | below 10 ng/dose |
| | Vero Host Cell Protein (HCP) ELISA | below 5 μg/mL |
| | Detection of Bovine Serum Albumin (BSA) by ELISA | below 500 ng/mL |

Process related impurities were determined using the following kits and assays: (i) for detection and quantification of residual Vero host cell DNA: Cygnus ELISA Kit; (ii) detection and quantification of residual Vero DNA in biological samples: Life Technologies qPCR assay; (iii) for detection of Bovine Serum Albumin: Cygnus ELISA Kit; and (iv) for detection of residual Benzonase: Merck ELISA Kit.

In a comparative Example, the value of host cell protein (HCP) was defined as detailed above for the material according to the present invention for material as obtainable according to Brandler et al. (supra) or for material as obtainable according to the disclosure of WO 2014/049094 A1. Vero cells were used as host cells for these comparative examples. Notably, both Brandler et al. and WO 2014/049094 A1 exclusively teach the use and further characterization of virus material and/or VLPs not subjected to any further purification and/or polishing step at all. When evaluating different charges of measles-chinkungunya material obtained according to the disclosure of Brandler et al. or WO 2014/049094 A1, HCP values of between 316.28 μg/mL to 861.31 μg/mL were obtained. On average, the values as obtained according to the present disclosure using the specific chromatographic purification schemes as disclosed herein were thus significantly better than the values obtained in the prior art.

Example 11: Separation of Virions from Virus-Like Particles

The material obtained from the above experiments as detailed in the Examples Section resulted in the provision of a mixture of fully infectious virus particles comprising both, measles virus based virions as well as virus-like particles (VLPs) of the Chikungunya virus antigens, which are obtained by expressing structural proteins of the Chikungunya virus within the measles virus scaffold (cf. WO 2014/049094 A1). To further allow the possibility to produce a virus material suitable as immunogenic or vaccine composition, further experiments were conducted to separate the nucleic acid containing virion fraction from the VLPs devoid of nucleic acid.

To this end several filtration, centrifugation or chromatography approaches were evaluated to obtain both, the virion and the VLP fraction. The following purification or polishing strategies were applied: membrane filtration/purification with other grafted media, ion-exchange chromatography, size-exclusion chromatography, affinity chromatography; aqueous two phase extraction; precipitation, tangential flow filtration (polishing); dialysis (polishing) and/or buffer exchange or size exclusion (polishing).

Example 12: Immunization Experiments

To evaluate the immunogenicity of the purified material, i.e. infectious virus particles derived from a measles virus scaffold (MV-Xp), in comparison to the crude, unpurified material (MV-Xup) two animal studies can be conducted:

1. Challenge study—lethal challenge after two immunizations

2. T cell response after one immunization

The animal model of choice would be a transgenic mouse carrying the human MV entry receptor CD46. In addition these mice are deficient in the type 1 interferon receptor ($CD46^{tg}/IFNAR^{-/-}$). In previous studies the immunogenicity of various MV/Schwarz based construct was demonstrated (MV-CHIK, MV-DEN, etc.). For MV-CHIK we showed that doses as low as $1\times10^3$ $TCID_{50}$ fully protect animals against a lethal dose of CHIKV. Thus, a lower dose would allow the comparison between two formulations in terms of potency. A result of this type of study would be:

Formulation A (purified, MV-Xp) protects x out of 10 mice

Formulation B (unpurified, MV-Xup) protects y out of 10 mice

For the challenge study we propose the following study set up:

$CD46^{tg}/IFNAR^{-/-}$ mice will receive two immunizations. The lethal challenge with the respective pathogen will show % protection against death. In addition, antibody levels as determined by ELISA can be quantified and compared.

TABLE 19

| Group | No of Mice | Treatment | Dose (MV-X) | Vaccination Schedule | Challenge |
|---|---|---|---|---|---|
| 1 | 10 | MV-Xp Formulation A | $1 \times 10^2$ | Day 0, 28 | Day 56 |
| 2 | 10 | MV-Xup Formulation B | $1 \times 10^2$ | Day 0, 28 | Day 56 |
| 4 | 5 | MV-Schw | — | Day 0, 28 | Day 56 |

T cell study - IFNγ producing cells after one immunization

Mice will be immunized with a low dose of MV-X (Formulation A (purified) or B (unpurified)) or a control MV/Schwarz. One week after immunization the mice will be sacrificed and spleenocytes will be harvested. The cells will be challenged in vitro with pathogen specific peptides and the number of interferon gamma (IFNγ) producing T cells will be determined by ELISPOT.

TABLE 20

| Group | No of Mice | Treatment | Dose | Vaccination Schedule | Spleenocyte harvest |
|---|---|---|---|---|---|
| 1 | 5 | Purified MV-Xp | $1 \times 10^3$ | Day 0 | Day 7 |
| 2 | 5 | Unpurified MV-Xup | $1 \times 10^3$ | Day 0 | Day 7 |
| 4 | 5 | MV/Schw | — | Day 0 | Day 7 |

Example 13: Toxicity Studies in Macaques

To evaluate the safety and potential toxicity of the immunogenic and vaccine compositions as produced according to the present invention, the following experiment can be performed under good laboratory proactive (GLP) conditions as pre-experiment potentially followed by Phase 1 clinical trials. One group of five male and five female purpose-bred cynomolgus macaques is treated on days 1, 22 and 36 by intramuscular route of the test immunogenic or vaccine composition. The animals were sero-negative to measles. Furthermore, animals have to be sero-negative for the antigen comprised by the measles virus scaffold and presented in the recombinant infectious virus particles. For pTM 2ATU MV CHIK (SEQ ID NOs:2/8) obtained after performing the methods according to the present invention, treatment is performed at a dose of $1.925\times10^6$ $TCID_{50}$/day of injection. Two other groups of two males and two females will receive received the composition at doses of $1.925\times10^4$ or $1.925\times10^5$ $TCID_{50}$/day of injection, here exemplified for the recombinant infectious virus particles derived from a measles virus scaffold obtained from SEQ ID NOs:2/8. A further control group of three males and three females will receive vehicle only (sterile saline). A summary of treatment groups is presented in Table 21 below. The person skilled in the art will readily be able to adapt said scheme to any recombinant infectious virus particle as immunogenic and vaccine composition purified according to the methods of the present invention.

TABLE 21

Summary of treatment groups for cynomolgus macaque toxicity studies

| | Males (M)/ Females (F) | Dose ($TCID_{50}$/day of injection) | Volume administered (mL) |
|---|---|---|---|
| Group 1 | 3M/3F | 0 | 2.5 |
| Group 2 | 2M/2F | $1.925 \times 10^4$ | 0.025 |
| Group 3 | 2M/2F | $1.925 \times 10^5$ | 0.25 |
| Group 4 | 5M/5F | $1.925 \times 10^6$ | 2.5 |

$TCID_{50}$ = 50% tissue culture infective dose

At the end of the treatment period (day 37), the animals will be sacrificed, except for the last two animals of each sex in Group 4, which were observed for a 13-day treatment-free period (and sacrificed on day 50). Blood samples will be taken for the determination of serum levels of antibodies against the vaccine antigen, for measles serology and for haematology and biochemistry. Other assessments known to the skilled person can comprise body weight, functional observation battery, rectal temperature, ECG and ophthalmology examinations. On completion of the treatment period or treatment-free period, the animals will be sacrificed and a full macroscopic post-mortem examination will be performed. Designated organs can be weighed and selected tissue specimens can be preserved. A microscopic examination can be performed on designated tissues from Group 1 and Group 4 animals sacrificed on completion of the treatment period.

For the immunogenic composition derived from SEQ ID NOs:2/8 no unscheduled deaths occurred during the study. There were no test item-related clinical signs during the treatment and treatment-free periods. In particular, no local reactions were reported. There were no test item-related findings at functional observation battery. There were no effects on the rectal temperature or body weight throughout the study. Qualitative and quantitative parameters at ECG examination were unaffected throughout the study. No test item-related ophthalmological findings were observed at the end of treatment or the treatment-free period. No remarkable changes were noted in haematological parameters at the end of the treatment period, while slightly increased lymphocyte counts were recorded in males and females at the end of the treatment-free period. After each round of vaccination and then in detail at the end of the treatment period injection site inflammatory lesions (e.g. increases in inflammatory mononuclear and/or granulocytic cell infiltrates or interstitial oedema).

Example 14: Purification of pTM 2ATU MV DVAX1

The same purification scheme as detailed above in Examples 1 to 10 was applied for the purification of a virus derived from pTM 2ATU MV DVAX1 (SEQ ID NOs:3/9). All experiments were conducted under GMP conditions. The same overall parameters as detailed above were applied. This series of experiments allowed the yield of infectious recombinant viruses comprising the Dengue antigens with a very high titer of 1.27E+07 $TCID_{50}$/mL. In sum, 425 mL were produced. The level of contaminating Vero host cell DNA for one of the product peak fractions was below the detection limit of the assay applied, i.e. below 1.1 pg/mL. Further testing for purity and immunogenicity is currently ongoing. Notably, no acute side effects were detected when administering a dose of $1\times10^2$ $TCID_{50}$ to five $CD46^{t9}$/$IFNAR^{-/-}$ mice.

Example 15: Purification of MV-Zika

The same purification scheme as detailed above in Examples 1 to 10 was applied for the purification of a measles virus scaffold carrying specific antigens derived from a Zika virus as disclosed in EP16162688.2 and as disclosed herein as a plasmid having the sequence of SEQ ID NOs: 5 and 6. The plasmids according to SEQ ID NOs: 5 and 6 can be propagated and purified as detailed above.

Following the purification, the material was tested in accordance with the specification in Table 22 below.

TABLE 22

Testing Specification

| Test Category | Test Method | Acceptance Criteria |
|---|---|---|
| Potency | Titration of measles virus by TCID50 (Infectivity) | ≥$10^4$ $TCID_{50}$/mL |
| Identity | Determination of identity of MV-sE (SEQ ID NO: 5) or RSP (SEQ ID NO: 6) vaccine by PCR | Amplification product of 321 bp observed for PCR1 Amplification product of 621 bp observed for PCR2 |
| Physico-chemical | Potentiometric determination of pH | 7.5 ± 0.5 |
| | Particulate contamination: visible particles | Clear to opaque colourless liquid (There may be product related particles visible) |
| Purity | Sterility | No growth |
| | Enzyme Immunoassay (EIA) for the detection and quantification of residual Benzonase in a test sample | below 100 ng/mL |
| | Detection and quantification of residual Vero DNA in biological samples | below 10 ng/dose |
| | Vero Host Cell Protein (HCP) ELISA | below 5 μg/mL |
| | Detection of Bovine Serum Albumin (BSA) by ELISA | below 500 ng/mL |

Process related impurities were determined using the following kits and assays: (i) for detection and quantification of residual Vero host cell DNA: Cygnus ELISA Kit; (ii) detection and quantification of residual Vero DNA in biological samples: Life Technologies qPCR assay; (iii) for detection of Bovine Serum Albumin: Cygnus ELISA Kit; and (iv) for detection of residual Benzonase: Merck ELISA Kit.

The invention claimed is:

1. A method for purifying recombinant infectious virus particles, comprising:

(i) providing at least one clarified virus sample comprising at least one recombinant infectious virus particle, wherein the at least one recombinant infectious virus particle comprises a measles virus scaffold and is obtained from at least one host cell infected with a virus stock comprising the at least one recombinant infectious virus particle, and wherein the clarification has been performed by a filtration method and the at least one virus sample is treated with a DNAse before or after clarification;

(ii) purifying the at least one recombinant infectious virus particle by means of chromatography performed using a stationary phase, wherein the stationary phase has a monolithic arrangement and has a pore size of at least 5 μm, at least 6 μm, or at least 7 μm, wherein the mode of adsorption is hydrophobic interaction; and (iii) directly obtaining purified recombinant infectious virus particles within at least one fraction from the chromatography of step (ii), wherein the purified infectious virus particles contain less than 33.33 ng/mL of contaminating host cell DNA with respect to 1 mL of the at least one fraction.

2. The method according to claim 1, wherein the DNAse is a genetically engineered endonuclease derived from *Serratia*.

3. The method according to claim 1, wherein the method further comprises the following steps preceding the steps as defined in claim 1:

(a) providing at least one host cell;

(b) providing a virus stock comprising at least one recombinant infectious virus particle, wherein the at least one recombinant infectious virus particle is encoded by at least one nucleic acid sequence, wherein the nucleic acid sequence comprises at least one first nucleic acid sequence encoding a virus scaffold and at least one second nucleic acid sequence operably linked to the first nucleic acid sequence, wherein the at least one second nucleic acid sequence encodes at least one virus antigen;

(c) infecting the at least one host cell of step (a) with the virus stock provided in step (b);

(d) incubating the at least one infected host cell at a temperature in the range of 32.0° C.+/−4° C.;

(e) obtaining at least one virus sample from the at least one infected host cell comprising the at least one recombinant infectious virus particle; and (f) clarifying the at least one virus sample of step (e) by a filtration method.

4. The method according to claim 3, wherein the at least one infected host cell is incubated at a temperature in the range of 32.0° C.+/−1° C.

5. The method according to claim 1, wherein the at least one host cell consists of cells selected from the group consisting of Vero cells, chicken embryo fibroblast cells, HEK293 cells, HeLa cells, and MRC5 cells.

6. The method according to claim 1, wherein the at least one recombinant infectious virus particle is encoded by at least one nucleic acid sequence, wherein the at least one nucleic acid sequence comprises at least one first nucleic acid sequence encoding a virus scaffold and at least one second nucleic acid sequence operably linked to the first nucleic acid sequence, wherein the at least one second nucleic acid sequence encodes at least one antigen of at least one virus, wherein the nucleic acid sequence encoding the at least one antigen is selected from the group consisting of a nucleic acid sequence from a virus belonging to the family of Flaviviridae, including a nucleic acid sequence from a West-Nile virus, a tick-borne encephalitis virus, a Japanese encephalitis virus, a yellow fever virus, a Zika virus, or a Dengue virus, a Chikungunya virus, a norovirus, a virus belonging to the family of Paramyxoviridae, including a nucleic acid sequence from a human respiratory syncytial virus, a measles virus or a metapneumovirus, a parvovirus, a coronavirus, including a nucleic acid sequence from a Middle East respiratory syndrome antigen or a severe acute respiratory syndrome antigen, a human enterovirus 71, a cytomegalovirus, a poliovirus, an Epstein-Barr virus, a hepatitis E virus, a human papilloma virus, including a human papilloma virus 16, a human papilloma virus 5, a human papilloma virus 4, a human papilloma virus 1 or a human papilloma virus 41, or a varicella zoster virus.

7. The method according to claim 1, wherein the measles virus scaffold is selected from an attenuated virus strain.

8. The method according to claim 7, wherein the attenuated virus strain is selected from the group consisting of the Schwarz strain, the Zagreb strain, the AIK-C strain, and the Moraten strain.

9. The method according to claim 1, wherein the purified recombinant infectious virus particles contain less than 30 ng/mL, less than 20 ng/mL, less than 10 ng/mL, less than 1 ng/mL, less than 100 pg/mL, less than 10 pg/mL, or less than 1.1 pg/mL of contaminating host cell DNA per one mL of the recombinant infectious virus particles as directly obtained within at least one fraction after chromatographic purification with respect to 1 mL of the at least one fraction.

10. The method according to claim 1, further comprising a purification step (iv), comprising:

further purifying the purified recombinant infectious virus particles by means of filtration, centrifugation, tangential flow filtration, membrane filtration, purification with grafted media, aqueous two phase extraction, precipitation, buffer exchange, dialysis, or chromatography, including size exclusion chromatography for separating the purified recombinant infectious virus particles into a fraction containing virions and another fraction containing virus-like particles.

* * * * *